(12) United States Patent
Martin et al.

(10) Patent No.: US 8,492,404 B2
(45) Date of Patent: Jul. 23, 2013

(54) BIS-ARYL AMIDE COMPOUNDS AND METHODS OF USE

(75) Inventors: Matthew W. Martin, Arlington, MA (US); David C. McGowan, Brussels (BE)

(73) Assignee: Amgen Inc., Thousand Oaks, CA (US)

(*) Notice: Subject to any disclaimer, the term of this patent is extended or adjusted under 35 U.S.C. 154(b) by 161 days.

(21) Appl. No.: 12/788,201

(22) Filed: May 26, 2010

(65) Prior Publication Data
US 2010/0234373 A1 Sep. 16, 2010

Related U.S. Application Data

(62) Division of application No. 11/503,551, filed on Aug. 11, 2006, now Pat. No. 7,754,717.

(60) Provisional application No. 60/708,720, filed on Aug. 15, 2005.

(51) Int. Cl.
| | | |
|---|---|---|
| A01N 43/42 | (2006.01) | |
| A61K 31/47 | (2006.01) | |
| C07D 215/46 | (2006.01) | |

(52) U.S. Cl.
USPC .......................................... 514/313; 546/162

(58) Field of Classification Search
None
See application file for complete search history.

(56) References Cited

U.S. PATENT DOCUMENTS

| | | | |
|---|---|---|---|
| 5,981,573 | A | 11/1999 | Iwasawa et al. |
| 6,048,894 | A | 4/2000 | Iwasawa et al. |
| 6,432,949 | B1 | 8/2002 | Brown et al. |
| 6,548,514 | B1 | 4/2003 | Brown et al. |
| 6,635,655 | B1 | 10/2003 | Jayyosi et al. |
| 6,794,378 | B2 | 9/2004 | Lino et al. |
| 6,794,380 | B2 | 9/2004 | Brown et al. |
| 6,821,965 | B1 | 11/2004 | Brown et al. |
| 2004/0087798 | A1 | 5/2004 | Yamada et al. |
| 2005/0256125 | A1 | 11/2005 | Kath et al. |

FOREIGN PATENT DOCUMENTS

| | | |
|---|---|---|
| EP | 039051 A2 | 4/1981 |
| WO | 99/32433 A1 | 7/1999 |
| WO | 00/07980 A1 | 2/2000 |
| WO | 01/45689 A2 | 6/2001 |
| WO | 01/96327 A1 | 12/2001 |
| WO | 02/34711 A1 | 5/2002 |
| WO | 03/002109 A2 | 1/2003 |
| WO | 2004/017969 A1 | 3/2004 |
| WO | 2005/061465 A1 | 7/2005 |
| WO | 2005/063689 | 7/2005 |
| WO | 2005/063689 A1 | 7/2005 |
| WO | 2005/073165 A1 | 11/2005 |
| WO | 2006/003378 A1 | 1/2006 |
| WO | 2006/028958 A2 | 3/2006 |
| WO | 2006/040568 A1 | 4/2006 |

OTHER PUBLICATIONS

Atwell, et. al., Journal of Medicinal Chemistry (1967), 10(4), 706-13.*
Hiratani, et. al., Bulletin of the Chemical Society of Japan (1990), 63(11), 3331-3.*
Abram, et al "Src Family Tyrosine Kinases and Growth Factor Signaling", *Exp. Cell Rsh.*, 254: 1-13 (2000).
Andoh, et al "Rapid intestinal ischaemia-reperfusion injury is suppressed in genetically mast cell-deficient Ws/Ws rats", *Clin. Experim. Immunol.*, 116: 90-93 (1999).
Boissan, et al "c-Kit and c-kit mutations in mastocytosis and other hematological diseases", *Jnl. of Leukoc. Biol.*, 67: 135-148 (2000).
Bradding, et al "Heterogeneity of Human Mast Cells Based on Cytokine Content", *Jnl. of Immunol.*, 155: 297-307 (1995).
Feng, et al "Decreased expression of the *c-kit* receptor is associated with increased apoptosis in subfertile human testes", *Fertil. and Steril.*, 71: 85-89 (1999).
Gaça, et al "Human and rat hepatic stellate cells produce stem cell factor: a possible mechanism for mast cell recruitment in liver fibrosis", *Jnl. Hep.*, 30: 850-858 (1999).
Parrott, et al "Kit-Ligand/Stem Cell Factor Induces Primordial Follicle Development and Initiates Folliculogenesis", *Endocrin.*, 140: 4262-4271 (1999).
Paul, et al "Src deficiency or blockade of Src activity in mice provides cerebral protection following stroke", *Nature Med.*, 7: 222-227 (2001).
Secor, et al "Mast Cells Are Essential for Early Onset and Severe Disease in a Murine Model of Multiple Sclerosis", *Jnl. of Experim. Med.*, 191: 813-821 (2000).

* cited by examiner

*Primary Examiner* — Jeffrey Murray
(74) *Attorney, Agent, or Firm* — G. Prabhakar Reddy

(57) ABSTRACT

The present invention comprises a new class of compounds useful for the prophylaxis and treatment of protein kinase mediated diseases, including autoimmune disease and inflammation. In one embodiment, the compounds have a general Formula I

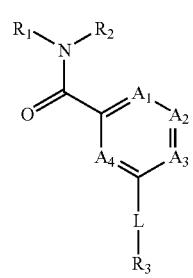

wherein $A^1, A^2, A^3, A^4, L, R^1, R^2$ and $R^3$ are defined herein. The invention also comprises pharmaceutical compositions including one or more compounds of the present invention, methods of use such as treatment of Lck and/or c-Kit kinase mediated diseases by administering the compounds of the invention, or compositions including one or more compounds of the invention, and intermediates and processes useful for the preparation of compounds of the present invention.

7 Claims, No Drawings

BIS-ARYL AMIDE COMPOUNDS AND METHODS OF USE

RELATED APPLICATIONS

This application claims the benefit of U.S. National patent application Ser. No. 11/503,551, filed Aug. 11, 2006, which in turn claims the benefit of U.S. Provisional patent Application No. 60/708,720, filed Aug. 15, 2005, each of which is hereby incorporated herein by reference in their entireties.

FIELD OF THE INVENTION

The present invention generally relates to bis-aryl amide compounds, pharmaceutical compositions comprising same and use for treatment of kinase mediated disorders.

BACKGROUND OF THE INVENTION

Inflammatory autoimmune diseases, such as rheumatoid arthritis, polyarthritis scleroderma, inflammatory bowel disease, type I diabetes, multiple sclerosis, ulcerative colitis, Crohn's disease, Sjogren's disease, polymyositis, dermatomyositis, vasculitis, myasthenia gravis, psoriasis, and lupus, typically activate various inflammatory factors, including T-cells. T cells play a pivotal role in the regulation of immune responses and are important for establishing immunity to pathogens. T cell activation is also an important component of organ transplantation rejection, allergic reactions, and asthma.

T cells are activated by specific antigens through T cell receptors (TCR) which are expressed on the cell surface. This activation triggers a series of intracellular signaling cascades mediated by enzymes expressed within the cell (Kane, L P et al. Current Opinion in Immunol. 2000, 12, 242). These cascades lead to gene regulation events that result in the production of cytokines, including interleukin-2 (IL-2). IL-2 is a critical cytokine in T cell activation, leading to proliferation and amplification of specific immune responses.

Kinase enzymes have been shown to be important in the intracellular signal transduction. One class of kinase enzymes involved in signal transduction is the Src-family of protein tyrosine kinases (PTK's), which includes, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the Src family of kinases would potentially lead to therapeutic benefit. Src(−/−) mice have abnormalities in bone remodeling or osteopetrosis (Soriano, P. Cell 1991, 64, 693), suggesting that inhibition of the Src kinase might be useful in diseases of bone resorption, such as osteoporosis. Lck(−/−) mice have defects in T cell maturation and activation (Anderson, S J et al. Adv. Immunol. 1994, 56, 151), suggesting that inhibition of the Lck kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

Src kinases have also been found to be activated in tumors including sarcoma, melanoma, breast, and colon cancers suggesting that Src kinase inhibitors may be useful anti-cancer agents (Abram, C L and Courtneidge, S A Exp. Cell Res. 2000, 254, 1). Src kinase inhibitors have also been reported to be effective in an animal model of cerebral ischemia (R. Paul et al. Nature Medicine 2001, 7, 222), suggesting that Src kinase inhibitors may be effective at limiting brain damage following stroke.

Another protein kinase believed to cause autoimmune disease is c-Kit. C-kit is a receptor tyrosine kinase expressed on the surface of mast cells, to which stem cell factor (SCF) is a ligand. Aberrant c-kit signaling is believed to be a mediator of certain autoimmune diseases. Binding of SCF to the c-kit receptor mediates various functions of the mast cell. As an important mediator of mast cell function, c-kit is thought to also play a role in pathologies associated with mast cells (MC). C-kit functions through mast cell generation, which plays an important role in triggering autoimmune diseases. Mast cells are tissue elements derived from a particular subset of hematopoietic stem cells that express CD34, c-kit and CD13 antigens (Kirshenbaum et al., *Blood* 94:2333-2342, 1999 and Ishizaka et al, *Curr. Opinion Immunol.* 5:937-943, 1993). Mast cells are characterized by their heterogeneity, not only regarding tissue location and structure but also at the functional and histochemical levels (Aldenberg and Enerback, *Histochem. J.* 26:587-596, 1994; Bradding et al., *J. Immunol.* 155:297-307, 1995; Irani et al., *J. Immunol.* 147:247-253, 1991).

Mast cells are thought to participate in the destruction of tissues by releasing various proteases and mediators categorized into three groups: pre-formed granule associated mediators (histamine, proteoglycans, and neutral proteases), lipid-derived mediators (prostaglandins, thromboxanes, and leucotrienes), and various cytokines, including IL-1, IL-2, IL-3, IL-4, IL-5, IL-6, IL-8, TNFα, GM-CSF, MIP-1a, MIP-1b, MIP-2 and IFNγ. The liberation of these mediators induces and activates various components of immune response involved in autoimmune diseases, and also promotes the tissue destruction process.

Activation of the auto-immune response is postulated to be caused by, or stimulated from, the degranulation of mast cells. Immature MC progenitors circulate in the blood stream and differentiate in the tissues. These differentiation and proliferation processes are influenced by various cytokines. Stem Cell Factor (SCF) and IFNγ are two cytokines which are important in influencing such processes. The SCF receptor is encoded by the proto-oncogene c-kit, which belongs to the type III receptor tyrosine kinase subfamily (Boissan and Arock, *J. Leukoc. Biol.* 67:135-148, 2000), along with PDGF and cFMS. Ligation of c-kit receptor by SCF induces its dimerization followed by its transphosphorylation, leading to the recruitment and activation of various intracytoplasmic substrates. IFNγ is another cytokine secreted by mast cells. It has been reported that IFNγ is responsible for major histocompatibility complexes associated with autoimmune diseases (Hooks et al., *New England J. of Med.*, 301:5-8, 1979). These activated substrates induce multiple intracellular signaling pathways responsible for cell proliferation and activation (Boissan and Arock, 2000).

TNF is another cytokine produced by mast cells. More recently, it has been reported that the TNF produced by mast cells is involved in the pathogenesis of auto-antibody mediated vasculitis (Watanabe et al., *Blood* 11:3855-3866, 1994).

Mast cells were also shown to control neutrophil recruitment during T-cell mediated delayed-type hypersensitivity reactions through TNF and macrophage inflammatory protein 2 (MIP-2). Accordingly, c-kit regulation may be useful in various types of inflammation including without limitation, rheumatoid arthritis, severe asthma, allergy associated chronic rhinitis, and the like.

Mast cells have also been implicated in liver allograph rejection (Yammaguchi et al., *Hematology* 29:133-139, 1999) and in liver fibrosis, where hepatic stallate cells produce the SCF that recruits the mast cells (Gaca et al., *J. Hematology* 30:850-858, 1999). These observations suggest that c-kit kinase inhibitors may help prevent organ rejection and fibrosis. Some possible related c-kit mediated therapeutic indications include idiopathic pulmonary fibrosis (IPF) and scleroderma. Mast cells have also been implicated in the pathology of multiple sclerosis (Secor et al., *J. Experimental Medicine* 191:813-822, 1999), and ischemia-reperfusion injury (Andoh et al, *Clinical & Experimental Immunology* 116:90-93, 1999) in experimental models using mice with mutant kit receptors that are deficient in mast cells. In both cases, the pathology of the diseases was significantly attenuated relative to mice with normal c-kit and mast cell populations. Thus, the role of mast cells in these diseases suggests that c-kit modulators might be useful therapeutics.

C-kit signaling is also important for fetal gonadal development, and plays a role in adult fertility (Mauduit et al, *Human Rep. Update* 5: 535-545, 1999). Spermatogenesis is inhibited through a reduction of c-Kit activity in c-kit signaling through the PI3 kinase pathway (Blume-Jensen et al, *Nature Genetics* 24:157-162, 2000). C-kit expression has been observed to be lower in sub-fertile testes than in normal testicular tissue (Feng et al, *Fertility and Sterility* 71:85-89, 1999). C-kit signaling is also important for oogenesis and folliculogenesis (Parrott and Skinner, *Endocrinology* 140:4262-4271, 1999). These reports suggest that modulation of c-kit enzymatic activity may be a method to reduce both male and female infertility.

While various groups have published on inhibitors of c-kit kinase, disclosing various chemical compounds, including 2-phenylamino-imidazo[4,5-h]isoquinolin-9-ones (Snow, R J et al, *J. Med. Chem.* 2002, 45, 3394), pyrazolo [3,4-d] pyrimidines (Burchat, A F et al, *Bioorganic and Med. Chem. Letters* 2002, 12, 1987 and Hanke, J H et al, *J. Biol. Chem.* 1996, 271, 695), pyrrolo[2,3-d]pyrimidines (Altmann, E et al, *Bioorganic and Med. Chem. Letters* 2001, 11, 853), anilinoquinazolines (Wang, Y D et al, *Bioorganic and Med. Chem. Letters* 2000, 10, 2477), imidazoquinoxalines (Chen, P. et al, *Bioorganic and Med. Chem. Letters* 2002, 12, 3153), PCT publication entitled, "Methods of Modulating C-kit Tyrosine Protein Kinase Function with Indoline Compounds" and PCT publication entitled, "Use of Tyrosine Kinase Inhibitors for Treating Autoimmune Diseases", none of these groups describe the compounds of the present invention, and particularly as modulators of kinase enzymes such as c-kit, and useful for the regulation of autoimmune disease(s), allergies, asthma, cancer and the like.

BRIEF DESCRIPTION OF EXEMPLARY
EMBODIMENTS OF THE INVENTION

The present invention provides compounds that are capable of modulating the activity of one or more kinase enzymes, thereby regulating various kinase-associated disorders including, without limitation, inflammation and autoimmune disease.

The compounds of the present invention, including stereoisomers, tautomers, solvates, pharmaceutically acceptable salts and derivatives, and prodrugs thereof, are represented by general Formula I:

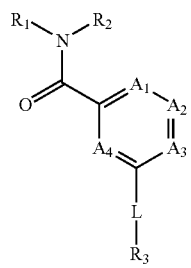

wherein $A^1$, $A^2$, $A^3$, $A^4$, L, $R^1$, $R^2$ and $R^3$ are defined in the Detailed Description below. The compounds of Formula I are capable of modulating protein tyrosine kinase enzymes of the Src family, such as Lck, as well as other protein kinase enzymes such as c-kit. Accordingly, these compounds are useful in the treatment, including preventative, prophylactic and therapeutic treatment, of protein tyrosine kinase-associated, or mediated, disorders, including but not limited to, T-cell mediated inflammatory disorders and mast cell regulated auto-immune diseases and other c-kit associated or mediated disorders.

"Protein kinase-associated disorders" are disorders which result from aberrant kinase activity, and/or which are alleviated by the regulation, and inhibition in particular, of one or more of these kinase enzymes. For example, Lck inhibitors are of value in the treatment of a number of such disorders (for example, the treatment of autoimmune diseases), as Lck inhibition blocks T cell activation. It is believed that the compounds of Formula I modulate T cell activation by way of inhibition of one or more of the multiple protein tyrosine kinases involved in early signal transduction steps leading to T cell activation, for example, by way of inhibition of Lck kinase.

Accordingly, in one embodiment of the invention, the compounds of Formula I are useful for the treatment of T cell mediated diseases, including inhibition of T cell activation and proliferation. Further, the compounds may block the activation of endothelial cell protein tyrosine kinase by oxidative stress thereby limiting surface expression of adhesion molecules that induce neutrophil binding, and they also can inhibit protein tyrosine kinase necessary for neutrophil activation. The compounds would be useful, therefore, in the treatment of ischemia and reperfusion injury. In another embodiment of the invention, there is provided a method for the treatment of protein tyrosine kinase-associated disorder, the method comprising administering to a subject at least one compound of Formula I in an amount effective to treat the disorder.

Additional tyrosine kinase-associated disorders, or which the compound(s) of the present invention are useful include, without limitation, arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracielma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides methods for treating the aforementioned disorders such as atopic dermatitis by administration of a therapeutically effective amount of a compound of the present invention, which is an inhibitor of protein tyrosine kinase, to a patient suffering from dermatitis and potentially in need of such treatment.

The compounds of the invention are also capable of modulating the activity of c-kit protein kinase and, therefore, are capable of regulating various c-kit related disorders. More specifically, these compounds are useful in the treatment, including preventative, prophylactic and therapeutic treatment, of c-kit kinase-associated or mediated disorders including, but not limited to, mast cell regulated autoimmune disorders and fibrotic diseases, including idiopathic pulmonary fibrosis. In one embodiment of the invention, the compounds of the invention are useful for the treatment of mast cell production, tumors related to mast cell proliferation and mastocytosis, allergic reactions including severe asthma, rheumatoid arthritis, scleroderma, multiple sclerosis and allergy associated chromic rhinitis, and c-kit mediated fibrotic and autoimmune disease.

In one embodiment of the invention, the compounds of the invention are useful for the treatment of an abnormal condition associated with inappropriate c-kit kinase mediated signal transduction in a subject, the treatment method comprising the step of administering to the subject an effective dosage amount of a compound according to the invention.

To treat patients for such disorders and conditions, another embodiment of the invention provides a composition comprising a compound of Formula I, or II or III, and a pharmaceutically acceptable carrier. Such a pharmaceutical composition, or medicament, can be administered to the subject, such as a human, for the purpose of treating the disorder. Other therapeutic agents such as those described below may be employed in combination with the inventive compounds, such as in a combined composition, in the present methods. Alternatively, such other therapeutic agent(s) may be administered prior to, simultaneously with, or following the administration of the compound(s) of the present invention.

The foregoing merely summarizes certain aspects of the invention and is not intended, nor should it be construed, as limiting the invention in any way.

DETAILED DESCRIPTION OF THE EXEMPLARY EMBODIMENTS OF THE INVENTION

In one embodiment, the present invention provides a compound of Formula I

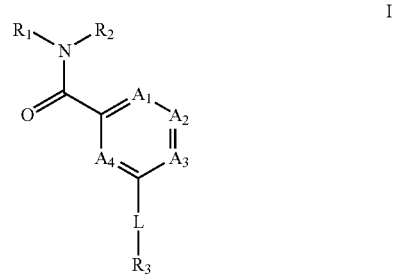

or stereoisomer, tautomer, solvate, pharmaceutically acceptable salt, derivative or prodrug thereof, wherein $A^1$ is $CR^4$ or N;

$A^2$ is $CR^5$ or N;

$A^3$ is $CR^6$ or N;

$A^4$ is $CR^7$ or N; provided that (1) no more than two of $A^1$, $A^2$, $A^3$ and $A^4$ is N and (2) when L is —NHC(O)—, $A^1$ is $CR^4$, $A^2$ is $CR^5$, $A^3$ is $CR^6$ and $A^4$ is $CR^7$, then $R^6$ is H;

L is —C(O)NR$^7$—, —C(S)NR$^7$—, —NR$^7$C(O)—, —NR$^7$C(S)—, —NR$^7$C(O)NR$^7$—, —NR$^7$C(S)NR$^7$—, —NR$^7$C(O)O—, —OC(O)NR$^7$—, —S(O)$_2$NR$^7$—, —NR$^7$S(O)$_2$NR$^7$— or —NR$^7$S(O)$_2$—;

$R^1$ is pyrimidyl, pyrazinyl, pyridazinyl, triazinyl, quinolinyl, isoquinolinyl, quinazolinyl, isoquinazolinyl, aza-quinazolinyl, phthalazinyl and aza-phthalazinyl, thiophenyl, furyl, pyrrolyl, pyrazolyl, imidazolyl, triazolyl, oxazolyl, isoxazolyl, indolyl, isoindolyl, benzofuranyl, benzothiophenyl, benzimidazolyl, benzoxazolyl, benzisoxazolyl, benzothiazolyl or oxo-dihydropyrrolopyridinyl, each ring of which is optionally substituted independently with one or more substituents of $R^8$, $R^9$, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^9$, $NR^8S(O)_2NR^8R^9$, $NR^8S(O)_2R^8$ or $NR^8S(O)_2R^9$;

$R^2$ is H, $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 1-3 heteroatoms selected from N, O and S and optionally substituted with one or more substituents of $R^9$ or $R^{10}$;

$R^3$ is $C_{1-10}$-alkyl, $C_{2-10}$-alkenyl, $C_{2-10}$-alkynyl, $C_{3-10}$-cycloalkyl, 5-6 membered monocyclic or 9-10 membered bicyclic non-aromatic heterocyclic ring system, or a 5-6 membered monocyclic or 9-10 membered bicyclic aromatic ring system, said aromatic ring system formed of carbon atoms optionally including 1-3 heteroatoms if monocyclic or 1-6 heteroatoms if bicyclic, said heteroatoms selected from O, N, or S, wherein said $C_{1-10}$-alkyl, $C_{2-10}$-alkenyl, $C_{2-10}$-alkynyl, $C_{3-10}$-cycloalkyl, non-aromatic heterocyclic ring system and aromatic ring system is optionally substituted independently with one or more substituents of $R^{11}$, $R^{12}$, $R^{13}$, $NR^{11}R^{11}$, $NR^{11}R^{12}$, $OR^{11}$, $SR^{11}$, $OR^{12}$, $SR^{12}$, $C(O)R^{11}$, $C(S)R^{11}$, $CN(CN)R^{11}$, $C(O)R^{12}$, $C(S)R^{12}$, $CN(CN)R^{12}$, $C(O)C(O)R^{11}$, $OC(O)R^{11}$, $COOR^{11}$, $C(O)SR^{11}$, $C(O)C(O)R^{12}$, $OC(O)R^{12}$, $COOR^{12}$, $C(O)SR^{12}$, $C(O)NR^{11}R^{11}$, $C(S)NR^{11}R^{11}$, $C(O)NR^{11}R^{12}$, $C(S)NR^{11}R^{12}$, $OC(O)NR^{11}R^{12}$, $NR^{11}C(O)$ $R^{11}$, $NR^{11}C(O)R^{12}$, $NR^{11}C(S)R^{11}$, $NR^{11}C(S)R^{12}$, $NR^{11}C(O)NR^{11}R^{11}$, $NR^{11}C(O)NR^{11}R^{12}$, $NR^{11}C(S)NR^{11}R^{11}$, $NR^{11}C(S)NR^{11}R^{12}$, $NR^{11}C(O)OR^{11}$, $NR^{11}C(O)OR^{12}$, $NR^{11}C(O)R^{11}$, $NR^{11}C(O)C(O)R^{12}$, $NR^{11}C(O)C(O)NR^{11}R^{12}$, $S(O)_2R^{11}$, $S(O)_2R^{12}$, $S(O)_2NR^{11}R^{11}$, $S(O)_2NR^{11}R^{12}$, $NR^{11}S(O)_2{}_{NR}{}^{11}R^{12}$, $NR^{11}S(O)_2R^{11}$ or $NR^{11}S(O)_2R^{12}$;

Each of $R^4$, $R^5$, $R^6$ and $R^7$, independently, is H, halo, haloalkyl, $NO_2$, CN, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$, $NR^8S(O)_2R^9$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$ or $R^{10}$;

alternatively, $R^5$ and $R^6$ taken together form a saturated or partially or fully unsaturated 5-6 membered monocyclic ring of carbon atoms optionally including 1-3 heteroatoms selected from O, N, or S, and the ring optionally substituted independently with 1-3 substituents of $R^8$, $R^9$ or $R^{10}$;

$R^8$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^9$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{10}$, oxo, $NR^{10}R^{10}$, $R^{10}$, $SR^{10}$, $C(O)R^{10}$, $COOR^{10}$, $C(O)NR^{10}R^{10}$, $NR^{10}C(O)R^{10}$, $NR^{10}C(O)NR^{10}R^{10}$, $OC(O)NR^{10}R^{10}$, $S(O)_2R^{10}$, $S(O)_2NR^{10}R^{10}$ or $NR^{10}S(O)_2R^{10}$;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{11}$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^{12}R^{13}$, $NR^{13}R^{13}$, $OR^{12}$, $SR^{12}$, $OR^{13}$, $SR^{13}$, $C(O)R^{12}$, $OC(O)R^{12}$, $COOR^{12}$, $C(O)R^{13}$, $OC(O)R^{13}$, $COOR^{13}$, $C(O)NR^{12}R^{13}$, $C(O)NR^{13}R^{13}$, $NR^{13}C(O)R^{12}$, $NR^{13}C(O)R^{13}$, $NR^{13}C(O)NR^{12}R^{13}$, $NR^{13}C(O)NR^{13}R^{13}$, $NR^{13}C(O)OR^{12}$, $NR^{13}C(O)OR^{13}$, $OC(O)NR^{12}R^{13}$, $OC(O)NR^{13}R^{13}$, $S(O)_2R^{13}$, $S(O)_2NR^{12}R^{13}$, $S(O)_2R^{13}$, $S(O)_2NR^{13}R^{13}$, $NR^{13}S(O)_2NR^{12}R^{13}$, $NR^{13}S(O)_2NR^{13}R^{13}$, $NR^{13}S(O)_2R^{12}$, $NR^{13}S(O)_2R^{13}$ or $R^{13}$;

$R^{12}$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{13}$, oxo, $NR^{13}R^{13}$, $OR^{13}$, $SR^{13}$, $C(O)R^{13}$, $COOR^{13}$, $C(O)NR^{13}R^{13}$, $NR^{13}C(O)R^{13}$, $NR^{13}C(O)NR^{13}R^{13}$, $OC(O)NR^{13}R^{13}$, $S(O)_2R^{13}$, $S(O)_2NR^{13}R^{13}$ or $NR^{13}S(O)_2R^{13}$;

alternatively, $R^{11}$ and $R^{12}$ taken together form a partially or fully saturated or unsaturated 5-6 membered ring of carbon atoms optionally including 1-3 heteroatoms selected from O, N, or S, and the ring optionally substituted independently with 1-5 substituents of $R^{13}$; and $R^{13}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

The compound groups and sub-groups described herein below reveal various embodiments of the present invention wherein compounds in that embodiment include the specified variables as defined in that embodiment. The scope of each defined variable may be taken with any other embodiment described hereinto form a compound of the present invention. For example, the embodiment immediately below described compounds wherein $A^1$ is $CR^4$ and not N, which may be combined with compounds where the remaining variables are as defined in any of the further embodiments described herein. All compounds resulting from such embodiment combinations are contemplated herein and included in the invention.

In another embodiment, in conjunction with any of the above or below embodiments, $A^1$ is $CR^4$.

In another embodiment, in conjunction with any of the above or below embodiments, $A^1$ is N.

In another embodiment, in conjunction with any of the above or below embodiments, $A^2$ is $CR^5$.

In another embodiment, in conjunction with any of the above or below embodiments, $A^2$ is N.

In another embodiment, in conjunction with any of the above or below embodiments, $A^3$ is $CR^6$.

In another embodiment, in conjunction with any of the above or below embodiments, $A^3$ is N.

In another embodiment, in conjunction with any of the above or below embodiments, $A^4$ is $CR^7$.

In another embodiment, in conjunction with any of the above or below embodiments, $A^4$ is N.

In another embodiment, in conjunction with any of the above or below embodiments, one of $A^1$, $A^2$, $A^3$ and $A^4$ is N.

In another embodiment, in conjunction with any of the above or below embodiments, $A^1$ is $CR^4$ or N, $A^2$ is $CR^5$ or N, $A^3$ is $CR^6$ or N, $A^4$ is $CR^7$ or N; provided that no more than two of $A^1$, $A^2$, $A^3$ and $A^4$ is N.

In another embodiment, in conjunction with any of the above or below embodiments, $A^1$ is $CR^4$, $A^2$ is $CR^5$, $A^3$ is $CR^6$; and $A^4$ is $CR^7$.

In another embodiment, in conjunction with any of the above or below embodiments, $A^1$ is $CR^4$, wherein $R^4$ is halo, haloalkyl, $NO_2$, CN, $NR^8R^8$, $OR^8$, $SR^8$, $C(O)R^8$ or $C_{1-10}$-alkyl; $A^2$ is CH; $A^3$ is CH; and $A^4$ is CH.

In another embodiment, in conjunction with any of the above or below embodiments, L is —C(O)NR$^7$—, —C(S)NR$^7$—, —NR$^7$C(O)—, —NR$^7$C(S)—, —NR$^7$C(O)NR$^7$—, —NR$^7$C(S)NR$^7$—, —NR$^7$C(O)O—, —OC(O)NR$^7$—, —S(O)$_2$NR$^7$—, —NR$^7$S(O)$_2$NR$^7$— or —NR$^7$S(O)$_2$—.

In another embodiment, in conjunction with any of the above or below embodiments, L is —C(O)NR$^7$—, —NR$^7$C(O)—, —NR$^7$C(O)NR$^7$—, —NR$^7$C(O)O—, —S(O)$_2$NR$^7$—, —NR$^7$S(O)$_2$NR$^7$— or —NR$^7$S(O)$_2$—.

In another embodiment, in conjunction with any of the above or below embodiments, L is —C(O)NH—, —NHC(O)—, —NHC(O)NH—, —NHC(O)O—, —S(O)$_2$NH—, —NHS(O)$_2$NH— or —NHS(O)$_2$—.

In another embodiment, in conjunction with any of the above or below embodiments, when L is —NHC(O)—, $A^1$ is $CR^4$, $A^2$ is $CR^5$, $A^3$ is $CR^6$ and $A^4$ is $CR^7$, then $R^6$ is H.

In another embodiment, in conjunction with any of the above or below embodiments, $R^1$ is pyrimidyl, pyrazinyl, pyridazinyl, triazinyl, quinolinyl, isoquinolinyl, quinazolinyl, isoquinazolinyl, aza-quinazolinyl, phthalazinyl and aza-phthalazinyl, thiophenyl, furyl, pyrrolyl, pyrazolyl, imidazolyl, triazolyl, oxazolyl, isoxazolyl, indolyl, isoindolyl, benzofuranyl, benzothiophenyl, benzimidazolyl, benzoxazolyl, benzisoxazolyl, benzothiazolyl or oxo-dihydropyrrolopyridine, each ring of which is optionally substituted independently with one or more substituents of $R^8$(alkyl), $R^9$(ring), $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$.

In another embodiment, in conjunction with any of the above or below embodiments, $R^1$ is selected from

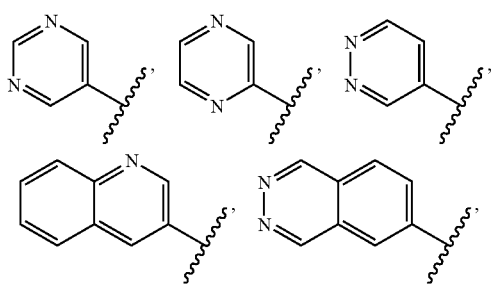

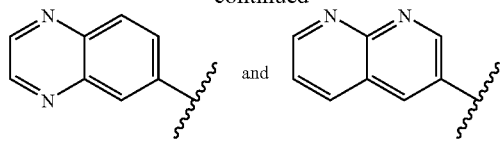

and wherein each ring is optionally substituted independently with one or more substituents of $R^8$(alkyl), $R^9$(ring), $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$.

In another embodiment, in conjunction with any of the above or below embodiments, $R^1$ is pyrimidyl, pyridazinyl, pyrazinyl, triazinyl, quinolinyl, isoquinolinyl, quinazolinyl, isoquinazolinyl, aza-quinazolinyl, phthalazinyl or aza-phthalazinyl.

In another embodiment, in conjunction with any of the above or below embodiments, $R^1$ is

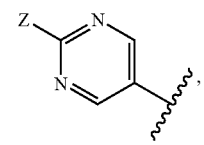

wherein Z is H, CN, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino-, heteroarylamino- or heterocyclylamino-, wherein each of the $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino, heteroarylamino- and heterocyclylamino- is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl, $R^9$(ring), $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$.

In another embodiment, in conjunction with any of the above or below embodiments, $R^2$ is H, $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 1-3 heteroatoms selected from N, O and S and optionally substituted with one or more substituents of $R^9$ or $R^{10}$.

In another embodiment, in conjunction with any of the above or below embodiments, $R^2$ is H or $C_{1-10}$-alkyl.

In another embodiment, in conjunction with any of the above or below embodiments, $R^3$ is $C_{1-10}$-alkyl, $C_{2-10}$-alkenyl, $C_{2-10}$-alkynyl, $C_{3-10}$-cycloalkyl, 5-6 membered monocyclic or 9-10 membered bicyclic non-aromatic heterocyclic ring system, or a 5-6 membered monocyclic or 9-10 membered bicyclic aromatic ring system, said aromatic ring system formed of carbon atoms optionally including 1-3 heteroatoms if monocyclic or 1-6 heteroatoms if bicyclic, said heteroatoms selected from O, N, or S, wherein said $C_{1-10}$-alkyl, $C_{2-10}$-alkenyl, $C_{2-10}$-alkynyl, $C_{3-10}$-cycloalkyl, non-aromatic heterocyclic ring system and aromatic ring system is optionally substituted independently with one or more substituents of $R^{11}$(alkyl), $R^{12}$(ring) $R^{13}$, $NR^{11}R^{11}$, $NR^{11}R^{12}$, $OR^{11}$, $SR^{11}$, $OR^{12}$, $SR^{12}$, $C(O)R^{11}$, $C(S)R^{11}$, $CN(CN)R^{11}$, $C(O)R^{12}$, $C(S)R^{12}$, $CN(CN)R^{12}$, $C(O)C(O)R^{11}$, $OC(O)R^{11}$, $COOR^{11}$, $C(O)SR^{11}$, $C(O)C(O)R^{12}$, $OC(O)R^{12}$, $COOR^{12}$, $C(O) SR^{12}$, $C(O)NR^{11}R^{11}$, $C(S)NR^{11}R^{11}$, $C(O)NR^{11}R^{12}$, $C(S)NR^{11}R^{12}$, $OC(O)NR^{11}R^{12}$, $NR^{11}C(O)R^{11}$, $NR^{11}C(O)R^{12}$, $NR^{11}C(S)R^{11}$, $NR^{11}C(S)R^{12}$, $NR^{11}C(O)NR^{11}R^{11}$, $NR^{11}C(O)NR^{11}R^{12}$, $NR^{11}C(S)NR^{11}R^{11}$, $NR^{11}C(S)NR^{11}R^{12}$, $NR^{11}C(O)OR^{11}$, $NR^{11}C(O)OR^{12}$, $NR^{11}C(O)C(O)R^{11}$, $NR^{11}C(O)C(O)R^{12}$, $NR^{11}C(O)C(O)NR^{11}R^{12}$, $S(O)_2R^{11}$, $S(O)_2R^{12}$, $S(O)_2NR^{11}R^{11}$, $S(O)_2NR^{11}R^{12}$, $NR^{11}S(O)_2NR^{11}R^{12}$, $NR^{11}S(O)_2R^{11}$ or $NR^{11}S(O)_2R^{12}$.

In another embodiment, in conjunction with any of the above or below embodiments, $R^3$ is $C_{1-10}$-alkyl, $C_{3-10}$-cycloalkyl, phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl or benzothiazolyl, each of which is optionally substituted as defined in the first described embodiment of the Detailed Description herein.

In another embodiment, the compounds of the present invention include compounds wherein $A^1$ is $CR^4$, wherein $R^4$ is halo, haloalkyl, CN, $NR^8R^8$, $OR^8$, $SR^8$, $C(O)R^8$ or $C_{1-10}$-alkyl;

$A^2$ is CH;

$A^3$ is CH;

$A^4$ is CH;

L is $-C(O)NR^7-$, $-NR^7C(O)-$, $-NR^7C(O)NR^7-$, $-NR^7C(O)O-$, $-S(O)_2NR^7-$, $-NR^7S(O)_2NR^7-$ or $-NR^7S(O)_2-$;

$R^1$ is

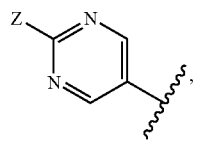

wherein Z is H, CN, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino-, heteroarylamino- or heterocyclylamino-, wherein each of the $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino, heteroarylamino- and heterocyclylamino- is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl, $R^9$(ring), $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$;

$R^2$ is H or $C_{1-6}$-alkyl; and $R^3$ is $C_{1-10}$-alkyl, $C_{3-10}$-cycloalkyl, phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl or benzothiazolyl, in conjunction with any of the above or below embodiments.

In another embodiment, in conjunction with any of the above or below embodiments, $R^4$ is H, halo, haloalkyl, $NO_2$, CN, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$, $NR^8S(O)_2R^9$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$ or $R^{10}$.

In another embodiment, the compounds of the present invention include compounds wherein $R^4$ is halo, haloalkyl, CN, $NR^8R^8$, $OR^8$, $SR^8$, $C(O)R^8$ or $C_{1-10}$-alkyl, in conjunction with any of the above or below embodiments.

In another embodiment, in conjunction with any of the above or below embodiments, $R^5$ is H, halo, haloalkyl, $NO_2$, CN, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$, $NR^8S(O)_2R^9$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$ or $R^{10}$.

In another embodiment, the compounds of the present invention include compounds wherein $R^5$ is H, in conjunction with any of the above or below embodiments.

In another embodiment, in conjunction with any of the above or below embodiments, $R^6$ is H, halo, haloalkyl, $NO_2$, CN, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$, $NR^8S(O)_2R^9$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$ or $R^{10}$.

In another embodiment, the compounds of the present invention include compounds wherein $R^6$ is H, in conjunction with any of the above or below embodiments.

In another embodiment, in conjunction with any of the above or below embodiments, $R^5$ and $R^6$ taken together form a saturated or partially or fully unsaturated 5-6 membered monocyclic ring of carbon atoms optionally including 1-3 heteroatoms selected from O, N, or S, and the ring optionally substituted independently with 1-3 substituents of $R^8$, $R^9$ or $R^{10}$.

In another embodiment, in conjunction with any of the above or below embodiments, $R^7$ is H, halo, haloalkyl, $NO_2$, CN, NR⁸R⁸, NR⁸R⁹, OR⁸, OR⁹, SR⁸, SR⁹, C(O)R⁸, C(O)R⁹, OC(O)R⁸, C(O)OR⁸, C(O)NR⁸R⁸, C(O)NR⁸R⁹, NR⁸C(O) R⁸, NR⁸C(O)R⁹, NR⁸C(O)NR⁸R⁸, NR⁸C(O)NR⁸R⁹, NR⁸C (O)OR⁸, NR⁸C(O)OR⁹, S(O)₂R⁸, S(O)₂R⁹, S(O)₂NR⁸R⁸, S(O)₂NR⁸R⁹, NR⁸S(O)₂NR⁸R⁸, NR⁸S(O)₂NR⁸R⁹, NR⁸S (O)₂R⁸, NR⁸S(O)₂R⁹, C₁₋₁₀-alkyl, C₂₋₁₀-alkenyl, C₂₋₁₀-alkynyl, C₃₋₁₀-cycloalkyl or C₄₋₁₀-cycloalkenyl, each of the C₁₋₁₀-alkyl, C₂₋₁₀-alkenyl, C₂₋₁₀-alkynyl, C₃₋₁₀-cycloalkyl and C₄₋₁₀-cycloalkenyl optionally comprising 1-4 heteroatoms selected from N, O and S and optionally substituted with one or more substituents of R⁹ or R¹⁰.

In another embodiment, the compounds of the present invention include compounds wherein R⁷ is H, in conjunction with any of the above or below embodiments.

In another embodiment, in conjunction with any of the above or below embodiments, R⁸ is H, halo, haloalkyl, CN, NO₂, acetyl, C₁₋₁₀-alkyl, C₂₋₁₀-alkenyl, C₂₋₁₀-alkynyl or C₃₋₁₀-cycloalkyl, each of the C₁₋₁₀-alkyl, C₂₋₁₀-alkenyl, C₂₋₁₀-alkynyl and C₃₋₁₀-cycloalkyl optionally comprising 1-4 heteroatoms selected from N, O and S and optionally substituted with one or more substituents of NR⁸R⁹, NR⁹R⁹, OR⁸, SR⁸, OR⁹, SR⁹, C(O)R⁸, OC(O)R⁸, COOR⁸, C(O)R⁹, OC(O)R⁹, COOR⁹, C(O)NR⁸R⁹, C(O)NR⁹R⁹, NR⁹C(O)R⁸, NR⁹C(O)R⁹, NR⁹C(O)NR⁸R⁹, NR⁹C(O) NR⁹R⁹, NR⁹ (COOR⁸), NR⁹(COOR⁹), OC(O)NR⁸R⁹, OC(O)NR⁹R⁹, S(O)₂R⁸, S(O)₂NR⁸R⁹, S(O)₂R⁹, S(O)₂NR⁹R⁹, NR⁹S(O)₂ NR⁸R⁹, NR⁹S(O)₂NR⁹R⁹, NR⁹S(O)₂R⁸, NR⁹S(O)₂R⁹ or R⁹.

In another embodiment, in conjunction with any of the above or below embodiments, R⁹ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R¹⁰, oxo, NR¹⁰R¹⁰ OR¹⁰, SR¹⁰, C(O)R¹⁰, COOR¹⁰, C(O)NR¹⁰R¹⁰, NR¹⁰C(O)R¹⁰, NR¹⁰C(O)NR¹⁰R¹⁰, OC(O)NR¹⁰R¹⁰, S(O)₂ R¹⁰, S(O)₂NR¹⁰R¹⁰ or NR¹⁰S(O)₂R¹⁰.

In another embodiment, in conjunction with any of the above or below embodiments, R¹⁰ is H, halo, haloalkyl, CN, OH, NO₂, NH₂, acetyl, C₁₋₁₀-alkyl, C₂₋₁₀-alkenyl, C₂₋₁₀-alkynyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C₁₋₁₀-alkyl, C₂₋₁₀-alkenyl, C₂₋₁₀-alkynyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl and ring of said ring system is optionally substituted independently with 1-3 substituents of halo, haloalkyl, CN, NO₂, NH₂, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, in conjunction with any of the above or below embodiments, R¹¹ is H, halo, haloalkyl, CN, NO₂, acetyl, C₁₋₁₀-alkyl, C₂₋₁₀-alkenyl, C₂₋₁₀-alkynyl or C₃₋₁₀-cycloalkyl, each of the C₁₋₁₀-alkyl, C₂₋₁₀-alkenyl, C₂₋₁₀-alkynyl and C₃₋₁₀-cycloalkyl optionally comprising 1-4 heteroatoms selected from N, O and S and optionally substituted with one or more substituents of NR¹²R¹³, NR¹³R¹³, OR¹², SR¹², OR¹³, SR¹³, C(O)R¹², OC(O)R¹², COOR¹², C(O)R¹³, OC(O)R¹³, COOR¹³, C(O)NR¹²R¹³, C(O)NR¹³R¹³, NR¹³C(O)R¹², NR¹³C(O)R¹³, NR¹³C(O) NR¹²R¹³, NR¹³C(O)NR¹³R¹³, NR¹³C (O)OR¹², NR¹³C(O) OR¹³, OC(O)NR¹²R¹³, OC(O)NR¹³R¹³, S(O)₂R¹², S(O)₂ NR¹²R¹³, S(O)₂R¹³, S(O)₂NR¹³R¹³, NR¹³S(O)₂NR¹²R¹³, NR¹³S(O)₂NR¹³R¹³, NR¹³S(O)₂R¹², NR¹³S(O)₂R¹³ or R¹³.

In another embodiment, in conjunction with any of the above or below embodiments, R¹² is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R¹³, oxo, NR¹³R¹³, OR¹³, SR¹³, C(O)R¹³, COOR¹³, C(O)NR¹³R¹³, NR¹³C(O)R¹³, NR¹³C(O)NR¹³R¹³, OC(O)NR¹³R¹³, S(O)₂ R¹³, S(O)₂NR¹³ R¹³ or NR¹³S(O)₂R¹³.

In another embodiment, in conjunction with any of the above or below embodiments, R¹¹ and R¹² taken together form a partially or fully saturated or unsaturated 5-6 membered ring of carbon atoms optionally including 1-3 heteroatoms selected from O, N, or S, and the ring optionally substituted independently with 1-5 substituents of R¹³.

In another embodiment, in conjunction with any of the above or below embodiments, R¹³ is H, halo, haloalkyl, CN, OH, NO₂, NH₂, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO₂, NH₂, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds of the present invention include compounds of Formula I:

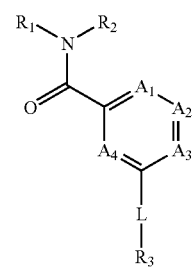

or stereoisomer, tautomer, solvate, pharmaceutically acceptable salt, derivative or prodrug thereof, wherein
A¹ is CR⁴ or N;
A² is CR⁵ or N;
A³ is CR⁶ or N;
A⁴ is CR⁷ or N; provided that (1) no more than two of A¹, A², A³ and A⁴ is N and (2) when L is —NHC(O)—, A¹ is CR⁴, A² is CR⁵, A³ is CR⁶ and A⁴ is CR⁷, then R⁶ is H;
L is —C(O)NR⁷—, —NR⁷C(O)—, —NR⁷C(O)NR⁷—, —S(O)₂NR⁷—, —NR⁷S(O)₂NR⁷— or —NR⁷S(O)₂—;

$R^1$ is 2-pyridyl, 3-pyridyl or 4-pyridyl, each of which is optionally substituted independently with one or more substituents of $R^8$, $R^9$, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$;

$R^2$ is H, $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 1-3 heteroatoms selected from N, O and S and optionally substituted with one or more substituents of $R^9$ or $R^{10}$;

$R^3$ is $C_{1-10}$-alkyl, $C_{2-10}$-alkenyl, $C_{2-10}$-alkynyl, $C_{3-10}$-cycloalkyl, 5-6 membered monocyclic or 9-10 membered bicyclic non-aromatic heterocyclic ring system, or a 5-6 membered monocyclic or 9-10 membered bicyclic aromatic ring system, said aromatic ring system formed of carbon atoms optionally including 1-3 heteroatoms if monocyclic or 1-6 heteroatoms if bicyclic, said heteroatoms selected from O, N, or S, wherein said $C_{1-10}$-alkyl, $C_{2-10}$-alkenyl, $C_{2-10}$-alkynyl, $C_{3-10}$-cycloalkyl, non-aromatic heterocyclic ring system and aromatic ring system is optionally substituted independently with one or more substituents of $R^{11}$, $R^{12}$, $R^{13}$, $NR^{11}R^{11}$, $NR^{11}R^{12}$, $OR^{11}$, $SR^{11}$, $OR^{12}$, $SR^{12}$, $C(O)R^{11}$, $C(S)R^{11}$, $CN(CN)R^{11}$, $C(O)R^{12}$, $C(S)R^{12}$, $CN(CN)R^{12}$, $C(O)C(O)R^{11}$, $OC(O)R^{11}$, $COOR^{11}$, $C(O)SR^{11}$, $C(O)C(O)R^{12}$, $OC(O)R^{12}$, $COOR^{12}$, $C(O)SR^{12}$, $C(O)NR^{11}R^{11}$, $C(S)NR^{11}R^{11}$, $C(O)NR^{11}R^{12}$, $C(S)NR^{11}R^{12}$, $OC(O)NR^{11}R^{12}$, $NR^{11}C(O)R^{11}$, $NR^{11}C(O)R^{12}$, $NR^{11}C(S)R^{11}$, $NR^{11}C(S)R^{12}$, $NR^{11}C(O)NR^{11}R^{11}$, $NR^{11}C(O)NR^{11}R^{12}$, $NR^{11}C(S)NR^{11}R^{11}$, $NR^{11}C(S)NR^{11}R^{12}$, $NR^{11}C(O)OR^{11}$, $NR^{11}C(O)OR^{12}$, $NR^{11}C(O)C(O)R^{11}$, $NR^{11}C(O)C(O)R^{12}$, $NR^{11}C(O)C(O)NR^{11}R^{12}$, $S(O)_2R^{11}$, $S(O)_2R^{12}$, $S(O)_2NR^{11}R^{11}$, $S(O)_2NR^{11}R^{12}$, $NR^{11}S(O)_2NR^{11}R^{12}$, $NR^{11}S(O)_2R^{11}$ or $NR^{11}S(O)_2R^{12}$;

each of $R^4$, $R^5$, $R^6$ and $R^7$, independently, is H, halo, haloalkyl, $NO_2$, CN, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$, $NR^8S(O)_2R^9$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^9$ or $R^{10}$;

alternatively, $R^5$ and $R^6$ taken together form a saturated or partially or fully unsaturated 5-6 membered monocyclic ring of carbon atoms optionally including 1-3 heteroatoms selected from O, N, or S, and the ring optionally substituted independently with 1-3 substituents of $R^8$, $R^9$ or $R^{10}$;

$R^8$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^9$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{10}$, oxo, $NR^{10}R^{10}$, $OR^{10}$, $SR^{10}$, $C(O)R^{10}$, $COOR^{10}$, $C(O)NR^{10}R^{10}$, $NR^{10}C(O)R^{10}$, $NR^{10}C(O)NR^{10}R^{10}$, $OC(O)NR^{10}R^{10}$, $S(O)_2R^{10}$, $S(O)_2NR^{10}R^{10}$ or $NR^{10}S(O)_2R^{10}$;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{2-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{2-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{11}$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^{12}R^{13}$, $NR^{13}R^{13}$, $OR^{12}$, $SR^{12}$, $OR^{13}$, $SR^{13}$, $C(O)R^{12}$, $OC(O)R^{12}$, $COOR^{12}$, $C(O)R^{13}$, $OC(O)R^{13}$, $COOR^{13}$, $C(O)NR^{12}R^{13}$, $C(O)NR^{13}R^{13}$, $NR^{13}C(O)R^{12}$, $NR^{13}C(O)R^{13}$, $NR^{13}C(O)NR^{12}R^{13}$, $NR^{13}C(O)NR^{13}R^{13}$, $NR^{13}C(O)OR^{12}$, $NR^{13}C(O)OR^{13}$, $OC(O)NR^{12}R^{13}$, $OC(O)NR^{13}R^{13}$, $S(O)_2R^{12}$, $S(O)_2NR^{12}R^{13}$, $S(O)_2R^{13}$, $S(O)_2NR^{13}R^{13}$, $NR^{13}S(O)_2NR^{12}R^{13}$, $NR^{13}S(O)_2NR^{13}R^{13}$, $NR^{13}S(O)_2R^{12}$, $NR^{13}S(O)_2R^{13}$ or $R^{13}$;

$R^{12}$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{13}$, oxo, $NR^{13}R^{13}$, $OR^{13}$, $SR^{13}$, $C(O)R^{13}$, $COOR^{13}$, $C(O)NR^{13}R^{13}$, $NR^{13}C(O)R^{13}$, $NR^{13}C(O)NR^{13}R^{13}$, $OC(O)NR^{13}R^{13}$, $S(O)_2R^{13}$, $S(O)_2NR^{13}R^{13}$ or $NR^{13}S(O)_2R^{13}$;

alternatively, $R^{11}$ and $R^{12}$ taken together form a partially or fully saturated or unsaturated 5-6 membered ring of carbon atoms optionally including 1-3 heteroatoms selected from O, N, or S, and the ring optionally substituted independently with 1-5 substituents of $R^{13}$; and $R^{13}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl, provided that (1) when $R^1$ is 3-pyridyl, then $L^1$ is not —$NR^7C(O)NR^7$— or (2) when $R^1$ is 2-pyridyl, then $R^3$ is not -2-pyridyl-3—$C(O)NHR^{11}$ or -2-pyridyl-3—$C(O)NHR^{11}$ or (3) the ring of $R^1$ does not contain a quaternary nitrogen atom or (4) the compound is not (a) 5-[(4-methylphenyl)sulfonylamino]-N-3-pyridinyl-6-(3-pyridinylmethoxy)-pyrazine carboxamide or (b) 5-bromo-N,N'-bis-[2-(phenylamino)-3-pyridinyl]-1,3-benzene dicarbaxamide.

In another embodiment, the compounds of the present invention include compounds of the immediately above embodiment wherein one of $A^1$, $A^2$, $A^3$ and $A^4$ is N, in conjunction with any of the above or below embodiments.

In another embodiment, the compounds of Formula I include compounds wherein $A^1$ is $CR^4$, wherein $R^4$ is halo, haloalkyl, $NO_2$, CN, $NR^8R^8$, $OR^8$, $SR^8$, $C(O)R^8$ or $C_{1-10}$-alkyl, $A^2$ is CH, $A^3$ is CH and $A^4$ is CH, in conjunction with any of the above or below embodiments.

In another embodiment, the compounds of Formula I include compounds wherein L is —$C(O)NR^7$— or —$S(O)_2NR^7$—, in conjunction with any of the above or below embodiments.

In another embodiment, the compounds of Formula I include compounds wherein $A^1$ is $CR^4$, wherein $R^4$ is halo, haloalkyl, $NO_2$, CN, $NR^8R^8$, $OR^8$, $SR^8$, $C(O)R^8$ or $C_{1-10}$-alkyl;
$A^2$ is CH;
$A^3$ is CH;
$A^4$ is CH;
L is —$C(O)NR^7$— or —$S(O)_2NR^7$—; and
$R^2$ is H or $C_{1-10}$-alkyl, in conjunction with any of the above or below embodiments.

In another embodiment, the compounds of Formula I include compounds wherein
$R^1$ is

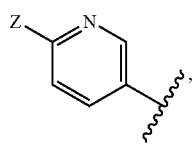

wherein Z is H, CN, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino-, heteroarylamino-, heterocyclylamino-, $C_{3-10}$-cycloalkylamido-, aryl-amido-, heteroarylamido- or heterocyclylamido-, wherein each of the $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino, heteroarylamino-, heterocyclylamino-, $C_{3-10}$-cycloalkylamido-, aryl-amido-, heteroarylamido- and heterocyclylamido- is optionally substituted independently with 1-3 substituents of halo, haloalkyl, haloalkoxyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, phenyl or benzyl, in conjunction with any of the above or below embodiments.

In another embodiment, the compounds of Formula I include compounds wherein $R^3$ is $C_{1-10}$-alkyl, $C_{3-10}$-cycloalkyl, phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl or benzothiazolyl, in conjunction with any of the above or below embodiments.

In another embodiment, the compounds of Formula I include compounds wherein $A^1$ is $CR^4$, wherein $R^4$ is halo, haloalkyl, $NO_2$, CN, $NR^8R^8$, $OR^8$, $SR^8$, $C(O)R^8$ or $C_{1-10}$-alkyl;
$A^2$ is CH;
$A^3$ is CH;
$A^4$ is CH;
L is —$C(O)NR^7$— or —$S(O)_2NR^7$—;
$R^1$ is

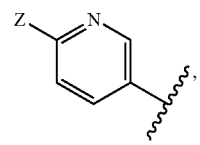

wherein Z is H, CN, $NH_2$, acetyl, halo, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino-, heteroarylamino-, heterocyclylamino-, $C_{3-10}$-cycloalkylamido-, aryl-amido-, heteroarylamido- or heterocyclylamido-, wherein each of the $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{3-10}$-cycloalkylamino-, aryl-amino, heteroarylamino-, heterocyclylamino-, $C_{3-10}$-cycloalkylamido-, aryl-amido-, heteroarylamido- and heterocyclylamido- is optionally substituted independently with 1-3 substituents of halo, haloalkyl, haloalkoxyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, phenyl or benzyl;
$R^2$ is H or $C_{1-10}$-alkyl; and
$R^3$ is $C_{1-10}$-alkyl, $C_{3-10}$-cycloalkyl, phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl or benzothiazolyl, in conjunction with any of the above or below embodiments.

In another embodiment, there is provided a compound defined by Formula II

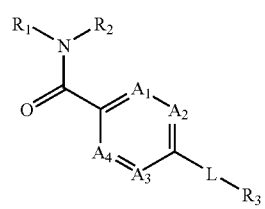

or stereoisomer, tautomer, solvate, pharmaceutically acceptable salt, derivative or prodrug thereof, wherein
$A^1$ is $CR^4$ or N;
$A^2$ is $CR^5$ or N;

A³ is CR⁶ or N;

A⁴ is CR⁷ or N; provided that no more than two of A¹, A², A³ and A⁴ is N and A² and A⁴ are both not N;

L is —C(O)NR⁷—, —C(S)NR⁷—, —NR⁷C(O)—, —NR⁷C(S)—, —NR⁷C(O)NR⁷—, —NR⁷C(S)NR⁷—, —NR⁷C(O)O—, —OC(O)NR⁷—, —S(O)₂NR⁷—, —NR⁷S(O)₂NR⁷— or —NR⁷S(O)₂—;

R¹ is 2-pyridyl, 3-pyridyl or 4-pyridyl pyrimidyl, pyrazinyl, pyridazinyl, triazinyl, quinolinyl, isoquinolinyl, quinazolinyl, isoquinazolinyl, aza-quinazolinyl, phthalazinyl and aza-phthalazinyl, thiophenyl, furyl, pyrrolyl, pyrazolyl, imidazolyl, triazolyl, oxazolyl, isoxazolyl, indolyl, isoindolyl, benzofuranyl, benzothiophenyl, benzimidazolyl, benzoxazolyl, benzisoxazolyl or benzothiazolyl, each ring of which is optionally substituted independently with one or more substituents of R⁸, R⁹, NR⁸R⁸, NR⁸R⁹, OR⁸, OR⁹, SR⁸, SR⁹, C(O)R⁸, C(O)R⁹, OC(O)R⁸, C(O)OR⁸, C(O)NR⁸R⁸, C(O)NR⁸R⁹, NR⁸C(O)R⁸, NR⁸C(O)R⁹, NR⁸C(O)NR⁸R⁸, NR⁸C(O)NR⁸R⁹, NR⁸C(O)OR⁸, NR⁸C(O)OR⁹, S(O)₂R⁸, S(O)₂R⁹, S(O)₂NR⁸R⁸, S(O)₂NR⁸R⁹, NR⁸S(O)₂NR⁸R⁸, NR⁸S(O)₂NR⁸R⁹, NR⁸S(O)₂R⁸ or NR⁸S(O)₂R⁹;

R² is H, C₁₋₁₀-alkyl, C₂₋₁₀-alkenyl or C₂₋₁₀-alkynyl, each of the C₁₋₁₀-alkyl, C₂₋₁₀-alkenyl and C₂₋₁₀-alkynyl optionally comprising 1-3 heteroatoms selected from N, O and S and optionally substituted with one or more substituents of R⁹ or R¹⁰;

R³ is C₁₋₁₀-alkyl, C₂₋₁₀-alkenyl, C₂₋₁₀-alkynyl, C₃₋₁₀-cycloalkyl, 5-6 membered monocyclic or 9-10 membered bicyclic non-aromatic heterocyclic ring system, or a 5-6 membered monocyclic or 9-10 membered bicyclic aromatic ring system, said aromatic ring system formed of carbon atoms optionally including 1-3 heteroatoms if monocyclic or 1-6 heteroatoms if bicyclic, said heteroatoms selected from O, N, or S, wherein said C₁₋₁₀-alkyl, C₂₋₁₀-alkenyl, C₂₋₁₀-alkynyl, C₃₋₁₀-cycloalkyl, non-aromatic heterocyclic ring system and aromatic ring system is optionally substituted independently with one or more substituents of R¹¹, R¹², R¹³, NR¹¹R¹¹, NR¹¹R¹², OR¹¹, SR¹¹, OR¹², SR¹², C(O)R¹¹, C(S)R¹¹, CN(CN)R¹¹, C(O)R¹², C(S)R¹², CN(CN)R¹², C(O)C(O)R¹¹, OC(O)R¹¹, COOR¹¹, C(O)SR¹¹, C(O)C(O)R¹², OC(O)R¹², COOR¹², C(O)SR¹², C(O)NR¹¹R¹¹, C(S)NR¹¹R¹¹, C(O)NR¹¹R¹², C(S)NR¹¹R¹², OC(O)NR¹¹R¹², NR¹¹C(O)R¹¹, NR¹¹C(O)R¹², NR¹¹C(S)R¹¹, N¹¹C(S)R¹², NR¹¹C(O)NR¹¹R¹¹, NR¹¹C(O)NR¹¹R¹², NR¹¹C(S)NR¹¹R¹¹, NR¹¹C(S)NR¹¹R¹², NR¹¹C(O)OR¹¹, NR¹¹C(O)OR¹², NR¹¹C(O)C(O)R¹¹, NR¹¹C(O)C(O)R¹², NR¹¹C(O)C(O)NR¹¹R¹², S(O)₂R¹¹, S(O)₂R¹², S(O)₂NR¹¹R¹¹, S(O)₂NR¹¹R¹², NR¹¹S(O)₂NR¹¹R¹², NR¹¹S(O)₂R¹¹ or NR¹¹S(O)₂R¹²;

each of R⁴, R⁵, R⁶ and R⁷, independently, is H, halo, haloalkyl, NO₂, CN, NR⁸R⁸, NR⁸R⁹, OR⁸, OR⁹, SR⁸, SR⁹, C(O)R⁸, C(O)R⁹, OC(O)R⁸, C(O) OR⁸, C(O)NR⁸R⁸, C(O)NR⁸R⁹, NR⁸C(O)R⁸, NR⁸C(O)R⁹, NR⁸C(O)NR⁸R⁸, NR⁸C(O)NR⁸R⁹, NR⁸C(O)OR⁸, NR⁸C(O)OR⁹, S(O)₂R⁸, S(O)₂R⁹, S(O)₂NR⁸R⁸, S(O)₂NR⁸R⁹, NR⁸S(O)₂NR⁸R⁸, NR⁸S(O)₂ NR⁸R⁹, NR⁸S(O)₂R⁸, NR⁸S(O)₂R⁹, C₁₋₁₀-alkyl, C₂₋₁₀-alkenyl, C₂₋₁₀-alkynyl, C₃₋₁₀-cycloalkyl or C₄₋₁₀-cycloalkenyl, each of the C₁₋₁₀-alkyl, C₂₋₁₀-alkenyl, C₂₋₁₀-alkynyl, C₃₋₁₀-cycloalkyl and C₄₋₁₀-cycloalkenyl optionally comprising 1-4 heteroatoms selected from N, O and S and optionally substituted with one or more substituents of R⁹ or R¹⁰;

alternatively, R⁴ and R⁵ taken together form a saturated or partially or fully unsaturated 5-6 membered monocyclic ring of carbon atoms optionally including 1-3 heteroatoms selected from O, N, or S, and the ring optionally substituted independently with 1-3 substituents of R⁸, R⁹ or R¹⁰;

R⁸ is H, halo, haloalkyl, CN, NO₂, acetyl, C₁₋₁₀-alkyl, C₂₋₁₀-alkenyl, C₂₋₁₀-alkynyl or C₃₋₁₀-cycloalkyl, each of the C₁₋₁₀-alkyl, C₂₋₁₀-alkenyl, C₂₋₁₀-alkynyl and C₃₋₁₀-cycloalkyl optionally comprising 1-4 heteroatoms selected from N, O and S and optionally substituted with one or more substituents of NR⁸R⁹, NR⁹R⁹, OR⁸, SR⁸, OR⁹, SR⁹, C(O)R⁸, OC(O)R⁸, COOR⁸, C(O)R⁹, OC(O)R⁹, COOR⁹, C(O)NR⁸R⁹, C(O)NR⁹R⁹, NR⁹C(O)R⁸, NR⁹C(O)R⁹, NR⁹C(O)NR⁸R⁹, NR⁹C(O)NR⁹R⁹,)NR⁹(COOR⁸), NR⁹(COOR⁹), OC(O)NR⁸R⁹, OC(O)NR⁹R⁹, S(O)₂R⁸, S(O)₂NR⁸R⁹, S(O)₂R⁹, S(O)₂NR⁹R⁹, NR⁹S(O)₂NR⁸R⁹, NR⁹S(O)₂NR⁹R⁹, NR⁹S(O)₂R⁸, NR⁹S(O)₂R⁹ or R⁹;

R⁹ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R¹⁰, oxo, NR¹⁰R¹⁰, OR¹⁰, SR¹⁰, C(O)R¹⁰, COOR¹⁰, C(O)NR¹⁰R¹⁰, NR¹⁰C(O)R¹⁰, NR¹⁰C(O)NR¹⁰R¹⁰, OC(O)NR¹⁰R¹⁰, S(O)₂R¹⁰, S(O)₂NR¹⁰R¹⁰ or NR¹⁰S(O)₂R¹⁰;

R¹⁰ is H, halo, haloalkyl, CN, OH, NO₂, NH₂, acetyl, C₁₋₁₀-alkyl, C₂₋₁₀-alkenyl, C₂₋₁₀-alkynyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C₁₋₁₀-alkyl, C₂₋₁₀-alkenyl, C₂₋₁₀-alkynyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl and ring of said ring system is optionally substituted independently with 1-3 substituents of halo, haloalkyl, CN, NO₂, NH₂, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

R¹¹ is H, halo, haloalkyl, CN, NO₂, acetyl, C₁₋₁₀-alkyl, C₂₋₁₀-alkenyl, C₂₋₁₀-alkynyl or C₃₋₁₀-cycloalkyl, each of the C₁₋₁₀-alkyl, C₂₋₁₀-alkenyl, C₂₋₁₀-alkynyl and C₃₋₁₀-cycloalkyl optionally comprising 1-4 heteroatoms selected from N, O and S and optionally substituted with one or more substituents of NR¹²R¹³, NR¹³R¹³, OR¹², SR¹², OR¹³, SR¹³, C(O)R¹², OC(O)R¹², COOR¹², C(O)R¹³, OC(O)R¹³, COOR¹³, C(O)NR¹²R¹³, C(O)NR¹³R¹³, NR¹³C(O)R¹², NR¹³C(O)R¹³, NR¹³C(O)NR¹²R¹³, NR¹³C(O)NR¹³R¹³, NR¹³C(O)OR¹², NR¹³C(O)OR¹³, OC(O)NR¹²R¹³, OC(O)NR¹³R¹³, S(O)₂R¹², S(O)₂NR¹²R¹³, S(O)₂R¹³, S(O)₂NR¹³R¹³, NR¹³S(O)₂NR¹²R¹³, NR¹³S(O)₂NR¹³R¹³, NR¹³S(O)₂R¹², NR¹³S(O)₂R¹³ or R¹³;

R¹² is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R¹³, oxo, NR¹³R¹³, OR¹³, SR¹³, C(O)R¹³, COOR¹³, C(O)NR¹³R¹³, NR¹³C(O)R¹³, NR¹³C(O)NR¹³R¹³, OC(O)NR¹³R¹³, S(O)₂R¹³, S(O)₂NR¹³R¹³ or NR¹³S(O)₂R¹³;

alternatively, R¹¹ and R¹² taken together form a partially or fully saturated or unsaturated 5-6 membered ring of carbon atoms optionally including 1-3 heteroatoms selected from O, N, or S, and the ring optionally substituted independently with 1-5 substituents of $R^{13}$; and $R^{13}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

provided that (1) when $R^1$ is 3-pyridyl, then $L^1$ is not —$NR^7C(O)$—; or (2) when $R^1$ is 3-pyridyl, then $L^1$ is not —$NR^7C(O)$-(ortho-Ph-Phenyl); or (3) when $R^1$ is 3-pyridyl, it does not contain a quaternary nitrogen atom; or (4) the compound is not (a) N,N'-bis(2,6-diamino-1,4-dihydro-4-oxo-5-pyrimidinyl-1,4)-benzenedicarboxamide or (b) N-(3-pyridyl)-4-[1,2,3,4-tetrahydro-2,4-dioxo-5-pyrimidyl)sulfonyl)amino]benzamide.

In many further embodiments of compounds related to Formula II, $A^1$, $A^2$, $A^3$, $A^4$, L, $R^1$, $R^2$, $R^3$ and R's$^{4-13}$ are as defined in any of the above embodiments in conjunction with compounds of Formula I hereinabove.

In another embodiment, the present invention provides a compound defined by Formula III

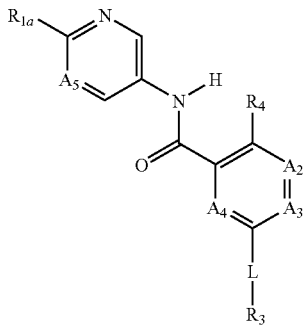

or stereoisomer, tautomer, solvate, pharmaceutically acceptable salt, derivative or prodrug thereof, wherein $A^2$ is $CR^5$ or N;

$A^3$ is CH or N;

$A^4$ is $CR^7$ or N, provided that (1) no more than one of $A^2$, $A^3$ and $A^4$ is N;

$A^5$ is CH or N;

L is —$C(O)NR^7$—, —$NR^7C(O)$—, —$S(O)_2NR^7$—, —$NR^7S(O)_2NR^7$— or —$NR^7S(O)_2$—;

$R^{1a}$ is H, $R^8$, $R^9$, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^8$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$;

$R^3$ is $C_{1-10}$-alkyl, $C_{2-10}$-alkenyl, $C_{2-10}$-alkynyl, $C_{3-10}$-cycloalkyl, 5-6 membered monocyclic or 9-10 membered bicyclic non-aromatic heterocyclic ring system, or 5-6 membered monocyclic or 9-10 membered bicyclic aromatic ring system, said aromatic ring system formed of carbon atoms optionally including 1-3 heteroatoms if monocyclic or 1-6 heteroatoms if bicyclic, said heteroatoms selected from O, N, or S, wherein said $C_{1-10}$-alkyl, $C_{2-10}$-alkenyl, $C_{2-10}$-alkynyl, $C_{3-10}$-cycloalkyl, non-aromatic heterocyclic ring system and aromatic ring system is optionally substituted independently with one or more substituents of $R^{11}$, $R^{12}$, $R^{13}$ $NR^{11}R^{11}$, $NR^{11}R^{12}$, $OR^{11}$, $SR^{11}$, $OR^{12}$, $SR^{12}$, $C(O)R^{11}$, $C(S)R^{11}$, $CN(CN)R^{11}$, $C(O)R^{12}$, $C(S)R^{12}$, $CN(CN)R^{12}$, $C(O)C(O)R^{11}$, $OC(O)R^{11}$, $COOR^{11}$, $C(O)SR^{11}$, $C(O)C(O)R^{12}$, $OC(O)R^{12}$, $COOR^{12}$, $C(O)SR^{12}$, $C(O)NR^{11}R^{11}$, $C(S)NR^{11}R^{11}$, $C(O)NR^{11}R^{12}$, $C(S)NR^{11}R^{12}$, $OC(O)NR^{11}R^{12}$, $NR^{11}C(O)R^{11}$, $NR^{11}C(O)R^{12}$, $NR^{11}C(S)R^{11}$, $NR^{11}C(S)R^{12}$, $NR^{11}C(O)NR^{11}R^{11}$, $NR^{11}C(O)NR^{11}R^{12}$, $NR^{11}C(S)NR^{11}R^{11}$, $NR^{11}C(S)$ $NR^{11}R^{12}$, $NR^{11}C(O)OR^{11}$, $NR^{11}C(O)OR^{12}$, $NR^{11}C(O)C(O)R^{11}$, $NR^{11}C(O)C(O)R^{12}$, $NR^{11}C(O)C(O)NR^{11}R^{12}$, $S(O)_2R^{11}$, $S(O)_2R^{12}$, $S(O)_2NR^{11}R^{11}$, $S(O)_2NR^{11}R^{12}$, $NR^{11}S(O)_2NR^{11}R^{12}$, $NR^{11}S(O)_2R^{11}$ or $NR^{11}S(O)_2R^{12}$;

$R^4$ is halo, haloalkyl, haloalkoxyl, $NO_2$, CN, $NH_2$, OH, or $C_{1-10}$-alkyl;

each of $R^5$ and $R^7$, independently, is H, halo, haloalkyl, haloalkoxyl, $NO_2$, CN, $NR^8R^8$, $NR^8R^9$, $OR^8$, $OR^9$, $SR^8$, $SR^9$, $C(O)R^8$, $C_{1-10}$-alkyl, $C_{2-10}$-alkenyl or $C_{3-10}$-cycloalkyl, each of the $C_{1-10}$-alkyl, $C_{2-10}$-alkenyl and $C_{3-10}$-cycloalkyl optionally comprising 1-4 heteroatoms selected from N, O and S and optionally substituted with one or more substituents of $R^9$ or $R^{10}$;

$R^8$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^9$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{10}$, oxo, $NR^{10}R^{10}$, $OR^{10}$, $SR^{10}$, $C(O)R^{10}$, $COOR^{10}$, $C(O)NR^{10}R^{10}$, $NR^{10}C(O)R^{10}$, $NR^{10}C(O)NR^{10}R^{10}$, $OC(O)NR^{10}R^{10}$, $S(O)_2R^{10}$, $S(O)_2NR^{10}R^{10}$ or $NR^{10}S(O)_2R^{10}$;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{2-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{11}$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^{12}R^{13}$, $NR^{13}R^{13}$, $OR^{12}$, $SR^{12}$, $OR^{13}$, $SR^{13}$, $C(O)R^{12}$, $OC(O)R^{12}$, $COOR^{12}$, $C(O)R^{13}$, $OC(O)R^{13}$, $COOR^{13}$, $C(O)NR^{12}R^{13}$, $C(O)NR^{13}R^{13}$, $NR^{13}C(O)R^{12}$, $NR^{13}C(O)R^{13}$, $NR^{13}C(O)NR^{12}R^{13}$, $NR^{13}C(O)NR^{13}R^{13}$, $NR^{13}C(O)OR^{12}$, $NR^{13}C(O)OR^{13}$, $OC(O)NR^{12}R^{13}$, $OC(O)NR^{13}R^{13}$, $S(O)_2R^{12}$, $S(O)_2NR^{12}R^{13}$, $S(O)_2R^{13}$, $S(O)_2NR^{13}R^{13}$, $NR^{13}S(O)_2NR^{12}R^{13}$, $NR^{13}S(O)_2NR^{13}R^{13}$, $NR^{13}S(O)_2R^{12}$, $NR^{13}S(O)_2R^{13}$ or $R^{13}$;

$R^{12}$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{13}$, oxo, $NR^{13}R^{13}$, $OR^{13}$, $SR^{13}$, $C(O)R^{13}$, $COOR^{13}$, $C(O)NR^{13}R^{13}$, $NR^{13}C(O)R^{13}$, $NR^{13}C(O)NR^{13}R^{13}$, $OC(O)NR^{13}R^{13}$, $S(O)_2R^{13}$, $S(O)_2NR^{13}R^{13}$ or $NR^{13}S(O)_2R^{13}$;

alternatively, $R^{11}$ and $R^{12}$ taken together form a partially or fully saturated or unsaturated 5-6 membered ring of carbon atoms optionally including 1-3 heteroatoms selected from O, N, or S, and the ring optionally substituted independently with 1-5 substituents of $R^{13}$; and $R^{13}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl, provided that the compound is not (a) 5-[(4-methylphenyl)sulfonylamino]-N-3-pyridinyl-6-(3-pyridinylmethoxy)-pyrazine carboxamide or (b) 5-bromo-N,N'-bis-[2-(phenylamino)-3-pyridinyl]-1,3-benzene dicarbaxamide.

In another embodiment, in conjunction with the above embodiment related to compounds of Formula III, $A^5$ is CH; and L is —C(O)NR$^7$—.

In another embodiment, in conjunction with the above embodiment related to compounds of Formula III, $R^{1a}$ is H, $NR^8R^8$, $NR^8R^9$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$, In another embodiment, in conjunction with the above embodiment related to compounds of Formula III $R^8$ is H or $C_{1-10}$-alkyl, wherein the $C_{1-10}$-alkyl is optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9$ ($COOR^8$), $NR^9$ ($COOR^9$), $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$; and $R^9$ is $C_{3-10}$-cycloalkyl, phenyl, naphthyl, pyridyl pyrimidinyl, triazinyl, piperidinyl, piperazinyl, pyrrolyl, imidazolyl, pyrazolyl, triazolyl, pyrrolidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, thiazolyl, oxazolyl, isoxazolyl, isothiazolyl, indolyl, isoindolyl, indolinyl, benzofuranyl, dihydrobenzofuranyl, benzothiophenyl, benzimidazolyl, benzoxazolyl, benzisoxazolyl or benzothiazolyl, each of which is optionally substituted independently with 1-3 substituents of $R^{10}$, oxo, $NR^{10}R^{10}$, $OR^{10}$, $SR^{10}$, $C(O)R^{10}$, $COOR^{10}$, $C(O)NR^{10}R^{10}$, $NR^{10}C(O)R^{10}$, $NR^{10}C(O)NR^{10} R^{10}$, $OC(O)NR^{10}R^{10}$, $S(O)_2 R^{10}$, $S(O)_2 NR^{10}R^{10}$ or $NR^{10}S(O)_2R^{10}$.

In another embodiment related to compounds of Formula III, in conjunction with any of the above or below embodiments, $A^1$ is $CR^4$, $A^2$ is $CR^5$, $A^3$ is CH and $A^4$ is $CR^7$.

In another embodiment related to compounds of Formula III, in conjunction with any of the above or below embodiments, $R^4$ is halo, haloalkyl, $NO_2$, CN, $NR^8R^8$, $OR^8$, $SR^8$, $C(O)R^8$ or $C_{1-10}$-alkyl; $R^5$ is H; and $R^7$ is H.

In another embodiment related to compounds of Formula III, in conjunction with any of the above or below embodiments, $R^2$ is H or $C_{1-10}$-alkyl.

In another embodiment related to compounds of Formula III, in conjunction with any of the above or below embodiments, $R^3$ is $C_{1-10}$-alkyl, $C_{3-10}$-cycloalkyl, phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl or benzothiazolyl, wherein said $C_{1-10}$-alkyl, $C_{3-10}$-cycloalkyl, and ring, independently, is optionally substituted as the embodiment generally describing compounds of Formula III.

In another embodiment related to compounds of Formula III, in conjunction with any of the above or below embodiments, $R^{12}$ is a ring selected from phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein the ring is optionally substituted independently with 1-3 substituents of $R^{13}$.

In yet another embodiment, there are provided the compounds of Examples 1-2 and 6-140 described herein, or a pharmaceutically acceptable salt thereof, selected from:

The compounds of Formulas I, II or III, and stereoisomers, solvates, tautomers, pharmaceutically acceptable salts and derivatives, and prodrugs of these compounds, are useful for treating subjects, typically mammals such as humans, with various conditions and/or disease states, as previously described. To this end, and in another embodiment, the invention provides pharmaceutical compositions comprising one or more of the compounds of Formula I, II or III, including compounds according to any of the various embodiments described above, and a pharmaceutically acceptable carrier or diluent.

The compounds of Formula I, II or III, or pharmaceutical composition comprising such compound(s), may be administered in an effective amount to the subject to modulate one or more target proteins, including receptors and/or kinase enzymes, in the subject thereby treating the target-mediated disease or condition. Accordingly, another embodiment of the invention relates to a method for treating a protein kinase-mediated disorder in a mammal, comprising administering to the mammal a therapeutically effective amount of a compound according to any one of the above embodiments. In another embodiment, the protein kinase is one of Lck or c-Kit.

Further embodiments of the present invention include methods for treating conditions, disorders or diseases related to the modulation of the activity of protein kinases. Accordingly, embodiments include a method of treating inflammation in a mammal, a method of inhibiting T cell activation in a mammal, a method of lowering plasma concentrations of any one or combination of TNF-a, IL-1, IL-6 or IL-8 in a subject, a method of treating the over-production of histamine in a subject, a method of treating an autoimmune disease, mastocytosis, mast cell tumors, asthma, chronic rhinitis, small cell lung caner, acute myelocytic leukemia, acute lymphocytic leukemia, myelodysplastic syndrome, chronic myelogenus leukemia, colorectal carcinoma, bastric carcinoma, gastrointestinal stromal tumor, testicular cancer, glioblastoma, astrocytoma or a combination thereof in a subject and a method of treating rheumatoid arthritis, Pagets disease, osteoporosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses, herpes zoster infection or a combination thereof in a subject, wherein each of the above methods, independently, comprise administering to the subject or mammal a therapeutically effective amount, or a therapeutically effective dosage amount, of a compound according to any one of the above embodiments related to Formulas I, II or III.

Another embodiment of the invention relates to a method of treating an abnormal condition associated with inappropriate c-kit kinase mediated signal transduction in a subject, the method comprising the step of administering to the subject an effective dosage amount of a compound according to any one of the above embodiments.

Another embodiment of the invention relates to a method of the immediately above embodiment wherein the condition is selected from the group consisting of fibrotic disease, mastocytosis, the presence of one or more mast cell tumors, severe asthma, rheumatoid arthritis, scleroderma, multiple sclerosis and allergy associated chromic rhinitis.

Another embodiment of the invention relates to a method of treating idiopathic pulmonary fibrosis in a mammal, the method comprising administering to the mammal a therapeutically effective amount of a compound according to any one of the above embodiments.

Another embodiment of the invention relates to a method of treating multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising administering to the mammal a therapeutically-effective amount of a compound according to any one of the above embodiments.

Another embodiment of the invention relates to a method of treating a proliferative disease in a mammal, the method comprising administering to the mammal a therapeutically effective amount of a compound according to any one of the above embodiments.

Various other embodiments of the invention relate to the manufacture of a medicament for the purposes of administering the compound of Formula I, II or III, or pharmaceutical composition comprising same, to the mammal for treatment thereof, as described herein.

For example, and in another embodiment, the invention relates to the manufacture of a medicament comprising a compound according to any one of the above embodiments related to Formulas I, II or III.

Another embodiment of the invention relates to a method of manufacturing a medicament for the treatment of a protein kinase-mediated disease, for the inhibition of T cell activation and proliferation, for the treatment of cancer, for the treatment of colon carcinoma or thymoma in a mammal, for the treatment of autoimmune disease(s), for the treatment of inflammation, for the treatment of arthritis, rheumatoid arthritis, psoriatic arthritis, or osteoarthritis in a mammal, for the treatment of organ transplant, acute transplant or heterograft or homograft rejection, or transplantation tolerance induction in a mammal, for the treatment of ischemic or reperfusion injury, myocardial infarction, or stroke in a mammal, each of the methods, independently, comprise combining a compound according to any one of the above embodiments with a pharmaceutically acceptable carrier to form the medicament.

Another embodiment of the invention relates to a method of manufacturing a medicament for the treatment of multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising combining a compound according to any one of the above embodiments with an pharmaceutically acceptable carrier to form the medicament.

Another embodiment of the invention relates to a method of making a compound according to Formula I or III, as described herein, comprising the step of reacting a compound 51

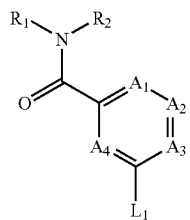

wherein $A^1$, $A^2$, $A^3$, $A^4$, $R^1$ and $R^2$ are as defined in Claim 1 and $L^1$ is $NH_2$, COOH, C(O)Cl, $SO_2$Cl, OC(O)OH or OC(O)Cl, with a compound having a general formula $L^2$-$R^3$, wherein $L^2$ is $NH_2$, COOH, C(O)Cl, $SO_2$Cl, OC(O)OH or OC(O)Cl, to make a compound of Formula I or III.

Another embodiment of the invention relates to a method of making a compound according to Formula II, as described herein, comprising the step of reacting a compound 52

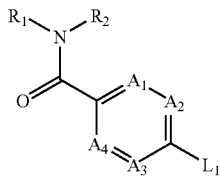

wherein $A^1$, $A^2$, $A^3$, $A^4$, $R^1$ and $R^2$ are as defined in Claim 1 and $L^1$ is $NH_2$, COOH, C(O)Cl, $SO_2$Cl, OC(O)OH or OC(O)Cl, with a compound having a general formula $L^2$-$R^3$, wherein $L^2$ is $NH_2$, COOH, C(O)Cl, $SO_2$Cl, OC(O)OH or OC(O)Cl, to make a compound of Formula II.

Meanings and Definitions

Unless otherwise specified, the following terms found in the specification and claims have the following meanings and/or definitions:

| aq: | Aqueous |
| ATP: | Adenosine triphosphate |
| BSA: | Bovine Serum Albumin |
| DBU: | 1,8-diazabicyclo[5.4.0]undec-7-ene |
| DCE: | Dichloroethane |
| DCM: | Dichloromethane |
| DIEA: | Diisopropylethylamine |
| DMA: | N,N-Dimethylacetamide |
| DME: | Dimethoxyethane |
| DMF: | N,N-Dimethylformamide |
| DMSO: | Dimethylsulfoxide |
| dppf: | 1,1'(diphenylphosphino)ferrocene |
| DTT: | Dithiothreitol |
| EDTA: | Ethylene diamine tetraacetic acid |
| EtOAc: | Ethyl acetate |
| EtOH: | Ethanol |
| FCS: | Fetal Calf Serum |
| g: | Gram(s) |
| h: | Hour(s) |
| HBTU: | O-Benzotriazol-1-yl-N,N,N',N'-tetramethyluronium hexafluorophosphate |
| Hepes: | N-[2-Hydroxyethyl]piperazine-N'-[2-ethanesulfonic acid] |
| $IC_{50}$ value: | The concentration of an inhibitor that causes a 50% reduction in a measured activity. |
| IPA | isopropyl alcohol |
| Lck: | Lymphocyte specific tyrosine kinase |
| LiHMDS: | Lithium bis(trimethylsilyl)amide |
| MeI: | Methyl iodide |
| MeCN: | Acetonitrile |
| MeOH: | Methanol |
| min: | Minute(s) |
| mmol: | Millimole(s) |
| NBS: | N-Bromo succinimide |
| Ni-NTA: | Nickel-nitriloacetic acid |
| NIS: | N-Iodosuccinimide |
| NMP: | N-methylpyrrolidone |
| RT, rt: | Room temperature |
| TFA: | Trifluoroacetic acid |
| THF: | Tetrahydrofuran |

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

In general, "substituted" as used herein refers to a group, such as those defined below, in which one or more bonds to a hydrogen atom contained therein are replaced by a bond to non-hydrogen or non-carbon atoms including, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfoxide groups, sulfone groups, and sulfonyl groups such as sulfonyl halides and sulfonomides; a nitrogen atom in groups such as amines, amides, alkylamines, dialkylamines, arylamines, alkylarylamines, diarylamines, N-oxides, ureas, imines, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carboxylic acid, ester and carbamate groups; and nitrogen in groups such as imines, oximes, hydrazones, and nitriles.

Substituents, including alkyl and ring groups, may be either monovalent or polyvalent depending on the context of their usage. For example, if description contained the group $R^1$-$R^2$-$R^3$ and $R^2$ was defined as $C_{1-6}$alkyl, then the $R^2$ alkyl would be considered polyvalent because it must be bonded to at least $R^1$ and $R^3$. Alternatively, if $R^1$ were defined as $C_{1-6}$alkyl, then the $R^1$ alkyl would be monovalent (excepting any further substitution language).

In general, "unsubstituted" as used herein with reference to a group, means that the group does not have one or more bonds to a hydrogen or carbon atom contained therein replaced by a bond to non-hydrogen or non-carbon atom, as described above.

The term "optionally substituted" as used herein with reference to a group, means that the group may be substituted with a specified number of defined substituents or the group may remain unsubstituted.

In general, "alkyl" as used herein either alone or within other terms such as "haloalkyl", "alkylamino" and "cycloalkyl", refers to linear, branched or cyclic radicals having one to about twelve carbon atoms. "Cycloalkyl" is also used exclusively herein to refer specifically to fully or partially saturated cyclic alkyl radicals. Examples of "alkyl" radicals include methyl, ethyl, n-propyl, isopropyl, n-butyl, isobutyl, sec-butyl, tert-butyl, pentyl, isoamyl, hexyl, cyclopropyl, cyclopentyl, cyclohexyl and the like.

In general, "$C_{a-b}$alkyl" as used herein refers to an alkyl group comprising from a to b carbon atoms in a branched, cyclical or linear relationship or any combination of the three. The alkyl groups described in this section may also contain double or triple bonds. Examples of $C_{1-8}$alkyl include, but are not limited to the following:

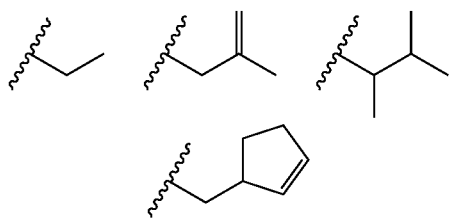

In general, "aralkyl" as used herein refers to linear or branched aryl-containing radicals each having alkyl portions of one to about ten carbon atoms. Examples of such radicals include benzyl, 2-phenyl-propane, and the like.

In general, "Halogen" and "halo" as used herein, refers to a halogen atoms selected from F, Cl, Br and I.

In general, "haloalkyl", as used herein refers to radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

In general, "$C_{a-b}$haloalkyl" as used herein refers to an alkyl group, as described above, wherein any number—at least one—of the hydrogen atoms attached to the alkyl chain are replaced by F, Cl, Br or I. Examples of haloalkyl includes, without limitation, trifluoromethyl, pentafluoroethyl and the like.

In general, "heteroalkyl" as used herein refers to an alkyl having one or more of the carbon atoms replaced by a heteroatom, selected from nitrogen, oxygen and sulfur. For example, a heteroalkyl would include an ether or a thioether chain, or an alkoxide moiety, wherein the heteroatom is in the linear region of the moiety. The term also includes moieties where the heteroatom is in a branched region. For example, the term includes 2-amino-n-hexane or 5-hydroxypentane.

In general, "hydroxyalkyl" as used herein refers to linear or branched alkyl radicals having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

In general, "alkoxy" as used herein refers to linear or branched oxy-containing radicals each having alkyl portions of one to about ten carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of lower haloalkoxy radicals having one to three carbon atoms include fluoromethoxy, chloromethoxy, trifluoromethoxy, trifluoroethoxy, fluoroethoxy and fluoropropoxy.

In general, "sulfonyl", as used herein whether alone or linked to other terms such as alkylsulfonyl, refers respectively to divalent radicals —$SO_2$—.

In general, the term "amino", as used herein whether alone or linked to other terms, refers to a nitrogen radical containing two hydrogen atoms ($NH_2$), a nitrogen radical which is mono-substituted such as an alkylamine (methylamine for example), or a nitrogen radical which is disubstituted such as a dialkylamine (dimethylamine for example). Generally, the amine nitrogen is the point of attachment to the group in question. Accordingly, the term "alkylamino" or dialkylamino" as used herein, means a mono-alkyl or bis-alkyl substituted amine-linked group. The term "cycloalkylamino" refers to an amine-linked cycloalkyl group. The term "arylamino" refers to an amine-linked aryl group. The term "heteroarylamino" refers to an amine-linked heteroaryl group. The term "heterocyclylamino" refers to an amino-linked heterocyclyl group.

In general, "aryl", as used herein alone or in combination, refers to a carbocyclic aromatic system containing one, two or three rings wherein such rings may be attached together in a fused manner. The term "aryl" includes, without limitation, aromatic radicals such as phenyl, naphthyl, indenyl, tetrahydronaphthyl, and indanyl. The "aryl" group may have 1 to 3 substituents such as alkyl, hydroxyl, halo, haloalkyl, nitro, cyano, alkoxy and alkylamino. "Aryl" also includes the moiety wherein the aromatic carbocycle is fused with a $C_{3-6}$cycloalkyl bridge, wherein the bridge optionally includes 1, 2 or 3 heteroatoms selected from N, O and S. For example, phenyl substituted with —O—$CH_2$—O— forms the aryl benzodioxolyl substituent.

In general, "heterocyclic" as used herein, refers to fully or partially saturated heteroatom-containing ring radicals, where the heteroatom(s) may be selected from nitrogen, sulfur and oxygen. "Heterocycle" is used herein synonymously with heterocycloalkyl.

In general, "heterocycloalkyl" as used herein, refers to saturated and partially saturated (or partially unsaturated) heteroatom-containing ring radicals, where the heteroatoms may be selected from nitrogen, sulfur and oxygen. It does not include rings containing —O—O—, —O—S— or —S—S— portions. Said "heterocycloalkyl" group may have 1 to 3 substituents such as hydroxyl, Boc, halo, haloalkyl, cyano, lower alkyl, oxo, alkoxy, amino and alkylamino.

Examples of saturated heterocycloalkyl radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

In general, "heteroaryl" as used herein, refers fully unsaturated or aromatic heteroatom-containing ring radicals, where the heteroatoms may be selected from nitrogen, sulfur and oxygen. Examples of heteroaryl radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroaryl" also embraces radicals where heterocyclic radicals are fused/condensed with aryl radicals (also referred to herein as "arylheterocycloalkyl"): unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Further examples of suitable heterocyclic and heteroaryl radicals, some of which have been described above, include, without limitation, the following:

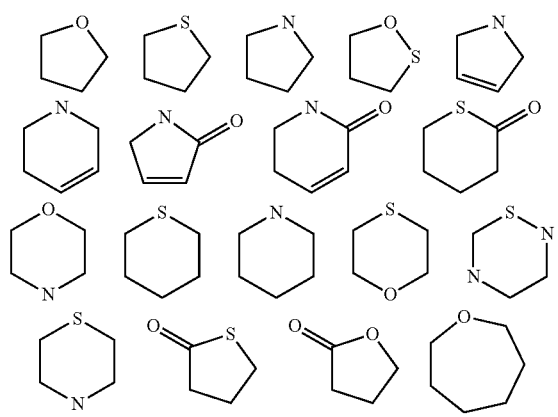

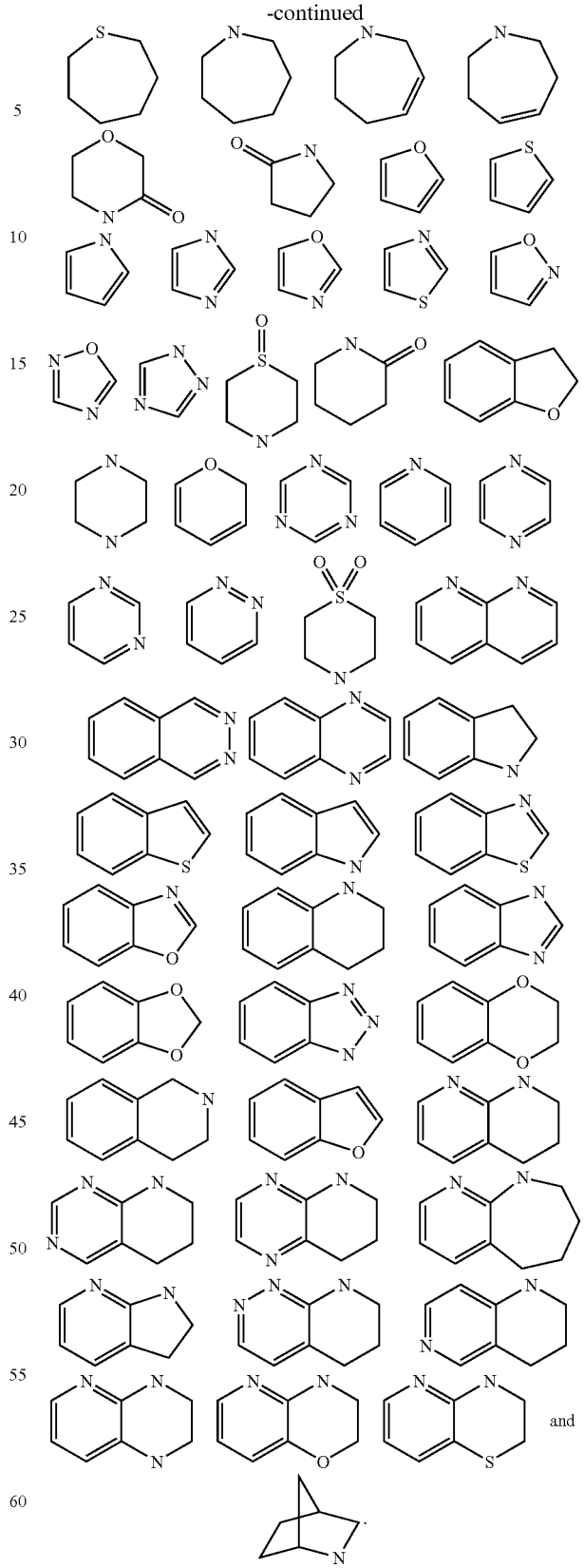

and

"Saturated or unsaturated" with reference to a group or substitution means a substituent that is completely saturated, completely unsaturated, or has any degree of unsaturation in between. Examples of a saturated or unsaturated 6-membered ring carbocycle would include phenyl, cyclohexyl, cyclohexenyl and cyclohexadienyl.

In general, the term "salt" refers to a salt form of a free base compound of the present invention, as appreciated by persons of ordinary skill in the art. Salts may be prepared by conventional means, known to those skilled in the art. In general, "pharmaceutically-acceptable", when used in reference to a salt, refers to salt forms of a given compound, which are within governmental regulatory safety guidelines for ingestion and/or administration to a subject. The term "pharmaceutically-acceptable salts" embraces salts commonly used to form alkali metal salts and to form addition salts of free acids or free bases. The nature of the salt is not critical, provided that it is safe and considered pharmaceutically-acceptable.

Suitable pharmaceutically-acceptable acid addition salts of compounds of Formula I-III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formula I-III include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine.

Additional examples of such acid and base addition salts can be found in Berge et al., J. Pharm. Sci., 66, 1 (1977). All of these salts may be prepared by conventional means from the corresponding compound of the invention by reacting, for example, the appropriate acid or base with the compound of Formula I-III.

Also, the basic nitrogen-containing groups of compounds of Formulas I-III can be quaternized with such agents as lower alkyl halides including, without limitation, methyl, ethyl, propyl, and butyl chloride, bromides and iodides; dialkyl sulfates including dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products may be obtained by quaternizing such basic nitrogen groups in compounds of Formula I-III. Certain quaternized nitrogen compounds of the present invention are not included in the invention, as specified herein in the claims.

In general, "Derivative" as used herein, refers to simple modifications, readily apparent to those of ordinary skill in the art, on the parent core structure of Formula I, II or III, which does not significantly affect (generally decrease) the activity of the compound in-vitro as well as in vivo, in a subject. The term, "derivative" as used herein, is contemplated to include pharmaceutically acceptable derivatives of compounds of Formula I, II or III.

In general, "Pharmaceutically acceptable" when used with reference to a derivative, is consistent in meaning with reference to a salt, and refers to a derivative that is pharmacologically safe for consumption, generally as determined by a governmental or authorized regulatory body.

In general, "Leaving group" as used herein, refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

In general, "Protecting group" as used herein, refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups, including aralkyl groups for example, are also suitable for protecting carboxy, hydroxy and mercapto groups. Alkyl groups are also suitable groups for protecting hydroxy and mercapto groups, such as tert-butyl.

Silyl protecting groups are groups containing silicon atoms which are optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

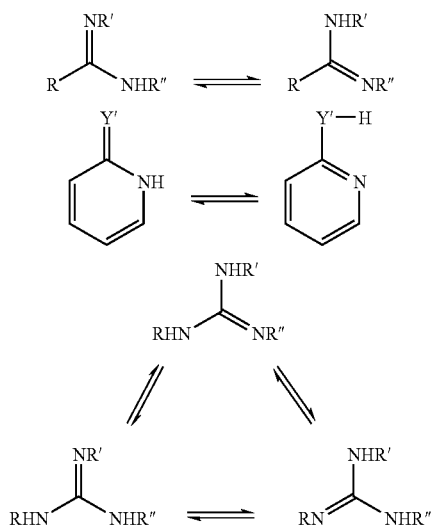

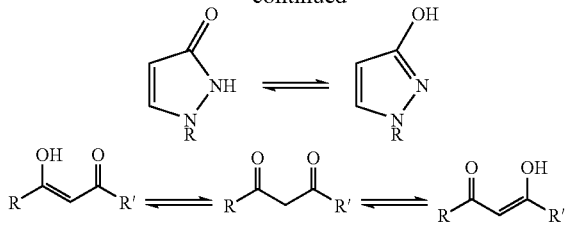

and though one form is named, described, displayed and/or claimed herein, all the tautomeric forms are intended to be inherently included in such name, description, display and/or claim.

Prodrugs of the compounds of this invention are also contemplated by this invention. The term "prodrug", as used herein, refers to a compound, which when administered to the body of a subject (such as a mammal), breaks down in the subject's metabolic pathway to provide an active compound of Formula I, II or III. More specifically, a prodrug is an active or inactive "masked" compound that is modified chemically through in vivo physiological action, such as hydrolysis, metabolism and the like, into a compound of this invention following administration of the prodrug to a subject or patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as phosphate esters, esters and ethers. EP 039,051 (Sloan and Little, Apr. 11, 1981) discloses Mannich-base hydroxamic acid prodrugs, their preparation and use.

In general, the term "stereoisomer" as used herein refers to a compound having one or more asymmetric centers. Chiral centers in a compound generally cause that compound to exist in many different conformations or stereoisomers. The term "stereoisomers" includes enantiomers, diastereomers, atropisomers and geometric isomers. Stereoisomers generally possess different chemical properties and/or biological activity, as appreciated by those skilled in the art. For example, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the present invention necessarily include mixtures of stereoisomers, including racemic mixtures, individual stereoisomers, and optically active forms.

In general, the term "solvate" when used with reference to a compound refers to a compound, which is associated with one or more molecules of a solvent, such as an organic solvent, inorganic solvent, aqueous solvent or mixtures thereof. The compounds of Formula I, II or III may also be solvated, especially hydrated. Hydration may occur during manufacturing of the compounds or compositions comprising the compounds, or the hydration may occur over time due to the hygroscopic nature of the compounds. Compounds of the invention may exist as organic solvates as well, including DMF, ether, and alcohol solvates among others. The identification and preparation of any particular solvate is within the skill of the ordinary artisan of synthetic organic or medicinal chemistry.

In general, the term "Cytokine" as used herein, refers to a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

In general, the term "treatment" as used herein, includes therapeutic treatment as well as prophylactic treatment (either preventing the onset of disorders altogether or delaying the onset of a pre-clinically evident stage of disorders in individuals).

In general, the term "therapeutically-effective" as used herein, is intended to qualify the amount of each compound of Formula I, II or III, which will achieve the goal of treatment, for example, improvement in disorder severity and the frequency of incidence over treatment of each agent by itself, while avoiding adverse side effects typically associated with alternative therapies.

In general, "Lck- or C-kit-mediated disease or disease states" refer to all disease states wherein Lck or C-kit plays a role, either directly as Lck and/or C-kit itself, or by Lck and/or C-kit inducing other proteins, cytokines, enzymes or disease-causing agents and the like to be released, activated or otherwise directly or indirectly regulated.

The specification and claims contain a listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

1. Synthesis

Compounds of Formula I, II and III can be synthesized according to one or more of the following schematic procedures and specific methods wherein the substituents are as defined for Formula I, II and III, above, except where further noted. The procedures and methods as shown relate to preparation of compounds having unspecified stereochemistry. However, such procedures and methods may generally be applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion. Compounds and examples taught herein are either named with conventional IUPAC naming system or with the naming system utilized in ChemDraw, software version 8.0, or the convention used by MDL.

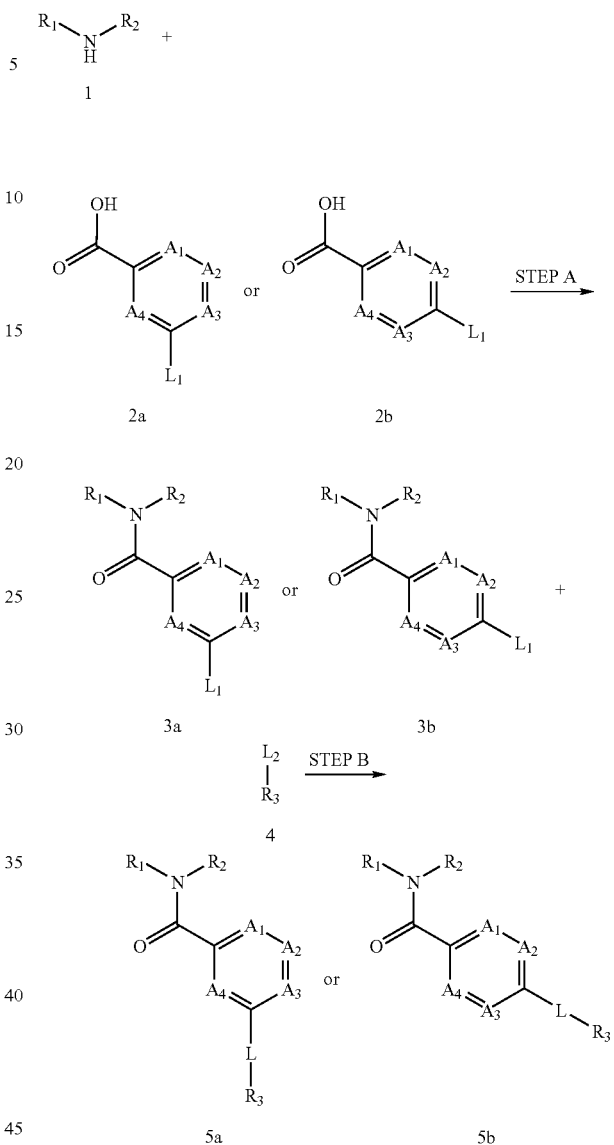

Scheme 1 describes a general method for preparing meta-substituted 5a and para-substituted 5b bis-aryl amide compounds, of Formulas I, II and III. As shown, an amine 1 can be reacted with an aromatic carboxylic acid 2a or 2b to generate the corresponding amide 3a or 3b by known methods (Step A), such as in the presence of a conventional coupling reagent, in a suitable basic media or solvent. Methods which are suitable and may be used to form the amide are described in further detail in Scheme 2 below, which generally describes various methods of forming the linker "L", in compounds 5a and 5b above, from linker pieces $L^1$ and $L^2$, as shown in compounds 3a and 3b, and 4, respectively. Note that intermediates 3a and 3b already have in place linker piece $L^1$ which may be reacted with linker piece $L^2$ on a desired $R^3$ ring. As shown, an $R^3$ intermediate 4 can be reacted with a compound 3a or a compound 3b utilizing known methods (Step B), such as those described in further detail in Scheme 3 below, to prepare a meta-substituted 5a or a para-substituted 5b bis-aryl amide compound, of Formula I, II or III.

Scheme 2

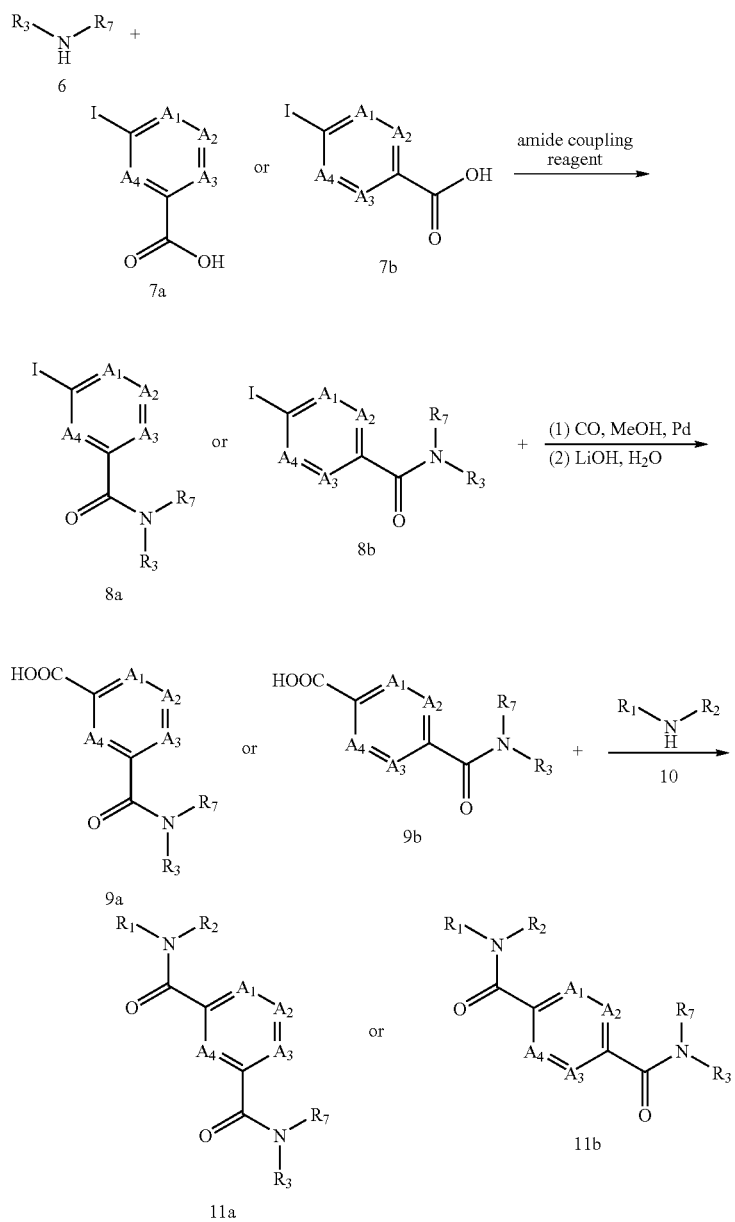

Scheme 2 describes a general method for preparing meta-substituted 11a and para-substituted 11b bis-aryl amide compounds, of Formulas I, II and III. As shown, an amine 6 can be reacted with an iodo-aromatic carboxylic acid 7a or 7b to generate the corresponding amide 8a or 8b by known methods, such as in the presence of a conventional coupling reagent, in a suitable basic media or solvent. Methods which are suitable and may be used to form the amide are described in further detail in Scheme 3 below. In this manner desired $R^1$ groups or rings may be installed first. The iodo-aromatic amides 8a or 8b may be reacted with carbon monoxide and methanol in the presence of a palladium catalyst to generate the corresponding methyl ester adduct, which ester may then be hydrolyzed by conventional methods, such as with a suitable base, such as aqueous LiOH, to provide the corresponding carboxylic acids 9a and 9b. As shown, an $R^3$ substituted amine 10 can be reacted with compound 9a or 9b utilizing known methods (scheme 3), to prepare a meta-substituted 11a or a para-substituted 11b bis-aryl amide compound, of Formula I, II or III.

Scheme 3

1.

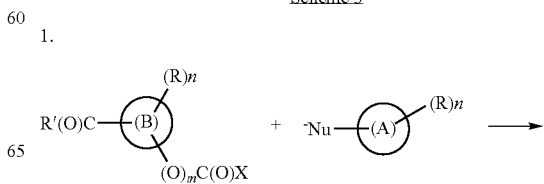

2.

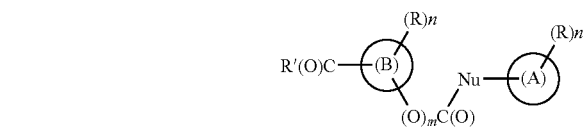

3.

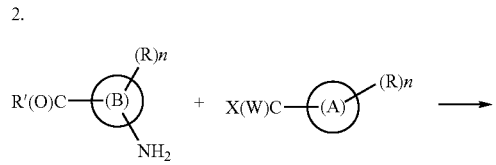

4.

5.

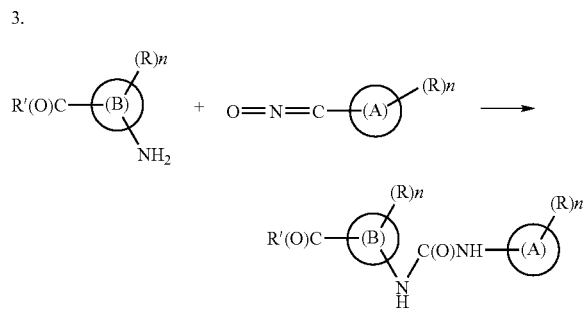

6.

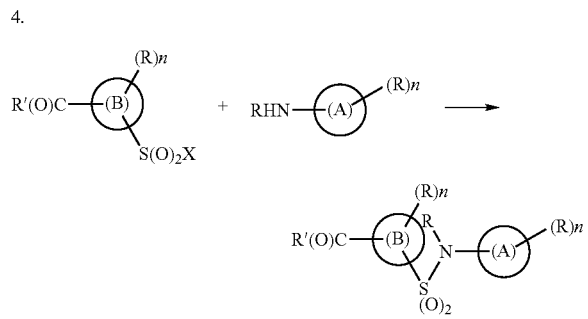

7.

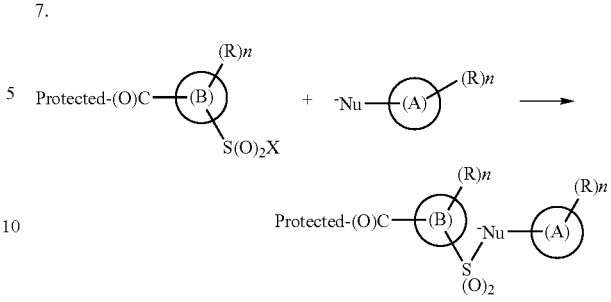

Scheme 3 describes various exemplary coupling methods whereby desired linkers "L" may be made or formed between the 6-membered central ring and a desired $R^3$ ring, as illustrated in Formulas I, II and III herein. The 6-membered central ring, illustrated in Formulas I, II and III, is generally designated and referred to in Scheme 3, and throughout the specification, as the "B" ring. The $R^3$ rings, illustrated in Formulas I, II and III, are generally designated and referred to in Scheme 3, and throughout the specification, as the "A" ring.

Each of the seven sub-schemes, numbered 1-7 above and described below, utilize the following meanings for R', $(R)_n$, X, Nu⁻, E⁺, W and m: R' in sub-schemes 1-4 represent $R^1R^2N$— as defined in Formulas I, II and III; $(R)_n$ refers to n number of $R^4$, $R^5$, $R^6$ and $R^7$ substitutions wherein n is an integer from 0-4; X refers generally to a "leaving group" such as a halide (bromine, chlorine, iodine or fluorine), alkylsulfonate and other known leaving groups (also see definitions herein); Nu⁻ refers generally to a nucleophile or nucleophilic species such as a primary or secondary amine, an oxygen, a sulfur or an anionic carbon species—examples of nucleophiles include, without limitation, amines, hydroxides, alkoxides and the like; E⁺ refers generally to an electrophile or electrophilic species, such as the carbon atom of a carbonyl or carbon atom attached to an activated leaving group, the carbon atom of which is susceptible to nucleophilic attack or readily eliminates—examples of suitable electrophilic carbonyl species include, without limitation, acid halides, mixed anhydrides, aldehydes, carbamoyl-chlorides, sulfonyl chlorides (sulfonyl electrophile), acid carbonyls activated with activating reagents such as TBTU, HBTU, HATU, HOBT, BOP, PyBOP, carbodiimides (DCC, EDC and the like), pentafluorophenyl, and other electrophilic species including halides, isocyanates (see ring A reagent of sub-scheme 3), diazonium ions and the like; W is either O or S; and m is either 0 or 1. The protected carbonyl, as shown in sub-schemes 5-7, allows one to take a desired B-linked-A ring intermediate and attach various "D" ring intermediates or selected $R^1$ coupled primary or secondary amines. This allows one the advantage of modifying the $R^1$ group in a single step.

The coupling of rings B and A, as shown as products in sub-schemes 1-7, can be brought about using various conventional methods to link rings B and A together. For example, an amide or a sulfonamide linker "L", as shown in sub-schemes 1 (where m=0), 2, 4, 5, 6 and 7 where the Nu– is an amine, respectively, can be made utilizing an amine on either the B or A rings and an acid chloride or sulfonyl chloride on the other of either the A or B rings. The reaction proceeds generally in the presence of a suitable solvent and/or base. The reaction proceeds generally in the presence of a suitable solvent and/or base. Suitable solvents include, without limitation, generally non-nucleophilic, aprotic solvents such as toluene, $CH_2Cl_2$, THF, DMF, DMSO, N,N-dimethylacetamide and the like, and solvent combinations thereof. The solvent(s) may range in polarity, as appreciated by those skilled in the art. Suitable bases include, for example, mild bases such as tertiary amine bases including, without limitation, DIEA, TEA, N-methylmorpholine; and stronger bases such as carbonate bases including, without limitation, $Na_2CO_3$, $K_2CO_3$, $Cs_2CO_3$; hydrides including, without limitation, NaH, KH, borohydrides, cyanoborohydrides and the like; and alkoxides including, without limitation, $NaOCH_3$, and the like. The base itself may also serve as a solvent. The reaction may optionally be run neat, i.e., without any base and/or solvent. For simple structurally unhindered substrates, these coupling reactions are generally fast and conversion occurs typically in ambient conditions. However, depending upon the particular substrate, steric hindrance, concentration and other stoichiometric factors, such reactions may be sluggish and may require a basicity adjustment or heat, as appreciated by those skilled in the art.

As another example, a urea linker (or a sulfonylurea linker), as shown in sub-scheme 3, may be made by reacting an amine with a desired isocyanate. As isocyanates are generally highly reactive species, the urea formation generally proceeds quickly, at ambient temperatures with a minimal amount of solvent, as appreciated by those of ordinary skill in the art. The reaction may optionally be run neat, i.e., without any base and/or solvent.

Similarly, carbamate linkers are illustrated in sub-scheme 1 (where m=1) where Nu– would be an amine, anhydride linkers are illustrated in sub-scheme 1 where Nu– would be an oxygen, reverse amide linkers are generally illustrated in sub-scheme 6 where Nu– would be an amine and E+ would be an acid chloride, urea linkers are illustrated in sub-scheme 3, thioamide and thiourea linkers are illustrated in sub-schemes 2 and 3 where the respective carbonyl oxygen is a sulfur, and thiocarbamates are illustrated in sub-schemes 1 where the respective carbonyl oxygen and/or carbamate oxygen is a sulfur. While the above methods are so described, they are not exhaustive, and other methods for linking rings A and B together may be utilized as appreciated by those skilled in the art.

Although sub-schemes 1-7 are illustrated as having the nucleophilic and electrophilic coupling groups, such as the amino group and acid chloride groups illustrated in sub-scheme 2, directly attached to the substrate, either the A or B ring, in question, the invention is not so limited. It is contemplated herein that these nucleophilic and/or electrophilic coupling groups may be tethered from their respective ring. For example, the amine group on the B ring, and/or the acid halide group on the A ring, as illustrated in sub-scheme 2, may be removed from direct attachment to the ring by a one or more atom spacer, such as by a methylene, ethylene, propylene spacer or the like. As appreciated by those skilled in the art, such spacer may or may not affect the coupling reactions described above, and accordingly, such reaction conditions may need to be modified to affect the desired transformation.

The coupling methods described in sub-schemes 1-7 are also applicable for coupling desired A rings to desired $R^1$—N($R^2$)C(O)—B ring intermediates (sub-schemes 1-4), to synthesize desired compounds of Formulas I, II and III. For example, an amine-protected B ring intermediate may be first coupled to a desired $R^1R^2N$— group, as illustrated in Formulas I, II and III and as R' in sub-schemes 1-4, to form the $R^1$—N($R^2$)C(O)—B intermediate. The protected amine may then be de-protected and used to form an amide linker, or converted to an isocyanate, for example, or any other desired group for coupling the A ring via the desired linker. Suitable B ring amino protecting groups include t-butoxycarbonyl group, which can be made with BOC—ON, exist as appreciated by those skilled in the art and further described herein.

The Specific Methods and Examples described in detail below further exemplify the synthesis of compounds of Formulas I, II and III, generally described in Schemes 1-3 above.

Analytical Methods:

Unless otherwise indicated all LC-MS sample analysis and/or HPLC analysis of exemplary compounds, intermediates and starting materials described here were conducted using one of the following methods:

Run on an HP-1000 or HP-1050 system with an HP Zorbax SB-$C_{18}$ (5μ) reverse phase column (4.6×150 mm) run at 30° C. with a flow rate of 1.00 mL/min. The mobile phase used solvent A ($H_2O$/0.1% TFA) and solvent B ($CH_3CN$/0.1% TFA) with a 20 min gradient from 10% to 90% $CH_3CN$. The gradient was followed by a 2 min return to 10% $CH_3CN$ and a 3 min flush.

Method A (LC-MS):

Samples were run on an HP-1100 system with an HP Zorbax SB-$C_8$ (5μ) reverse phase column (4.6×50 mm) run at 30° C. with a flow rate of 0.75 mL/min. The mobile phase used solvent A ($H_2O$/0.1% AcOH) and solvent B ($CH_3CN$/0.1% AcOH) with a 10 min gradient from 10% to 90% $CH_3CN$. The gradient was followed by a 1 min return to 10% $CH_3CN$ and a 2 min flush.

Method B (LC-MS):

Samples were run on an HP-1100 system with an HP Zorbax SB-$C_8$ (5μ) reverse phase column (4.6×50 mm) run at 30° C. with a flow rate of 1.5 mL/min. The mobile phase used solvent A ($H_2O$/0.1% AcOH) and solvent B ($CH_3CN$/0.1% AcOH) with a 5 min gradient from 10% to 90% $CH_3CN$. The gradient was followed by a 0.5 min return to 10% $CH_3CN$ and a 1.5 min flush.

Method C:

Samples were run on an Agilent-1100 system with a Phenomenex Luna $C_8$ (5μ) reverse phase column (4.6×100 mm) run at 40° C. with a flow rate of 1.0 mL/min. The mobile phase used solvent A ($H_2O$/0.1% TFA) and solvent B ($CH_3CN$/0.1% TFA) with a 7 min gradient from 10% to 100% $CH_3CN$, and a 2.5 min hold at 100% $CH_3CN$. The gradient was followed by a 1 min return to 10% $CH_3CN$ and a 2 min flush.

Method D:

Samples were run on an Agilent 1100 system with a Phenomenex-Synergy MAX (4μ) reverse phase column (2.0×50 mm) run at 40° C. with a flow rate of 0.8 mL/min. The mobile phase used solvent A ($H_2O$/0.1% TFA) and solvent B ($CH_3CN$/0.1% TFA) with a 3 min gradient from 10% to 100% $CH_3CN$. The gradient was followed by a 0.5 min return to 10% $CH_3CN$ and a 1.5 min flush.

Proton NMR Spectra:

Unless otherwise indicated all $^1H$ NMR spectra were run on an Varian series Mercury 300 or 400 MHz instrument, or Bruker 400 MHz instrument. All observed protons, where reported, are as parts per million (ppm) downfield from tetramethylsilane (TMS) or other internal reference in the appropriate solvent indicated.

EXAMPLE 1

Method A

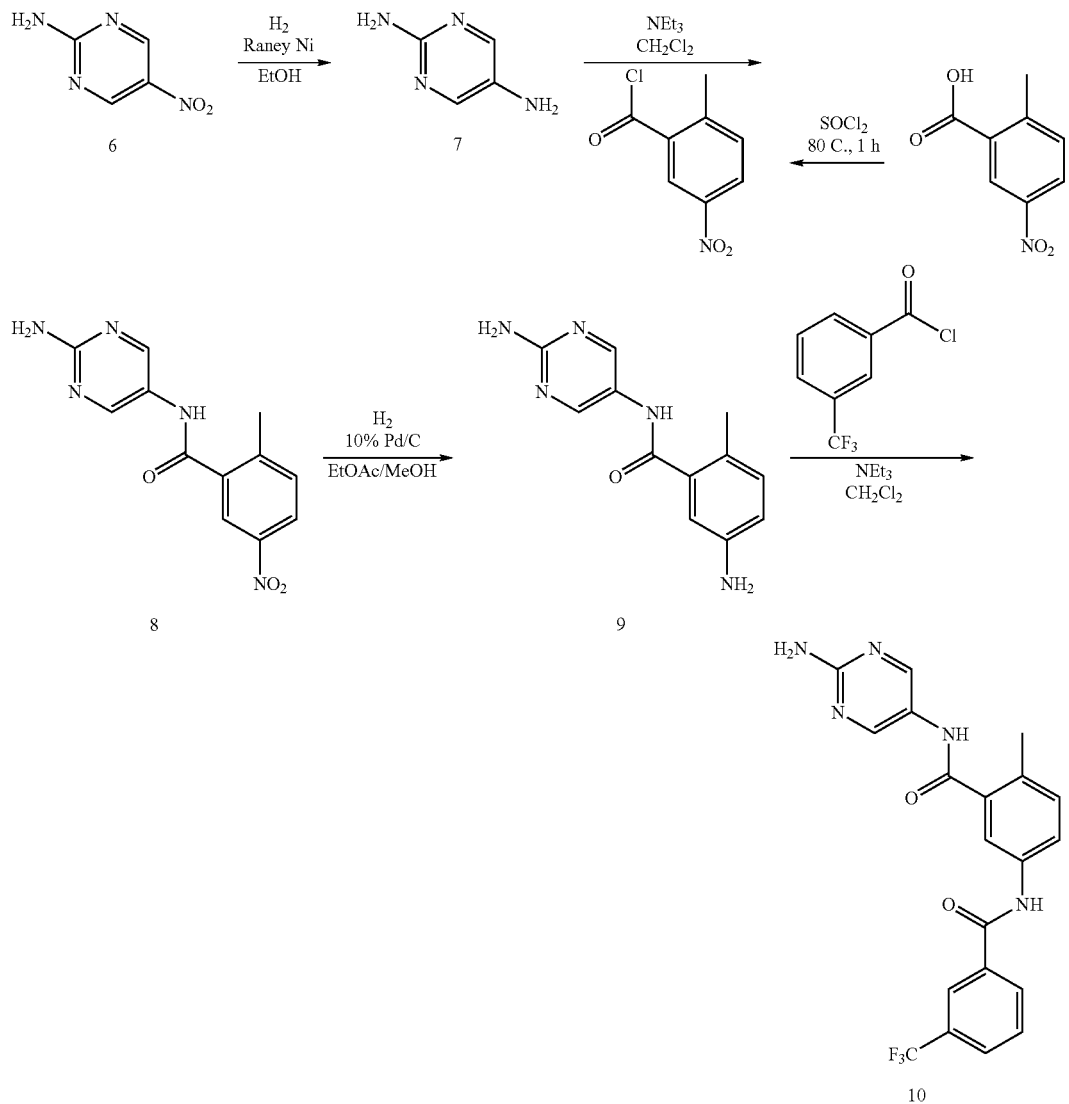

Synthesis of N-(2-amino-5-pyrimidinyl)-2-methyl-5-(((3-(trifluoromethyl)phenyl)carbonyl)amino)benzamide

Step 1. Pyrimidine-2,5-diamine

A round bottom flask equipped with a stir bar was charged with 5-nitropyrimidin-2-amine 6 (3.0 g, 21.4 mmol), wet Raney Ni (~8 g) and EtOH (30 mL). The mixture was purged with $H_2$ (3 vacuum and back-fill cycles) then allowed to stir under an $H_2$ balloon. The reaction was monitored by TLC and LCMS for the complete consumption of starting material, which occurred after about 20 h. The mixture was filtered through a pad of Celite with EtOH and $CH_2Cl_2$. The crude material was purified on a short plug using automated medium pressure chromatography (Isco—40 g column; eluting with a linear gradient from 100% $CH_2Cl_2$ (A line) to 100% 90/10/1 $CH_2Cl_2$/MeOH/$NH_3$ (B line) on silica gel) to afford pyrimidine-2,5-diamine 7 as an orange solid.

Step 2. N-(2-Aminopyrimidin-5-yl)-2-methyl-5-nitrobenzamide 2-methyl-5-nitrobenzoic acid (659 mg, 3.64 mmol) was heated to reflux in $SOCl_2$ (6 mL) for 1 h. After cooling to room temperature and concentrating to dryness, the crude acid chloride was taken up in $CH_2Cl_2$ (25 mL). Pyrimidine-2,5-diamine 7 (400 mg, 3.64 mmol) was added to the solution and the mixture was allowed to stir at rt over night. The mixture became a thick white suspension. $NEt_3$ (700 L, 4.73 mmol) was added. After 2 h, a thick white suspension remained. The mixture was filtered through a Buchner funnel and washed with copious amounts of $CH_2Cl_2$ to remove $NEt_3HCl$ salt, affording N-(2-aminopyrimidin-5-yl)-2-methyl-5-nitrobenzamide 8 as an off-white solid.

Step 3. 5-Amino-N-(2-aminopyrimidin-5-yl)-2-methylbenzamide

A round bottom flask equipped with a stir bar was charged with N-(2-aminopyrimidin-5-yl)-2-methyl-5-nitrobenzamide 8 (300 mg, 1.1 mmol), 10% Pd/C (~150 mg), EtOAc (24 mL) and MeOH (6 mL). The mixture was purged with $H_2$ (3× evacuation and back-fill cycles) then allowed to stir under an $H_2$ balloon. After 24 h, TLC and LCMS indicated that the starting material was completely consumed. The mixture was filtered through a pad of Celite, washing with MeOH and $CH_2Cl_2$. Recrystallization from MeOH/$CH_2Cl_2$ afforded 5-amino-N-(2-aminopyrimidin-5-yl)-2-methylbenzamide 9 as a pale yellow crystalline solid.

Step 4. N-(2-amino-5-pyrimidinyl)-2-methyl-5-(((3-(trifluoromethyl)phenyl)carbonyl)amino)benzamide 5-Amino-N-(2-aminopyrimidin-5-yl)-2-methylbenzamide 9 (86 mg, 0.353 mmol) was taken up in $CH_2Cl_2$ (3 mL) and 3-(trifluoromethyl)benzoyl chloride (0.052 mL, 0.353 mmol) was added. The mixture was allowed to stir at rt for 2 h, becoming a thick yellow suspension. $NEt_3$ (0.064 mL, 0.459 mmol) was added. After 0.5 h, a thick yellow suspension remained. Complete consumption of the amine starting material was indicated by LCMS. The crude reaction mixture was concentrated and the title compound was purified using automated medium pressure chromatography (Isco—40 g column; eluting with a linear gradient from 100% $CH_2Cl_2$ (A line) to 100% 90/10/1 $CH_2Cl_2$/MeOH/$NH_3$ (B line) on silica gel) to afford N-(2-amino-5-pyrimidinyl)-2-methyl-5-(((3-(trifluoromethyl)phenyl)carbonyl)amino)benzamide 10 as an off-white solid. MS: m/z found 416 [MH+] (by ESI, positive ion); MS calculated for $C_{20}H_{16}F_3N_5O_2$=415.13.

Alternatively, compound 10 may be made using the following conditions: Step 1. $H_2$, $PtO_2$; Step 2. acid chloride, $NEt_3$, THF; Step 3. $H_2$, 10% -Pd/C, 2-methoxyethanol; and Step 4: same as above.

EXAMPLE 2

Method Q

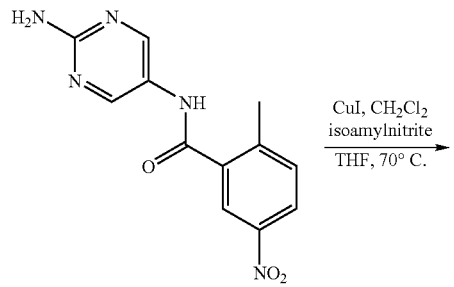

8

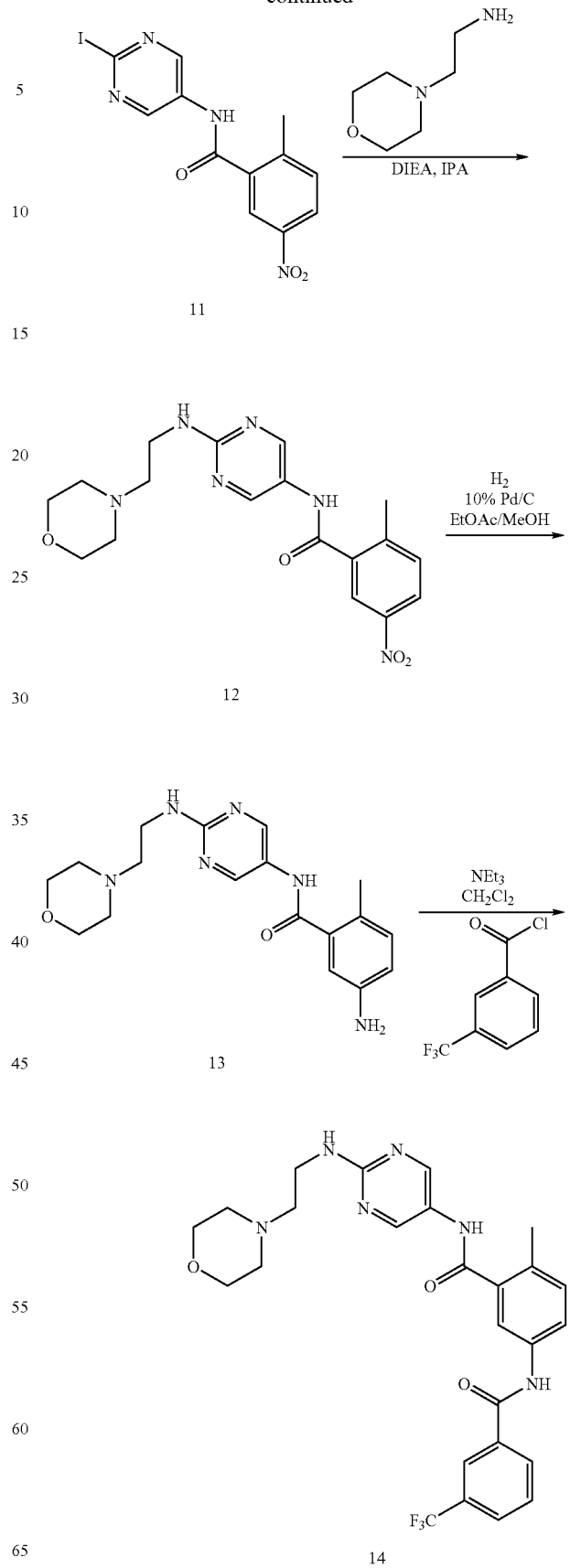

Synthesis of 2-methyl-N-(2-((2-(4-morpholino)ethyl)amino)-5-pyrimidinyl)-5-(((3-trifluoromethyl)phenyl)carbonyl)amino)benzamide

Step 1.
N-(2-iodopyrimidin-5-yl)-2-methyl-5-nitrobenzamide

N-(2-Aminopyrimidin-5-yl)-2-methyl-5-nitrobenzamide [prepared according to Specific Method 1] (200 mg, 0.732 mmol), CuI (140 mg, 0.732 mmol) and CH$_2$I$_2$ (0.30 mL, 3.73 mmol) were taken up in THF (3.7 mL) in a 16×100 mm resealable pyrex tube. The tube was sealed and the mixture was heated at 70° C. for 2 h. After cooling to rt, the crude reaction mixture was taken up in 1:1 EtOAc:1N HCl and the layers were separated. The organics were washed with saturated NH$_4$Cl then dried over Na$_2$SO$_4$. Purification by MPLC (Isco—100% EtOAc eluent) afforded N-(2-iodopyrimidin-5-yl)-2-methyl-5-nitrobenzamide as a pale yellow solid.

Step 2. 2-Methyl-N-(2-(2-morpholinoethylamino)pyrimidin-5-yl)-5-nitrobenzamide N-(2-iodopyrimidin-5-yl)-2-methyl-5-nitrobenzamide (60 mg, 0.156 mmol), 2-morpholinoethanamine (~200 mg, 1.5 mmol), and DIEA (0.041 mL, 0.234 mmol) were taken up in IPA (2.5 mL) in a 16×100 mm resealable pyrex tube and heated at 70° C. for 4 h. The mixture was concentrated and purified by preparative TLC (2.5% MeOH/CH$_2$Cl$_2$) to afford 2-methyl-N-(2-(2-morpholinoethylamino)pyrimidin-5-yl)-5-nitrobenzamide.

Step 3. 5-Amino-2-methyl-N-(2-(2-morpholinoethylamino)pyrimidin-5-yl)benzamide The title intermediate was prepared in a manner analogous to the method described in Step 3 of Example 1.

Step 4. 2-methyl-N-(2-((2-(4-morpholino)ethyl)amino)-5-pyrimidinyl)-5-(((3-trifluoromethyl)phenyl)carbonyl)amino)benzamide The title compound was prepared in a manner analogous to the method described in Step 4 of Example 1. MS: m/z found 529.0 [MH+] (by ESI, positive ion); MS calculated for C$_{26}$H$_{27}$F$_3$N$_6$O$_3$=528.

2-NR$^8$R$^9$ substituted diamino-pyrimidine R$^1$ groups may be made utilizing the methods described in Examples 3-8

EXAMPLE 3

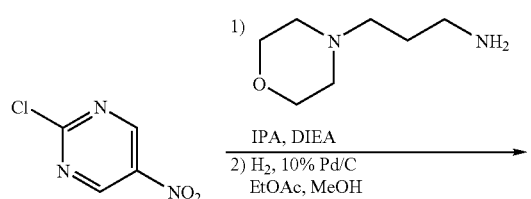

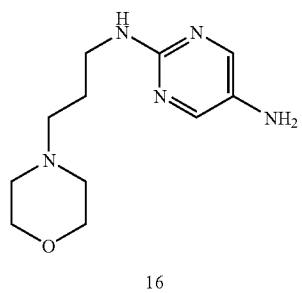

16

Synthesis of N2-(3-morpholinopropyl)pyrimidine-2,5-diamine 16

Step 1

2-Chloro-5-nitropyrimidine 15 (500 mg, 3.13 mmol), 3-morpholinopropan-1-amine (1.35 g, 9.39 mmol) and DIEA (3.4 mL, 4.7 mmol) were taken up in IPA (20 mL) in a resealable pyrex tube and heated at 70° C. for 20 h. After cooling to rt, N-(3-morpholinopropyl)-5-nitropyrimidin-2-amine precipitated out of solution and was collected by filtration through a Buchner micro membrane, and washing with MeOH, then drying to afford the 5-nitro intermediate as a pale yellow solid.

Step 2

The crude N-(3-morpholinopropyl)-5-nitropyrimidin-2-amine was combined with 10% Pd/C (500 mg) in EtOAc (20 mL) and MeOH (10 mL) was added. The mixture was purged with H$_2$ and allowed to stir under 1 atm H$_2$ overnight. Filtration through a pad of celite and concentration afforded N2-(1-methylpiperidin-4-yl)pyrimidine-2,5-diamine 16 as a thick rust colored oil, which may be used without further purification. MS: m/z found 270 [MH+].

EXAMPLE 4

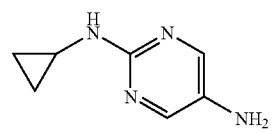

Synthesis of N2-cyclopropylpyrimidine-2,5-diamine

The title compound was prepared by a method similar to that described in Example 3, starting with 2-chloro-5-nitropyrimidine 15. MS: m/z found 151 [MH+].

EXAMPLE 5

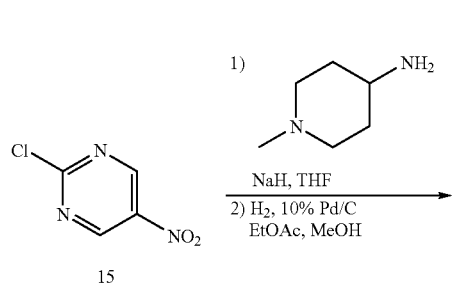

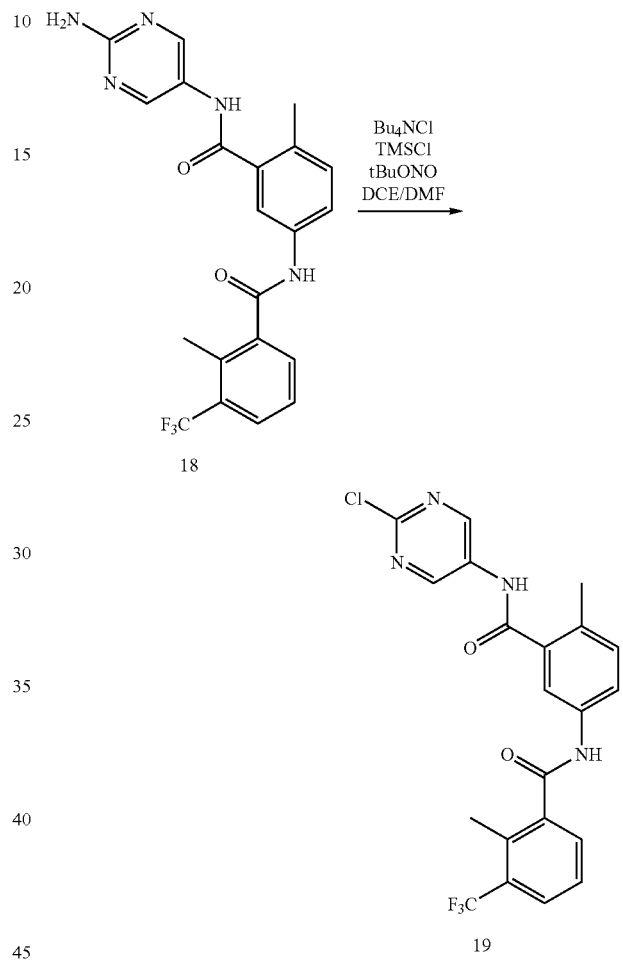

Synthesis of N2-(1-methylpiperidin-4-yl)pyrimidine-2,5-diamine 17

Step 1

1-Methylpiperidin-4-amine (358 mg, 3.13 mmol) and NaH (60% dispersion in mineral oil) (126 mg, 3.13 mmol) were taken up in THF (16 mL) under an atmosphere of dry $N_2$. After stirring at rt for 10 min, 2-chloro-5-nitropyrimidine 15 (500 mg, 3.13 mmol) was added. The mixture was allowed to stir at rt for 1 h then quenched with 1 N HCl and concentrated to dryness.

Step 2

The crude N-(1-methylpiperidin-4-yl)-5-nitropyrimidin-2-amine was combined with 10% Pd/C (500 mg) in EtOAc (8 mL) and MeOH (20 mL) was added. The mixture was purged with $H_2$ and allowed to stir under 1 atm $H_2$ overnight. Filtration through a pad of celite and concentration afforded N2-(1-methylpiperidin-4-yl)pyrimidine-2,5-diamine 17 as a tan solid, which may be used without further purification. MS: m/z found 285 [MH+].

2-Chloro-pyrimidin-5-yl compounds may be synthesized from the 2-amino pyrimidine intermediate directly in a single step utilizing the method described in Example 6 below.

EXAMPLE 6

Synthesis of 2-methyl-N-(((2-chloro)-5-pyrimidinyl)-5-((((2-methyl)-3-trifluoromethyl)phenyl)carbonyl)aminobenzamide In a 16×120 mm resealable pyrex tube, 2-methyl-N-(((2-amino)-5-pyrimidinyl)-5-((((2-methyl)-3-trifluoromethyl)phenyl)carbonyl)aminobenzamide 18 (0.100 g, 0.23 mmol) was taken up in DCE (2.0 mL) and DMF (0.2 mL). The solution was treated in one portion with tetrabutylammonium chloride (0.065 g, 0.23 mmol). After 5 min, trimethylsilyl chloride (0.030 ml, 0.23 mmol) was added slowly. After 15 min, tert-butyl nitrite (0.028 ml, 0.23 mmol) was added dropwise and the mixture was purged with $N_2$ then the tube was sealed and the mixture was heated at 50° C. for 7 h. After cooling, the crude reaction mixture was taken up in minimal $CH_2Cl_2$ and purified by MPLC (Isco—Redi-Sep® prepacked silica gel column (40 g); eluent gradient: 5-80%

EtOAc in hexanes over 20 min) to afford the title compound 19 as a white solid. MS: m/z found 449 [MH+].

EXAMPLE 7

Method I

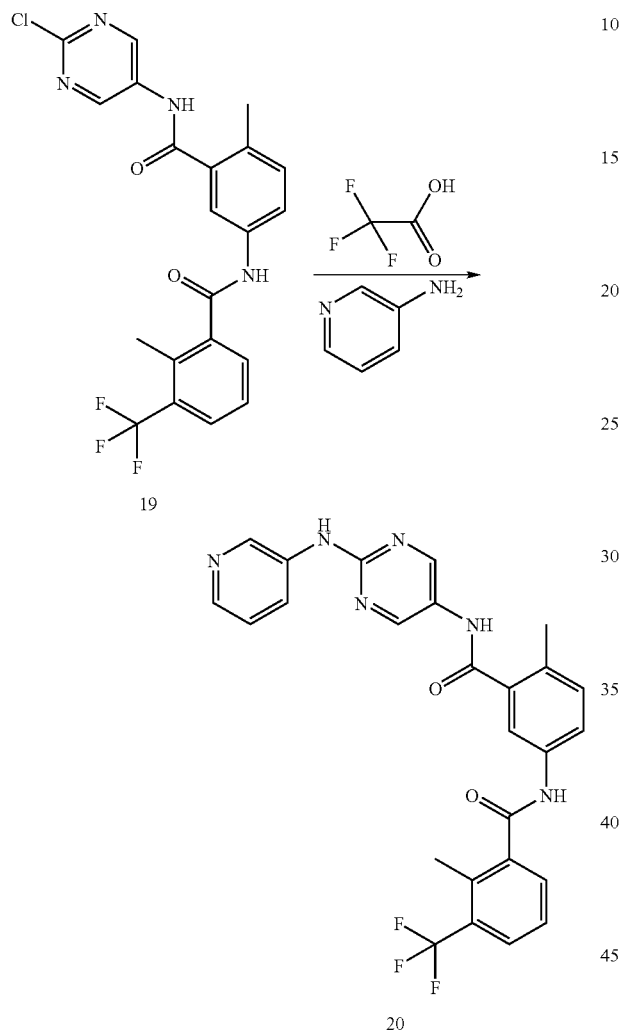

Synthesis of 2-methyl-N-(4-methyl-3-(((2-(3-pyridinylamino)-5-pyrimidinyl)amino)carbonyl)phenyl)-3-(trifluoromethyl)benzamide A small microwave reaction vessel was charged with N-(3-(((2-chloro-5-pyrimidinyl)amino)carbonyl)-4-methylphenyl)-2-methyl-3-(trifluoromethyl)benzamide 19 (0.100 g, 0.22 mmol), and pyridin-3-amine (0.10 g, 1.1 mmol) in IPA (1.0 mL). Trifluoroacetic acid (0.034 ml, 0.45 mmol) was added and the vessel was sealed. The reaction mixture was stirred and heated in a Smith Synthesizer® microwave reactor (Personal Chemistry, Inc., Upssala, Sweden) at 140° C. for 10 min. Monitored the reaction by LCMS and found 50% conversion. Added another 105 mg aniline and 0.05 mL TFA and resumed microwave heating the reaction at 140° C. for 15 min. After about >90% conversion was found by LCMS, the crude reaction mixture was filtered through a Buchner apparatus with micromembrane filter, and the filtrate was washed with copius amounts of MeOH to afford 2-methyl-N-(4-methyl-3-(((2-(3-pyridinylamino)-5-pyrimidinyl)amino)carbonyl)phenyl)-3-(trifluoromethyl)benzamide 20 as an off-white solid after drying. MS m/z found 507.1 [MH+], calc. for C26H21F3N6O2=506.17.

EXAMPLE 8

Method J

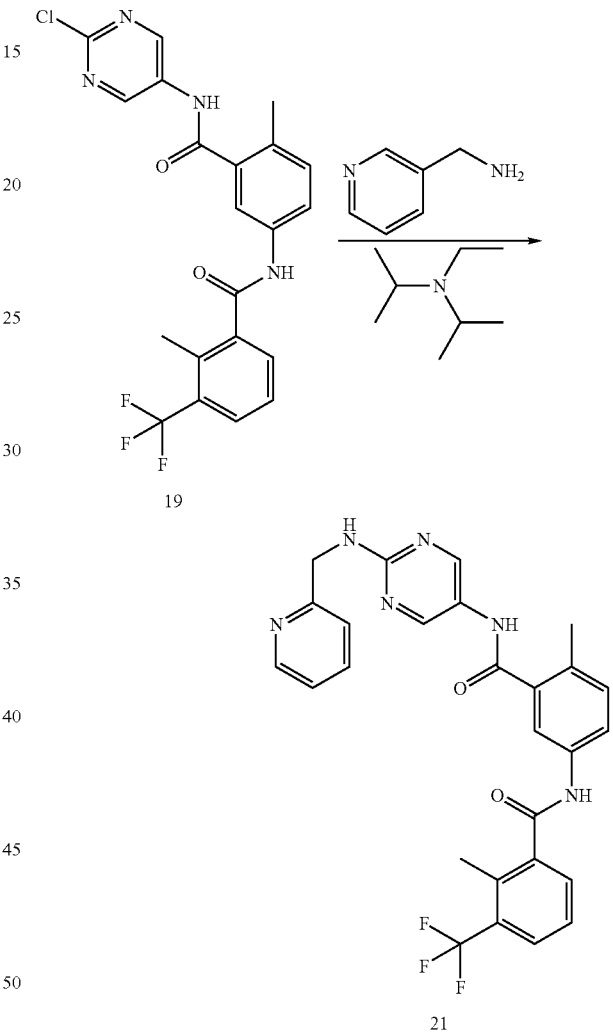

Synthesis of 2-methyl-N-(4-methyl-3-(((2-((2-pyridinylmethyl)amino)-5-pyrimidinyl)amino)carbonyl) phenyl)-3-(trifluoromethyl)benzamide A small microwave reaction vessel was charged with N-(3-(((2-chloro-5-pyrimidinyl)amino)carbonyl)-4-methylphenyl)-2-methyl-3-(trifluoromethyl)benzamide 19 (0.100 g, 0.22 mmol), pyridin-3-ylmethanamine (0.091 ml, 0.89 mmol) and IPA (1 mL). DIEA (0.058 ml, 0.33 mmol) was added and the vessel was sealed. The reaction mixture was stirred and heated in a Smith Synthesizer® microwave reactor (Personal Chemistry, Inc., Upssala, Sweden) at 140° C. for 30 min. After monitoring the reaction by LCMS and finding >95% conversion, the reaction was concentrated to dryness, and taken up in minimal CH2Cl2/MeOH. The crude reaction solution was injected onto the Isco {Redi-Sep® pre-packed silica gel column (40 g); eluent gradient: 3-80% 90/10/1 CH$_2$Cl$_2$/MeOH/NH$_3$ in CH$_2$Cl$_2$ over 20 min} to afford pure 2-methyl-N-(4-methyl-3-(((2-((2-pyridinylmethyl)amino)-5-pyrimidinyl)amino)carbonyl)phenyl)-3-(trifluoromethyl)benzamide 21 as a white solid. MS m/z found 521.1 [MH+]; calc. for C$_{27}$H$_{23}$F$_3$N$_6$O$_2$=520.18.

The following compounds, Examples 9-86 were made using a procedure similar to that described in Examples 1-8.

| Ex. No. | Structure | Name | MS | Method |
|---|---|---|---|---|
| 9 | 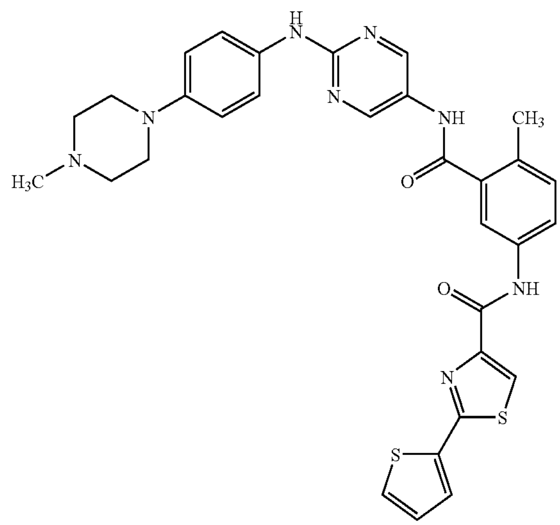 [SMILES: Cc1ccc(NC(=O)c2csc(-c3cccs3)n2)cc1C(=O)Nc1cnc(Nc2ccc(N3CCN(C)CC3)cc2)nc1] | N-(4-methyl-3-((2-(4-(4-methylpiperazin-1-yl)phenylamino)pyrimidin-5-yl)carbamoyl)phenyl)-2-(thiophen-2-yl)thiazole-4-carboxamide | 611.1 | A |
| 10 | 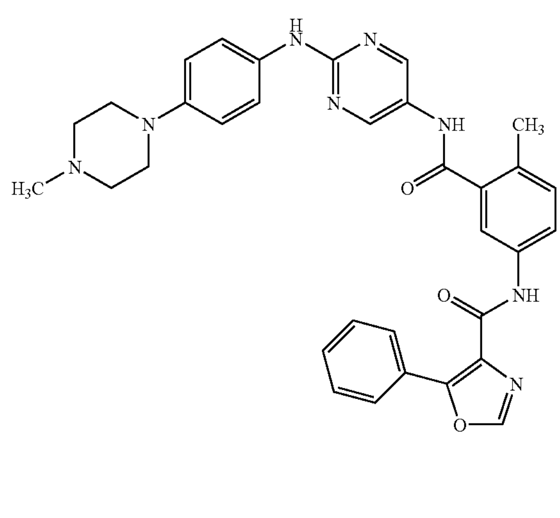 [SMILES: Cc1ccc(NC(=O)c2ncoc2-c2ccccc2)cc1C(=O)Nc1cnc(Nc2ccc(N3CCN(C)CC3)cc2)nc1] | N-(4-methyl-3-((2-(4-(4-methylpiperazin-1-yl)phenylamino)pyrimidin-5-yl)carbamoyl)phenyl)-5-phenyloxazole-4-carboxamide | 589.2 | A |

| Ex. No. | Structure | Name | MS | Method |
|---|---|---|---|---|
| 11 | 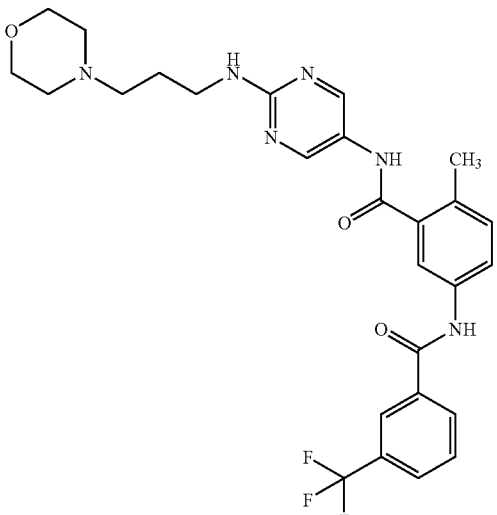 | 2-methyl-N-(2-((3-(4-morpholinyl)propyl)amino)-5-pyrimidinyl)-5-(((3-(trifluoromethyl)phenyl)carbonyl)amino)benzamide | 543 | A |
| 12 | 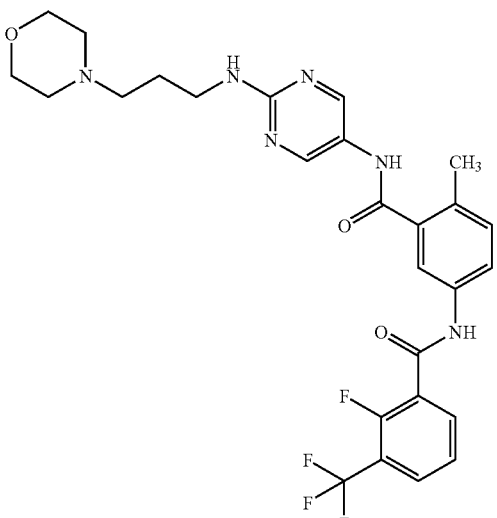 | 2-fluoro-N-(4-methyl-3-(((2-((3-(4-morpholinyl)propyl)amino)-5-pyrimidinyl)amino)carbonyl)phenyl)-3-(trifluoromethyl)benzamide | 561 | A |
| 13 | 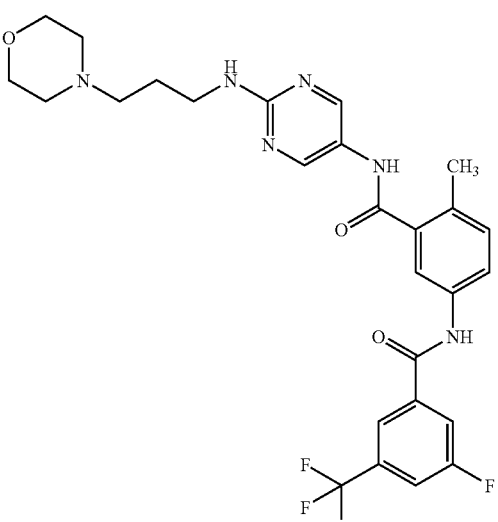 | 5-(((3-fluoro-5-(trifluoromethyl)phenyl)carbonyl)amino)-2-methyl-N-(2-((3-(4-morpholinyl)propyl)amino)-5-pyrimidinyl)benzamide | 561.2 | A |

-continued

| Ex. No. | Structure | Name | MS | Method |
|---|---|---|---|---|
| 14 | 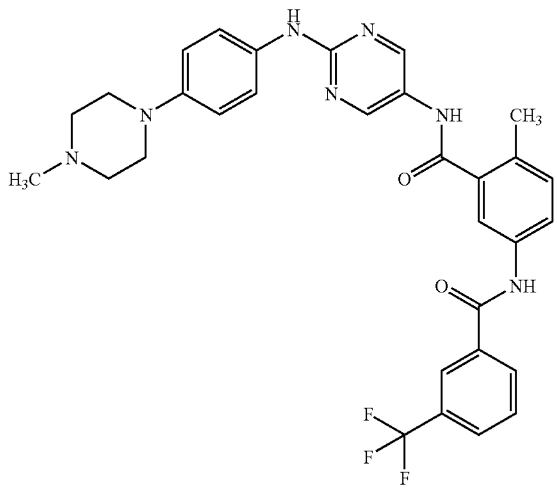 [SMILES: Cc1ccc(NC(=O)c2cccc(C(F)(F)F)c2)cc1C(=O)Nc1cnc(Nc2ccc(N3CCN(C)CC3)cc2)nc1] | 2-methyl-N-(2-((4-(4-methyl-1-piperazinyl)phenyl)amino)-5-pyrimidinyl)-5-(((3-(trifluoromethyl)phenyl)carbonyl)amino)benzamide | 590.2 | A |
| 15 | 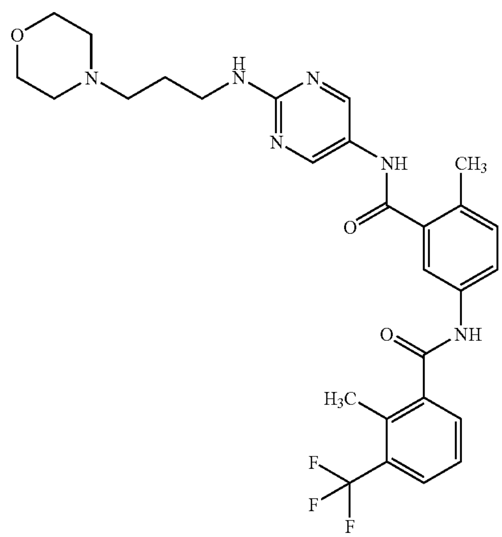 [SMILES: Cc1ccc(NC(=O)c2cccc(C(F)(F)F)c2C)cc1C(=O)Nc1cnc(NCCCN2CCOCC2)nc1] | 2-methyl-N-(4-methyl-3-(((2-((3-(4-morpholinyl)propyl)amino)-5-pyrimidinyl)amino)carbonyl)phenyl)-3-(trifluoromethyl)benzamide | 557.1 | A |
| 16 | 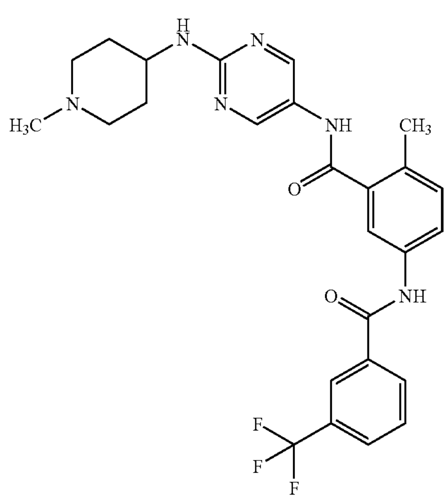 [SMILES: Cc1ccc(NC(=O)c2cccc(C(F)(F)F)c2)cc1C(=O)Nc1cnc(NC2CCN(C)CC2)nc1] | 2-methyl-N-(2-((1-methyl-4-piperidinyl)amino)-5-pyrimidinyl)-5-(((3-(trifluoromethyl)phenyl)carbonyl)amino)benzamide | 513.2 | A |

| Ex. No. | Structure | Name | MS | Method |
|---|---|---|---|---|
| 17 | 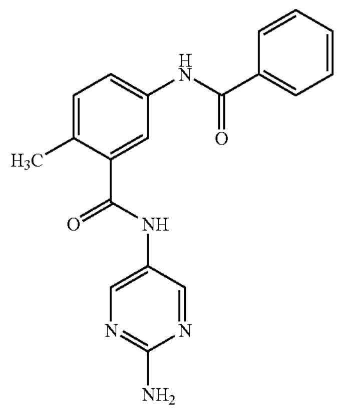 [SMILES: Cc1ccc(NC(=O)c2ccccc2)cc1C(=O)Nc1cnc(N)nc1] | N-(2-amino-5-pyrimidinyl)-2-methyl-5-((phenylcarbonyl)amino)benzamide | 348 | A |
| 18 | 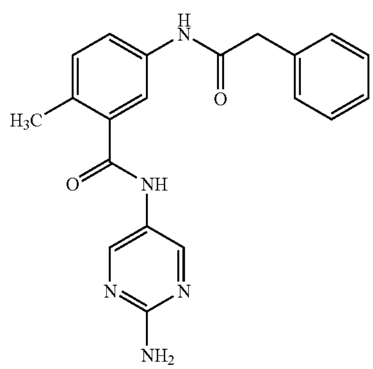 [SMILES: Cc1ccc(NC(=O)Cc2ccccc2)cc1C(=O)Nc1cnc(N)nc1] | N-(2-amino-5-pyrimidinyl)-2-methyl-5-((phenylacetyl)amino)benzamide | 362.0 | A |
| 19 | 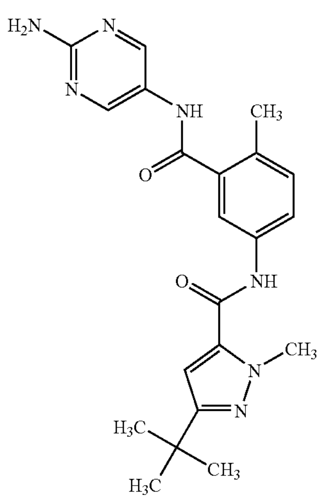 [SMILES: Cc1ccc(NC(=O)c2cc(C(C)(C)C)nn2C)cc1C(=O)Nc1cnc(N)nc1] | N-(3-(((2-amino-5-pyrimidinyl)amino)carbonyl)-4-methylphenyl)-3-(1,1-dimethylethyl)-1-methyl-1H-pyrazole-5-carboxamide | 407.8 | A |

-continued
| Ex. No. | Structure | Name | MS | Method |
|---|---|---|---|---|
| 20 | 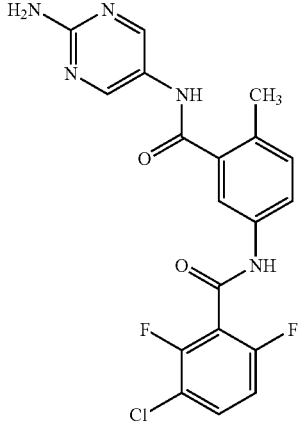 [SMILES: Cc1ccc(NC(=O)c2c(F)ccc(Cl)c2F)cc1C(=O)Nc1cnc(N)nc1] | N-(3-(((2-amino-5-pyrimidinyl)amino)carbonyl)-4-methylphenyl)-3-chloro-2,6-difluorobenzamide | 417.8 | A |
| 21 | 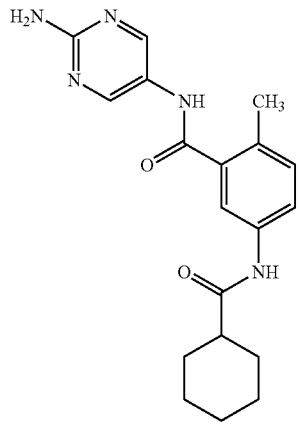 [SMILES: Cc1ccc(NC(=O)C2CCCCC2)cc1C(=O)Nc1cnc(N)nc1] | N-(2-aminopyrimidin-5-yl)-5-(cyclohexanecarboxamido)-2-methylbenzamide | 353.9 | A |
| 22 | 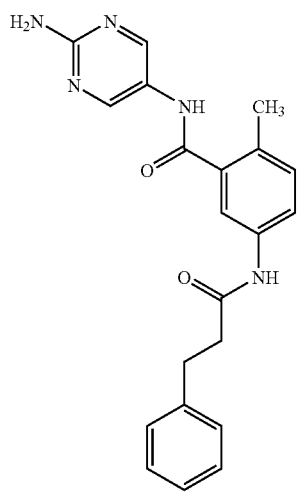 [SMILES: Cc1ccc(NC(=O)CCc2ccccc2)cc1C(=O)Nc1cnc(N)nc1] | N-(2-aminopyrimidin-5-yl)-2-methyl-5-(3-phenylpropanamido)benzamide | 375.9 | A |

-continued
| Ex. No. | Structure | Name | MS | Method |
|---|---|---|---|---|
| 23 | 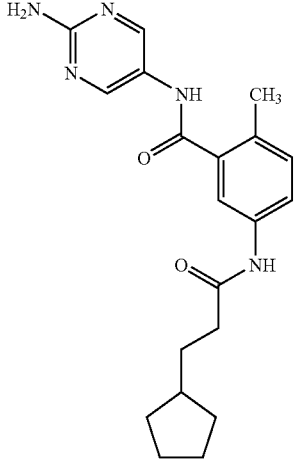 [SMILES: Cc1ccc(NC(=O)CCC2CCCC2)cc1C(=O)Nc1cnc(N)nc1] | N-(2-aminopyrimidin-5-yl)-5-(3-cyclopentylpropanamido)-2-methylbenzamide | 367.9 | A |
| 24 | 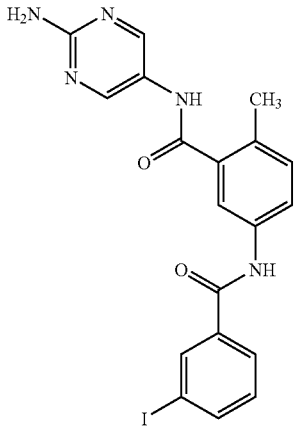 | N-(2-Amino-pyrimidin-5-yl)-5-(3-iodo-benzoylamino)-2-methyl-benzamide | 473.7 | A |
| 25 | 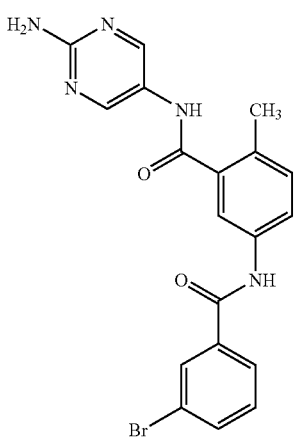 | N-(2-Amino-pyrimidin-5-yl)-5-benzoylamino)-2-(3-bromo-methyl-benzamide | 425.8 | A |

-continued
| Ex. No. | Structure | Name | MS | Method |
|---|---|---|---|---|
| 26 | 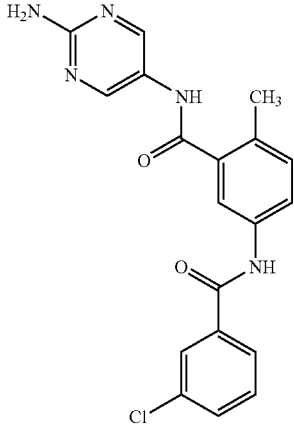 | N-(2-Amino-pyrimidin-5-yl)-5-(3-chloro-benzoylamino)-2-methyl-benzamide | 381.8 | A |
| 27 | 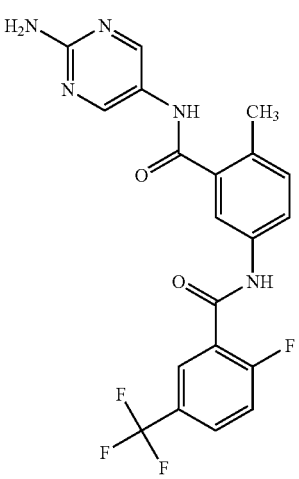 [SMILES: Cc1ccc(NC(=O)c2cc(C(F)(F)F)ccc2F)cc1C(=O)Nc1cnc(N)nc1] | N-(3-(((2-amino-5-pyrimidinyl)amino)carbonyl)-4-methylphenyl)-2-fluoro-5-(trifluoromethyl)benzamide | 433.8 | A |
| 28 | 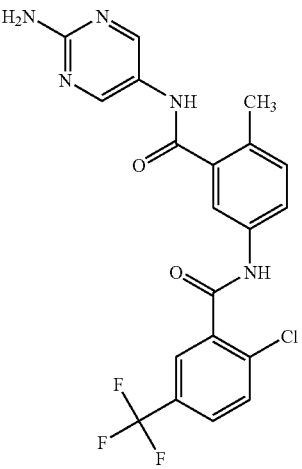 [SMILES: Cc1ccc(NC(=O)c2cc(C(F)(F)F)ccc2Cl)cc1C(=O)Nc1cnc(N)nc1] | N-(3-(((2-amino-5-pyrimidinyl)amino)carbonyl)-4-methylphenyl)-2-chloro-5-(trifluoromethyl)benzamide | 449.8 | A |

-continued

| Ex. No. | Structure | Name | MS | Method |
|---|---|---|---|---|
| 29 | 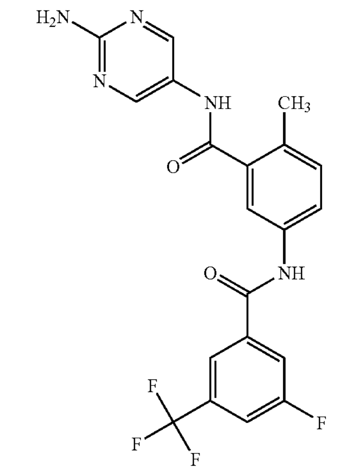 [SMILES: Cc1ccc(NC(=O)c2cc(F)cc(C(F)(F)F)c2)cc1C(=O)Nc1cnc(N)nc1] | N-(2-amino-5-pyrimidinyl)-5-(((3-fluoro-5-(trifluoromethyl)phenyl)carbonyl)amino)-2-methylbenzamide | 433.8 | A |
| 30 | 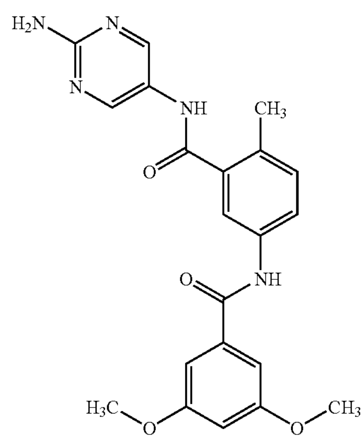 [SMILES: COc1cc(OC)cc(C(=O)Nc2ccc(C)c(C(=O)Nc3cnc(N)nc3)c2)c1] | N-(2-amino-5-pyrimidinyl)-5-(((3,5-bis(methyloxy)phenyl)carbonyl)amino)-2-methylbenzamide | 407.9 | A |
| 31 | 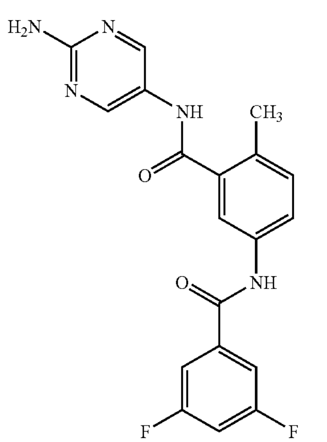 [SMILES: Cc1ccc(NC(=O)c2cc(F)cc(F)c2)cc1C(=O)Nc1cnc(N)nc1] | N-(2-amino-5-pyrimidinyl)-5-(((3,5-difluorophenyl)carbonyl)amino)-2-methylbenzamide | 383.8 | A |

| Ex. No. | Structure | Name | MS | Method |
|---|---|---|---|---|
| 32 | 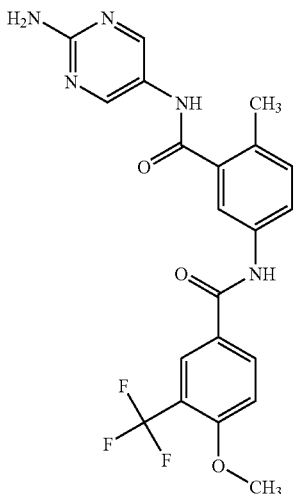 | N-(2-amino-5-pyrimidinyl)-2-methyl-5-(((4-(methyloxy)-3-(trifluoromethyl)phenyl)carbonyl)amino)benzamide | 445.8 | A |
| 33 | 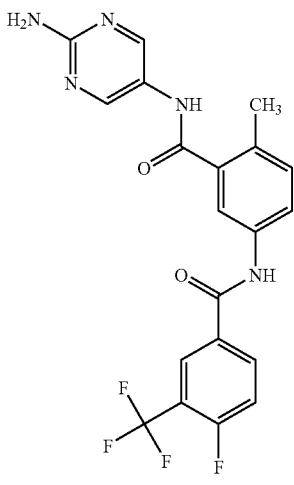 [SMILES: Cc1ccc(NC(=O)c2ccc(F)c(C(F)(F)F)c2)cc1C(=O)Nc1cnc(N)nc1] | N-(2-amino-5-pyrimidinyl)-5-(((4-fluoro-3-(trifluoromethyl)phenyl)carbonyl)amino)-2-methylbenzamide | 433.8 | A |
| 34 | 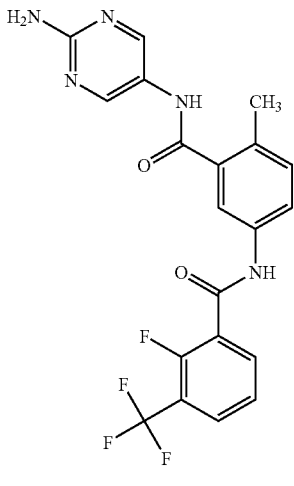 [SMILES: Cc1ccc(NC(=O)c2cccc(C(F)(F)F)c2F)cc1C(=O)Nc1cnc(N)nc1] | N-(3-(((2-amino-5-pyrimidinyl)amino)carbonyl)-4-methylphenyl)-2-fluoro-3-(trifluoromethyl)benzamide | 433.8 | A |

-continued

| Ex. No. | Structure | Name | MS | Method |
|---|---|---|---|---|
| 35 | 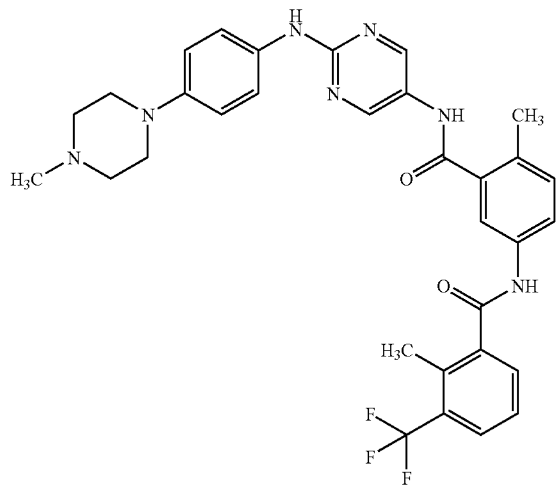 [SMILES: Cc1ccc(NC(=O)c2cccc(C(F)(F)F)c2C)cc1C(=O)Nc1cnc(Nc2ccc(N3CCN(C)CC3)cc2)nc1] | 2-methyl-N-(4-methyl-3-(((2-((4-(4-methyl-1-piperazinyl)phenyl)amino)-5-pyrimidinyl)amino)carbonyl)phenyl)-3-(trifluoromethyl)benzamide | 604.3 | A |
| 36 | 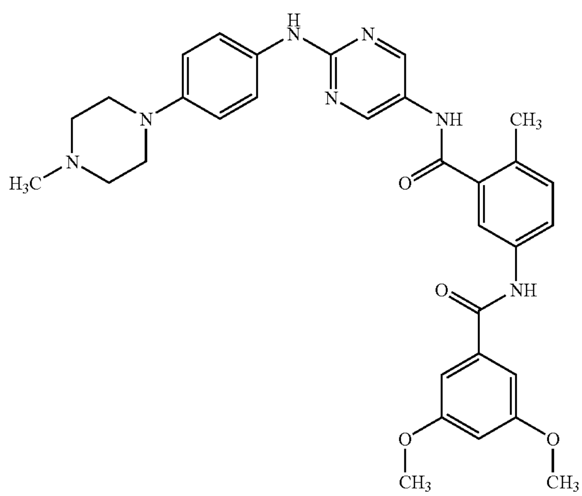 | 5-(((3,5-bis(methyloxy)phenyl)carbonyl)amino)-2-methyl-N-(2-((4-(4-methyl-1-piperazinyl)phenyl)amino)-5-pyrimidinyl)benzamide | 582.3 | A |
| 37 | 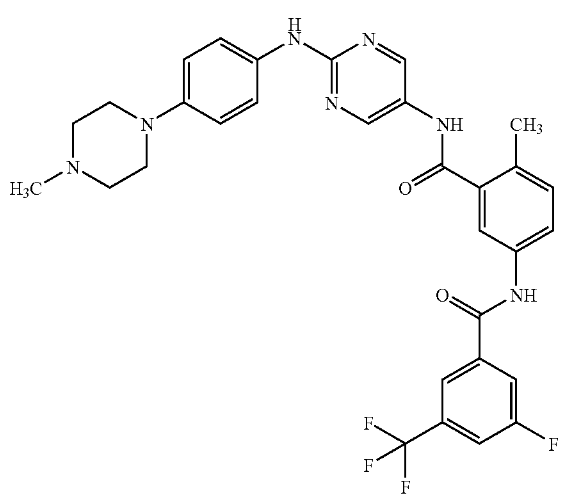 [SMILES: Cc1ccc(NC(=O)c2cc(F)cc(C(F)(F)F)c2)cc1C(=O)Nc1cnc(Nc2ccc(N3CCN(C)CC3)cc2)nc1] | 5-(((3-fluoro-5-(trifluoromethyl)phenyl)carbonyl)amino)-2-methyl-N-(2-((4-(4-methyl-1-piperazinyl)phenyl)amino)-5-pyrimidinyl)benzamide | 608.1 | A |

| Ex. No. | Structure | Name | MS | Method |
|---|---|---|---|---|
| 38 | 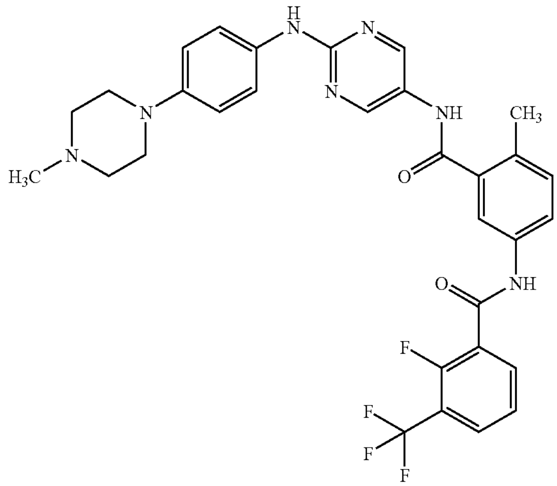 [SMILES: Cc1ccc(NC(=O)c2cccc(C(F)(F)F)c2F)cc1C(=O)Nc1cnc(Nc2ccc(N3CCN(C)CC3)cc2)nc1] | 2-fluoro-N-(4-methyl-3-(((2-((4-(4-methyl-1-piperazinyl)phenyl)amino)-5-pyrimidinyl)amino)carbonyl)phenyl)-3-(trifluoromethyl)benzamide | 608.2 | A |
| 39 | 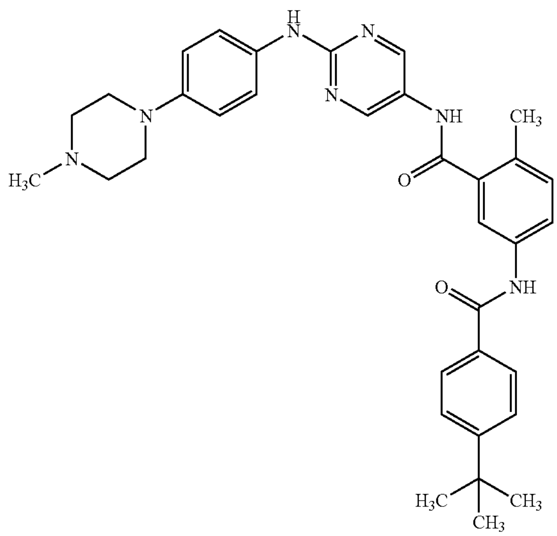 [SMILES: Cc1ccc(NC(=O)c2ccc(C(C)(C)C)cc2)cc1C(=O)Nc1cnc(Nc2ccc(N3CCN(C)CC3)cc2)nc1] | 5-(((4-(1,1-dimethylethyl)phenyl)carbonyl)amino)-2-methyl-N-(2-((4-(4-methyl-1-piperazinyl)phenyl)amino)-5-pyrimidinyl)benzamide | 578.2 | A |
| 40 | 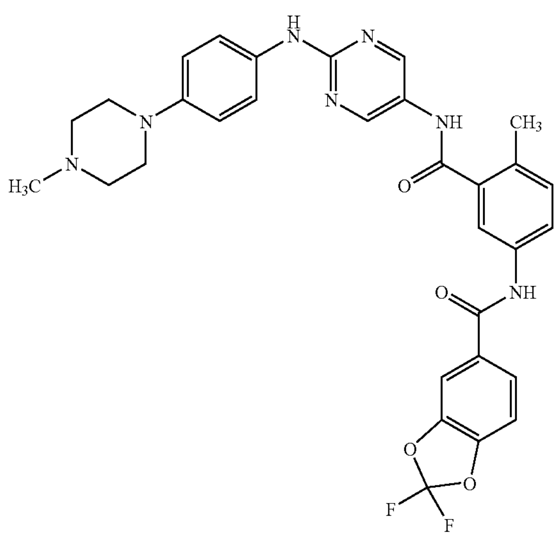 [SMILES: Cc1ccc(NC(=O)c2ccc3c(c2)OC(F)(F)O3)cc1C(=O)Nc1cnc(Nc2ccc(N3CCN(C)CC3)cc2)nc1] | 2,2-difluoro-N-(4-methyl-3-((2-(4-(4-methylpiperazin-1-yl)phenylamino)pyrimidin-5-yl)carbamoyl)phenyl)benzo[d][1,3]dioxole-5-carboxamide | 602.2 | A |

| Ex. No. | Structure | Name | MS | Method |
|---|---|---|---|---|
| 41 | 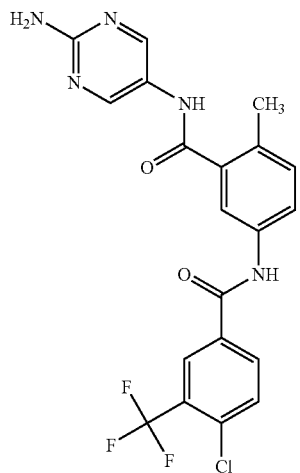 [SMILES: Cc1ccc(NC(=O)c2ccc(Cl)c(C(F)(F)F)c2)cc1C(=O)Nc1cnc(N)nc1] | N-(2-amino-5-pyrimidinyl)-5-(((4-chloro-3-(trifluoromethyl)phenyl)carbonyl)amino)-2-methylbenzamide | 449.8 | A |
| 42 | 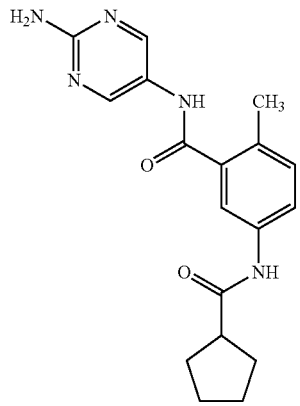 [SMILES: Cc1ccc(NC(=O)C2CCCC2)cc1C(=O)Nc1cnc(N)nc1] | N-(2-aminopyrimidin-5-yl)-5-(cyclopentanecarboxamido)-2-methylbenzamide | 340.2 | A |
| 43 | 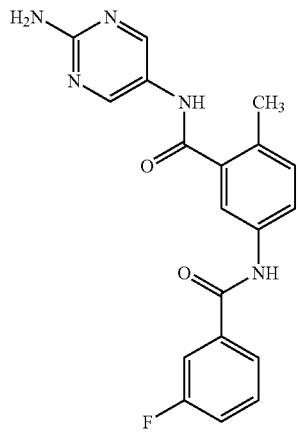 | N-(2-Amino-pyrimidin-5-yl)-5-(3-fluoro-benzoylamino)-2-methyl-benzamide | 366.2 | A |

| Ex. No. | Structure | Name | MS | Method |
|---|---|---|---|---|
| 44 | 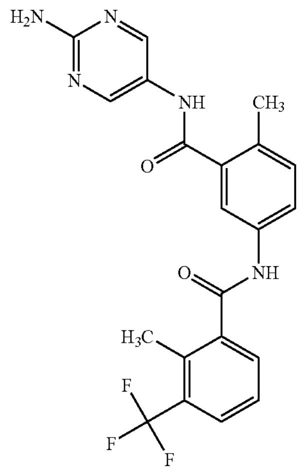 [SMILES: Cc1ccc(NC(=O)c2cccc(C(F)(F)F)c2C)cc1C(=O)Nc1cnc(N)nc1] | N-(3-(((2-amino-5-pyrimidinyl)amino)carbonyl)-4-methylphenyl)-2-methyl-3-(trifluoromethyl)benzamide | 429.8 | A |
| 45 | 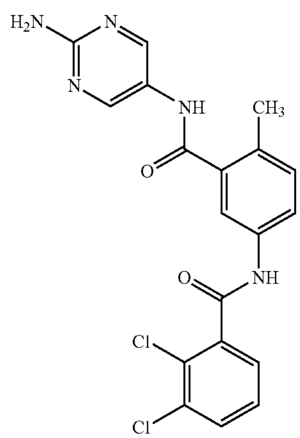 [SMILES: Cc1ccc(NC(=O)c2cccc(Cl)c2Cl)cc1C(=O)Nc1cnc(N)nc1] | N-(3-(((2-amino-5-pyrimidinyl)amino)carbonyl)-4-methylphenyl)-2,3-dichlorobenzamide | 415.7 | A |
| 46 | 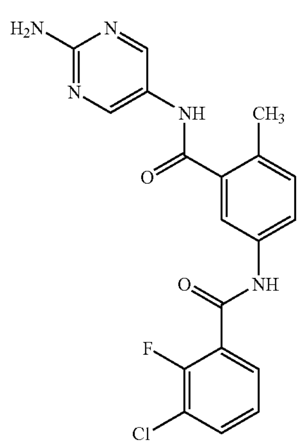 [SMILES: Cc1ccc(NC(=O)c2cccc(Cl)c2F)cc1C(=O)Nc1cnc(N)nc1] | N-(3-(((2-amino-5-pyrimidinyl)amino)carbonyl)-4-methylphenyl)-3-chloro-2-fluorobenzamide | 399.8 | A |

-continued

| Ex. No. | Structure | Name | MS | Method |
|---|---|---|---|---|
| 47 | 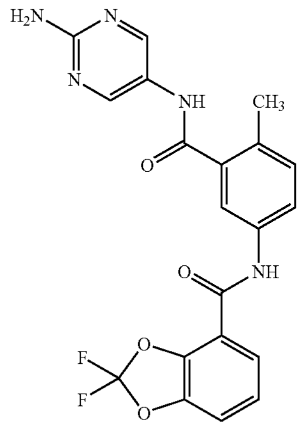 [SMILES: Cc1ccc(NC(=O)c2cccc3c2OC(F)(F)O3)cc1C(=O)Nc1cnc(N)nc1] | N-(3-((2-aminopyrimidin-5-yl)carbamoyl)-4-methylphenyl)-2,2-difluorobenzo[d][1,3]dioxole-4-carboxamide | 428.1 | A |
| 48 | 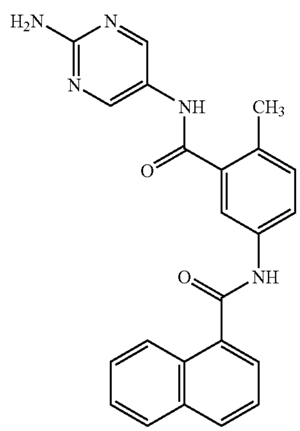 [SMILES: Cc1ccc(NC(=O)c2cccc3ccccc23)cc1C(=O)Nc1cnc(N)nc1] | N-(3-((2-aminopyrimidin-5-yl)carbamoyl)-4-methylphenyl)-1-naphthamide | 398.2 | A |
| 49 | 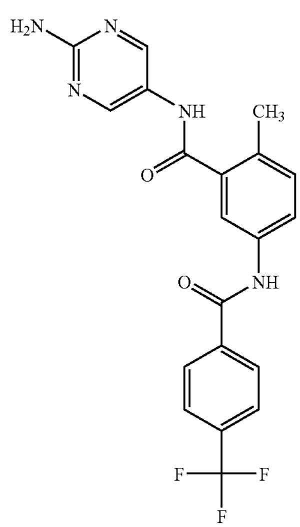 [SMILES: Cc1ccc(NC(=O)c2ccc(C(F)(F)F)cc2)cc1C(=O)Nc1cnc(N)nc1] | N-(2-Amino-pyrimidin-5-yl)-2-methyl-5-(4-trifluoromethyl-benzoylamino)-benzamide | 416.1 | A |

-continued

| Ex. No. | Structure | Name | MS | Method |
|---|---|---|---|---|
| 50 | 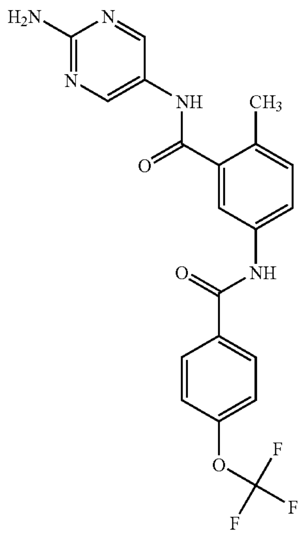 [SMILES: Cc1ccc(NC(=O)c2ccc(OC(F)(F)F)cc2)cc1C(=O)Nc1cnc(N)nc1] | N-(2-Amino-pyrimidin-5-yl)-2-methyl-5-(4-trifluoromethoxy-benzoylamino)-benzamide | 432.1 | A |
| 51 | 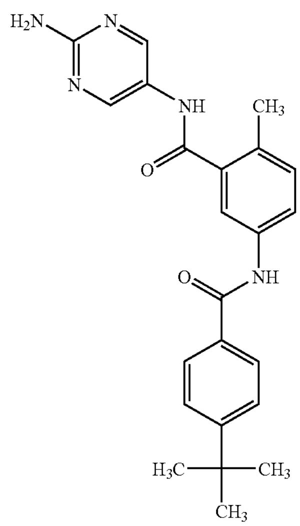 [SMILES: Cc1ccc(NC(=O)c2ccc(C(C)(C)C)cc2)cc1C(=O)Nc1cnc(N)nc1] | N-(2-Amino-pyrimidin-5-yl)-5-(4-tert-butyl-benzoylamino)-2-methyl-benzamide | 404.3 | A |
| 52 | 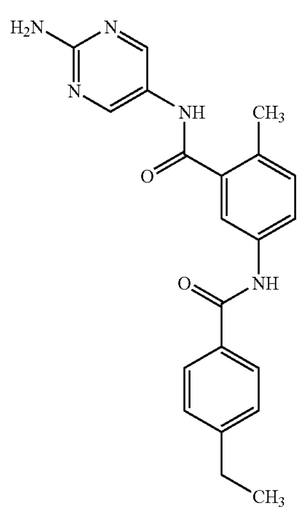 [SMILES: CCc1ccc(C(=O)Nc2ccc(C)c(C(=O)Nc3cnc(N)nc3)c2)cc1] | N-(2-Amino-pyrimidin-5-yl)-5-(4-ethyl-benzoylamino)-2-methyl-benzamide | 376.2 | A |

-continued

| Ex. No. | Structure | Name | MS | Method |
|---|---|---|---|---|
| 53 | 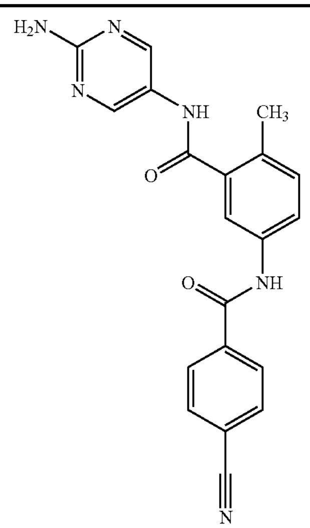 | N-(2-Amino-pyrimidin-5-yl)-5-(4-cyano-benzoylamino)-2-methyl-benzamide | 373.2 | A |
| 54 | 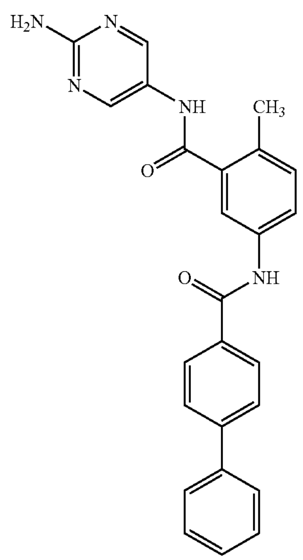 [SMILES: Cc1ccc(NC(=O)c2ccc(-c3ccccc3)cc2)cc1C(=O)Nc1cnc(N)nc1] | Biphenyl-4-carboxylic acid [3-(2-amino-pyrimidin-5-ylcarbamoyl)-4-methyl-phenyl]-amide | 424.2 | A |
| 55 | 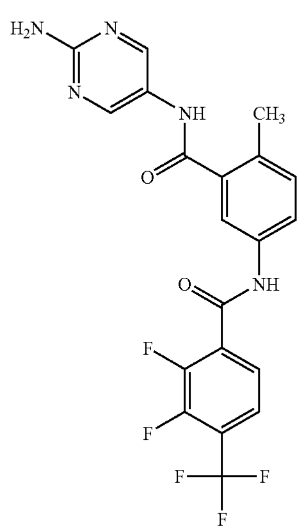 [SMILES: Cc1ccc(NC(=O)c2ccc(C(F)(F)F)c(F)c2F)cc1C(=O)Nc1cnc(N)nc1] | N-[3-(2-Amino-pyrimidin-5-ylcarbamoyl)-4-methyl-phenyl]-2,3-difluoro-4-trifluoromethyl-benzamide | 452.2 | A |

-continued

| Ex. No. | Structure | Name | MS | Method |
|---|---|---|---|---|
| 56 | 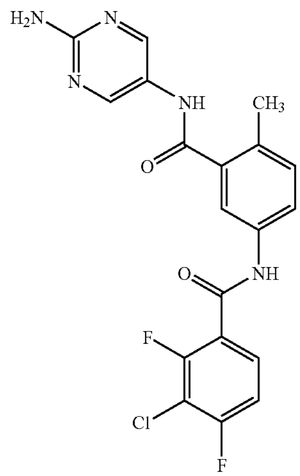 [SMILES: Cc1ccc(NC(=O)c2ccc(F)c(Cl)c2F)cc1C(=O)Nc1cnc(N)nc1] | N-[3-(2-Amino-pyrimidin-5-ylcarbamoyl)-4-methyl-phenyl]-3-chloro-2,4-difluoro-benzamide | 418.1 | A |
| 57 | 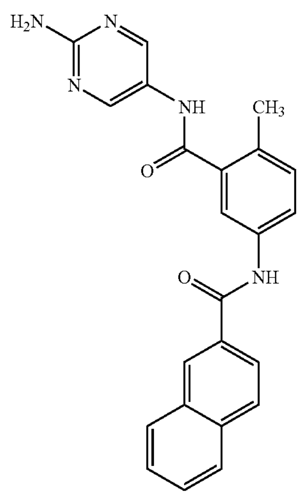 [SMILES: Cc1ccc(NC(=O)c2ccc3ccccc3c2)cc1C(=O)Nc1cnc(N)nc1] | N-(3-((2-aminopyrimidin-5-yl)carbamoyl)-4-methylphenyl)-2-naphthamide | 398.2 | A |
| 58 | 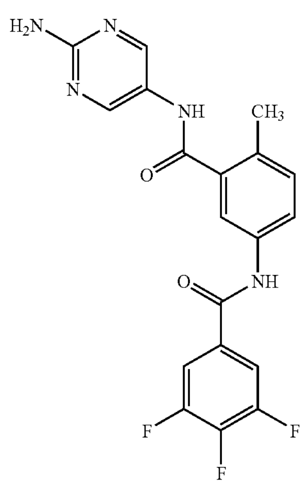 [SMILES: Cc1ccc(NC(=O)c2cc(F)c(F)c(F)c2)cc1C(=O)Nc1cnc(N)nc1] | N-[3-(2-Amino-pyrimidin-5-ylcarbamoyl)-4-methyl-phenyl]-3,4,5-trifluoro-benzamide | 402.2 | A |

-continued

| Ex. No. | Structure | Name | MS | Method |
|---|---|---|---|---|
| 59 | 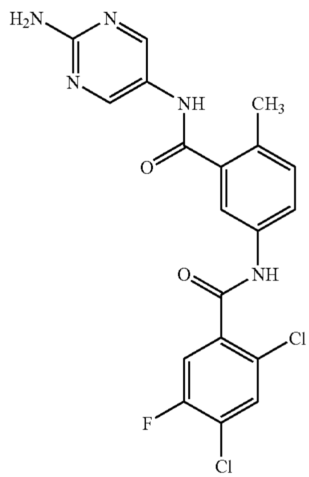 [SMILES: Cc1ccc(NC(=O)c2cc(F)c(Cl)cc2Cl)cc1C(=O)Nc1cnc(N)nc1] | N-[3-(2-Amino-pyrimidin-5-ylcarbamoyl)-4-methyl-phenyl]-2,4-dichloro-5-fluoro-benzamide | 434.2 | A |
| 60 | 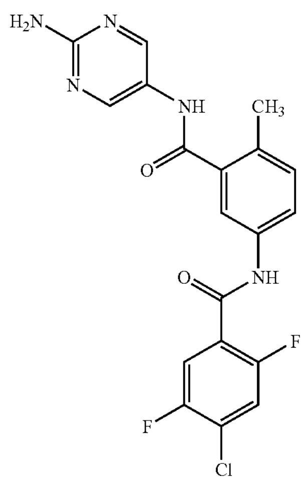 [SMILES: Cc1ccc(NC(=O)c2cc(F)c(Cl)cc2F)cc1C(=O)Nc1cnc(N)nc1] | N-[3-(2-Amino-pyrimidin-5-ylcarbamoyl)-4-methyl-phenyl]-4-chloro-2,5-difluoro-benzamide | 417.4 | A |
| 61 | 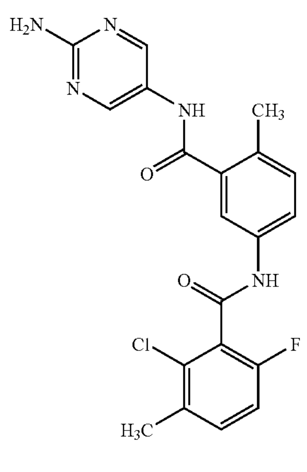 [SMILES: Cc1ccc(NC(=O)c2c(F)ccc(C)c2Cl)cc1C(=O)Nc1cnc(N)nc1] | N-[3-(2-Amino-pyrimidin-5-ylcarbamoyl)-4-methyl-phenyl]-2-chloro-6-fluoro-3-methyl-benzamide | 414.2 | A |

| Ex. No. | Structure | Name | MS | Method |
|---|---|---|---|---|
| 62 | 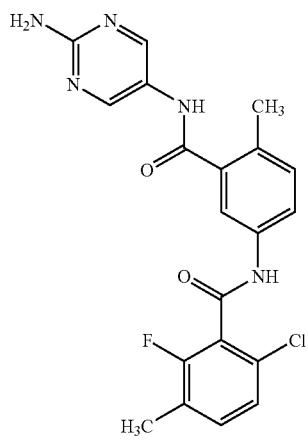 [SMILES: Cc1ccc(NC(=O)c2c(Cl)ccc(C)c2F)cc1C(=O)Nc1cnc(N)nc1] | N-[3-(2-Amino-pyrimidin-5-ylcarbamoyl)-4-methyl-phenyl]-6-chloro-2-fluoro-3-methyl-benzamide | 414.2 | A |
| 63 | 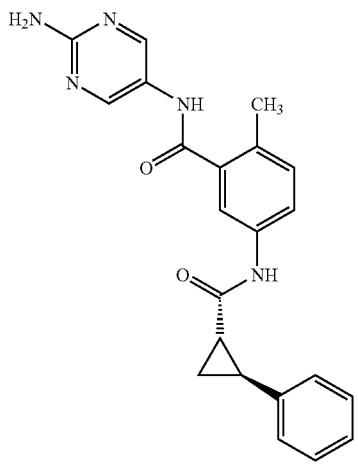 | N-(2-aminopyrimidin-5-yl)-2-methyl-5-(((1S,2S)-2-phenylcyclopropanecarboxamido)benzamide | 387.5 | A |
| 64 | 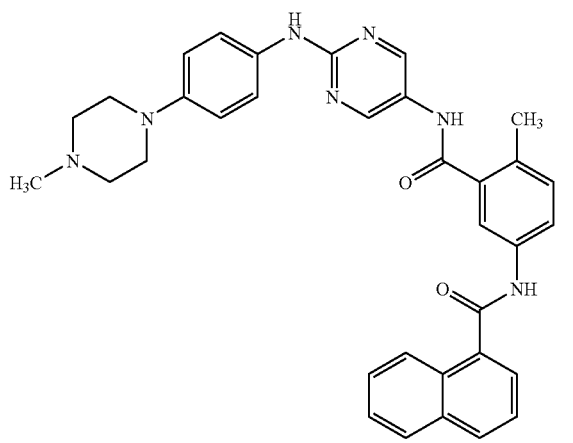 [SMILES: Cc1ccc(NC(=O)c2cccc3ccccc23)cc1C(=O)Nc1cnc(Nc2ccc(N3CCN(C)CC3)cc2)nc1] | N-(4-methyl-3-((2-(4-(4-methylpiperazin-1-yl)phenylamino)pyrimidin-5-yl)carbamoyl)phenyl)-1-naphthamide | 572.3 | A |

| Ex. No. | Structure | Name | MS | Method |
|---|---|---|---|---|
| 65 | 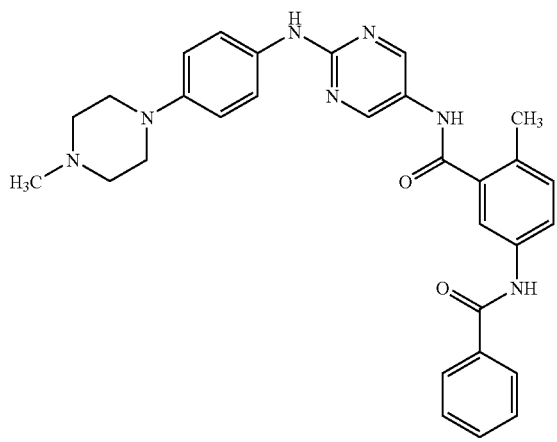 [SMILES: Cc1ccc(NC(=O)c2ccccc2)cc1C(=O)Nc1cnc(Nc2ccc(N3CCN(C)CC3)cc2)nc1] | 5-Benzoylamino-2-methyl-N-{2-[4-(4-methyl-piperazin-1-yl)-phenylamino]-pyrimidin-5-yl}-benzamide | 522.2 | A |
| 66 | 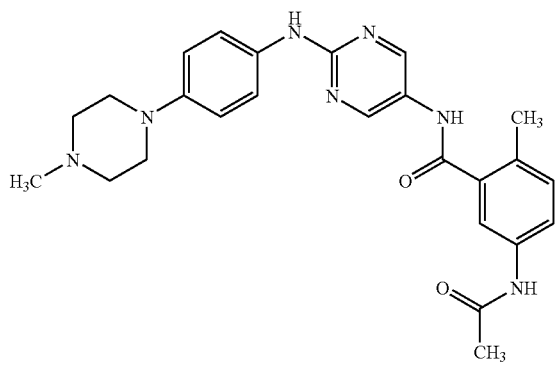 [SMILES: CC(=O)Nc1ccc(C)c(C(=O)Nc2cnc(Nc3ccc(N4CCN(C)CC4)cc3)nc2)c1] | 5-acetamido-2-methyl-N-(2-(4-(4-methylpiperazin-1-yl)phenylamino)pyrimidin-5-yl)benzamide | 460.2 | A |
| 67 | 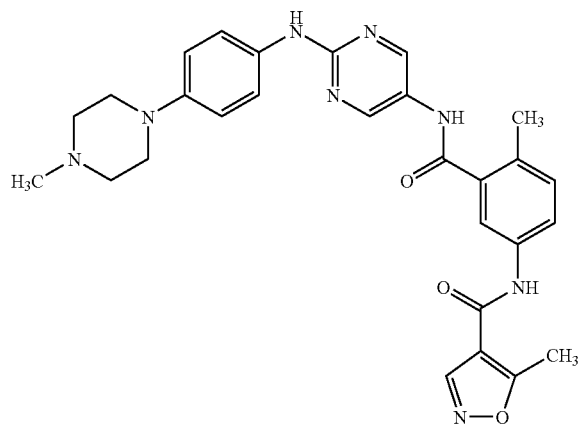 [SMILES: Cc1ccc(NC(=O)c2cnoc2C)cc1C(=O)Nc1cnc(Nc2ccc(N3CCN(C)CC3)cc2)nc1] | 5-methyl-N-(4-methyl-3-((2-(4-(4-methylpiperazin-1-yl)phenylamino)pyrimidin-5-yl)carbamoyl)phenyl)isoxazole-4-carboxamide | 527.2 | A |

-continued

| Ex. No. | Structure | Name | MS | Method |
|---|---|---|---|---|
| 68 | 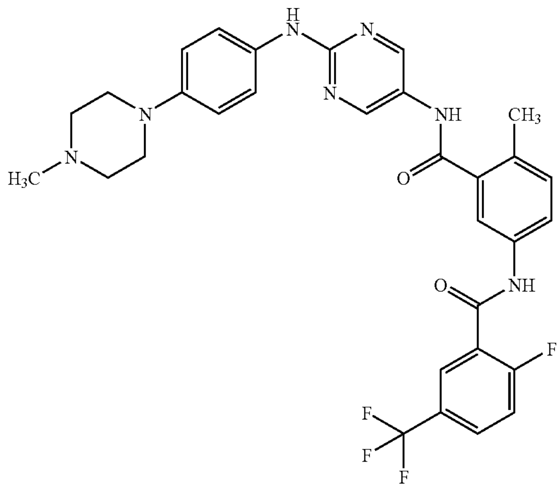 [SMILES: Cc1ccc(NC(=O)c2cc(C(F)(F)F)ccc2F)cc1C(=O)Nc1cnc(Nc2ccc(N3CCN(C)CC3)cc2)nc1] | 2-fluoro-N-(4-methyl-3-(((2-((4-(4-methyl-1-piperazinyl)phenyl)amino)-5-pyrimidinyl)amino)carbonyl)phenyl)-5-(trifluoromethyl)benzamide | 608.1 | A |
| 69 | 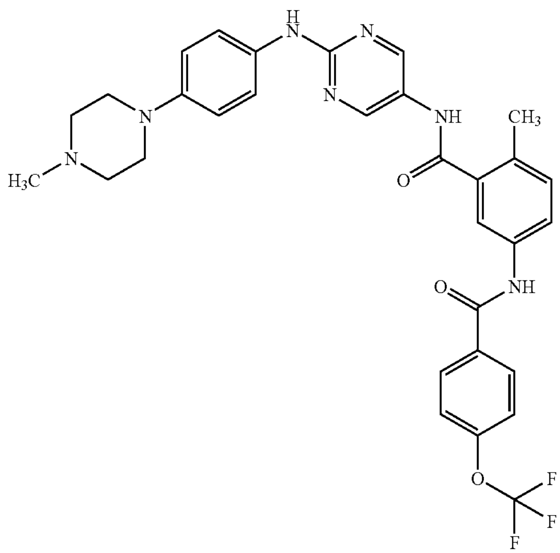 [SMILES: Cc1ccc(NC(=O)c2ccc(OC(F)(F)F)cc2)cc1C(=O)Nc1cnc(Nc2ccc(N3CCN(C)CC3)cc2)nc1] | 2-Methyl-N-{2-[4-(4-methyl-piperazin-1-yl)-phenylamino]-pyrimidin-5-yl}-5-(4-trifluoromethoxy-benzoylamino)-benzamide | 606.2 | A |
| 70 | 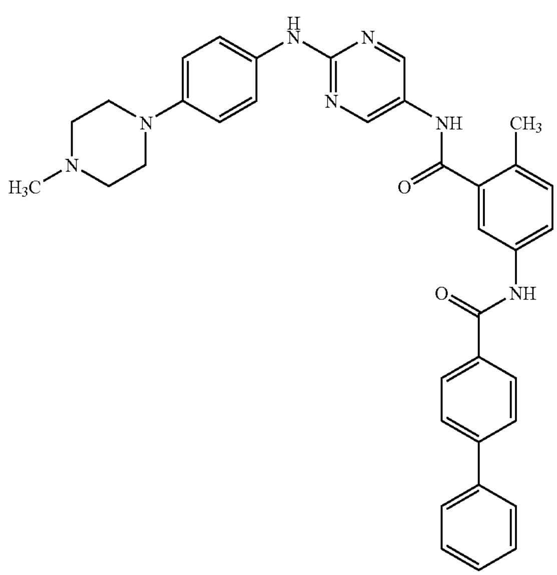 [SMILES: Cc1ccc(NC(=O)c2ccc(-c3ccccc3)cc2)cc1C(=O)Nc1cnc(Nc2ccc(N3CCN(C)CC3)cc2)nc1] | Biphenyl-4-carboxylic acid (4-methyl-3-{2-[4-(4-methyl-piperazin-1-yl)-phenylamino]-pyrimidin-5-ylcarbamoyl}-phenyl)-amide | 598.2 | A |

-continued

| Ex. No. | Structure | Name | MS | Method |
|---|---|---|---|---|
| 71 | 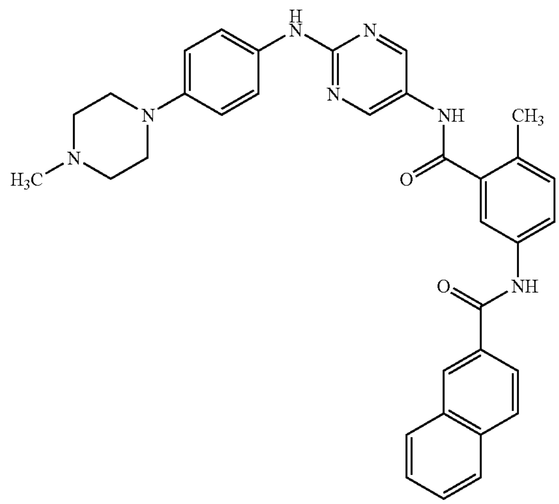 [SMILES: Cc1ccc(NC(=O)c2ccc3ccccc3c2)cc1C(=O)Nc1cnc(Nc2ccc(N3CCN(C)CC3)cc2)nc1] | N-(4-methyl-3-((2-(4-(4-methylpiperazin-1-yl)phenylamino)pyrimidin-5-yl)carbamoyl)phenyl)-2-naphthamide | 572.3 | A |
| 72 | 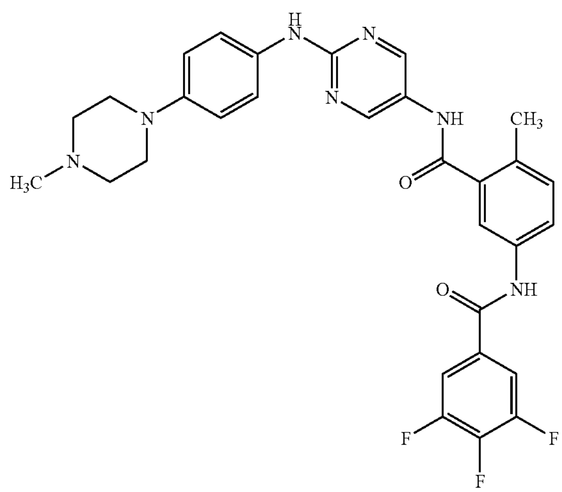 [SMILES: Cc1ccc(NC(=O)c2cc(F)c(F)c(F)c2)cc1C(=O)Nc1cnc(Nc2ccc(N3CCN(C)CC3)cc2)nc1] | 3,4,5-Trifluoro-N-(4-methyl-3-{2-[4-(4-methyl-piperazin-1-yl)-phenylamino]-pyrimidin-5-ylcarbamoyl}-phenyl)-benzamide | 576.2 | A |
| 73 | 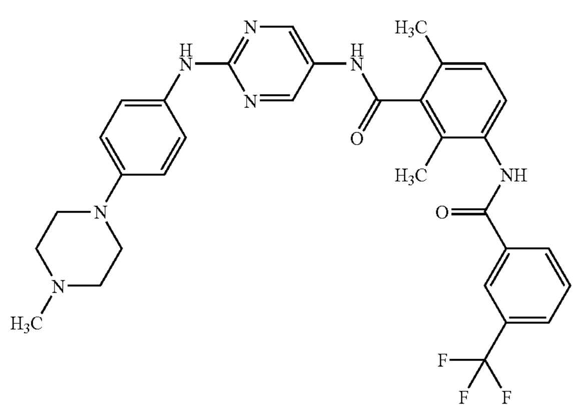 [SMILES: Cc1ccc(NC(=O)c2cccc(C(F)(F)F)c2)c(C)c1C(=O)Nc1cnc(Nc2ccc(N3CCN(C)CC3)cc2)nc1] | 2,6-Dimethyl-N-{2-[4-(4-methyl-piperazin-1-yl)-phenylamino]-pyrimidin-5-yl}-3-(3-trifluoromethyl-benzoylamino)-benzamide | 604.2 | A |

| Ex. No. | Structure | Name | MS | Method |
|---|---|---|---|---|
| 74 | 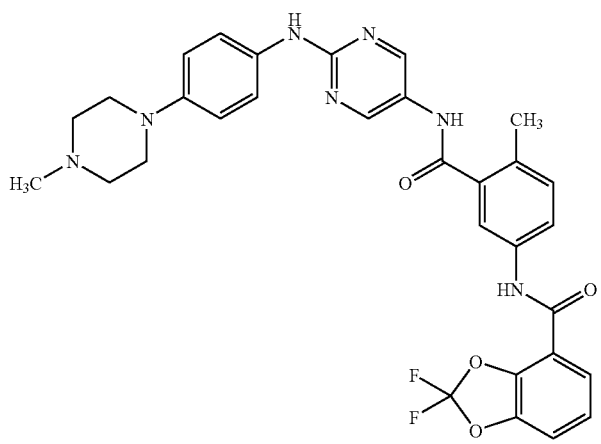 [SMILES: Cc1ccc(NC(=O)c2cccc3c2OC(F)(F)O3)cc1C(=O)Nc1cnc(Nc2ccc(N3CCN(C)CC3)cc2)nc1] | 2,2-difluoro-N-(4-methyl-3-((2-(4-(4-methylpiperazin-1-yl)phenylamino)pyrimidin-5-yl)carbamoyl)phenyl)benzo[d][1,3]dioxole-4-carboxamide | 602.2 | A |
| 75 | 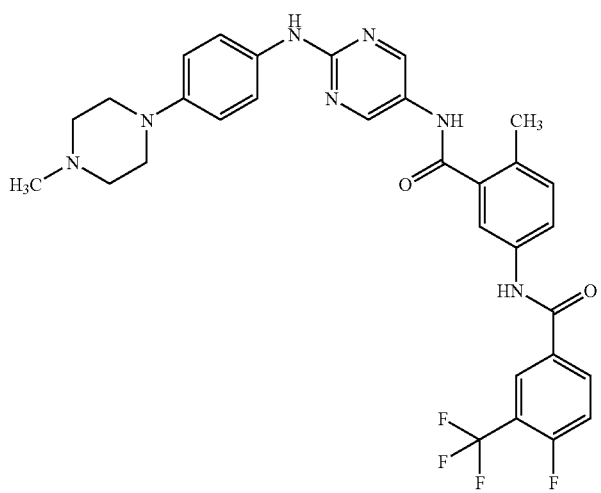 [SMILES: Cc1ccc(NC(=O)c2ccc(F)c(C(F)(F)F)c2)cc1C(=O)Nc1cnc(Nc2ccc(N3CCN(C)CC3)cc2)nc1] | 4-fluoro-N-(4-methyl-3-(((2-((4-(4-methyl-1-piperazinyl)phenyl)amino)-5-pyrimidinyl)amino)carbonyl)phenyl)-3-(trifluoromethyl)benzamide | 608.2 | A |
| 76 | 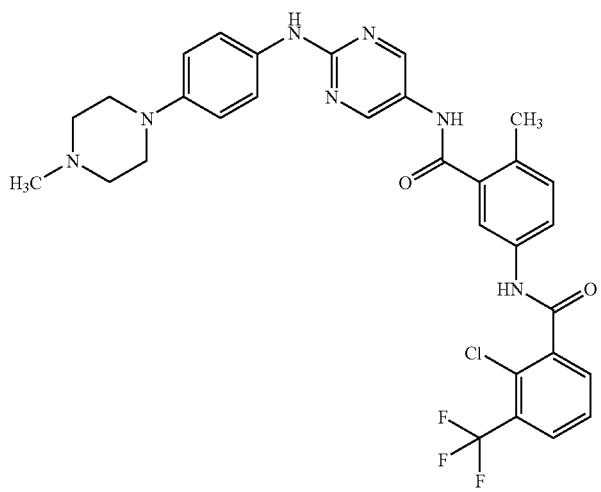 [SMILES: Cc1ccc(NC(=O)c2cccc(C(F)(F)F)c2Cl)cc1C(=O)Nc1cnc(Nc2ccc(N3CCN(C)CC3)cc2)nc1] | 2-chloro-N-(4-methyl-3-(((2-((4-(4-methyl-1-piperazinyl)phenyl)amino)-5-pyrimidinyl)amino)carbonyl)phenyl)-3-(trifluoromethyl)benzamide | 624.1 | A |

| Ex. No. | Structure | Name | MS | Method |
|---|---|---|---|---|
| 77 | 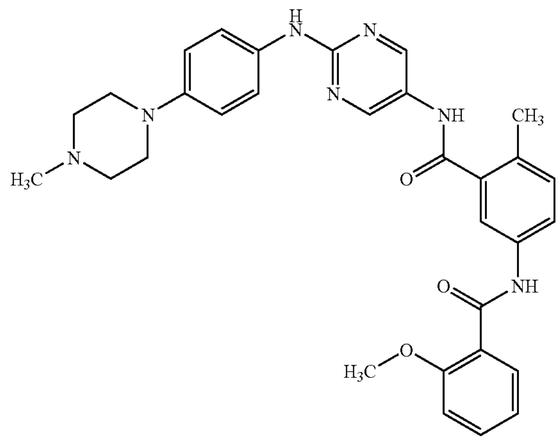 [SMILES: COc1ccccc1C(=O)Nc1ccc(C)c(C(=O)Nc2cnc(Nc3ccc(N4CCN(C)CC4)cc3)nc2)c1] | 2-methoxy-N-(4-methyl-3-(((2-((4-(4-methyl-1-piperazinyl)phenyl)amino)-5-pyrimidinyl)amino)carbonyl)phenyl)benzamide | 552 | A |
| 78 | 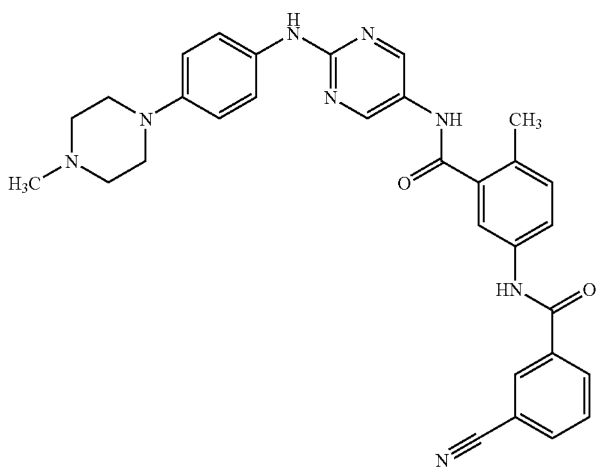 [SMILES: Cc1ccc(NC(=O)c2cccc(C#N)c2)cc1C(=O)Nc1cnc(Nc2ccc(N3CCN(C)CC3)cc2)nc1] | 3-cyano-N-(4-methyl-3-(((2-((4-(4-methyl-1-piperazinyl)phenyl)amino)-5-pyrimidinyl)amino)carbonyl)phenyl)benzamide | 547 | A |
| 79 | 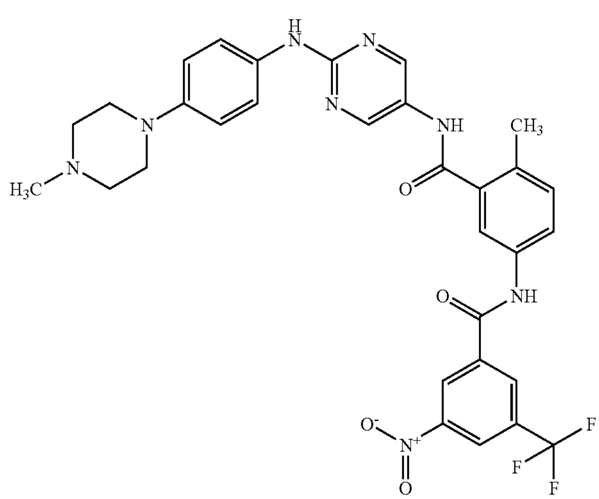 [SMILES: Cc1ccc(NC(=O)c2cc([N+](=O)[O-])cc(C(F)(F)F)c2)cc1C(=O)Nc1cnc(Nc2ccc(N3CCN(C)CC3)cc2)nc1] | N-(4-methyl-3-(((2-((4-(4-methyl-1-piperazinyl)phenyl)amino)-5-pyrimidinyl)amino)carbonyl)phenyl)3-nitro-5-(trifluoromethyl)benzamide | 635 | A |

| Ex. No. | Structure | Name | MS | Method |
|---|---|---|---|---|
| 80 | 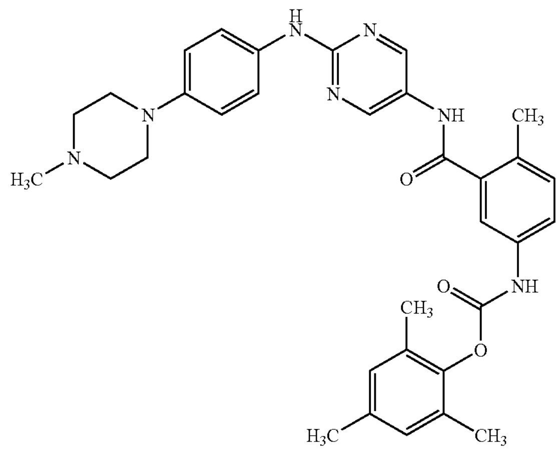 [SMILES: Cc1cc(C)c(OC(=O)Nc2ccc(C)c(C(=O)Nc3cnc(Nc4ccc(N5CCN(C)CC5)cc4)nc3)c2)c(C)c1] | mesityl 4-methyl-3-((2-(4-(4-methylpiperazin-1-yl)phenylamino)pyrimidin-5-yl)carbamoyl)phenylcarbamate | 580 | A |
| 81 | 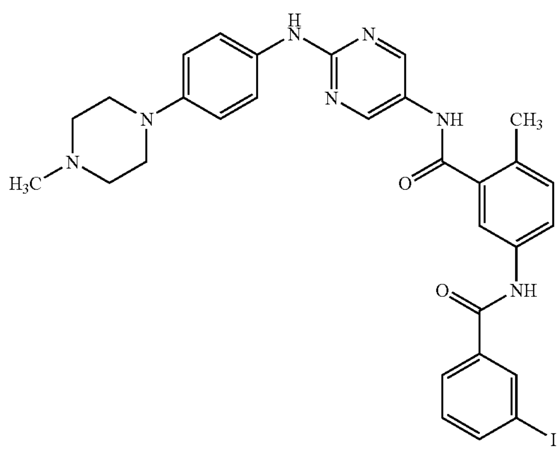 [SMILES: Cc1ccc(NC(=O)c2cccc(I)c2)cc1C(=O)Nc1cnc(Nc2ccc(N3CCN(C)CC3)cc2)nc1] | 3-iodo-N-(4-methyl-3-(((2-((4-(4-methyl-1-piperazinyl)phenyl)amino)-5-pyrimidinyl)amino)carbonyl)phenyl)benzamide | 648 | A |
| 82 | 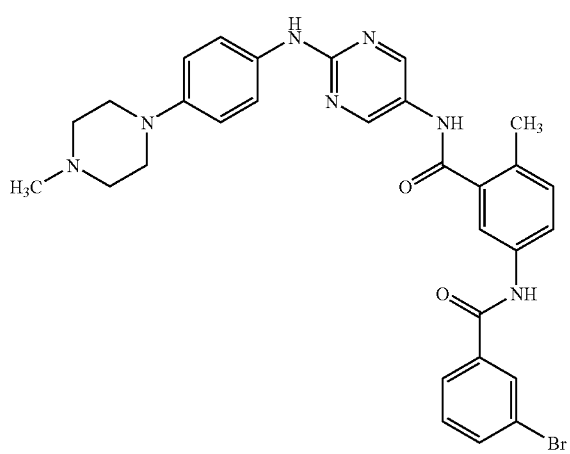 [SMILES: Cc1ccc(NC(=O)c2cccc(Br)c2)cc1C(=O)Nc1cnc(Nc2ccc(N3CCN(C)CC3)cc2)nc1] | 3-bromo-N-(4-methyl-3-(((2-((4-(4-methyl-1-piperazinyl)phenyl)amino)-5-pyrimidinyl)amino)carbonyl)phenyl)benzamide | 601 | A |

| Ex. No. | Structure | Name | MS | Method |
|---|---|---|---|---|
| 83 | 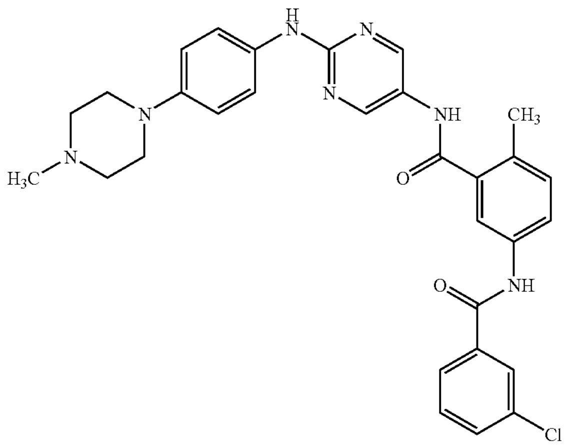 [SMILES: Cc1ccc(NC(=O)c2cccc(Cl)c2)cc1C(=O)Nc1cnc(Nc2ccc(N3CCN(C)CC3)cc2)nc1] | 3-chloro-N-(4-methyl-3-(((2-((4-(4-methyl-1-piperazinyl)phenyl)amino)-5-pyrimidinyl)amino)carbonyl)phenyl)benzamide | 557 | A |
| 84 | 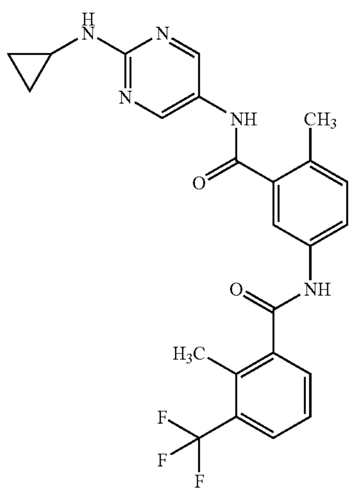 [SMILES: Cc1ccc(NC(=O)c2cccc(C(F)(F)F)c2C)cc1C(=O)Nc1cnc(NC2CC2)nc1] | N-(3-(((2-(cyclopropylamino)-5-pyrimidinyl)amino)carbonyl)-4-methylphenyl)-2-methyl-3-(trifluoromethyl)benzamide | 470 | A |
| 85 | 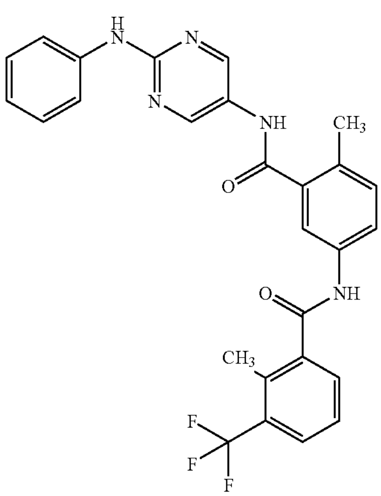 [SMILES: Cc1ccc(NC(=O)c2cccc(C(F)(F)F)c2C)cc1C(=O)Nc1cnc(Nc2ccccc2)nc1] | 2-methyl-N-(4-methyl-3-(((2-(3-phenylamino)-5-pyrimidinyl)amino)carbonyl)phenyl)-3-(trifluoromethyl)benzamide | 505.1 | I |

| Ex. No. | Structure | Name | MS | Method |
|---|---|---|---|---|
| 86 | 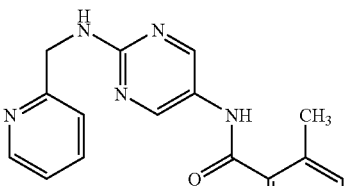 | 2-methyl-N-(4-methyl-3-(((2-((2-pyridinylmethyl)amino)-5-pyrimidinyl)amino)carbonyl)phenyl)-3-(trifluoromethyl)benzamide | 521.1 | J |

Urea linkers "L" between the B rings and $R^3$ groups may be synthesized from $N-R^1R^2$-5-amino-2-methylbenzamide intermediates directly in a single step utilizing desired isocyanates, as described in Example 87 below.

Example 87 illustrates how desired $-NR^8R^9$ groups can be made on a pyrimidyl $R^1$ ring. The methodology described in Example 87 is also applicable to amino substitutions of other heterocyclic $R^1$ rings as well, including those defined for $R^1$ herein.

EXAMPLE 87

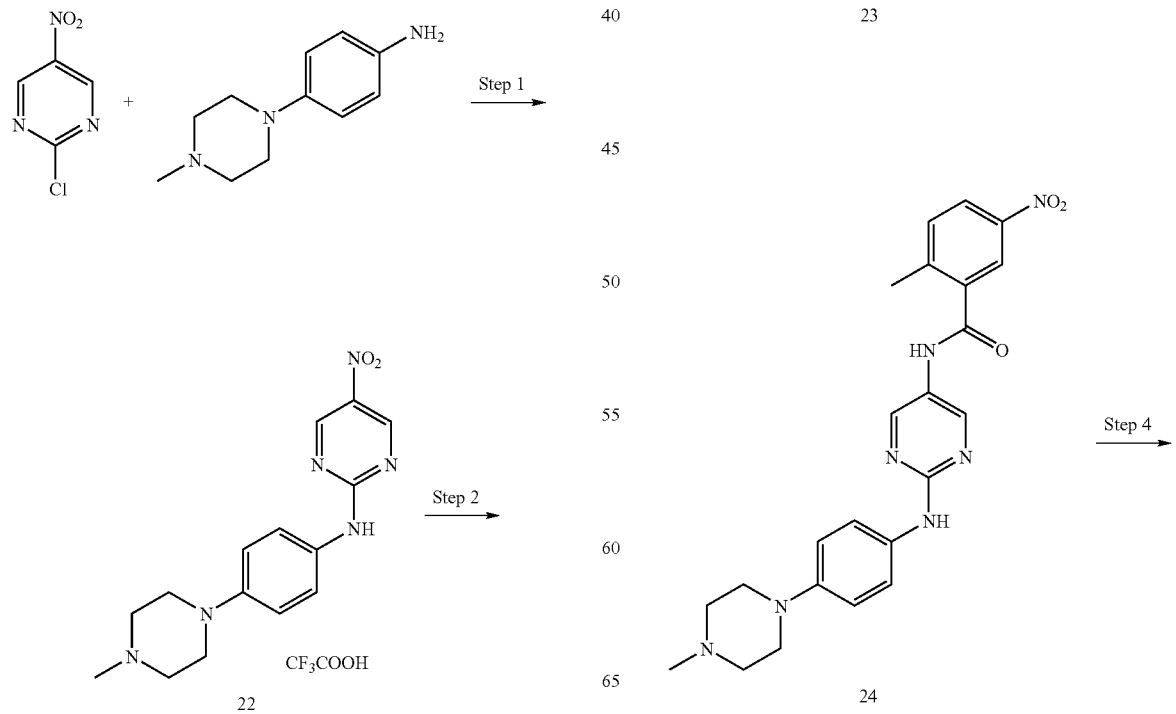

-continued

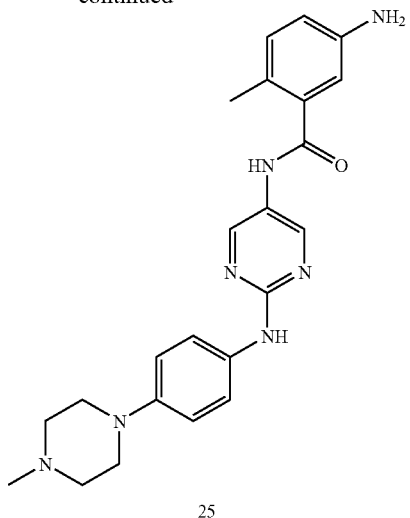

25

Synthesis of 5-amino-2-methyl-N-(2-(4-(4-methylpiperazin-1-yl)phenylamino)pyrimidin-5-yl)benzamide

Step 1. Preparation of 5-nitro-N-(2-(4-(4-methylpiperazin-1-yl)phenylamino)pyrimidine To a mixture of 4-(4-Methylpiperazino)aniline (57.7 g, 302 mmol), 2-chloro-5-nitropyrimidine (48.1 g, 302 mmol) in IPA (500 mL) was added trifluoroacetic acid (46 mL, 603 mmol). The mixture was heated to 80 C for 4 h then allowed to cool to room temperature. The solid was collected by suction filtration, washed twice with IPA (80 mL), methanol (100 mL) then dried under vacuum. Obtained the title compound 22 as a yellowish solid. MS m/z found 315 [MH+]; Calc'd for $C_{15}H_{18}N_6O_2$: 314.35.

Step 2. Preparation of N2-(4-(4-methylpiperazin-1-yl)phenyl)pyrimidine-2,5-diamine A mixture of the salt 22 of Step 1 (96 g, 224 mmol) was suspended in water (400 mL) and 2 N NaOH was added until the aqueous layer was pH=14. The brick red solid was collected by suction filtration and dried under vacuum overnight. The compound was taken up in EtOH (500 mL) and Palladium on Carbon added (10 g, 10% by weight wet). The mixture was placed in a stirred pressure vessel under 50 psi Hydrogen atmosphere for 48 hrs. The catalyst was removed by suction filtration and washed with EtOH. The organics were concentrated under reduced pressure and dried under vacuum. The crude N2-(4-(4-methylpiperazin-1-yl)phenyl)pyrimidine-2,5-diamine 23 was used without any additional purification.

Step 3. Preparation of 5-nitro-2-methyl-N-(2-(4-(4-methylpiperazin-1-yl)phenylamino)pyrimidin-5-yl)benzamide To a mixture of 2-Methyl-5-nitrobenzoic acid (46.0 g, 181 mmol) in methylene chloride (2 L) was added EDC (61.0 g, 318 mmol). The mixture was allowed to stir for 30 min at rt. N2-(4-(4-methylpiperazin-1-yl)phenyl)pyrimidine-2,5-diamine 23 (60 g, 211 mmol) was added and the mixture allowed to stir 70 hrs. Water (2 L) was added and 2N NaOH added until pH=14. The organics were extracted into EtOAc (4 L). The aqueous layer was extracted with additional EtOAc (2 L). The combined organics were dried over anhydrous magnesium sulfate and concentrated under reduced pressure. The residue was taken up in 1 L methylene chloride. The solid formed was collected by suction filtration and washed twice with methylene chloride (250 mL). The solid was dried under vacuum to obtain the title compound 24. MS m/z found 448 [MH+]; Calc'd for $C_{23}H_{25}N_7O_3$: 447.5.

Step 4. 5-amino-2-methyl-N-(2-(4-(4-methylpiperazin-1-yl)phenylamino)pyrimidin-5-yl)benzamide In a 2 L stainless steel pressure vessel with overhead stirring was charged a mixture of the product 24 of Step C (25 g, 55.9 mmol), Absolute ethanol (300 mL), EtOAc (200 mL) and Palladium on Carbon (15 g, 10% by weight wet). The reactor was charged with 65 psi Hydrogen atmosphere for 72 hrs. The catalyst was removed by suction filtration and washed with EtOH. The organics were concentrated under reduced pressure and dried under vacuum. The solid was dried under vacuum to obtain 5-amino-2-methyl-N-(2-(4-(4-methylpiperazin-1-yl)phenylamino)pyrimidin-5-yl)benzamide 25. MS m/z found 418 [MH+]; Calc'd for $C_{23}H_{27}N_7O_1$: 417.5.

EXAMPLE 88

Method B

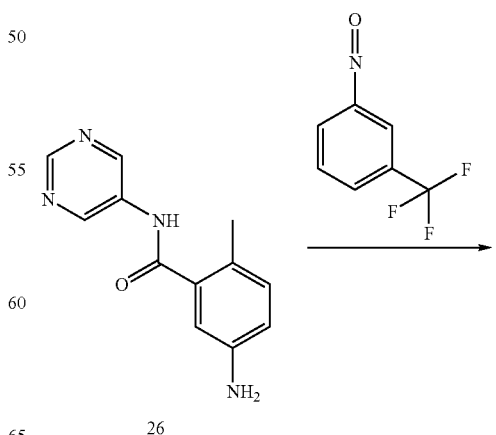

26

111
-continued

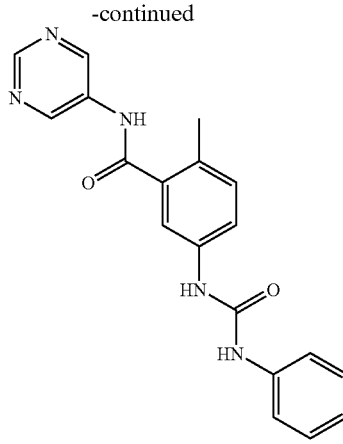

27

112

1-(4-methyl-3-(pyrimidin-5-ylcarbamoyl)phenyl)-3-(3-(trifluoromethyl)phenyl)urea To a suspension of 5-amino-2-methyl-N-(pyrimidin-5-yl) benzamide 26 (0.068 g, 0.30 mmol) in benzene (5 mL) was added 1-isocyanato-3-(trifluoromethyl)benzene (0.046 mL, 0.33 mmol). The reaction was heated at 75° C. for 2 hours, producing a solid precipitate. The mixture was concentrated and chromatographed on silica gel with 94/6 $CH_2Cl_2$/MeOH to afford 1-(4-methyl-3-(pyrimidin-5-ylcarbamoyl)phenyl)-3-(3-(trifluoromethyl)phenyl)urea 27 as a white solid. MS m/z: found 416 [MH+], calc. for $C_{20}H_{16}F_3N_5O_2$=415.13.

The following compounds, Examples 89-91 were made using a procedure similar to that described in Examples 87 and 88.

| Ex. No. | Structure | Name | MS | Method |
|---|---|---|---|---|
| 89 | 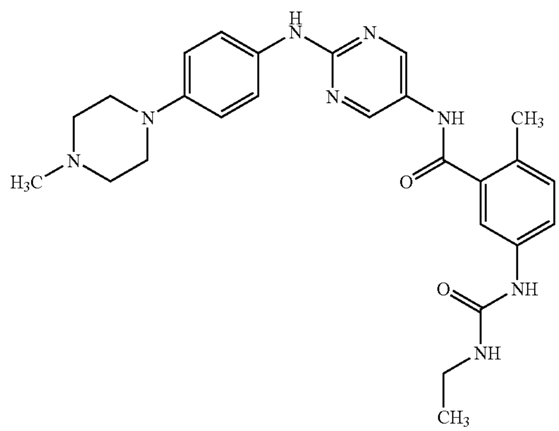 [SMILES: CCNC(=O)Nc1ccc(C)c(C(=O)Nc2cnc(Nc3ccc(N4CCN(C)CC4)cc3)nc2)c1] | 1-ethyl-3-(4-methyl-3-((2-(4-(4-methylpiperazin-1-yl)phenylamino)pyrimidin-5-yl)carbamoyl)phenyl)urea | 489.1 | B |
| 90 | 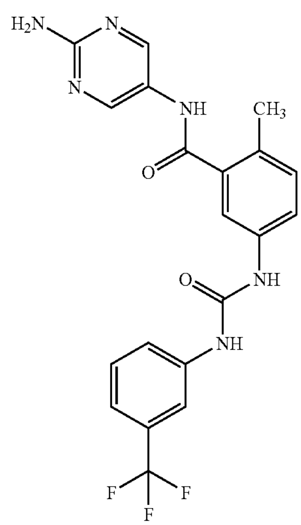 [SMILES: Cc1ccc(NC(=O)Nc2cccc(C(F)(F)F)c2)cc1C(=O)Nc1cnc(N)nc1] | N-(2-amino-5-pyrimidinyl)-2-methyl-5-((((3-(trifluoromethyl)phenyl)amino)carbonyl)amino)benzamide | 431 | B |

| Ex. No. | Structure | Name | MS | Method |
|---|---|---|---|---|
| 91 | 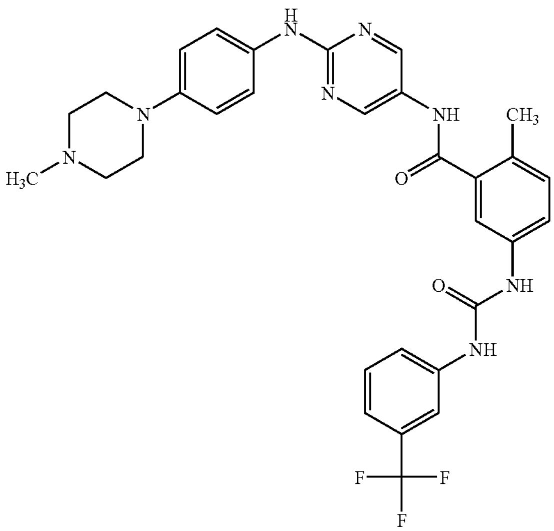 [SMILES: Cc1ccc(NC(=O)Nc2cccc(C(F)(F)F)c2)cc1C(=O)Nc1cnc(Nc2ccc(N3CCN(C)CC3)cc2)nc1] | 2-methyl-N-(2-((4-(4-methyl-1-piperazinyl)phenyl)amino)-5-pyrimidinyl)-5-((((3-(trifluoromethyl)phenyl)amino)carbonyl)amino)benzamide | 605.1 | B |

EXAMPLE 92

Method C

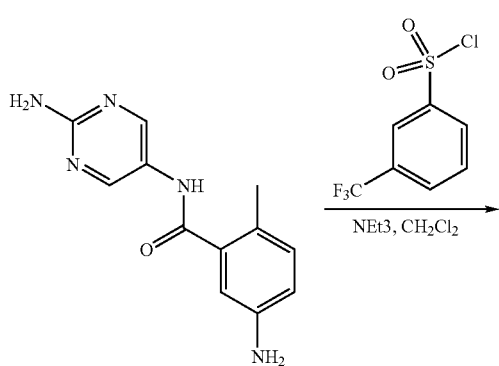

Synthesis of N-(2-aminopyrimidin-5-yl)-2-methyl-5-(3-(trifluoromethyl)phenylsulfonamido)benzamide To a solution of 5-amino-N-(2-aminopyrimidin-5-yl)-2-methylbenzamide 28 (85 mg, 0.349 mmol) in CHCl$_3$ (2 mL) was added triethylamine (0.453 mmol) and 3-(trifluoromethyl)benzene-1-sulfonyl chloride (0.064 mL, 0.401 mmol). The reaction mixture was heated to reflux for 12 h, cooled to rt and concentrated in vacuo. The crude residue was adsorbed on SiO$_2$ and purified by flash chromatography (CH$_2$Cl$_2$/MeOH 99:1) on SiO$_2$ to afford N-(2-aminopyrimidin-5-yl)-2-methyl-5-(3-(trifluoromethyl)phenylsulfonamido)benzamide 29. MS m/z found 452 [MH+]; calc. for C$_{19}$H$_{16}$F$_3$N$_5$O$_3$S=451.09.

The following compounds, Examples 93-95 were made using a procedure similar to that described in Example 92.

| Ex. No. | Structure | Name | MS | Method |
|---|---|---|---|---|
| 93 | 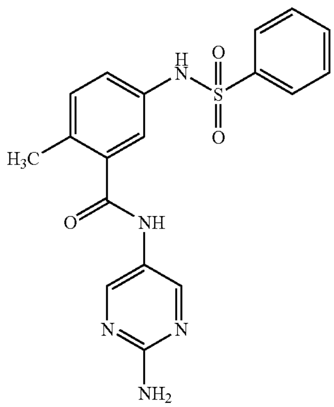 [SMILES: Cc1ccc(NS(=O)(=O)c2ccccc2)cc1C(=O)Nc1cnc(N)nc1] | N-(2-amino-5-pyrimidinyl)-2-methyl-5-((phenylsulfonyl)amino)benzamide | 384.0 | C |
| 94 | 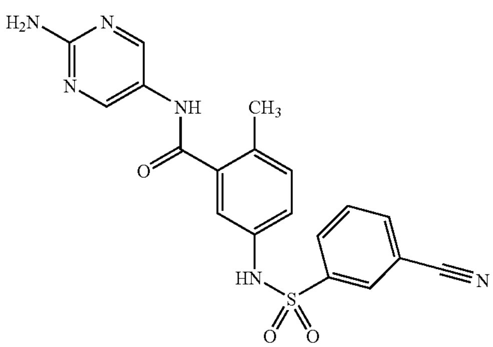 [SMILES: Cc1ccc(NS(=O)(=O)c2cccc(C#N)c2)cc1C(=O)Nc1cnc(N)nc1] | N-(2-aminopyrimidin-5-yl)-5-(3-cyanophenylsulfon-amido)-2-methylbenzamide | 408.8 | C |
| 95 | 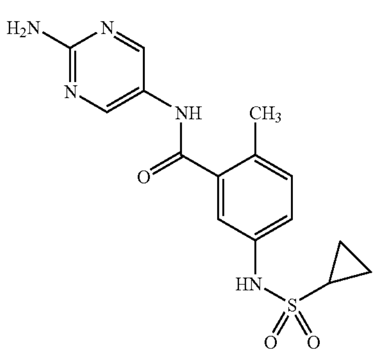 [SMILES: Cc1ccc(NS(=O)(=O)C2CC2)cc1C(=O)Nc1cnc(N)nc1] | N-(2-aminopyrimidin-5-yl)-5-(cyclopropanesulfon-amido)-2-methylbenzamide | 347.5 | C |

EXAMPLE 96

Method D

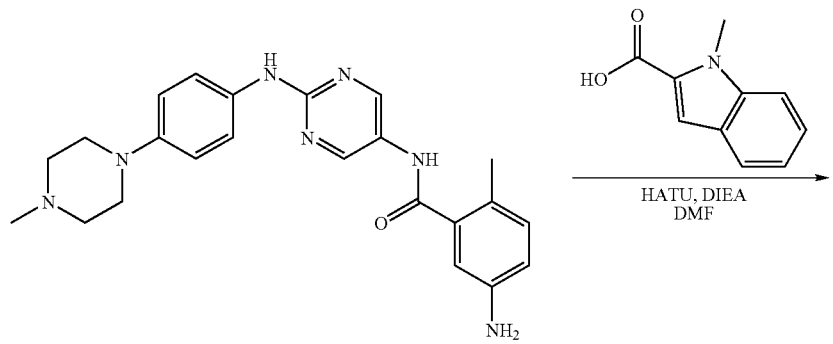

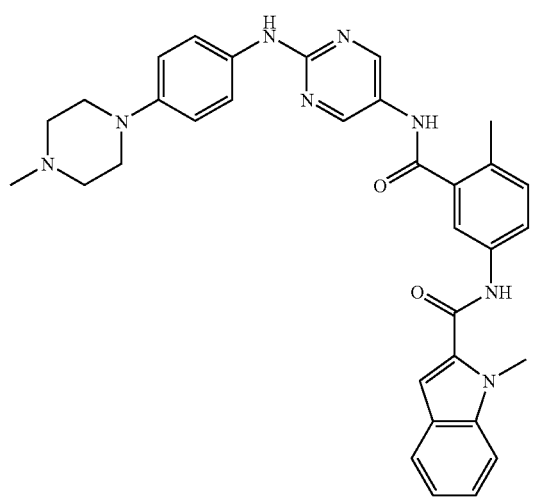

Synthesis of 1-methyl-N-(4-methyl-3-((2-(4-(4-methylpiperazin-1-yl)phenylamino)pyrimidin-5-yl)carbamoyl)phenyl)-1H-indole-2-carboxamide In a 16×120 mm resealable pyrex tube, 1-methyl-1H-indole-2-carboxylic acid (0.11 g, 0.62 mmol), HATU (0.24 g, 0.62 mmol), and N-ethyl-N-isopropylpropan-2-amine (0.17 ml, 0.96 mmol) were taken up in DMF (5 mL) and allowed to stir at rt for 30 min. 5-amino-2-methyl-N-(2-(4-(4-methylpiperazin-1-yl)phenylamino)pyrimidin-5-yl)benzamide 30 (0.200 g, 0.48 mmol) was added and the mixture was stirred at rt overnight. The crude reaction mixture was taken up in minimal MeOH/DMSO and purified by preparative HPLC (acidic Shimadzu: 15-85% (0.1% TFA in CH$_3$CN) in H2O over 20 min). Clean fractions were combined and neutralized with saturated NaHCO$_3$ then extracted with CH$_2$Cl$_2$, dried over Na$_2$SO$_4$, filtered and concentrated to afford 1-methyl-N-(4-methyl-3-((2-(4-(4-methylpiperazin-1-yl)phenylamino)pyrimidin-5-yl)carbamoyl)phenyl)-1H-indole-2-carboxamide 31 as a tan solid. MS m/z found 575.2 [MH+]; calc. for C$_{33}$H$_{34}$N$_8$O$_2$=574.28.

Alternatively, compound 31 may be made using the following various conditions:

a) desired A-ring acid (RCO$_2$H), EDC.HCl, HOBt.H$_2$O, DIEA, DMF;

b) desired A-ring acid (RCO$_2$H), HATU, HOAt, DIEA, DMF; or c) desired A-ring acid (RCO$_2$H), EDC, HOAt, DIEA, DMF The following compounds, Examples 97-113 were made using a procedure similar to that described in Examples 96.

| Ex. No. | Structure | Name | MS | Method |
|---|---|---|---|---|
| 97 | 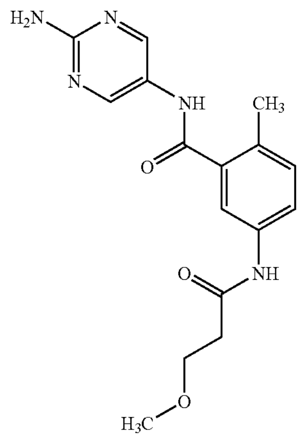 [SMILES: COCCC(=O)Nc1ccc(C)c(C(=O)Nc2cnc(N)nc2)c1] | N-(2-amino-5-pyrimidinyl)-2-methyl-5-((3-(methyloxy)propanoyl)amino)benzamide | 329.9 | D |
| 98 | 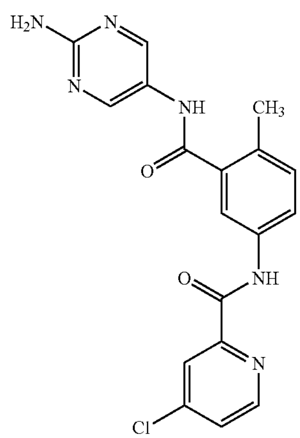 [SMILES: Cc1ccc(NC(=O)c2cc(Cl)ccn2)cc1C(=O)Nc1cnc(N)nc1] | N-(3-(((2-amino-5-pyrimidinyl)amino)carbonyl)-4-methylphenyl)-4-chloro-2-pyridinecarboxamide | 383.0 | D |
| 99 | 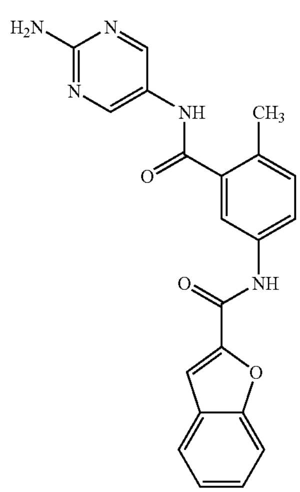 [SMILES: Cc1ccc(NC(=O)c2cc3ccccc3o2)cc1C(=O)Nc1cnc(N)nc1] | N-(3-(((2-amino-5-pyrimidinyl)amino)carbonyl)-4-methylphenyl)-1-benzofuran-2-carboxamide | 387.8 | D |

| Ex. No. | Structure | Name | MS | Method |
|---|---|---|---|---|
| 100 | 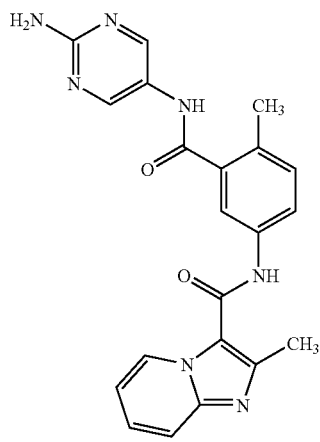 [SMILES: Cc1ccc(NC(=O)c2c(C)nc3ccccn23)cc1C(=O)Nc1cnc(N)nc1] | N-(3-(((2-amino-5-pyrimidinyl)amino)carbonyl)-4-methylphenyl)-2-methylimidazo[1,2-a]pyridine-3-carboxamide | 402 | D |
| 101 | 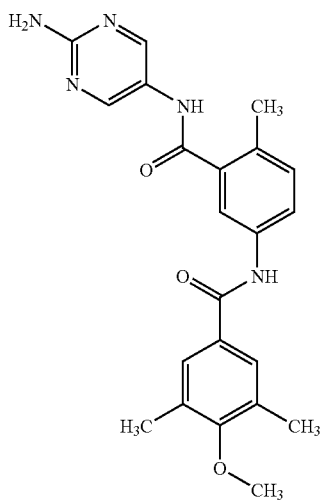 [SMILES: COc1c(C)cc(C(=O)Nc2ccc(C)c(C(=O)Nc3cnc(N)nc3)c2)cc1C] | N-(3-(((2-amino-5-pyrimidinyl)amino)carbonyl)-4-methylphenyl)-3,5-dimethyl-4-(methyloxy)benzamide | 406 | D |
| 102 | 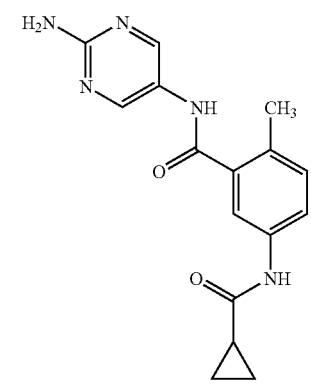 [SMILES: Cc1ccc(NC(=O)C2CC2)cc1C(=O)Nc1cnc(N)nc1] | N-(2-amino-5-pyrimidinyl)-5-((cyclopropylcarbonyl)amino)-2-methylbenzamide | 311.9 | D |

| Ex. No. | Structure | Name | MS | Method |
|---|---|---|---|---|
| 103 | 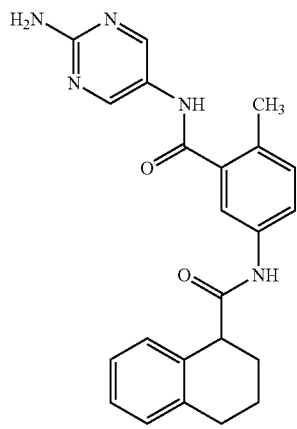 [SMILES: Cc1ccc(NC(=O)C2CCCc3ccccc32)cc1C(=O)Nc1cnc(N)nc1] | N-(3-(((2-amino-5-pyrimidinyl)amino)carbonyl)-4-methylphenyl)-1,2,3,4-tetrahydro-1-naphthalenecarboxamide | 401.9 | D |
| 104 | 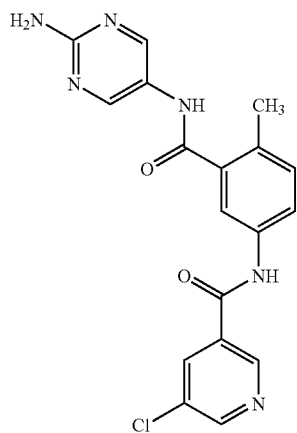 [SMILES: Cc1ccc(NC(=O)c2cncc(Cl)c2)cc1C(=O)Nc1cnc(N)nc1] | N-(3-(((2-amino-5-pyrimidinyl)amino)carbonyl)-4-methylphenyl)-5-chloro-3-pyridinecarboxamide | 382.8 | D |
| 105 | 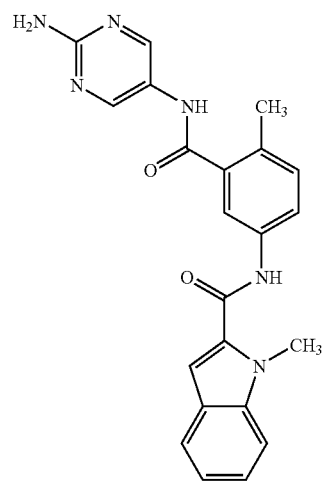 [SMILES: Cc1ccc(NC(=O)c2cc3ccccc3n2C)cc1C(=O)Nc1cnc(N)nc1] | N-(3-(((2-amino-5-pyrimidinyl)amino)carbonyl)-4-methylphenyl)-1-methyl-1H-indole-2-carboxmaide | 400.8 | D |

| Ex. No. | Structure | Name | MS | Method |
|---|---|---|---|---|
| 106 | 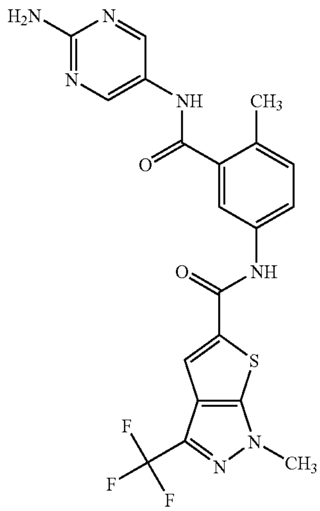 [SMILES: Cc1ccc(NC(=O)c2cc3c(C(F)(F)F)nn(C)c3s2)cc1C(=O)Nc1cnc(N)nc1] | N-(3-(((2-amino-5-pyrimidinyl)amino)carbonyl)-4-methylphenyl)-1-methyl-3-(trifluoromethyl)-1H-thieno[2,3-c]pyrazole-5-carboxamide | 476 | D |
| 107 | 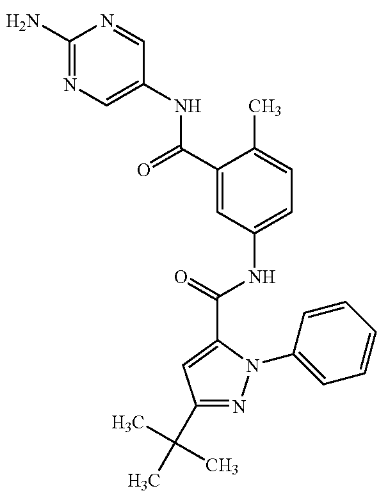 [SMILES: Cc1ccc(NC(=O)c2cc(C(C)(C)C)nn2-c2ccccc2)cc1C(=O)Nc1cnc(N)nc1] | N-(3-(((2-amino-5-pyrimidinyl)amino)carbonyl)-4-methylphenyl)-3-(1,1-dimethylethyl)-1-phenyl-1H-pyrazole-5-carboxamide | 469.9 | D |
| 108 | 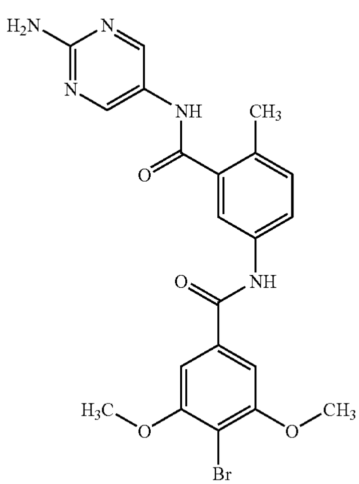 [SMILES: COc1cc(C(=O)Nc2ccc(C)c(C(=O)Nc3cnc(N)nc3)c2)cc(OC)c1Br] | N-(3-(((2-amino-5-pyrimidinyl)amino)carbonyl)-4-methylphenyl)-4-bromo-3,5-bis(methyloxy)benzamide | 487.7 | D |

| Ex. No. | Structure | Name | MS | Method |
|---|---|---|---|---|
| 109 | 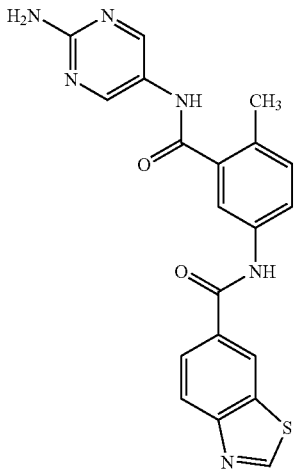 [SMILES: Cc1ccc(NC(=O)c2ccc3ncsc3c2)cc1C(=O)Nc1cnc(N)nc1] | N-(3-((2-aminopyrimidin-5-yl)carbamoyl)-4-methylphenyl)benzo[d]thiazole-6-carboxamide | 404.8 | D |
| 110 | 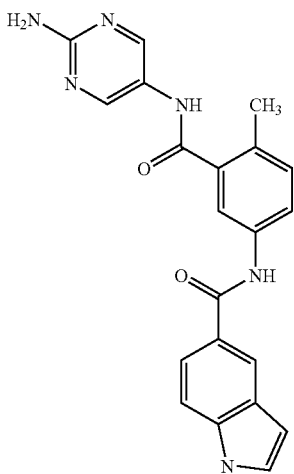 | N-(3-((2-aminopyrimidin-5-yl)carbamoyl)-4-methylphenyl)-1H-indole-5-carboxamide | 387.2 | D |
| 111 | 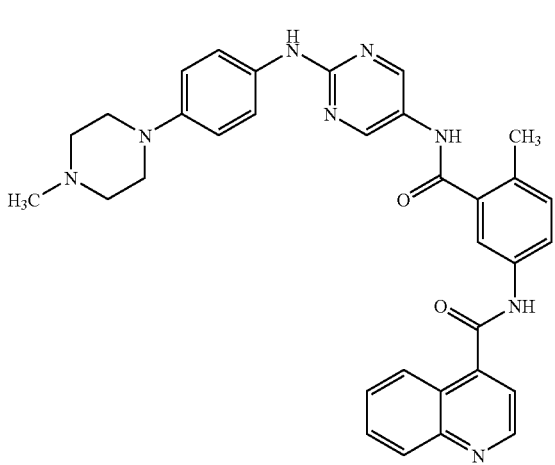 [SMILES: Cc1ccc(NC(=O)c2ccnc3ccccc23)cc1C(=O)Nc1cnc(Nc2ccc(N3CCN(C)CC3)cc2)nc1] | N-(4-methyl-3-((2-(4-(4-methylpiperazin-1-yl)phenylamino)pyrimidin-5-yl)carbamoyl)phenyl)quinoline-4-carboxamide | 573 | D |

| Ex. No. | Structure | Name | MS | Method |
|---|---|---|---|---|
| 112 | 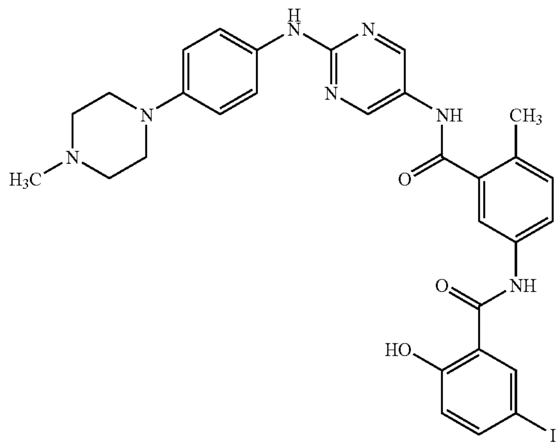 [SMILES: Cc1ccc(NC(=O)c2cc(I)ccc2O)cc1C(=O)Nc1cnc(Nc2ccc(N3CCN(C)CC3)cc2)nc1] | 2-hydroxy-5-iodo-N-(4-methyl-3-(((2-((4-(4-methyl-1-piperazinyl)phenyl)amino)-5-pyrimidinyl)amino)carbonyl)phenyl)benzamide | 664 | D |
| 113 | 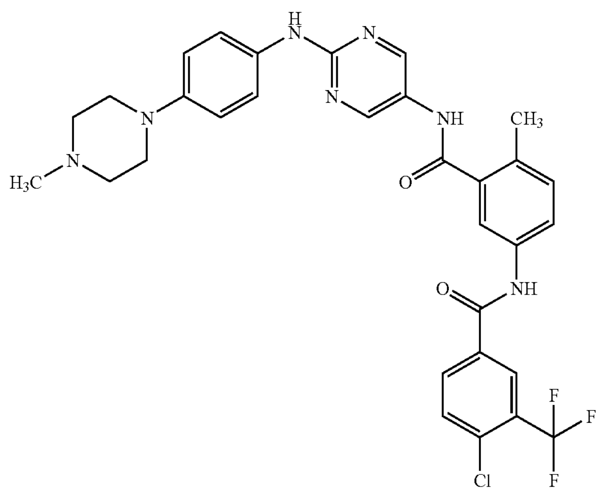 [SMILES: Cc1ccc(NC(=O)c2ccc(Cl)c(C(F)(F)F)c2)cc1C(=O)Nc1cnc(Nc2ccc(N3CCN(C)CC3)cc2)nc1] | 4-chloro-N-(4-methyl-3-(((2-((4-(4-methyl-1-piperazinyl)phenyl)amino)-5-pyrimidinyl)amino)carbonyl)phenyl)-3-(trifluoromethyl)benzamide | 625 | D |
EXAMPLE 114
Method E
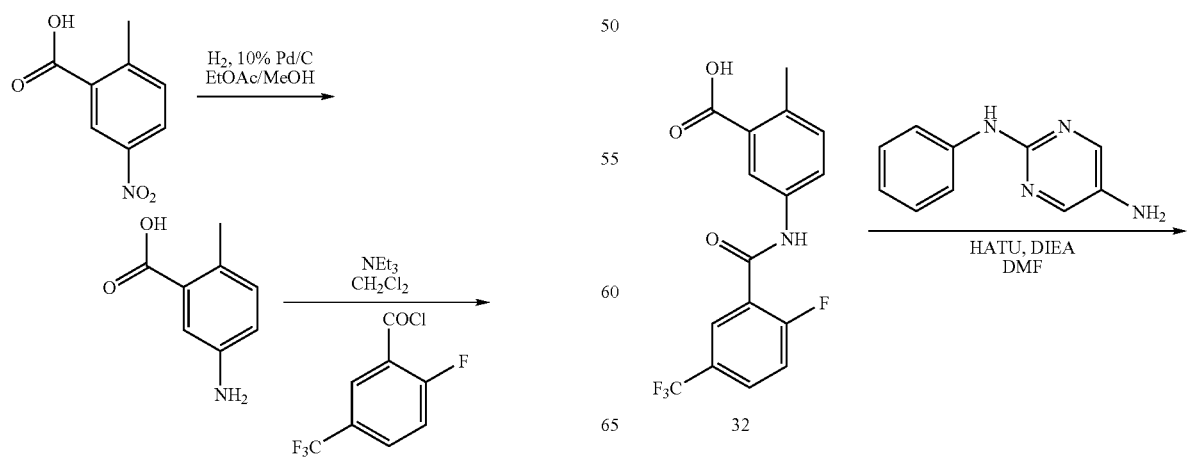

-continued

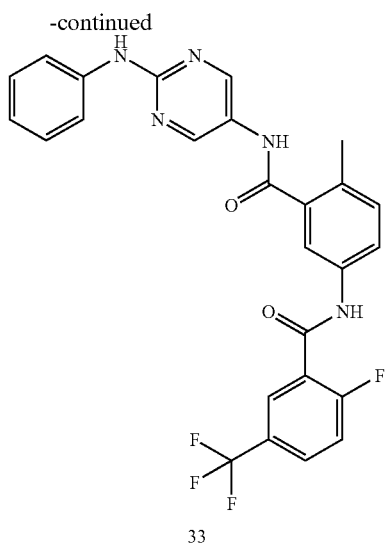

33

Synthesis of 2-fluoro-N-(4-methyl-3-(((2-(phenylamino)-5-pyrimidinyl)amino)carbonyl)phenyl)-5-(trifluoromethyl)benzamide 33

Step 1. Preparation of 5-(2-fluoro-5-(trifluoromethyl)benzamido)-2-methylbenzoic acid To a 250 mL round-bottomed flask was added 2-methyl-5-nitrobenzoic acid (5.0 g, 28 mmol) and palladium 10% on carbon (1.5 g, 14 mmol). The mixture was taken up in EtOAc (30 mL) then EtOH (70 mL) was added. The mixture was purged with H₂ then allowed to stir at 1 atm. H₂ for 24 h. LCMS indicated about 10% conversion to product. About 0.5 g 10% Pd/C and ~30 mL MeOH was added to the reaction. The reaction was purged with H₂ and let to stir at 1 atm H₂ for 20 h. They reaction was monitored for complete conversion by LCMS. The mixture was passed through a pad of celite, washing with MeOH and concentrated to afford 5-amino-2-methylbenzoic acid as an off-white solid MS m/z found 152.1 (ESI, neg. ion).

Step 2

To a 100 mL round-bottomed flask containing 2-fluoro-5-(trifluoromethyl)benzoyl chloride (0.44 ml, 2.9 mmol) in CH₂Cl₂ (30 mL) was added triethylamine (0.48 ml, 3.4 mmol). After 10 min, 5-amino-2-methylbenzoic acid (0.400 g, 2.6 mmol) was added. The solution was stirred at rt overnight. After cooling, the crude reaction mixture was concentrated to remove excess NEt₃ then diluted with CH₂Cl₂ and washed with 1 N HCl once, and brine & salt once then dried over Na₂SO₄ to afford 5-(2-fluoro-5-(trifluoromethyl)benzamido)-2-methylbenzoic acid 32 as an off-white solid. MS m/z found: 342.1 (ESI, pos. ion).

Step 3

5-(2-fluoro-5-(trifluoromethyl)benzamido)-2-methylbenzoic acid 32 (0.25 g, 0.73 mmol), HATU (0.28 g, 0.73 mmol), and N-ethyl-N-isopropylpropan-2-amine (0.20 mL, 1.1 mmol) were taken up in DMF (6 mL). The solution was stirred at rt for 30 min then N2-phenylpyrimidine-2,5-diamine (0.105 g, 0.56 mmol) was added and the mixture was allowed to stir at rt overnight. The crude reaction mixture was taken up in minimal MeOH/DMSO and purified by preparative HPLC (acidic Gilson: 10-90% (0.1% TFA in CH₃CN) in H2O over 15 min). Clean fractions were combined and allowed to stand for 2 h. Some product.TFA salt crashed out and was collected and neutralized with saturated NaHCO₃ then extracted with CH₂Cl₂, dried over Na₂SO₄, filtered and concentrated to afford 2-fluoro-N-(4-methyl-3-(((2-(phenylamino)-5-pyrimidinyl)amino)carbonyl)phenyl)-5-(trifluoromethyl)benzamide 33 as a white solid. MS m/z found 510.1 [MH+]; calc. for $C_{26}H_{19}F_4N_5O_2$=509.15.

The following compounds, Examples 115-126 were made using a procedure similar to that described in Examples 114.

| Ex. No. | Structure | Name | MS | Method |
|---|---|---|---|---|
| 115 | 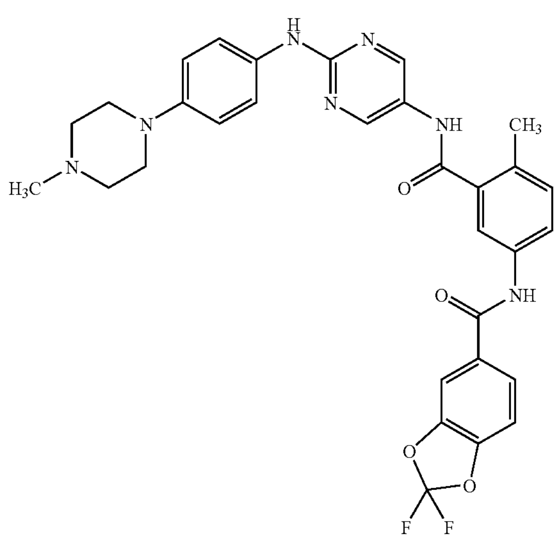 [SMILES: Cc1ccc(NC(=O)c2ccc3c(c2)OC(F)(F)O3)cc1C(=O)Nc1cnc(Nc2ccc(N3CCN(C)CC3)cc2)nc1] | N-(4-chloro-3-((2-(4-(4-methylpiperazin-1-yl)phenylamino)pyrimidin-5-yl)carbamoyl)phenyl)-2,2-difluorobenzo[d][1,3]dioxole-5-carboxamide | 622 | E |

| Ex. No. | Structure | Name | MS | Method |
|---|---|---|---|---|
| 116 | 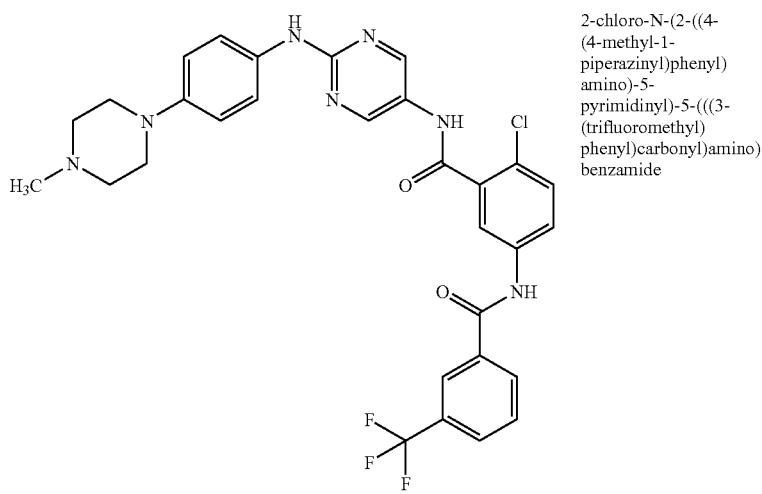 | 2-chloro-N-(2-((4-(4-methyl-1-piperazinyl)phenyl)amino)-5-pyrimidinyl)-5-(((3-(trifluoromethyl)phenyl)carbonyl)amino)benzamide | 610.2 | E |
| 117 | 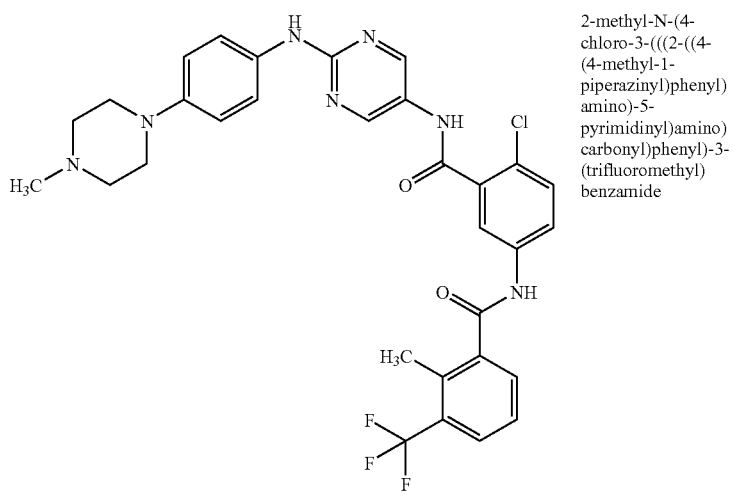 | 2-methyl-N-(4-chloro-3-(((2-((4-(4-methyl-1-piperazinyl)phenyl)amino)-5-pyrimidinyl)amino)carbonyl)phenyl)-3-(trifluoromethyl)benzamide | 624.1 | E |
| 118 | 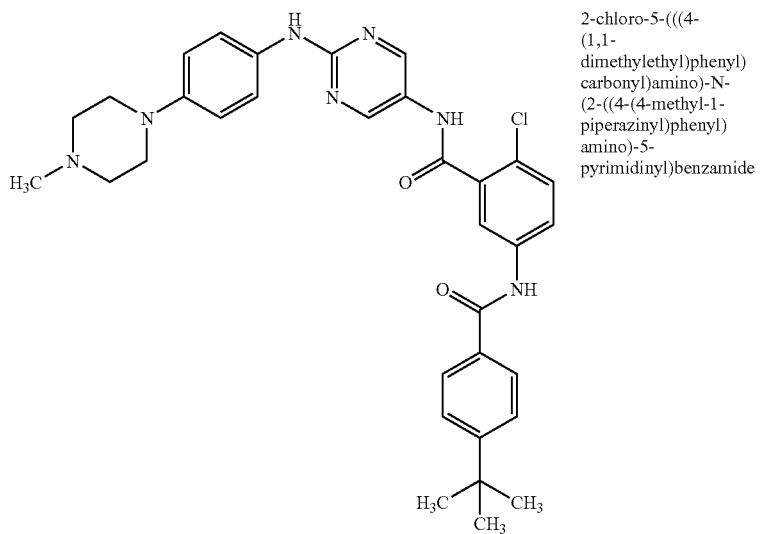 | 2-chloro-5-(((4-(1,1-dimethylethyl)phenyl)carbonyl)amino)-N-(2-((4-(4-methyl-1-piperazinyl)phenyl)amino)-5-pyrimidinyl)benzamide | 598.3 | E |

| Ex. No. | Structure | Name | MS | Method |
|---|---|---|---|---|
| 119 | 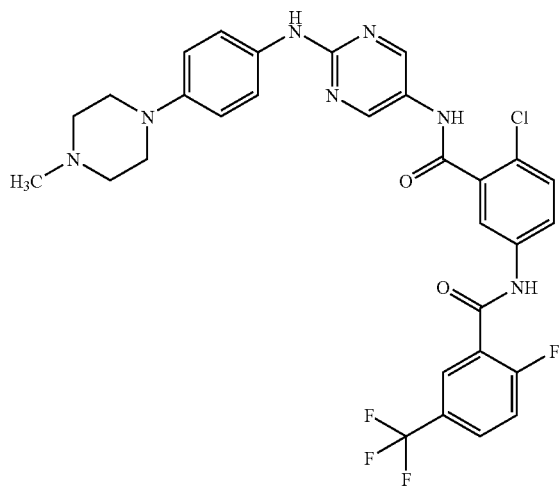 | 2-fluoro-N-(4-chloro-3-(((2-((4-(4-methyl-1-piperazinyl)phenyl)amino)-5-pyrimidinyl)amino)carbonyl)phenyl)-5-(trifluoromethyl)benzamide | 628.2 | E |
| 120 | 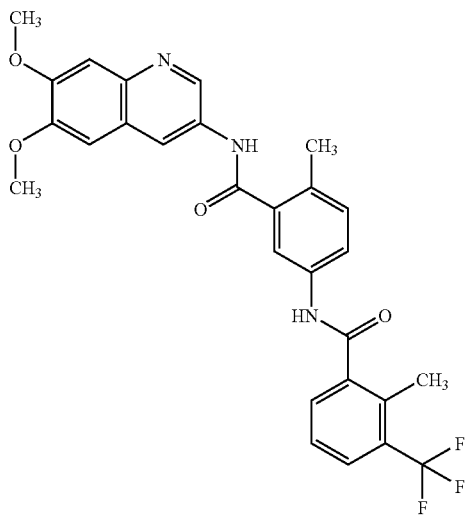 [SMILES: COc1cc2cc(NC(=O)c3cc(NC(=O)c4cccc(C(F)(F)F)c4C)ccc3C)cnc2cc1OC] | N-(3-((6,7-dimethoxyquinolin-3-yl)carbamoyl)-4-methylphenyl)-2-methyl-3-(trifluoromethyl)benzamide | 524 | E |
| 121 | 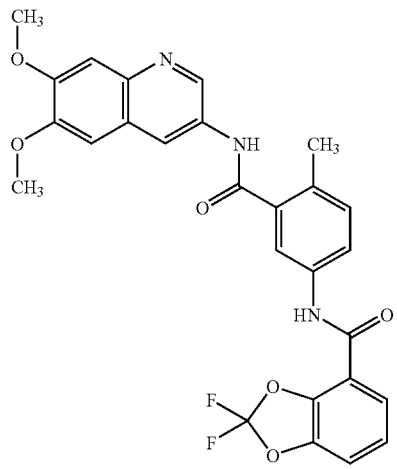 [SMILES: COc1cc2cc(NC(=O)c3cc(NC(=O)c4cccc5c4OC(F)(F)O5)ccc3C)cnc2cc1OC] | N-(3-((6,7-dimethoxyquinolin-3-yl)carbamoyl)-4-methylphenyl)-2,2-difluorobenzo[d][1,3]dioxole-4-carboxamide | 522.1 | E |

-continued

| Ex. No. | Structure | Name | MS | Method |
|---|---|---|---|---|
| 122 | 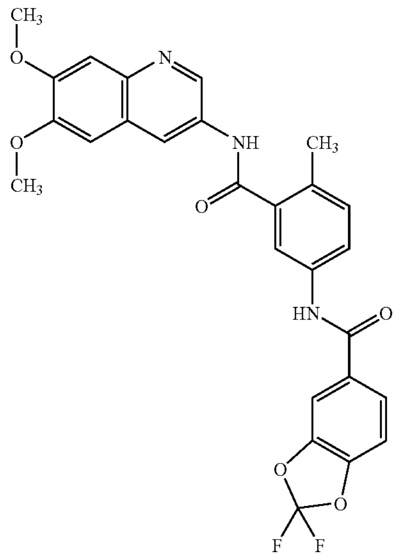 [SMILES: COc1cc2cc(NC(=O)c3cc(NC(=O)c4ccc5c(c4)OC(F)(F)O5)ccc3C)cnc2cc1OC] | N-(3-((6,7-dimethoxyquinolin-3-yl)carbamoyl)-4-methylphenyl)-2,2-difluorobenzo[d][1,3]dioxole-5-carboxamide | 522.1 | E |
| 123 | 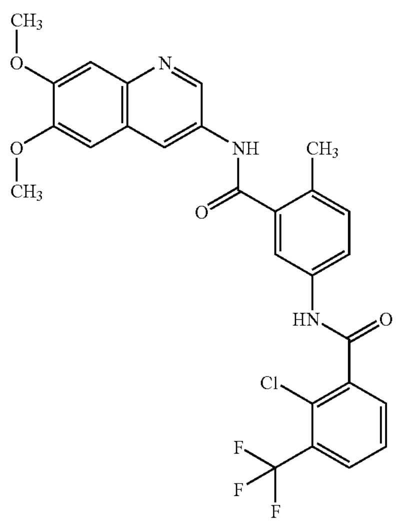 [SMILES: COc1cc2cc(NC(=O)c3cc(NC(=O)c4cccc(C(F)(F)F)c4Cl)ccc3C)cnc2cc1OC] | 2-chloro-N-(3-((6,7-dimethoxyquinolin-3-yl)carbamoyl)-4-methylphenyl)-3-(trifluoromethyl)benzamide | 544 | E |
| 124 | 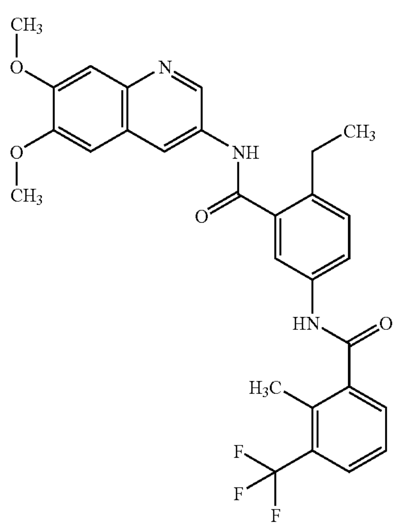 [SMILES: CCc1ccc(NC(=O)c2cccc(C(F)(F)F)c2C)cc1C(=O)Nc1cnc2cc(OC)c(OC)cc2c1] | N-(3-((6,7-dimethoxyquinolin-3-yl)carbamoyl)-4-ethylphenyl)-2-methyl-3-(trifluoromethyl)benzamide | 538.2 | E |

| Ex. No. | Structure | Name | MS | Method |
|---|---|---|---|---|
| 125 | 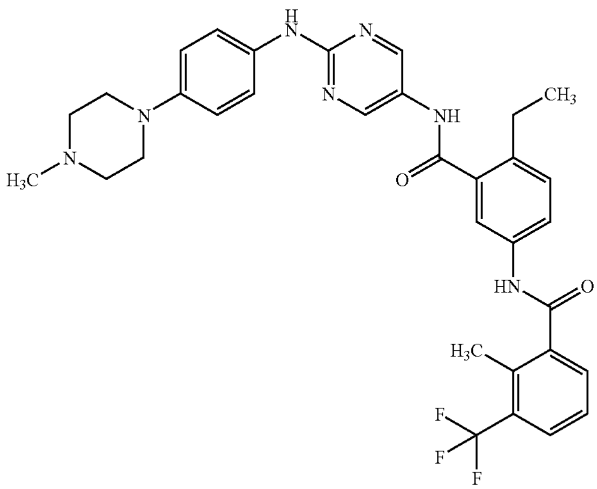 [SMILES: CCc1ccc(NC(=O)c2cccc(C(F)(F)F)c2C)cc1C(=O)Nc1cnc(Nc2ccc(N3CCN(C)CC3)cc2)nc1] | 2-methyl-N-(4-ethyl-3-(((2-((4-(4-methyl-1-piperazinyl)phenyl)amino)-5-pyrimidinyl)amino)carbonyl)phenyl)-3-(trifluoromethyl)benzamide | 618.2 | E |
| 126 | 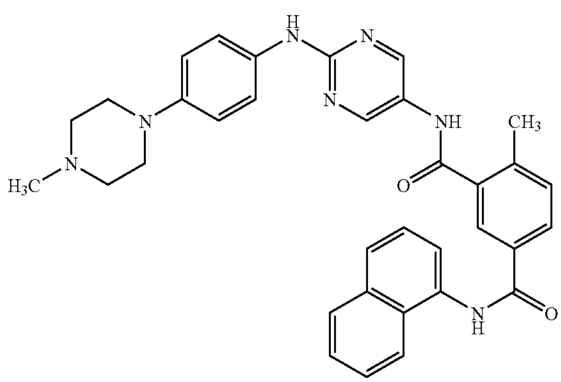 [SMILES: Cc1ccc(C(=O)Nc2cccc3ccccc23)cc1C(=O)Nc1cnc(Nc2ccc(N3CCN(C)CC3)cc2)nc1] | 4-methyl-N3-(2-(4-(4-methylpiperazin-1-yl)phenylamino)pyrimidin-5-yl)-N1-(naphthalen-1-yl)isophthalamide | 572 | E |
EXAMPLE 127
Method F
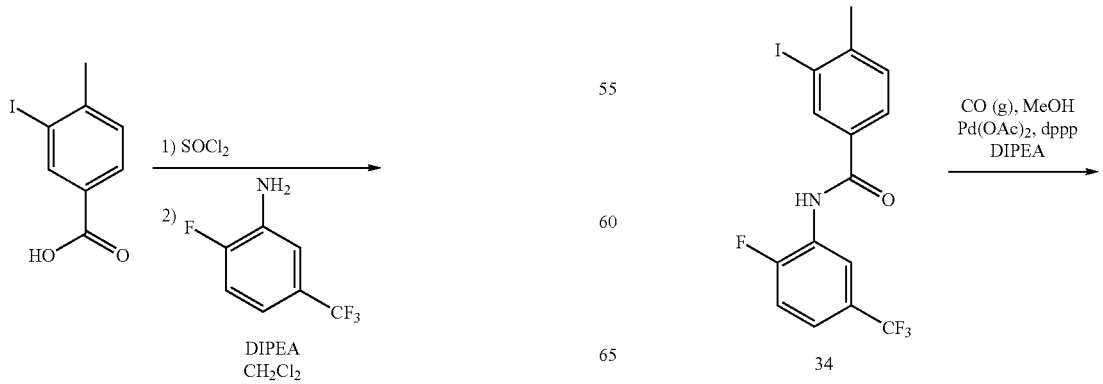

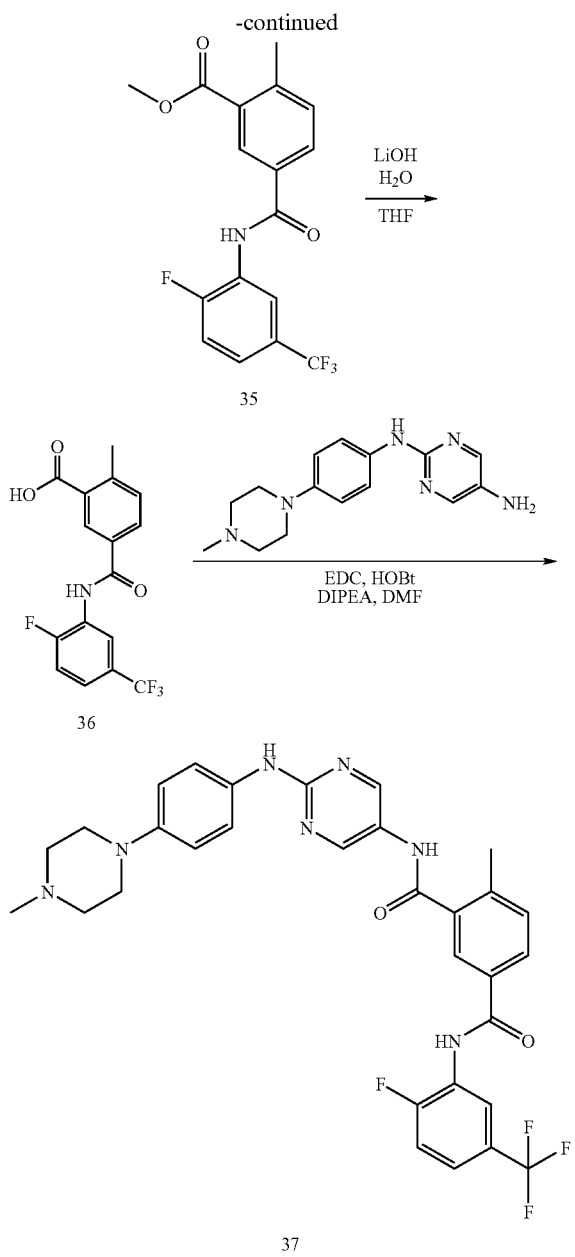

Synthesis of N1-(2-fluoro-5-(trifluoromethyl)phenyl)-4-methyl-N3-(2-(4-(4-methylpiperazin-1-yl)phenylamino)pyrimidin-5-yl)isophthalamide Step 1. N-(2-Fluoro-5-(trifluoromethyl)phenyl)-3-iodo-4-methylbenzamide A solution of 3-iodo-4-methylbenzoic acid (10.0 g, 38.2 mmol) in thionyl chloride (30.0 mL) was heated at reflux for 3 hours. The resulting yellow solution was cooled to room temperature and concentrated under reduced pressure to afford 3-iodo-4-methylbenzoyl chloride. A solution of 3-iodo-4-methylbenzoyl chloride (1 g, 4 mmol) in dichloromethane (10 mL) was added slowly to a 0° C. solution of 3-amino-4-fluorobenzotrifluoride (0.7 ml, 4 mmol) and diisopropylethylamine (0.9 ml, 5 mmol) in dichloromethane (10 mL). The reaction stirred at 0° C. and warmed to room temperature over 20 hours. The reaction mixture was purified via column chromatography on silica gel (gradient elution with 0 to 100% ethyl acetate-hexane) to afford N-(2-fluoro-5-(trifluoromethyl)phenyl)-3-iodo-4-methylbenzamide 34 MS m/z found 423.9 [MH+]; calc. for $C_{15}H_{10}F_4INO$=423.14.

Step 2. Methyl 5-((2-fluoro-5-(trifluoromethyl)phenyl)carbamoyl)-2-methylbenzoate A stainless steel cylinder equipped with a glass liner was charged with N-(2-fluoro-5-(trifluoromethyl)phenyl)-3-iodo-4-methylbenzamide 34 (1.089 g, 2.57 mmol), methanol (20 mL), and a magnetic stir bar. Argon gas was bubbled through this solution for one minute, and then triethylamine (0.358 ml, 2.57 mmol), 1,3-bis(diphenylphosphino)propane (0.0584 g, 0.142 mmol), and palladium(II) acetate (0.0289 g, 0.129 mmol) were added. The cylinder was sealed, charged to 200 psi of CO gas, placed into an oil bath at 75° C. and stirred for 2 hours. The reaction was cooled to room temperature, and palladium(II) acetate (0.0289 g, 0.129 mmol), DMF (2 mL), 1,3-bis(diphenylphosphino)propane (0.0584 g, 0.142 mmol), and triethylamine (0.358 ml, 2.57 mmol) were added. The cylinder was sealed, charged to 200 psi of CO gas, placed into an oil bath at 75° C. and stirred 48 hours. The reaction mixture was cooled to room temperature and concentrated. The residue was purified via column chromatography on silica gel (gradient elution 0 to 100% ethylacetate in hexane) to afford methyl 5-((2-fluoro-5-(trifluoromethyl)phenyl)carbamoyl)-2-methylbenzoate 35 as pale yellow solid. MS m/z found 356 [MH+]; calc. for $C_{17}H_{13}F_4NO_3$=355.28.

Step 3. 5-((2-fluoro-5-(trifluoromethyl)phenyl)carbamoyl)-2-methylbenzoic acid

A solution of methyl 5-((2-fluoro-5-(trifluoromethyl)phenyl)carbamoyl)-2-methylbenzoate 35 (0.904 g, 2.5 mmol), THF (20 mL), lithium hydroxide (0.18 g, 7.6 mmol), and water (5 mL) was heated at 55° C. for 24 hours and then cooled to room temperature. The aqueous layer was separated, cooled in an ice-water bath, and acidified with 6 M HCl (aq) to pH 1. This solution was extracted with ethyl acetate (3×10 mL), and the combined organic phases were dried over anhydrous sodium sulfate, filtered, and concentrated to afford 5-((2-fluoro-5-(trifluoromethyl)phenyl)carbamoyl)-2-methylbenzoic acid 36. MS m/z found 342 [MH+]; calc. for $C_{16}H_{11}F_4NO_3$=341.26.

Step 4. N1-(2-fluoro-5-(trifluoromethyl)phenyl)-4-methyl-N3-(2-(4-(4-methylpiperazin-1-yl)phenylamino)pyrimidin-5-yl)isophthalamide A 16×100 mm vial was charged with 5-((2-fluoro-5-(trifluoromethyl)phenyl)carbamoyl)-2-methylbenzoic acid 36 (0.100 g, 0.293 mmol), dichloromethane (3 mL), diisopropylethylamine (0.200 ml, 1.15 mmol), 1-hydroxybenzotriazole (0.0396 g, 0.293 mmol), EDC.HCl (0.0562 g, 0.293 mmol), and N2-(4-(4-methylpiperazin-1-yl)phenyl)pyrimidine-2,5-diamine (0.0875 g, 0.308 mmol), and the mixture stirred at room temperature for 24 hours. The reaction mixture was purified via column chromatography on silica gel (gradient elution with 0 to 20% methanol in dichloromethane) to afford N1-(2-fluoro-5-(trifluoromethyl)phenyl)-4-methyl-N3-(2-(4-(4-methylpiperazin-1-yl)phenylamino)pyrimidin-5-yl) isophthalamide 37 as a light yellow solid. MS m/z found 608 [MH+]; calc. for $C_{31}H_{29}F_4N_7O_2$=607.60.

The following compounds, Examples 128-134 were made using a procedure similar to that described in Examples 127.

| Ex. No. | Structure | Name | MS | Method |
|---|---|---|---|---|
| 128 | 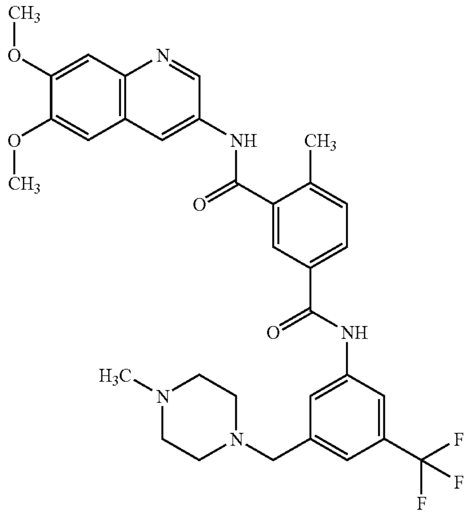 [SMILES: COc1cc2cc(NC(=O)c3cc(C(=O)Nc4cc(CN5CCN(C)CC5)cc(C(F)(F)F)c4)ccc3C)cnc2cc1OC] | N3-(6,7-dimethoxyquinolin-3-yl)-4-methyl-N1-(3-((4-methylpiperazin-1-yl)methyl)-5-(trifluoromethyl)phenyl)isophthalamide | 622.2 | F |
| 129 | 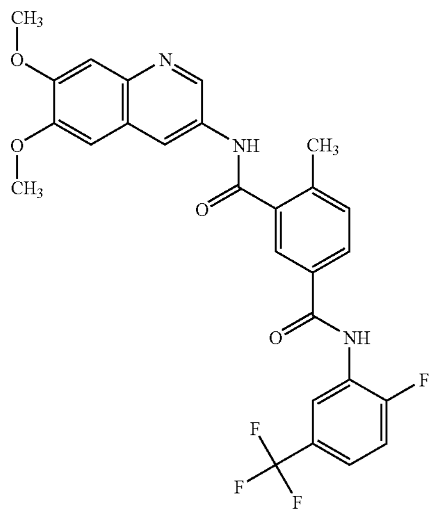 [SMILES: COc1cc2cc(NC(=O)c3cc(C(=O)Nc4cc(C(F)(F)F)ccc4F)ccc3C)cnc2cc1OC] | N3-(6,7-dimethoxyquinolin-3-yl)-N1-(2-fluoro-5-(trifluoromethyl)phenyl)-4-methylisophthalamide | 528.1 | F |
| 130 | 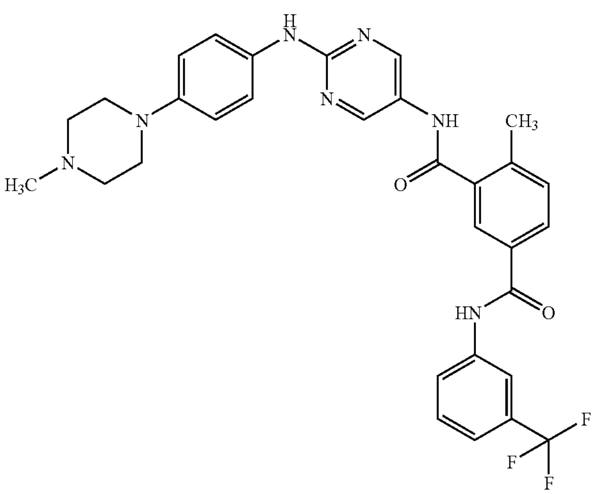 [SMILES: Cc1ccc(C(=O)Nc2cccc(C(F)(F)F)c2)cc1C(=O)Nc1cnc(Nc2ccc(N3CCN(C)CC3)cc2)nc1] | 4-methyl-N3-(2-(4-(4-methylpiperazin-1-yl)phenylamino)pyrimidin-5-yl)-N1-(3-(trifluoromethyl)phenyl)isophthalamide | 590.2 | F |

| Ex. No. | Structure | Name | MS | Method |
|---|---|---|---|---|
| 131 | 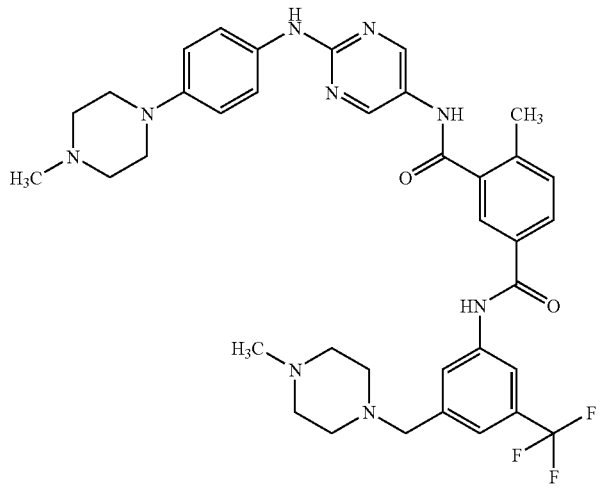 [SMILES: Cc1ccc(C(=O)Nc2cc(CN3CCN(C)CC3)cc(C(F)(F)F)c2)cc1C(=O)Nc1cnc(Nc2ccc(N3CCN(C)CC3)cc2)nc1] | 4-methyl-N1-(3-((4-methylpiperazin-1-yl)methyl)-5-(trifluoromethyl)phenyl)-N3-(2-(4-(4-methylpiperazin-1-yl)phenylamino)pyrimidin-5-yl)isophthalamide | 351.7 | F |
| 132 | 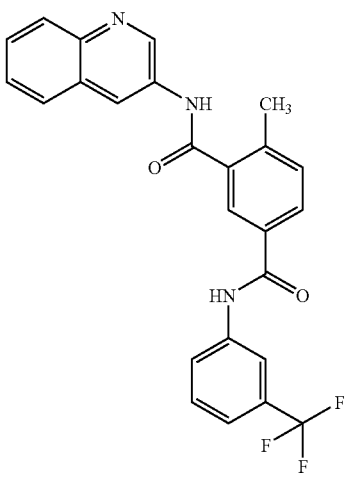 [SMILES: Cc1ccc(C(=O)Nc2cccc(C(F)(F)F)c2)cc1C(=O)Nc1cnc2ccccc2c1] | 4-methyl-N3-(quinolin-3-yl)-N1-(3-(trifluoromethyl)phenyl)isophthalamide | 450.1 | F |
| 133 | 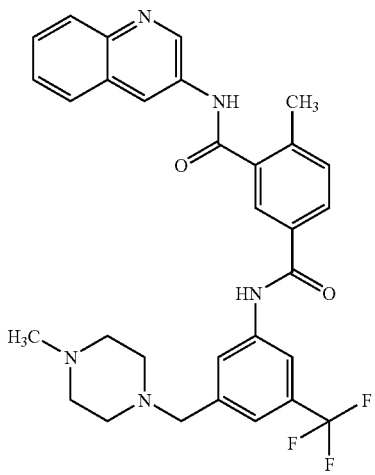 [SMILES: Cc1ccc(C(=O)Nc2cc(CN3CCN(C)CC3)cc(C(F)(F)F)c2)cc1C(=O)Nc1cnc2ccccc2c1] | 4-methyl-N1-(3-((4-methylpiperazin-1-yl)methyl)-5-(trifluoromethyl)phenyl)-N3-(quinolin-3-yl)isophthalamide | 562 | F |

| Ex. No. | Structure | Name | MS | Method |
|---|---|---|---|---|
| 134 | 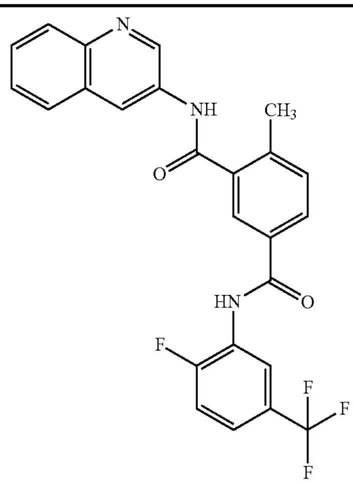 | N1-(2-fluoro-5-(trifluoromethyl)phenyl)-4-methyl-N3-(quinolin-3-yl)isophthalamide | 468 | F |

EXAMPLE 135

Method G

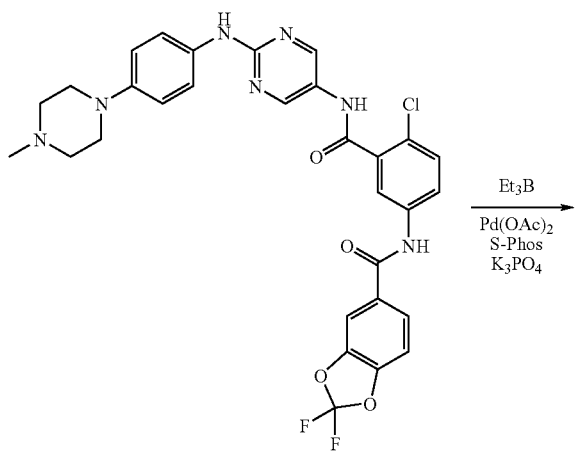

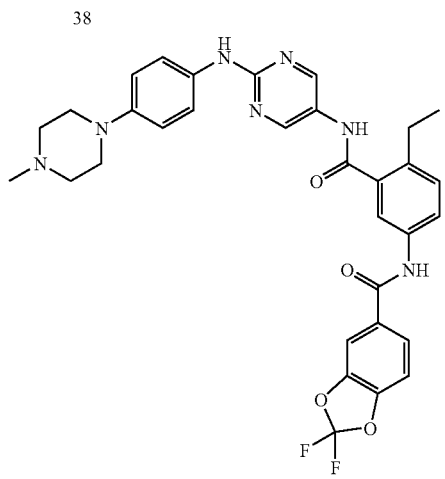

Synthesis of N-(4-ethyl-3-((2-(4-(4-methylpiperazin-1-yl)phenylamino)pyrimidin-5-yl)carbamoyl)phenyl)-2,2-difluorobenzo[d][1,3]dioxole-5-carboxamide A resealable tube was charged with N-(4-chloro-3-((2-(4-(4-methylpiperazin-1-yl)phenylamino)pyrimidin-5-yl)carbamoyl)phenyl)-2,2-difluorobenzo[d][1,3]dioxole-5-carboxamide 38 (0.050 g, 0.080 mmol), palladium(II) acetate (0.0018 g, 0.0080 mmol), 2-(dicyclohexylphosphino)-2',6'-dimethoxy-1,1'-biphenyl (0.0066 g, 0.016 mmol), potassium phosphate (0.068 g, 0.32 mmol), and DMF (2.0 mL). A solution of triethylborane (0.12 mL, 0.12 mmol) (1M in THF) was added. The reaction tube was evacuated and purged with argon, and then sealed. The mixture stirred at 100° C. for 6 h. The reaction mixture was filtered through a pad of Celite and concentrated to afford a yellow green solid. This material was purified via preparative thin layer chromatography (eluting three times with 95:5:0.5, dichloromethane/methanol/ammonium hydroxide) to afford N-(4-ethyl-3-((2-(4-(4-methylpiperazin-1-yl)phenylamino)pyrimidin-5-yl)carbamoyl)phenyl)-2,2-difluorobenzo[d][1,3]dioxole-5-carboxamide 39 as an off-white solid. MS m/z found 616.2 [MH+]; calc. for $C_{32}H_{31}F_2N_7O_4=615.63$.

EXAMPLE 136

Method H

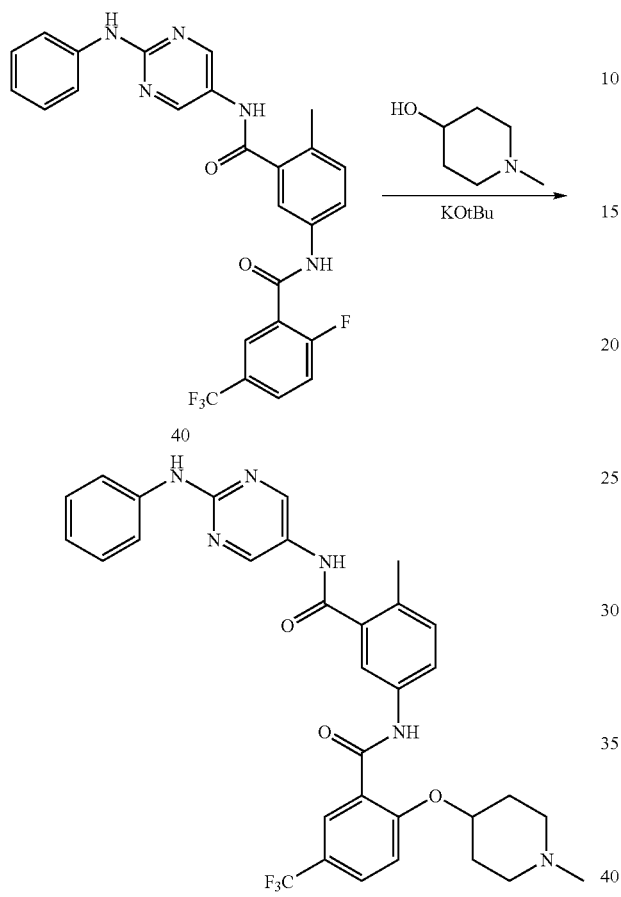

Synthesis of 2-methyl-5-(((2-((1-methyl-4-piperidinyl)oxy)-5-(trifluoromethyl)phenyl)carbonyl)amino)-N-(2-(phenylamino)-5-pyrimidinyl)benzamide To a suspension of potassium t-butoxide (17 mg, 0.151 mmol) in THF (2 mL) was added 1-methylpiperidin-4-ol (15 mg, 0.130 mmol). The mixture was allowed to stir at rt for 15 min, at which time 2-fluoro-N-(4-methyl-3-(((2-(phenylamino)-5-pyrimidinyl)amino)carbonyl)phenyl)-5-(trifluoromethyl)benzamide 40 (55 mg, 0.108 mmol) was added. The reaction mixture was stirred at room temperature for 24 h, at which time the LCMS showed complete conversion. The reaction mixture was diluted with $CH_2Cl_2$, washed with water (3×20 mL), dried over $Na_2SO_4$ and concentrated. The crude residue was taken up in MeOH/DMSO and purified on the Shimadzu reversed phase HPLC with a 15-85% gradient. Pure fractions were combined, basified with saturated sodium bicarbonate and extracted with $CH_2Cl_2$ (4×20 mL). Combined organic extracts were dried over sodium sulfate and concentrated to afford 2-methyl-5-(((2-((1-methyl-4-piperidinyl)oxy)-5-(trifluoromethyl)phenyl)carbonyl)amino)-N-(2-(phenylamino)-5-pyrimidinyl)benzamide 41. MS m/z found 605.3 [MH+]; calc. for $C_{32}H_{31}F_3N_6O_3$=604.24.

EXAMPLE 137

Method K

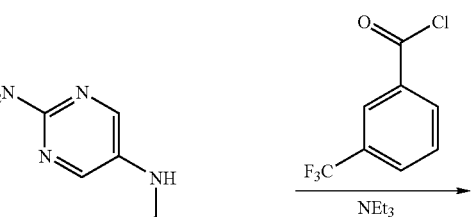

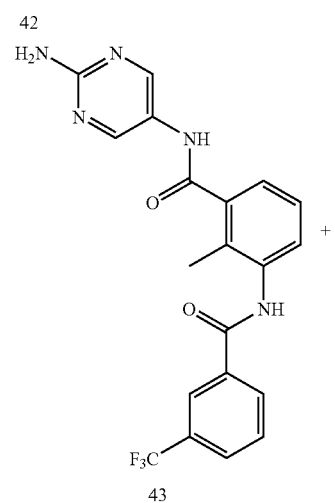

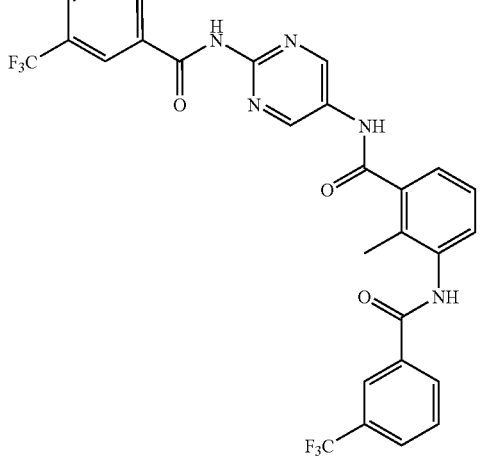

Synthesis of N-(2-amino-5-pyrimidinyl)-2-methyl-3-(((3-(trifluoromethyl)phenyl)carbonyl)amino)benzamide 3-amino-N-(2-aminopyrimidin-5-yl)-2-methylbenzamide 42 (113 mg, 0.464 mmol) [prepared according to the procedure described for methylbenzamide5-amino-N-(2-aminopyrimidin-5-yl)-2-methylbenzamide in Example 1] was taken up in $CH_2Cl_2$ (4 mL) and pyridine (3 mL) and 3-(trifluoromethyl)benzoyl chloride (0.31 mL, 2.09 mmol) was added followed by $NEt_3$ (0.13 mL, 0.928 mmol). Complete consumption of the amine starting material was indicated by LCMS. The crude reaction mixture was concentrated and the product purified using automated medium pressure chromatography (Isco—40 g column; eluting with a linear gradient from 97% $CH_2Cl_2$ (A line) to 100% 90/10/1 $CH_2Cl_2$/MeOH/$NH_3$ (B line) on silica gel) to afford N-(2-amino-5-pyrimidinyl)-2-methyl-3-(((3-(trifluoromethyl)phenyl)carbonyl)amino)benzamide 43 as an off-white solid. MS m/z found 416 [MH+]; calc. for $C_{20}H_{16}F_3N_5O_2$=415.13; and 2-methyl-3-(((3-(trifluoromethyl)phenyl)carbonyl)amino)-N-(2-(((3-(trifluoromethyl)phenyl)carbonyl)amino)-5-pyrimidinyl)benzamide 44 as an off-white solid. MS m/z found 588 [MH+]; calc. for $C_{28}H_{19}F_6N_5O_3$=587.14.

EXAMPLE 138

Method L

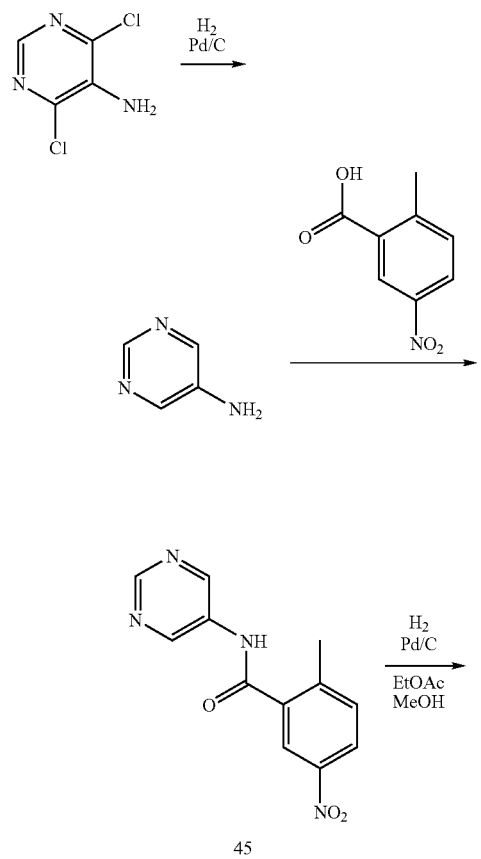

45

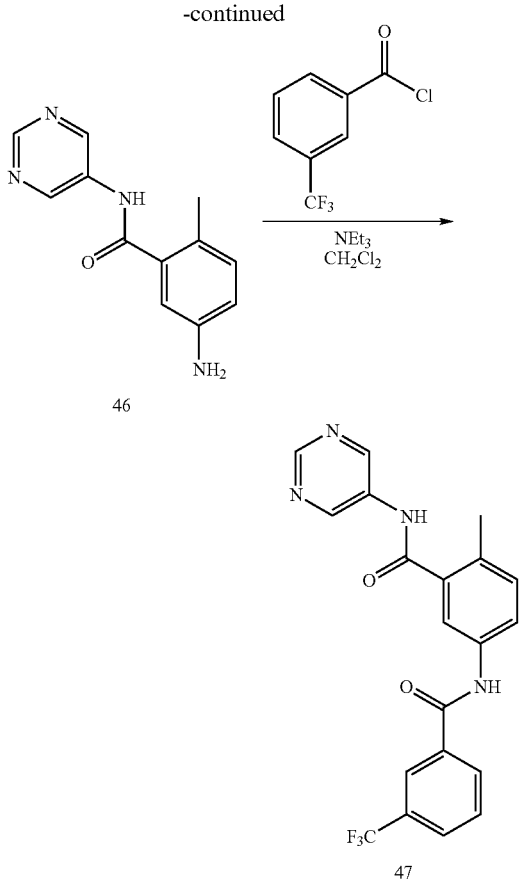

Synthesis of 2-methyl-N-(5-pyrimidinyl)-5-(((3-(trifluoromethyl)phenyl)carbonyl)amino)benzamide

Step 1

The method followed in step 1 was analogous to that described in Can. J. Chem. vol. 77, 216-222 (1999). A high-pressure 1L reaction vessel was charged with ether (300 mL) and a catalyst, palladium 10% on carbon wet (50% water) (1.68 g) was added, followed by 4,6-dichloropyrimidin-5-amine (21 g). A sodium hydroxide solution 50% (168 mL) was diluted with water (150 mL) and added to the previous mixture. The biphasic mixture was pressurized at 35 psi of $H_2$ and mechanically stirred for 24 h. More catalyst was added at this point (1.5 g) and the reaction was resubmitted to $H_2$ for 24 h. The reaction was complete as monitored by LCMS and was filtered through celite and rinsed with water. The biphasic mixture was separated and the aqueous phase was extracted 3 times with ether. The organics were combined, dried over $MgSO_4$, filtered and concentrated down to afford the crude 5-amino-pyrimidine product as a yellow solid. It was recrystallized from toluene/MeOH. The ageous phase was re-extracted twice using EtOAc, the organics were dried over $MgSO_4$, filtered and concentrated down to afford more desired product. The solids were all combined to yield product pyrimidin-5-amine.

Step 2

In a 2L round bottom flask with mechanical stirring was charged with 2-methyl-5-nitrobenzoic acid (20 g), HATU (38 g) and diisopropylamine (32 mL) in DMF (90 mL). This mixture was stirred for 30 min then pyrimidin-5-amine was added and the reaction was stirred for 18 hr. The LCMS showed complete conversion. DMF was removed under vacuum as much as possible then water was added and a solid precipitated out (use mechanical stirring). The tan solid was filtered and rinsed with water, then taken up in EtOAc, washed with brine, dried over MgSO₄, filtered and concentrated down. The crude was taken up in EtOAc and the product 45 precipitated out. This was filtered and the filtrate was concentrated down and taken up in EtOAc/Hex. After standing overnight, more solids were filtered and were combined with the first crop. 2-methyl-5-nitro-N-(pyrimidin-5-yl)benzamide 45 was obtained as a light yellow solid.

Step 3.
5-amino-2-methyl-N-(pyrimidin-5-yl)benzamide

A 2L high-pressure vessel was charged with Palladium 10% on carbon wet (50% water) and EtOAc (50 mL). 2-methyl-5-nitro-N-(pyrimidin-5-yl)benzamide 45 (18.79 g) was dissolved in methanol (400 mL) and added to the previous mixture. The reaction vessel was pressurized to 30 psi of H₂ and mechanically stirred until the hydrogen intake stopped. The reduction of the nitro group was complete by LCMS and the mixture was filtered off through paper and glass paper. The crude 5-amino-2-methyl-N-(pyrimidin-5-yl)benzamide 46 was obtained as a yellow solid and used without further purification.

Step 4

The title compound, 2-methyl-N-(5-pyrimidinyl)-5-(((3-(trifluoromethyl)phenyl)carbonyl)amino)benzamide, was prepared from compound 46 obtained in Step 3 according to the procedure described in the Step 4 of Example 1. MS m/z found 400.7 [MH+]; calc. for C₂₀H₁₅F₃N₄O₂=400.11.

EXAMPLE 139

Method N

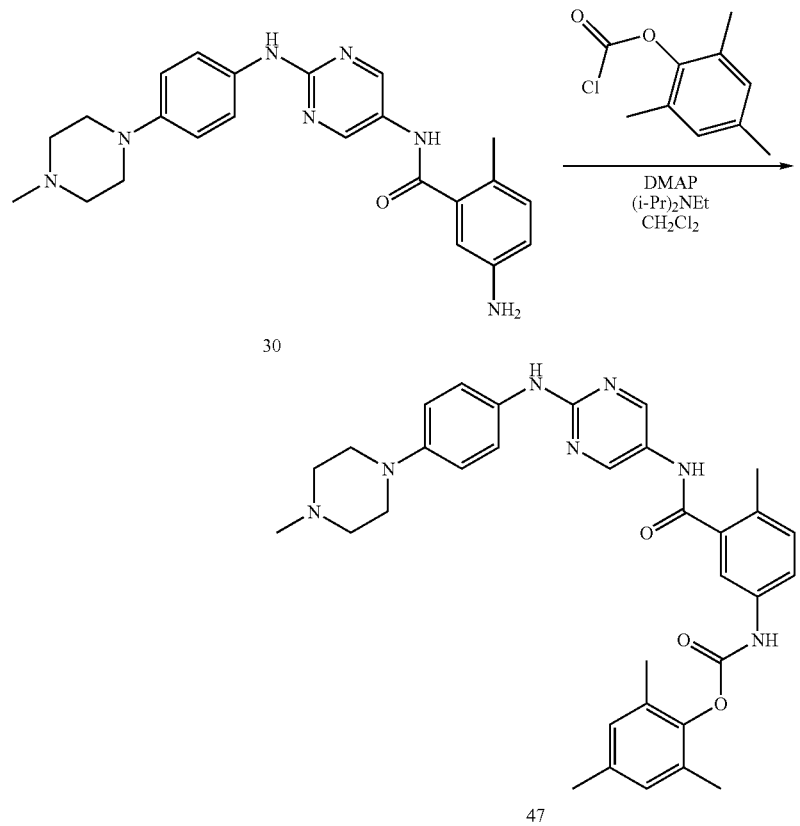

Synthesis of mesityl 4-methyl-3-((2-(4-(4-methylpiperazin-1-yl)phenylamino)pyrimidin-5-yl)carbamoyl)phenylcarbamate A 16×100 mm vial was charged with 5-amino-2-methyl-N-(2-(4-(4-methylpiperazin-1-yl)phenylamino)pyrimidin-5-yl)benzamide 30 (0.100 g, 0.24 mmol), 4-(dimethylamino)pyridine (0.0059 g, 0.048 mmol), dichloromethane (2 mL), and diisopropylethylamine (0.050 ml, 0.29 mmol). A solution of mesityl carbonochloridate (0.048 g, 0.24 mmol) in dichloromethane (1 mL) was added dropwise and the reaction mixture stirred at room temperature for 20 hours. The reaction mixture was purified via column chromatography on silica gel (gradient elution with 0 to 20% methanol in dichloromethane) to afford mesityl 4-methyl-3-((2-(4-(4-methylpiperazin-1-yl)phenylamino)pyrimidin-5-yl)carbamoyl)

phenylcarbamate 47 as a bright yellow solid. MS m/z found 580 [MH+]; calc. for $C_{33}H_{37}N_7O_3$=579.69.

EXAMPLE 140

Method O

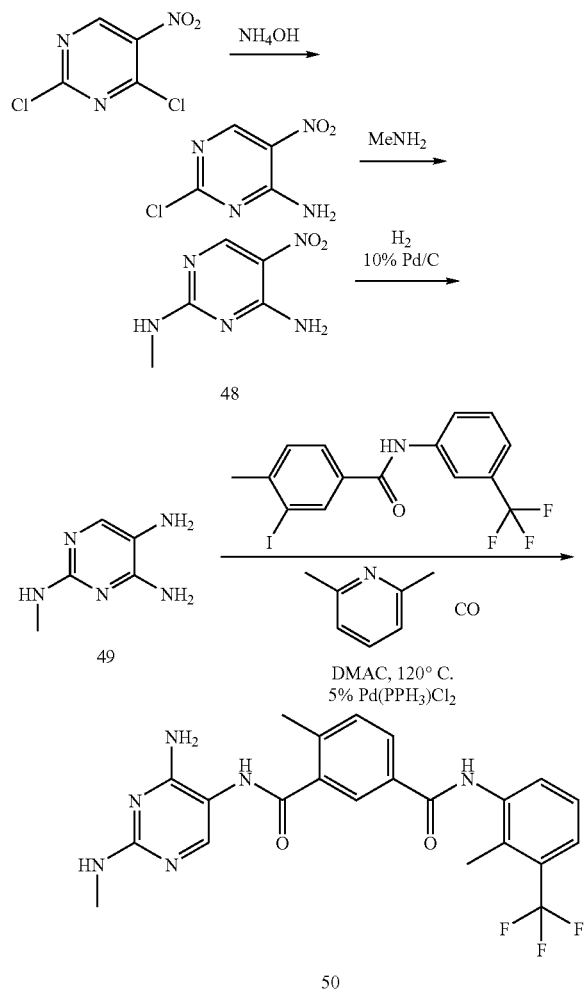

Synthesis of N3-(4-amino-2-(methylamino)pyrimidin-5-yl)-4-methyl-N1-(2-methyl-3-(trifluoromethyl)phenyl)isophthalamide

Step 1. 2-chloro-5-nitropyrimidin-4-amine

To a rapidly stirred solution of saturated aqueous ammonium hydroxide (50 mL) and ice in a 0 deg. C. bath was added 2,4-dichloro-5-nitropyrimidine (6.0 g, 31 mmol) in portions. The resulting yellow foamy mixture was allowed to stir for 30 min, at which point the precipitate was isolated by filtration. The solid was rinsed several times with ice-cold water and once with ice cold ethanol to give a peach-colored solid. The crude solid was purified by adsorption onto 18 g silica gel, followed by silica gel chromatography, eluting with 0-20% MeOH/dichloromethane to give 2-chloro-5-nitropyrimidin-4-amine as an off-white solid. MS (ES$^+$): 175 (M+H)$^+$; Calc. for $C_4H_3ClN_4O_2$=174.55.

Step 2. N2-methyl-5-nitropyrimidine-2,4-diamine

A mixture of 2-chloro-5-nitropyrimidin-4-amine (1.0 g, 5.8 mmol) and methylamine (2.0 M solution in THF, 14 mL, 28 mmol) was allowed to stir in a sealed vessel for 1 h. The mixture was then heated to 60 deg. C. for 30 min. The reaction was cooled to ambient temperature, and an additional amount of methylamine (2.0 M solution in THF, 8 mL, 16 mmol) was added and the reaction was sealed and heated to 60 deg. C. for 30 min. The reaction was cooled, diluted with water, and the precipitate was collected by filtration. The solid was rinsed with small portions of water followed by diethyl ether. The material was dried in under reduced pressure to give N2-methyl-5-nitropyrimidine-2,4-diamine 48 as a light yellow solid. MS (ES'): 170 (M+H)$^+$; Calc. for $C_5H_7N_5O_2$=169.14.

Step 3. N2-methylpyrimidine-2,4,5-triamine

N2-methyl-5-nitropyrimidine-2,4-diamine 48 (0.83 g, 4.9 mmol) and 10% palladium on carbon (0.52 g, 0.49 mmol) were combined under nitrogen. Methanol (16 mL) was added, and the atmosphere replaced with hydrogen from a balloon. The reaction was stirred rapidly for 6 h, at which point the atmosphere was replaced with nitrogen and the reaction mixture was filtered through celite, rinsing with methanol. The filtrate was concentrated in vacuo to give N2-methylpyrimidine-2,4,5-triamine 49 as a light pink solid. MS (ES$^+$): 140 (M+H)$^+$; Calc. for $C_5H_9N_5$=139.16.

Step 4. N3-(4-amino-2-(methylamino)pyrimidin-5-yl)-4-methyl-N1-(2-methyl-3-(trifluoromethyl)phenyl)isophthalamide To a small glass vessel was added N2-methylpyrimidine-2,4,5-triamine 49 (0.050 g, 0.36 mmol), 3-iodo-4-methyl-N-(2-methyl-3-(trifluoromethyl)phenyl)benzamide (0.15 g, 0.36 mmol) [prepared from 3-iodo-4-methylbenzoic acid and 2-methyl-3-(trifluoromethyl)benzenamine as shown in the first step of Example 127], and Bis(triphenylphosphine)palladium(II) dichloride (0.013 g, 0.018 mmol). A septum was attached and the mixture was purged with $N_2$. 2,6-Lutidine (0.054 ml, 0.47 mmol) was added via syringe and the mixture was flushed with CO(g) in a pressure reaction vessel and placed under 95 psi then heated at 120 C for 24 h. The reaction was allowed to cool to rt then the pressure was released and the sticky red residue was analyzed by LCMS. MS for the title compound was found to be (ESI, pos. ion) m/z: 459.1 [M+1]. The crude residue was triturated with MeOH and allowed to stir at rt overnight. The crude reaction mixture was filtered through a Buchner apparatus with micromembrane filter, and the filtrate was washed with copius amounts of MeOH. The mother liquors were concentrated to a sticky deep red solid after drying. This material was taken up in minimal amount of $CH_2Cl_2$ and the solution was injected onto the Isco {Redi-Sep® pre-packed silica gel column (40 g); eluent gradient: 3-80% 90/10/1 $CH_2Cl_2$/MeOH/NH$_3$ in $CH_2Cl_2$ over 20 min} to afford N3-(4-amino-2-(methylamino)pyrimidin-5-yl)-4-methyl-N1-(2-methyl-3-(trifluoromethyl)phenyl)isophthalamide 50 as off-white solid. MS m/z found 459.1 [M+]; calc. for $C_{22}H_{21}F_3N_6O_2$=459.17.

Additional examples 141-143 were prepared by methods described above.
EXAMPLE 141
EXAMPLE 142
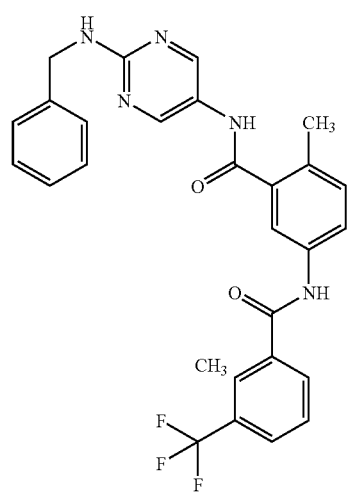
EXAMPLE 143
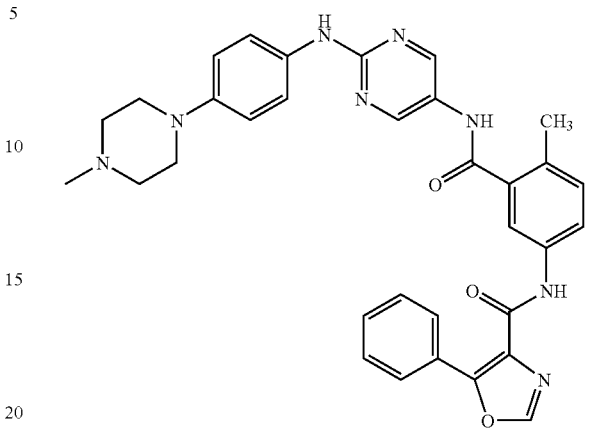
EXAMPLE 144
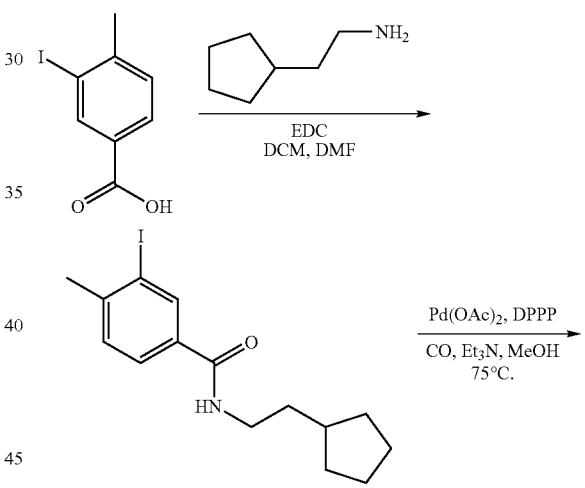
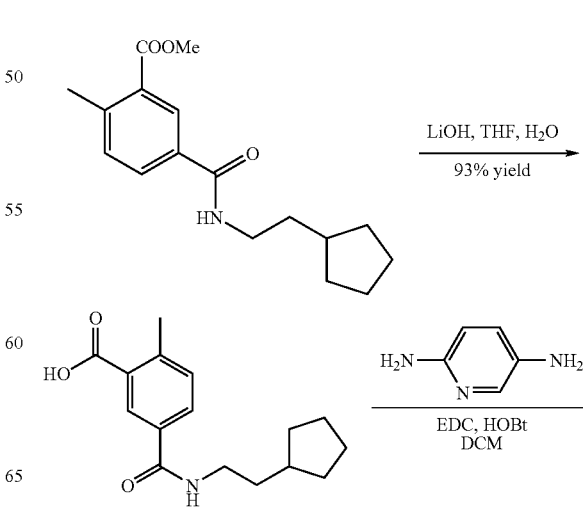

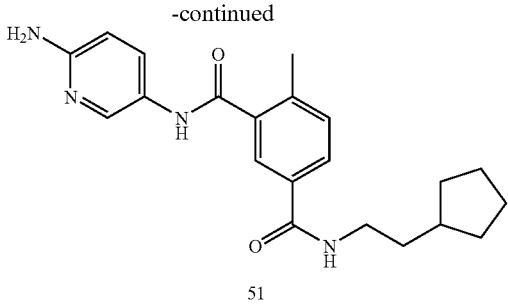

51

Synthesis of N3-(6-aminopyridin-3-yl)-N1-(2-cyclopentylethyl)-4-methylisophthalamide (51)

Step 1

In a round-bottomed flask was charged 3-iodo-4-methylbenzoic acid (1.4 g, 5.4 mmol), dicloromethane (4 ml), and DMF (2 ml). This mixture was cooled to 0° C. and 1-(3-dimethylaminopropyl)-3-ethylcarbodiimide hydrochloride (1.2 g, 6.3 mmol) was added. The reaction mixture was stirred for 10 min before 2-cyclopentylethanamine (0.47 g, 4.2 mmol) was introduced. The reaction mixture was stirred at 0° C. for 1 h, then at RT under $N_2$ for 16 h. The reaction was partitioned between DCM (60 ml) and brine (50 mL). The aqueous layer was back exacted with DCM (4×20 mL) and the combined DCM layer was dried ($Na_2SO_4$) and concentrated. The crude product was dissolved in DCM and purified by chromatography through a Redi-sep pre-packed silica gel column (330 g), eluting with a gradient of 5% to 15% EtOAc in hexane, to provide N-(2-cyclopentylethyl)-3-iodo-4-methylbenzamide as a white solid. MS (ESI, pos. ion) m/z: 358.1 (M+1).

Step 2

Into a 120 mL pressure cylinder with glass liner was placed N-(2-cyclopentylethyl)-3-iodo-4-methylbenzamide (1.7 g, 4.9 mmol) and methanol (25 mL). Nitrogen was bubbled through this mixture, then palladium acetate (55 mg, 0.24 mmol), 1,3-bis(diphenylphosphino)propane (0.11 g, 0.27 mmol), and triethylamine (1.6 ml, 11.6 mmol) were added. The cylinder was capped with a pressure gauge and charged to 40 psi of CO gas. The reaction was heated in a 75° C. oil bath for 20 h. The orange precipitate was filtered off and the filtrate was concentrated under vacuum. The red residue was dissolved in DCM and purified by chromatography through a Redi-Sep® pre-packed silica gel column (120 g), eluting with a gradient of 10% to 25% of EtOAc in hexane, to provide methyl 5-((2-cyclopentylethyl)carbamoyl)-2-methylbenzoate as a white solid. MS (ESI, pos. ion) m/z: 290.2 (M+1).

Step 3

To methyl 5-((2-cyclopentylethyl)carbamoyl)-2-methylbenzoate (1.2 g, 4.3 mmol) dissolved in THF (15 mL) was added a solution of LiOH, monohydrate (0.27 g, 6.4 mmol) in water (15 mL). The reaction mixture was stirred at RT for 18 h. THF was removed, the residue was extracted with ether (5 mL) and the layers were separated. To the aqueous layer was added 2N HCl until pH 4-5 (a lot of precipitate formed). The solid was collected by filtration, washed with water, dried to give 5-((2-cyclopentylethyl)carbamoyl)-2-methylbenzoic acid as a white solid. MS (ESI, pos. ion) m/z: 276.2 (M+1).

Step 4

In a RBF was charged 5-((2-cyclopentylethyl)carbamoyl)-2-methylbenzoic acid (0.25 g, 0.91 mmol), DCM (3 ml), n,n-diisopropylethylamine (0.6 ml, 3.5 mmol), HOBt (0.14 g, 1.0 mmol), 1-(3-dimethylaminopropyl)-3-ethylcarbodiimide hydrochloride (0.21 g, 1.1 mmol), and 2,5-diaminopyridine (0.1 g, 0.91 mmol) in that order. This mixture was stirred at RT under N2 for 18 h. The reaction was partitioned between DCM (30 ml) and brine (20 mL). The precipitate formed was collected, washed with water, dried in a vacuum oven overnight to give N3-(6-aminopyridin-3-yl)-N1-(2-cyclopentylethyl)-4-methylisophthalamide as a purple solid. MS (ESI, pos. ion) m/z: 367.2 (M+1).

EXAMPLE 145

Synthesis of N1-(2-cyclopentylethyl)-4-methyl-N3-(6-(3-methylbutanamido)pyridin-3-yl)isophthalamide (52)

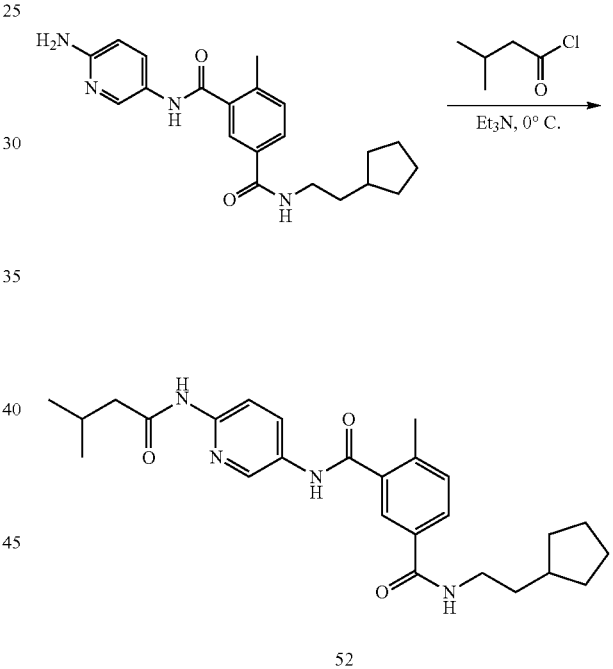

52

To a 25 mL round-bottomed flask was added N3-(6-aminopyridin-3-yl)-N1-(2-cyclopentylethyl)-4-methylisophthalamide (0.19 g, 0.52 mmol) and Triethylamine (0.18 ml, 1.3 mmol) to stir at 0° C. Isovaleryl chloride (0.14 ml, 1.0 mmol) was added to the solution dropwise. The reaction was allowed to stir for one hour. At which time was shown to be at completion by LC/MS. DI water was added to the reaction. The reaction was transferred to a separatory funnel, where the aqueous layer was extracted 3 times with DCM. The combined organic layers were washed with brine, saturated $NaHCO_3$, dried with $MgSO_4$, filtered, and concentrated. The crude product was adsorbed onto a plug of silica gel and chromatographed through a Biotage pre-packed silica gel column (25M), eluting with a gradient of 1% to 10% MeOH in CH2Cl2, to provide N1-(2-cyclopentylethyl)-4-methyl- N3-(6-(3-methylbutanamido)pyridin-3-yl)isophthalamide as a white solid. MS (ESI, pos. ion) m/z: 451.3 (M+1).

EXAMPLE 146

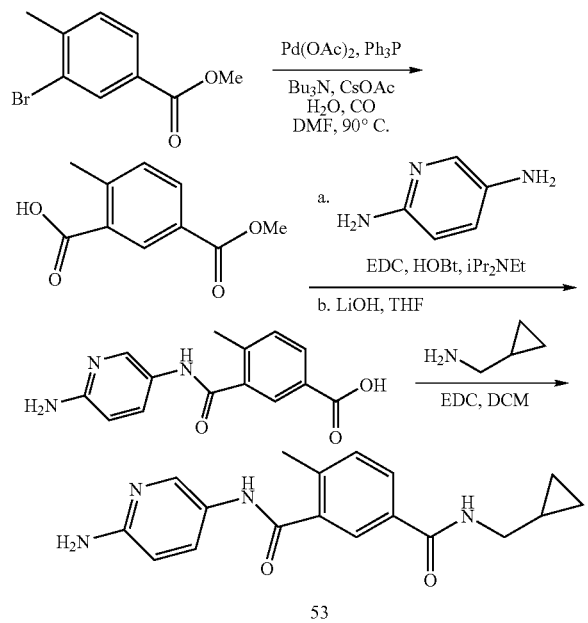

Synthesis of N3-(6-aminopyridin-3-yl)-N1-(cyclopropylmethyl)-4-methylisophthalamide (53)

Step 1

A pressure vessel was charged with methyl 3-bromo-4-methylbenzoate (5.0 g, 22 mmol), DMF (20 ml), water (1.25 ml) and tributylamine (8 ml, 34 mmol). Cesium acetate (2.1 g, 11 mmol) was then added and the flask was purged with $N_2$. Palladium acetate (0.25 g, 1.0 mmol) and triphenylphosphine (2.9 g, 11 mmol) were added and the flask was purged with CO gas. The reaction mixture was then heated at 90° C. under 20 psi of CO gas with vigorous stirring overnight. The reaction mixture was diluted with 50 mL of toluene and extracted with saturated $NaHCO_3$ (3×50 ml). The combined aqueous layer was washed with EtOAc (10 mL), then acidified using 2 N HCl to pH 5. The volume was reduced to about 50 mL and the resulting precipitate was collected by filtration, washed with water and dried to give 5-(methoxycarbonyl)-2-methylbenzoic acid as a white solid. MS (ESI, pos. ion) m/z: 193.1 (M−1).

Step 2

In a round-bottomed flask was charged 5-(methoxycarbonyl)-2-methylbenzoic acid (0.2 g, 1.0 mmol), dicloromethane (3 ml), n,n-diisopropylethylamine (0.7 ml, 4.0 mmol), HOBt (0.16 g, 1.2 mmol), 1-(3-dimethylaminopropyl)-3-ethylcarbodiimide hydrochloride (0.24 g, 1.2 mmol), and 2,5-diaminopyridine (0.11 g, 1.0 mmol) in that order. The reaction mixture was stirred at RT under N2 for 18 h. The reaction was partitioned between DCM (30 ml) and brine (20 mL). The aqueous layer was back extracted with DCM (3×15 mL) and the combined DCM layer was dried ($Na_2SO_4$) and concentrated. The crude product was dissolved in MeOH and absorbed on silica gel, pyrified by chromatography through a Redi-Sep 40 g column, eluting with a gradient of 0% to 10% MeOH in CH2Cl2, to provide methyl 3-((6-aminopyridin-3-yl)carbamoyl)-4-methylbenzoate as a tan solid. MS (ESI, pos. ion) m/z: 286.2 (M+1).

Step 3

To methyl 3-((6-aminopyridin-3-yl)carbamoyl)-4-methylbenzoate (0.11 g, 0.39 mmol) dissolved in tetrahydrofuran (1.5 mL) was added a solution of lithium hydroxide, monohydrate (24 mg, 0.58 mmol) in water (1.5 mL). The reaction mixture was stirred at RT for 4 h. THF was removed in vacuo and to the aqueous layer was added 2N HCl until pH 4-5. The precipitate formed was collected by filtration, washed with water, dried to give 3-((6-aminopyridin-3-yl)carbamoyl)-4-methylbenzoic acid as a tan solid. MS (ESI, pos. ion) m/z: 272.1 (M+1).

Step 4

In a round-bottomed flask was charged 3-((6-aminopyridin-3-yl)carbamoyl)-4-methylbenzoic acid (70 mg, 0.26 mmol), DCM (1 ml), and DMF (1 ml). 1-(3-dimethylaminopropyl)-3-ethylcarbodiimide hydrochloride (74 mg, 0.39 mmol) was then added. The reaction mixture was stirred for 10 min before (aminomethyl)cyclopropane (27 μl, 0.31 mmol) was introduced. The reaction mixture was stirred at RT under $N_2$ for 16 h. The reaction was partitioned between DCM (15 ml) and brine (10 mL). The aqueous layer was back exacted with DCM (3×10 mL) and the combined DCM layer was dried ($Na_2SO_4$) and concentrated. The crude product was dissolved in DCM and purified by chromatography through a Redi-Sep® pre-packed silica gel column (40 g), eluting with a gradient of 0% to 10% MeOH in CH2Cl2, to provide N3-(6-aminopyridin-3-yl)-N1-(cyclopropylmethyl)-4-methylisophthalamide as an off-white solid. m/z: 325.2 (M+1).

Examples 147 and 148, building block materials for compounds of Formulas I-III, were prepared according to the literature references provided below.

EXAMPLE 147

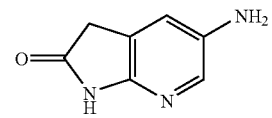 [SMILES: Nc1cnc2c(c1)CC(=O)N2]

U.S. Pat. Appl. Publ. (2005), 43 pp. CODEN: USXXCO US 2005256125 A1 20051117 CAN 143:460185 AN 2005: 1224270

EXAMPLE 148

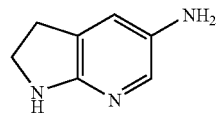

Synthesis 2005, 15, 2503-2506.

Each of the following examples 149-221 of Formulas I-III were made using a procedure analogous to that described in examples 1, 2, 88, 96, 114, 127, 136-140 or 144-146.

| Ex. No. | M + H | Compound Name |
|---|---|---|
| 149 | 421.1 | 2-chloro-N-5-pyrimidinyl-5-(((3-(trifluoromethyl)phenyl)carbonyl)amino)benzamide |
| 150 | 452.2 | 2-chloro-5-(((4-(4-morpholinylmethyl)phenyl)carbonyl)amino)-N-5-pyrimidinylbenzamide |
| 151 | 381.1 | 2-chloro-5-(((4-ethylphenyl)carbonyl)amino)-N-5-pyrimidinylbenzamide |
| 152 | | 2-chloro-5-((3-cyclopentylpropanoyl)amino)-N-5-pyrimidinylbenzamide |
| 153 | | 5-(acetylamino)-2-chloro-N-5-pyrimidinylbenzamide |
| 154 | | 2-chloro-N-5-pyrimidinyl-5-((3-(1-pyrrolidinyl)propanoyl)amino)benzamide |
| 155 | 400.1 | 4-methyl-N~3~-3-pyridinyl-N~1~-(3-(trifluoromethyl)phenyl)-1,3-benzenedicarboxamide |
| 156 | 434 | N~3~-(6-chloro-3-pyridinyl)-4-methyl-N~1~-(3-(trifluoromethyl)phenyl)-1,3-benzenedicarboxamide |
| 157 | 418 | N~1~-(2-fluoro-5-(trifluoromethyl)phenyl)-4-methyl-N~3~-3-pyridinyl-1,3-benzenedicarboxamide |
| 158 | 433 | N~3~-(6-amino-3-pyridinyl)-N~1~-(2-fluoro-5-(trifluoromethyl)phenyl)-4-methyl-1,3-benzenedicarboxamide |
| 159 | 401.1 | 4-methyl-N~3~-5-pyrimidinyl-N~1~-(3-(trifluoromethyl)phenyl)-1,3-benzenedicarboxamide |
| 160 | 401.1 | 4-methyl-N~3~-2-pyrimidinyl-N~1~-(3-(trifluoromethyl)phenyl)-1,3-benzenedicarboxamide |
| 161 | 401.1 | 4-methyl-N~3~-2-pyrazinyl-N~1~-(3-(trifluoromethyl)phenyl)-1,3-benzenedicarboxamide |
| 162 | 415.1 | N~3~-(6-amino-3-pyridinyl)-4-methyl-N~1~-(3-(trifluoromethyl)phenyl)-1,3-benzenedicarboxamide |
| 163 | 416.1 | N~3~-(2-amino-5-pyrimidinyl)-4-methyl-N~1~-(3-(trifluoromethyl)phenyl)-1,3-benzenedicarboxamide |
| 164 | 401.1 | 4-methyl-N~3~-4-pyridazinyl-N~1~-(3-(trifluoromethyl)phenyl)-1,3-benzenedicarboxamide |
| 165 | 418.1 | N~3~-(3,5-dimethyl-4-isoxazolyl)-4-methyl-N~1~-(3-(trifluoromethyl)phenyl)-1,3-benzenedicarboxamide |
| 166 | 457.1 | N~3~-(6-(acetylamino)-3-pyridinyl)-4-methyl-N~1~-(3-(trifluoromethyl)phenyl)-1,3-benzenedicarboxamide |
| 167 | 458.2 | N~3~-(2-(acetylamino)-5-pyrimidinyl)-4-methyl-N~1~-(3-(trifluoromethyl)phenyl)-1,3-benzenedicarboxamide |
| 168 | 353.2 | N~1~-(2-cyclopentylethyl)-4-methyl-N~3~-5-pyrimidinyl-1,3-benzenedicarboxamide |
| 169 | 367.2 | N~3~-(6-amino-3-pyridinyl)-N~1~-(2-cyclopentylethyl)-4-methyl-1,3-benzenedicarboxamide |
| 170 | 415.1 | N~3~-(6-amino-3-pyridinyl)-4-methyl-N~1~-(4-(trifluoromethyl)phenyl)-1,3-benzenedicarboxamide |
| 171 | 401.1 | 4-methyl-N~3~-5-pyrimidinyl-N~1~-(4-(trifluoromethyl)phenyl)-1,3-benzenedicarboxamide |
| 172 | 445.1 | N~3~-(6-amino-3-pyridinyl)-4-methyl-N~1~-(4-(methyloxy)-3-(trifluoromethyl)phenyl)-1,3-benzenedicarboxamide |
| 173 | 409.2 | N~3~-(6-(acetylamino)-3-pyridinyl)-N~1~-(2-cyclopentylethyl)-4-methyl-1,3-benzenedicarboxamide |
| 174 | 431.1 | 4-methyl-N~1~-(4-(methyloxy)-3-(trifluoromethyl)phenyl)-N~3~-5-pyrimidinyl-1,3-benzenedicarboxamide |
| 175 | 395.2 | N~1~-(2-cyclopentylethyl)-N~3~-(6-(ethylamino)-3-pyridinyl)-4-methyl-1,3-benzenedicarboxamide |
| 176 | 368.2 | N~3~-(2-amino-5-pyrimidinyl)-N~1~-(2-cyclopentylethyl)-4-methyl-1,3-benzenedicarboxamide |
| 177 | 410.2 | N~3~-(2-(acetylamino)-5-pyrimidinyl)-N~1~-(2-cyclopentylethyl)-4-methyl-1,3-benzenedicarboxamide |
| 178 | 381.2 | N~3~-(6-amino-5-methyl-3-pyridinyl)-N~1~-(2-cyclopentylethyl)-4-methyl-1,3-benzenedicarboxamide |
| 179 | 382.2 | N~1~-(2-cyclopentylethyl)-4-methyl-N~3~-(6-(methyloxy)-3-pyridinyl)-1,3-benzenedicarboxamide |
| 180 | 391.3 | N~1~-(2-cyclopentylethyl)-4-methyl-N~3~-1H-pyrrolo[2,3-b]pyridin-5-yl-1,3-benzenedicarboxamide |
| 181 | 420.2 | N~1~-(2-cyclopentylethyl)-4-methyl-N~3~-(6-(trifluoromethyl)-3-pyridinyl)-1,3-benzenedicarboxamide |
| 182 | 381.3 | N~3~-(6-amino-3-pyridinyl)-N~1~-(2-cyclohexylethyl)-4-methyl-1,3-benzenedicarboxamide |
| 183 | 451.3 | N~1~-(2-cyclopentylethyl)-N~3~-(6-((2,2-dimethylpropanoyl)amino)-3-pyridinyl)-4-methyl-1,3-benzenedicarboxamide |
| 184 | 435.2 | N~1~-(2-cyclopentylethyl)-N~3~-(6-((cyclopropylcarbonyl)amino)-3-pyridinyl)-4-methyl-1,3-benzenedicarboxamide |
| 185 | 449.2 | N~1~-(2-cyclopentylethyl)-4-methyl-N~3~-(6-((3-methyl-2-butenoyl)amino)-3-pyridinyl)-1,3-benzenedicarboxamide |
| 186 | 393.3 | N~1~-(2-cyclopentylethyl)-N~3~-(2,3-dihydro-1H-pyrrolo[2,3-b]pyridin-5-yl)-4-methyl-1,3-benzenedicarboxamide |

| Ex. No. | M + H | Compound Name |
| --- | --- | --- |
| 187 | 424.2 | N~1~-(2-cyclopentylethyl)-4-methyl-N~3~-(6-(((methylamino)carbonyl)amino)-3-pyridinyl)-1,3-benzenedicarboxamide |
| 188 | 368.3 | N~3~-(6-amino-3-pyridinyl)-4-methyl-N~1~-(2-(1-pyrrolidinyl)ethyl)-1,3-benzenedicarboxamide |
| 189 | 449.3 | N~3~-(6-(cyclohexylamino)-3-pyridinyl)-N~1~-(2-cyclopentylethyl)-4-methyl-1,3-benzenedicarboxamide |
| 190 | 402.2 | N~1~-(2-cyclopentylethyl)-4-methyl-N~3~-3-quinolinyl-1,3-benzenedicarboxamide |
| 191 | 395.2 | N~1~-(2-cyclopentylethyl)-N~3~-(6-(dimethylamino)-3-pyridinyl)-4-methyl-1,3-benzenedicarboxamide |
| 192 | 381.2 | N~1~-(2-cyclopentylethyl)-4-methyl-N~3~-(6-(methylamino)-3-pyridinyl)-1,3-benzenedicarboxamide |
| 193 | 463.2 | N~1~-(2-cyclopentylethyl)-4-methyl-N~3~-(6-((trifluoroacetyl)amino)-3-pyridinyl)-1,3-benzenedicarboxamide |
| 194 | 451.3 | N~1~-(2-cyclopentylethyl)-4-methyl-N~3~-(6-((3-methylbutanoyl)amino)-3-pyridinyl)-1,3-benzenedicarboxamide |
| 195 | 461.2 | N~1~-(2-cyclopentylethyl)-N~3~-(6-((2-furanylcarbonyl)amino)-3-pyridinyl)-4-methyl-1,3-benzenedicarboxamide |
| 196 | 407.3 | N~1~-(2-cyclopentylethyl)-4-methyl-N~3~-(2-oxo-2,3-dihydro-1H-pyrrolo[2,3-b]pyridin-5-yl)-1,3-benzenedicarboxamide |
| 197 | 421.3 | N~1~-(2-cyclopentylethyl)-N~3~-(6-((cyclopropylmethyl)amino)-3-pyridinyl)-4-methyl-1,3-benzenedicarboxamide |
| 198 | 370.2 | N~1~-(2-cyclopentylethyl)-N~3~-(6-fluoro-3-pyridinyl)-4-methyl-1,3-benzenedicarboxamide |
| 199 | 452.3 | N~1~-(2-cyclopentylethyl)-4-methyl-N~3~-(6-(((1-methylethyl)amino)carbonyl)amino)-3-pyridinyl)-1,3-benzenedicarboxamide |
| 200 | 471.2 | N~1~-(2-cyclopentylethyl)-4-methyl-N~3~-(6-((phenylcarbonyl)amino)-3-pyridinyl)-1,3-benzenedicarboxamide |
| 201 | 477.2 | N~1~-(2-cyclopentylethyl)-4-methyl-N~3~-(6-((2-thienylcarbonyl)amino)-3-pyridinyl)-1,3-benzenedicarboxamide |
| 202 | 449.2 | N~3~-(6-((cyclobutylcarbonyl)amino)-3-pyridinyl)-N~1~-(2-cyclopentylethyl)-4-methyl-1,3-benzenedicarboxamide |
| 203 | 501.2 | N~1~-(2-cyclopentylethyl)-4-methyl-N~3~-(6-(((3-(methyloxy)phenyl)carbonyl)amino)-3-pyridinyl)-1,3-benzenedicarboxamide |
| 204 | 366.3 | N~1~-(2-cyclopentylethyl)-4-methyl-N~3~-(6-methyl-3-pyridinyl)-1,3-benzenedicarboxamide |
| 205 | 463.3 | N~3~-(6-((cyclopentylcarbonyl)amino)-3-pyridinyl)-N~1~-(2-cyclopentylethyl)-4-methyl-1,3-benzenedicarboxamide |
| 206 | 461.2 | N~1~-(2-cyclopentylethyl)-N~3~-(6-((1H-imidazol-4-ylcarbonyl)amino)-3-pyridinyl)-4-methyl-1,3-benzenedicarboxamide |
| 207 | 464.2 | N~1~-(2-cyclopentylethyl)-4-methyl-N~3~-(6-(D-prolylamino)-3-pyridinyl)-1,3-benzenedicarboxamide |
| 208 | 355.2 | N~3~-(6-amino-3-pyridinyl)-4-methyl-N~1~-(tetrahydro-2-furanylmethyl)-1,3-benzenedicarboxamide |
| 209 | 396.2 | N~3~-(6-amino-3-pyridinyl)-4-methyl-N~1~-(3-(2-oxo-1-pyrrolidinyl)propyl)-1,3-benzenedicarboxamide |
| 210 | 325.2 | N~3~-(6-amino-3-pyridinyl)-N~1~-(cyclopropylmethyl)-4-methyl-1,3-benzenedicarboxamide |
| 211 | 371.3 | N~3~-(6-amino-3-pyridinyl)-4-methyl-N~1~-(3-((1-methylethyl)oxy)propyl)-1,3-benzenedicarboxamide |
| 212 |  | N~1~-(2-cyclopentylethyl)-4-methyl-N~3~-(6-(((1R,2R)-2-phenylcyclopropyl)carbonyl)amino)-3-pyridinyl)-1,3-benzenedicarboxamide |
| 213 | 379.3 | N~3~-(6-amino-3-pyridinyl)-N~1~-(2-(1-cyclohexen-1-yl)ethyl)-4-methyl-1,3-benzenedicarboxamide |
| 214 | 381.2 | N~3~-(6-amino-3-pyridinyl)-4-methyl-N~1~-(2-(2-thienyl)ethyl)-1,3-benzenedicarboxamide |
| 215 | 355.2 | N~3~-(6-amino-3-pyridinyl)-N~1~-(3,3-dimethylbutyl)-4-methyl-1,3-benzenedicarboxamide |
| 216 | 401.2 | N~3~-(6-amino-3-pyridinyl)-N~1~-(2,3-dihydro-1H-inden-2-ylmethyl)-4-methyl-1,3-benzenedicarboxamide |
| 217 | 421 | 4-chloro-N~3~-5-pyrimidinyl-N~1~-(3-(trifluoromethyl)phenyl)-1,3-benzenedicarboxamide |
| 218 | 387.2 | N~3~-(6-amino-3-pyridinyl)-4-chloro-N~1~-(2-cyclopentylethyl)-1,3-benzenedicarboxamide |
| 219 | 469.2 | 4-chloro-N~1~-(2-cyclopentylethyl)-N~3~-(6-((3-methyl-2-butenoyl)amino)-3-pyridinyl)-1,3-benzenedicarboxamide |

The following compounds in Tables 1 and 2 are additional representative examples of compounds of Formula I, II and III, as provided by the present invention.

TABLE 1

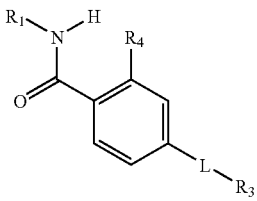

| Ex. No. | R¹ | L | R⁴ | R³ |
|---|---|---|---|---|
| 220 | cyclohexyl-HN-(CH₂)₂-pyridin-2-yl- | —NHCO— | Methyl | acetyl-indoline |
| 221 | piperidine-(CH₂)₂-pyrimidinyl- | —NHCO— | chloro | dimethyl-indoline |
| 222 | NH₂-pyridin-3-yl- | —CONH— | Methyl | pyrimidine |
| 223 | Pyrimidin-5-yl | —CONH— | Methyl or chloro | 2-CH₃-phenyl |
| 224 | NH₂-pyrimidin-5-yl- | —CONH— | Methyl or chloro | 4-CF₃-phenyl |
| 225 | 1-piperidinyl-N-pyridin-3-yl- | —CONH— | Methyl or chloro | 3-CF₃-phenyl |
| 226 | cyclohexyl-N-pyridin-3-yl- | —NHCO— | Methyl or chloro | 6-CH₃-phenyl |
| 227 | morpholine-(CH₂)₂—N-pyridin-3-yl- | —NHCONH— | Methyl or chloro | 6-CH₃-phenyl |
| 228 | (CH₃)₂N—(CH₂)₂—N-pyridin-3-yl-- | —NHCONH— | Methyl or chloro | 4-OCH₃-phenyl |
| 229 | (C₂H₅)₂N—(CH₂)₂-pyrimidin-5-yl- | —NHCO— | Methyl or chloro | pyridine |
| 230 | 3-OH-pyrimidin-5-yl | —NHCO— | Methyl or chloro | indole |
| 231 | 3-amido-pyridinyl | —CONH— | Methyl or chloro | indoline |
| 232 | 4-amido-2-pyridinyl | —CONH— | Methyl or chloro | benzofuran |
| 233 | 3-amido-5-pyrimidinyl | —CONH— | Methyl or chloro | 2-F-phenyl |
| 234 | 4-CH₃-pyridazinyl | —CONH— | Methyl or chloro | 4-F-phenyl |
| 235 | NH₂-pyrazinyl | —NHCO— | Methyl or chloro | Dihydrobenzofuran |
| 236 | NH₂-quinazolinyl | —NHCONH— | Methyl or chloro | cyclohexyl-(CH₂)₂— |
| 237 | CH₃-isoquinazolinyl | —NHCONH— | Methyl or chloro | cyclopropyl-(CH₂)₂— |
| 238 | cyclohexyl-HN—(CH₂)₂-pyridin-2-yl- | —NHCO— | Methyl or chloro | 2-CH₃-phenyl |
| 239 | piperidine-(CH₂)₂-pyrimidinyl- | —NHCO— | Methyl or chloro | 4-CF₃-phenyl |
| 240 | NH₂-pyridin-3-yl- | —CONH— | Methyl or chloro | 3-CF₃-phenyl |
| 241 | Pyrimidin-5-yl | —CONH— | Methyl or chloro | 6-CH₃-phenyl |
| 242 | NH₂-pyrimdin-5-yl- | —CONH— | Methyl or chloro | 2-OCH₃-phenyl |
| 243 | 1-piperidinyl-N-pyridin-3-yl- | —CONH— | Methyl or chloro | 4-OCH₃-phenyl |
| 244 | cyclohexyl-N-pyridin-3-yl- | —NHCO— | Methyl or chloro | pyridine |
| 245 | morpholin-(CH₂)₂—N-pyridin-3-yl- | —NHCONH— | Methyl or chloro | indole |
| 246 | (CH₃)₂N—(CH₂)₂—N-pyridin-3-yl-- | —NHCO— | Methyl or chloro | indoline |
| 247 | (C₂H₅)₂N—(CH₂)₂-pyrimidin-5-yl- | —NHCO— | Methyl or chloro | benzofuran |
| 248 | 3-OH-pyrimidin-5-yl | —CONH— | Methyl or chloro | 2-F-phenyl |
| 249 | 3-amido-pyridinyl | —CONH— | Methyl or chloro | 4-F-phenyl |
| 250 | 4-amino-2-pyridinyl | —CONH— | Methyl or chloro | dihydrobenzofuran |
| 251 | 3-amido-5-pyrimidinyl | —CONH— | Methyl or chloro | 2-CH₃-phenyl |
| 252 | 4-CH₃-pyridazinyl | —NHCO— | Methyl or chloro | 4-CF₃-phenyl |
| 253 | cyclohexyl-HN—(CH₂)₂-pyridin-2-yl- | —NHCONH— | Methyl or chloro | 3-CF₃-phenyl |
| 254 | piperidine-(CH₂)₂-pyrimidinyl- | —NHCONH— | Methyl or chloro | 6-CH₃-phenyl |
| 255 | NH₂-pyridin-3-yl- | —NHCO— | Methyl or chloro | 2-OCH₃-phenyl |
| 256 | Pyrimidin-5-yl | —NHCO— | Methyl or chloro | 4-OCH₃-phenyl |
| 257 | NH₂-pyrimidin-5-yl- | —CONH— | Methyl or chloro | pyridine |
| 258 | 1-piperidinyl-N-pyridin-3-yl- | —CONH— | Methyl or chloro | indole |
| 259 | cyclohexyl-N-pyridin-3-yl- | —CONH— | Methyl or chloro | indoline |
| 260 | morpholine-(CH₂)₂—N-pyridin-3-yl- | —CONH— | Methyl or chloro | benzofuran |
| 261 | (CH₃)₂N—(CH₂)₂—N-pyridin-3-yl-- | —NHCO— | Methyl or chloro | 2-F-phenyl |
| 262 | (C₂H₅)₂N—(CH₂)₂-pyrimidin-5-yl- | —NHCONH— | Methyl or chloro | 4-F-phenyl |
| 263 | 3-OH-pyrimidin-5-yl | —NHCONH— | Methyl or chloro | dihydrobenzofuran |
| 264 | 3-amido-pyridinyl | —NHCO— | Methyl or chloro | cyclohexyl-(CH₂)₂— |

TABLE 1-continued

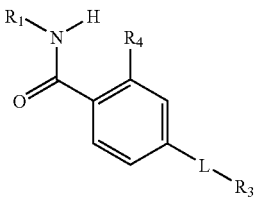

| Ex. No. | R¹ | L | R⁴ | R³ |
|---|---|---|---|---|
| 265 | 4-amido-2-pyridinyl | —NHCO— | Methyl or chloro | cylcopropyl-(CH₂)₂— |
| 266 | 3-amido-5-pyrimidinyl | —CONH— | Methyl or chloro | 2-CH₃-phenyl |
| 267 | 4-CH₃-pyridazinyl | —CONH— | Methyl or chloro | 4-CF₃-phenyl |
| 268 | cyclohexyl-HN—(CH₂)₂-pyridin-2-yl- | —CONH— | Methyl or chloro | 3-CF₃-phenyl |
| 269 | piperidine-(CH₂)₂-pyrimidinyl- | —CONH— | Methyl or chloro | 6-CH₃-phenyl |
| 270 | NH₂-pyridin-3-yl- | —NHCO— | Methyl or chloro | 2-OCH₃-phenyl |
| 271 | Pyrimidin-5-yl | —NHCONH— | Methyl or chloro | 4-OCH₃-phenyl |
| 272 | NH₂-pyrimidin-5-yl- | —NHCONH— | Methyl or chloro | pyridine |
| 273 | 1-piperidinyl-N-pyridin-3-yl- | —NHCO— | Methyl or chloro | indole |
| 274 | cyclohexyl-N-pyridin-3-yl- | —NHCO— | Methyl or chloro | indoline |
| 275 | morpholin-(CH₂)₂—N-pyridin-3-yl- | —CONH— | Methyl or chloro | benzofuran |
| 276 | (CH₃)₂N—(CH₂)₂—N-pyridin-3-yl- | —CONH— | Methyl or chloro | 2-F-phenyl |
| 277 | (C₂H₅)₂N—(CH₂)₂-pyrimidin-5-yl- | —CONH— | Methyl or chloro | 4-F-phenyl |
| 278 | 3-OH-pyrimidin-5-yl | —CONH— | Methyl or chloro | dihydrobenzofuran |
| 279 | 3-pyridinyl-amido-pyridin-3-yl | —NHCO— | Methyl or chloro | cyclohexyl-(CH₂)₂— |
| 280 | N-phenyl-amido-3-pyridinyl | —NHCONH— | Methyl or chloro | cylcopropyl-(CH₂)₂— |
| 281 | 3-amido-5-pyrimidinyl | —NHCONH— | Methyl or chloro | 2-thiophene |
| 282 | 4-CH₃-pyridazinyl | —NHCO— | Methyl or chloro | 3-thiophene |
| 283 | cyclohexyl-HN—(CH₂)₂-pyridin-2-yl- | —NHCO— | Methyl or chloro | 2-pyridine |
| 284 | piperidin-(CH₂)₂-pyrimidinyl- | —CONH— | Methyl or chloro | 1-morpholinyl |
| 285 | NH₂-pyridin-3-yl- | —CONH— | Methyl or chloro | 1-piperazinyl |

TABLE 1-continued

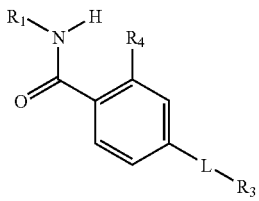

| Ex. No. | R¹ | L | R⁴ | R³ |
|---|---|---|---|---|
| 286 | Pyrimidin-5-yl | —CONH— | Methyl or chloro | 1-piperidinyl |

TABLE 2

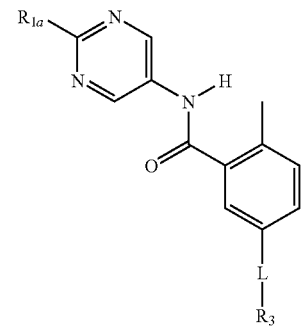

| Ex. No. | R¹ᵃ | A⁵ | L | R³ |
|---|---|---|---|---|
| 287 | cyclohexyl-HN—(CH₂)₂-pyridin-2-yl- | N | —NHCO— | 2-CH₃-phenyl |
| 288 | piperidine-(CH₂)₂-pyrimidinyl- | N | —NHCO— | 4-CF₃-phenyl |
| 289 | NH₂-pyridin-3-yl- | N | —CONH— | 3-CF₃-phenyl |
| 290 | Pyrimidin-5-yl | N | —CONH— | 6-CH₃-phenyl |
| 291 | NH₂-pyrimidin-5-yl- | CH | —CONH— | 2-OCH₃-phenyl |
| 292 | 1-piperidinyl-N-pyridin-3-yl- | CH | —CONH— | 4-OCH₃-phenyl |
| 293 | cyclohexyl-N-pyridin-3-yl- | CH | —NHCO— | pyridine |
| 294 | morpholine-(CH₂)₂—N-pyridin-3-yl- | CH | —NHCONH— | indole |
| 295 | (CH₃)₂N—(CH₂)₂—N-pyridin-3-yl-- | CH | —NHCONH— | indoline |
| 296 | (C₂H₅)₂N—(CH₂)₂-pyrimidin-5-yl- | CH | —NHCO— | benzofuran |
| 297 | 3-OH-pyrimidin-5-yl | CH | —NHCO— | 2-F-phenyl |
| 298 | 3-amido-pyridinyl | CH | —CONH— | 4-F-phenyl |
| 299 | 4-amido-2-pyridinyl | N | —CONH— | Dihydro-benzofuran |
| 300 | 3-amido-5-pyrimidinyl | N | —CONH— | cyclohexyl-(CH₂)₂— |
| 301 | 4-CH₃-pyridazinyl | N | —CONH— | cyclopropyl-(CH2)2— |
| 302 | NH₂-pyrazinyl | N | —NHCO— | 2-CH₃-phenyl |
| 303 | NH₂-quinazolinyl | N | —NHCONH— | 4-CF₃-phenyl |
| 304 | CH₃-isoquinazolinyl | CH | —NHCONH— | 3-CF₃-phenyl |
| 305 | cyclohexyl-HN—(CH₂)₂-pyridin-2-yl- | CH | —NHCO— | 6-CH₃-phenyl |
| 306 | piperidine-(CH₂)₂-pyrimidinyl- | CH | —NHCO— | 2-OCH₃-phenyl |
| 307 | NH₂-pyridin-3-yl- | CH | —CONH— | 4-OCH₃-phenyl |
| 308 | Pyrimidin-5-yl | CH | —CONH— | pyridine |

TABLE 2-continued

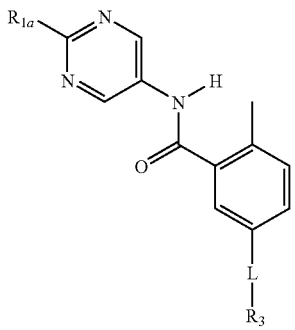

| Ex. No. | $R^{1a}$ | $A^5$ | L | $R^3$ |
|---|---|---|---|---|
| 309 | $NH_2$-pyrimidin-5-yl- | CH | —CONH— | indole |
| 310 | 1-piperidinyl-N-pyridin-3-yl- | CH | —CONH— | indoline |
| 311 | cyclohexyl-N-pyridin-3-yl- | CH | —NHCO— | benzofuran |
| 312 | morpholin-$(CH_2)_2$—N-pyridin-3-yl- | N | —NHCONH— | 2-F-phenyl |
| 313 | $(CH_3)_2N$—$(CH_2)_2$—N-pyridin-3-yl- | N | —NHCO— | 4-F-phenyl |
| 314 | $(C_2H_5)_2N$—$(CH_2)_2$-pyrimidin-5-yl- | N | —NHCO— | dihydro-benzofuran |
| 315 | 3-OH-pyrimidin-5-yl | N | —CONH— | 2-$CH_3$-phenyl |
| 316 | 3-amido-pyridinyl | N | —CONH— | 4-$CF_3$-phenyl |
| 317 | 4-amido-2-pyridinyl | N | —CONH— | 3-$CF_3$-phenyl |
| 318 | 3-amido-5-pyrimidinyl | N | —CONH— | 6-$CH_3$-phenyl |
| 319 | 4-$CH_3$-pyridazinyl | N | —NHCO— | 2-$OCH_3$-phenyl |
| 320 | cyclohexyl-HN—$(CH_2)_2$-pyridin-2-yl- | N | —NHCONH— | 4-$OCH_3$-phenyl |
| 321 | piperidine-$(CH_2)_2$-pyrimidinyl- | N | —NHCONH— | pyridine |
| 322 | $NH_2$-pyridin-3-yl- | N | —NHCO— | indole |
| 323 | Pyrimidin-5-yl | N | —NHCO— | indoline |
| 324 | $NH_2$-pyrimidin-5-yl- | CH | —CONH— | benzofuran |
| 325 | 1-piperidinyl-N-pyridin-3-yl- | CH | —CONH— | 2-F-phenyl |
| 326 | cyclohexyl-N-pyridin-3-yl- | CH | —CONH— | 4-F-phenyl |
| 327 | morpholine-$(CH_2)_2$—N-pyridin-3-yl- | CH | —CONH— | dihydro-benzofuran |
| 328 | $(CH_3)_2N$—$(CH_2)_2$—N-pyridin-3-yl- | CH | —NHCO— | cyclohexyl-$(CH_2)_2$— |
| 329 | $(C_2H_5)_2N$—$(CH_2)_2$-pyrimidin-5-yl- | CH | —NHCONH— | cyclopropyl-$(CH_2)_2$— |
| 330 | 3-OH-pyrimidin-5-yl | CH | —NHCONH— | 2-$CH_3$-phenyl |
| 331 | 3-amido-pyridinyl | CH | —NHCO— | 4-$CF_3$-phenyl |
| 332 | 4-amido-2-pyridinyl | CH | —NHCO— | 3-$CF_3$-phenyl |
| 333 | 3-amido-5-pyrimidinyl | CH | —CONH— | 6-$CH_3$-phenyl |
| 334 | 4-$CH_3$-pyridazinyl | CH | —CONH— | 2-$OCH_3$-phenyl |
| 335 | cyclohexyl-HN—$(CH_2)_2$-pyridin-2-yl- | CH | —CONH— | 4-$OCH_3$-phenyl |
| 336 | piperidine-$(CH_2)_2$-pyrimidinyl- | CH | —CONH— | pyridine |
| 337 | $NH_2$-pyridin-3-yl- | N | —NHCO— | indole |
| 338 | Pyrimidin-5-yl | N | —NHCONH— | indoline |
| 339 | $NH_2$-pyrimidin-5-yl- | N | —$NHSO_2NH$— | benzofuran |
| 340 | 1-piperidinyl-N-pyridin-3-yl- | N | —NHCO— | 2-F-phenyl |
| 341 | cyclohexyl-N-pyridin-3-yl- | N | —NHCO— | 4-F-phenyl |
| 342 | morpholine-$(CH_2)_2$—N-pyridin-3-yl- | N | —CONH— | dihydro-benzofuran |
| 343 | $(CH_3)_2N$—$(CH_2)_2$—N-pyridin-3-yl- | N | —CONH— | cyclohexyl-$(CH_2)_2$— |
| 344 | $(C_2H_5)_2N$—$(CH_2)_2$-pyrimidin-5-yl- | N | —CONH— | cyclopropyl-$(CH_2)_2$— |
| 345 | 3-OH-pyrimidin-5-yl | N | —$SO_2NH$— | 2-thiophene |
| 346 | 3-pyridinyl-amido-pyridin-3-yl | N | —$NHSO_2$— | 3-thiophene |
| 347 | N-phenyl-amido-3-pyridinyl | N | —NHCONH— | 2-pyridine |
| 348 | 3-amido-5-pyrimidinyl | N | —NHCONH— | 1-morpholinyl |
| 349 | 4-$CH_3$-pyridazinyl | CH | —NHCO— | 1-piperazinyl |
| 350 | cyclohexyl-HN—$(CH_2)_2$-pyridin-3-yl- | N | —$NHSO_2$— | 1-piperidinyl |

The following compounds are additional representative examples of compounds of the present invention:

N~3~-(6-isopropoylamino-3-pyridinyl)-N~1~-(2-cyclopentylethyl)-4-methyl-1,3-benzenedicarboxamide;

N~3~-(6-(3,3,3-trifluoroethanoylamino)-3-pyridinyl)-N~1~-(2-cyclopentylethyl)-4-methyl-1,3-benzenedicarboxamide;

N~3~-(6-methoxyacetylamino-3-pyridinyl)-N~1~-(2-cyclopentylethyl)-4-methyl-1,3-benzenedicarboxamide;

N~3~-(6-(phenoxyacetylamino)-3-pyridinyl)-N~1~-(2-cyclopentylethyl)-4-methyl-1,3-benzenedicarboxamide;

N~3~-(6-(trans-2-phenyl-1-cyclopropanoylamino)-3-pyridinyl)-N~1~-(2-cyclopentylethyl)-4-methyl-1,3-benzenedicarboxamide;

N~3~-(6-(1s-trans-2-fluorocyclopropanoylamino)-3-pyridinyl)-N~1~-(2-cyclopentylethyl)-4-methyl-1,3-benzenedicarboxamide;

N~3~-(6-®-(-)-2-pheylglycinecarbonylamino)-3-pyridinyl)-N~1~-(2-cyclopentylethyl)-4-methyl-1,3-benzenedicarboxamide;

N~3~-(6-phenacylamino-3-pyridinyl)-N~1~-(2-cyclopentylethyl)-4-methyl-1,3-benzenedicarboxamide;

N~3~-(6-(2-chlorobenzoylamino)-3-pyridinyl)-N~1~-(2-cyclopentylethyl)-4-methyl-1,3-benzenedicarboxamide;

N~3~-(6-(2-methoxybenoylamino)-3-pyridinyl)-N~1~-(2-cyclopentylethyl)-4-methyl-1,3-benzenedicarboxamide;

N~3~-(6-(2-truifluoromethylbenzoylamino)-3-pyridinyl)-N~1~-(2-cyclopentylethyl)-4-methyl-1,3-benzenedicarboxamide;

N~3~-(6-(o-toluoylamino)-3-pyridinyl)-N~1~-(2-cyclopentylethyl)-4-methyl-1,3-benzenedicarboxamide;

N~3~-(6-(2-trifluromethoxybenzoylamino)-3-pyridinyl)-N~1~-(2-cyclopentylethyl)-4-methyl-1,3-benzenedicarboxamide;

N~3~-(6-(2-fluorobenzoylamino)-3-pyridinyl)-N~1~-(2-cyclopentylethyl)-4-methyl-1,3-benzenedicarboxamide;
N~3~-(6-(3-fluorobenzoylamino)-3-pyridinyl)-N~1~-(2-cyclopentylethyl)-4-methyl-1,3-benzenedicarboxamide;
N~3~-(6-(4-fluorobenzoylamino)-3-pyridinyl)-N~1~-(2-cyclopentylethyl)-4-methyl-1,3-benzenedicarboxamide;
N~3~-(6-(6-chloronicotinoylamino)-3-pyridinyl)-N~1~-(2-cyclopentylethyl)-4-methyl-1,3-benzenedicarboxamide;
N~3~-(6-(thiophene-2-carbonylamino)-3-pyridinyl)-N~1~-(2-cyclopentylethyl)-4-methyl-1,3-benzenedicarboxamide;
N~3~-(6-(4-methyloxazole-5-carbonylamino)-3-pyridinyl)-N~1~-(2-cyclopentylethyl)-4-methyl-1,3-benzenedicarboxamide;
N~3~-(6-(4-methyl-1,2,3-thiadiazole-5-carbonylamino)-3-pyridinyl)-N~1~-(2-cyclopentylethyl)-4-methyl-1,3-benzenedicarboxamide;
N~3~-(6-(N,N-dimethylcarbamoylamino)-3-pyridinyl)-N~1~-(2-cyclopentylethyl)-4-methyl-1,3-benzenedicarboxamide;
N~3~-(6-(N-methyl-N-phenylcarbamoylamino)-3-pyridinyl)-N~1~-(2-cyclopentylethyl)-4-methyl-1,3-benzenedicarboxamide;
N~3~-(6-(phenylcarbamoylamino)-3-pyridinyl)-N~1~-(2-cyclopentylethyl)-4-methyl-1,3-benzenedicarboxamide;
N~3~-(6-(isopropylcarbamoylamino)-3-pyridinyl)-N~1~-(2-cyclopentylethyl)-4-methyl-1,3-benzenedicarboxamide;
N~3~-(6-(4-methyl-1-piperazinecarbonylamino)-3-pyridinyl)-N~1~-(2-cyclopentylethyl)-4-methyl-1,3-benzenedicarboxamide;
N~3~-(6-(1-piperidinecarbonylamino)-3-pyridinyl)-N~1~-(2-cyclopentylethyl)-4-methyl-1,3-benzenedicarboxamide;
N~3~-(6-(4-morpholinecarbonylamino)-3-pyridinyl)-N~1~-(2-cyclopentylethyl)-4-methyl-1,3-benzenedicarboxamide;
N~3~-(6-(1-pyrrolidinecarbonylamino)-3-pyridinyl)-N~1~-(2-cyclopentylethyl)-4-methyl-1,3-benzenedicarboxamide;
N~3~-(6-amino-4-methyl-3-pyridinyl)-N~1~-(2-cyclopentylethyl)-4-methyl-1,3-benzenedicarboxamide;
N~3~-(6-amino-2-methly-3-pyridinyl)-N~1~-(2-cyclopentylethyl)-4-methyl-1,3-benzenedicarboxamide;
N~3~-(6-cyclopropylamino-3-pyridinyl)-N~1~-(2-cyclopentylethyl)-4-methyl-1,3-benzenedicarboxamide;
N~3~-(6-phenylamino-3-pyridinyl)-N~1~-(2-cyclopentylethyl)-4-methyl-1,3-benzenedicarboxamide;
N~3~-(6-quinolinyl)-N~1~-(2-cyclopentylethyl)-4-methyl-1,3-benzenedicarboxamide;
N~3~-(6-methoxy-3-quinolinyl)-N~1~-(2-cyclopentylethyl)-4-methyl-1,3-benzenedicarboxamide;
N~3~-(6-quinoxalinyl)-N~1~-(2-cyclopentylethyl)-4-methyl-1,3-benzenedicarboxamide;
N~3~-(1,3,4-thiadiazol-2-yl)-N~1~-(2-cyclopentylethyl)-4-methyl-1,3-benzenedicarboxamide;
N~3~-(5-methly-pyrazol-3-yl)-N~1~-(2-cyclopentylethyl)-4-methyl-1,3-benzenedicarboxamide;
N~3~-(5-methyl-isoxazol-3-yl)-N~1~-(2-cyclopentylethyl)-4-methyl-1,3-benzenedicarboxamide;
N~3~-(imidazol-4-yl)-N~1~-(2-cyclopentylethyl)-4-methyl-1,3-benzenedicarboxamide;
N~3~-(6-chloro-3-pyridinyl)-N~1~-(2-cyclopentylethyl)-4-methyl-1,3-benzenedicarboxamide;
N~3~-(6-pyridin-2-ylamino-3-pyridinyl)-N~1~-(2-cyclopentylethyl)-4-methyl-1,3-benzenedicarboxamide;
N~3~-(6-pyrimidylamino-3-pyridinyl)-N~1~-(2-cyclopentylethyl)-4-methyl-1,3-benzenedicarboxamide;
N~3~-(6-benzimidazolylmino-3-pyridinyl)-N~1~-(2-cyclopentylethyl)-4-methyl-1,3-benzenedicarboxamide;
N~3~-(6-(5-methyl-1,3,4-thiadiazol-2-yl-amino)-3-pyridinyl)-N~1~-(2-cyclopentylethyl)-4-methyl-1,3-benzenedicarboxamide;
N~3~-(6-cyano-3-pyridinyl)-N~1~-(2-cyclopentylethyl)-4-methyl-1,3-benzenedicarboxamide;
N~3~-(6-(5-methylimidazolylamino)-3-pyridinyl)-N~1~-(2-cyclopentylethyl)-4-methyl-1,3-benzenedicarboxamide;
N~3~-(6-(1,2,4-triazolylamino)-3-pyridinyl)-N~1~-(2-cyclopentylethyl)-4-methyl-1,3-benzenedicarboxamide;
N~3~-(6-(5-methylisoxazolylamino)-3-pyridinyl)-N~1~-(2-cyclopentylethyl)-4-methyl-1,3-benzenedicarboxamide;
N~3~-(6-(pyrimidinemethyamino)-3-pyridinyl)-N~1~-(2-cyclopentylethyl)-4-methyl-1,3-benzenedicarboxamide; and
N~3~-(6-(3-methylpyridinemethylamino)-3-pyridinyl)-N~1~-(2-cyclopentylethyl)-4-methyl-1,3-benzenedicarboxamide.

All process steps described herein can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, water, esters, typically lower alkyl-lower alkanoates, e.g EtOAc, ethers, typically aliphatic ethers, e.g. Et$_2$O, or cyclic ethers, e.g. THF, liquid aromatic hydrocarbons, typically benzene or toluene, alcohols, typically MeOH, EtOH, IPA or 1-propanol, nitriles, typically AcCN, halogenated hydrocarbons, typically CH$_2$Cl$_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient species and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I, II or III, including their salts, are also obtainable in the form of hydrates, or their crystals can include for example the solvent used for crystallization (present as solvates).

New starting materials and/or intermediates, as well as processes for the preparation thereof, are likewise the subject of this invention. In one embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The examples above serve to illustrate various embodiments of the invention. The tables also contain the method by which these examples were prepared, with respect to the various schemes and examples presented above. The schematic illustrations, detailed description of the methods and preparation of compounds of Formulas I, II or III, and compounds described above fall within the scope, and serve to exemplify the scope of compounds contemplated in the invention. These detailed method descriptions are presented for illustrative purposes only and are not intended as a restriction on the scope of the present invention.

Biological Assays

The following assays can be employed to determine the degree of activity of a compound as a protein kinase inhibitor. Compounds described herein have been tested in one or more of these assays, and have shown activity. Representative compounds of the invention were tested and found to exhibit IC50 values of at least <10 μM in any one of the described assays, thereby demonstrating and confirming the utility of the compounds of the invention as protein kinase inhibitors and in the prophylaxis and treatment of autoimmune diseases, hyperproliferative disorders, etc.

LCK-Homogeneous Time Resolved Fluorescent (HTRF) Kinase Assay:

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents. The LCK HTRF assay is comprised of 10 μL of compound in 100% DMSO, 15 μL of ATP and biotinylated Gastrin, and 15 μL of LCK KD GST (225-509) for a final volume of 40 μL. The final concentration of gastrin is 1.2 μM. The final concentration of ATP is 0.5 μM (Km app=0.6 μM+/−0.1) and the final concentration of LCK is 250 pM. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Assays for other kinases are done in a similar way as described above, varying the concentrations of enzyme, peptide substrate, and ATP added to the reaction, depending on the specific activity of the kinase and measured Km's for the substrates.

Of the compounds which were tested, exemplary compounds 1, 2, 11-20, 22-72, 74-86, 88, 90-94, 96, 98-101, 103-136 and 140-143 exhibited an average $IC_{50}$ value of 10 uM or less in a human HTRF assay, for the inhibition of the Lck kinase enzyme. The majority of the exemplary compounds tested above exhibited an average $IC_{50}$ value of 1 uM or less in the human Lck kinase HTRF assay.

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; $2\times10^5$/well) are incubated with mitomycin C-treated B lymphoblastoid cells (JY cell line; $1\times10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay:

The purpose of this assay is to test the general anti-proliferative/cytotoxic effect of compounds on the Jurkat human T cell line. Jurkat cells ($1\times10^5$/well) are plated in 96-well flat-bottom tissue culture plates with or without compound dilutions and cultured for 72 h at 37° C. in 5% $CO_2$. Viable cell number is determined during the last 4 h of culture by adding 10 μL/well WST-1 dye. WST-1 dye conversion relies on active mitochondrial electron transport for reduction of the tetrazolium dye. The dye conversion is read by OD at 450-600 nm.

Anti-CD3/CD28-Induced T Cell IL-2 Secretion and Proliferation Assay:

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1\times10^5$ T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

cKIT-Homogeneous Time Resolved Fluorescent (HTRF) Kinase Assay:

The purpose of this assay is to measure the inhibition of cKIT enzyme activity (autophosphorylation and phosphorylation of substrate) by small molecule test compounds. The cKIT HTRF assay begins with cKIT-catalyzed phosphorylation of biotinylated peptide Her-2 (N-GGMEDIYFEFMG-GKKK-C) in the presence of ATP. The cKIT enzyme reaction is comprised of 1 µL of compound in 100% DMSO, 15 µL of 2× substrate mix (50 µM ATP and 2 µM biotinylated Her-2) and 15 µL of 2× cKIT (6.25 µM) (catalytic domain, N-terminal GST tagged, unphosphorylated) in 4 mM DTT all diluted in enzyme buffer (25 mM HEPES pH 7.5, 12.5 mM NaCl, 50 mM MgCl, 0.05% BSA). The reaction incubates for 90 min at room temperature. One-hundred and sixty microliters of detection mixture containing 0.47 µg/mL streptavidin allophycocyanin and 29.7 pM europylated anti-phosphotyrosine Ab (PT66, Perkin Elmer) in HTRF buffer (100 mM Hepes pH 7.5, 100 mM NaCl, 0.1% BSA, 0.05% Tween 20) is then added to stop the reaction by diluting out the enzyme as well as to enable quantitation of phosphorylated Her-2. After 3 h at room temperature, the detection reaction is read in a Packard Discovery™ (model BD1000) plate reader. The wells are excited with coherent 320 nM light and the ratio of delayed (50 ms post excitation) emissions at 620 nM (native europium fluorescence) and 665 nm (europium fluorescence transferred to allophycocyanin—an index of substrate phosphorylation) is determined. The proportion of substrate phosphorylated in the kinase reaction in the presence of compound compared with that phosphorylated in the presence of DMSO vehicle alone (HI control) is calculated using the formula: % control (POC)=(cpd−average LO)/(average HI−average LO)*100. Data (consisting of POC and inhibitor concentration in µM) is fitted to a 4-parameter equation ($y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm.

Of the compounds tested, exemplary compounds 1, 2, 11-40, 22-40, 42-46, 48-63, 69-72, 74-76, 81-86, 88, 90, 96, 98-100, 102-105, 109, 110, 112, 113, 120-130, 134-138, 141, 144-146, 149-152, 154-159, 161-164, 166-174, 176-180, 182, 184-190, 192-204, 206 and 217-219 exhibited an average $IC_{50}$ value of 10 uM or less in a human HTRF assay, for the inhibition of the c-kit kinase enzyme. The majority of the exemplary compounds tested above exhibited an average $IC_{50}$ value of 1 uM or less in the human c-kit kinase HTRF assay.

M07e phosphorylated-c-kit (Tyr721) Electrochemiluminescent Immunoassay:

The purpose of this assay is to test the potency of small molecule and biologic compounds on SCF-stimulated c-kit receptor phosphorylation of tyrosine 721 (Tyr721) in MO7e cells. Activation of c-kit upon binding with it's ligand, stem cell factor (SCF), leads to dimerization/oligomerization and autophosphorylation. Activation of c-kit results in the recruitment and tyrosine phosphorylation of downstream SH2-containing signaling components—such as the p85 subunit of PI3 kinase (Sattler, M. et al. (1997) *J. Biol. Chem.* 272, 10248-10253). C-kit phosphorylated at Tyr721 binds to the p85 subunit of PI3 kinase (Blume-Jensen, P et al. (2000) *Nature Genet.* 24, 157-162). MO7e cells are a human megakaryoblastic factor dependent leukemia cell line (these cells have been confirmed to carry wild type c-kit receptor). Cells are maintained in growth media (IMDM, 10% HI-FBS, 1× PGS, 5 ng/mL GM-CSF). To measure SCF-induced c-kit phosphorylation, cells are washed and re-suspended to 3.3E5c/mL in assay media (RPMI 1640/4% HI-FBS, 1× PGS) and plated at 30 uL/well for 10000 c/well. Small molecule compounds are diluted in 100% DMSO, antibodies and other biologics are diluted in assay media only. Cells are pre-incubated with 0.5-2 µL compound for 1 h at room temperature. Ten microliters of 4× SCF (100 ng/mL) in room temperature assay media is then added. After 30 min incubation at room temperature, the cells are lysed with the addition of 20 µL of ice cold 3× lysis buffer (20 mM Tris-Cl, 1 mM EDTA, 150 mM NaCl, 1% NP-40, 2 mM NaF, 20 mM -glycerophosphate, 1 mM $Na_3VO_4$ and 1 Complete Proteinase inhibitor tablet/50 mL 1× lysis buffer (Roche Cat #1697498, in stock room)). Twenty-five microliters of lysate is transferred to blocked MSD plates (blocked with 5% BSA in Tris-buffered saline, 0.01% Tween (TBS-T) for 1 h with shaking, then washed 3× with TBS-T) coated with anti-c-kit antibody (Labvision MS-289). After the plates are incubated with shaking for 1 h at room temperature, 25 µL of 10 nM ruthenylated detection antibody (Zymed 34-9400) is added and the plate is incubated again with shaking for 1 h at room temperature. The plates are then washed 3× with TBS-T, 150 µL of MSD Read Buffer T is added, and the electrochemiluminescence (ECL) reaction is read on the Sector Imager™ 6000. A low voltage is applied to the ruthenylated phos-c-kit (Tyr721) immune complexes, which in the presence of TPA (the active component in the ECL reaction buffer, Read Buffer T), results in a cyclical redox reaction generating light at 620 nm. The amount of phosphorylated c-kit (Tyr721) in the presence of compounds compared with that in the presence of vehicle alone (HI control) is calculated using the formula: % control (POC)=(cpd−average LO)/(average HI−averageLO)*100. Data (consisting of POC and inhibitor concentration in µM) is fitted to a 4-parameter equation ($y=A+((B-A)/(1+((x/C)^D)))$), where A is the minimum y (POC) value, B is the maximum y (POC), C is the x (cpd concentration) at the point of inflection and D is the slope factor) using a Levenburg-Marquardt non-linear regression algorithm.

SCF and GM-CSF Stimulated UT7 Proliferation/Survival Assay:

The purpose of this assay is to test the general anti-proliferative/cytotoxic effect of small molecule and biologic compounds on SCF or GM-CSF-stimulated UT-7 cells. Preventing SCF stimulated proliferation/survival is consistent with an on-mechanism effect whereas inhibition of GM-CSF driven proliferation/survival is indicative of off-target effects. UT-7 is a factor dependent human megakaryoblastic leukemia cell line that can be grown in either IL-3, GM-CSF, EPO or SCF (these cells have been confirmed to carry wild type c-kit receptor). Cells are maintained in growth media (IMDM, 10% HI-FBS, 1× PGS, 1 ng/mL GM-CSF). To measure SCF or GM-CSF-induced proliferation, cells are washed and re-suspended to 5e4c/mL in assay media (RPMI 1640/4% HI-FBS, 1× PGS) and plated at 50 uL/well for 2500 c/well. Small molecule compounds are first diluted in 100% DMSO, then diluted 1:4 in room temperature assay media. Antibodies and other biologics are diluted in assay media only. Five microliters of 11× SCF (55 ng/mL) or 11× GM-CSF (11 ng/mL) in assay media plus 1 µL of diluted drug are added to the cell plates. The treated cells are incubated in a 37° C. humidified incubator with 5% $CO_2$ for 3 days. The amount of ATP is then measured as a surrogate marker for cell viability. This is accomplished by adding 50 µL of Perkin Elmer ATP 1step reagent (as per instructed in the reagent manual, Cat. No. 6016739), incubating at room temperature for 15 min and reading the luminescence with a Perkin Elmer Topcount NXT™HTS (model c384) plate reader. The amount of SCF or GM-CSF stimulated viable cells in the presence of compound compared with in the presence of vehicle alone (HI control) is calculated using the formula: % control (POC)=(cpd−average LO)/(average HI−average LO)*100. Data (consisting of POC and inhibitor concentration in µM) is fitted to a 4-parameter equation $(y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm.

Methods of Use

For the treatment of Lck-mediated diseases, c-kit mediated diseases and/or other diseases listed above, the compounds of the present invention may be administered by several different modes, including without limitation, oral, parental, by spray inhalation, rectal, or topical, as discussed herein. The term parenteral as used herein, includes subcutaneous, intravenous, intramuscular, intrasternal, infusion techniques or intraperitoneal administration.

Treatment of diseases and disorders herein is intended to also include therapeutic administration of a compound of the invention (or a pharmaceutical salt, derivative or prodrug thereof) or a pharmaceutical composition containing said compound to a subject (i.e., an animal, preferably a mammal, most preferably a human) believed to be in need of preventative treatment, such as, for example, pain, inflammation and the like. Treatment also encompasses administration of the compound or pharmaceutical composition to subjects not having been diagnosed as having a need thereof, i.e., prophylactic administration to the subject. Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

"Treating" or "treatment of" within the context of the instant invention, means an alleviation, in whole or in part, of symptoms associated with a disorder or disease, or halt of further progression or worsening of those symptoms, or prevention or prophylaxis of the disease or disorder. Similarly, as used herein, an "effective amount" or "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. For example, within the context of treating patients in need of an inhibitor of c-kit, successful treatment may include a reduction in tumor adhesion and anchorage; an alleviation of symptoms related to a cancerous growth or tumor, or proliferation of diseased tissue; a halting in the progression of a disease such as cancer or in the growth of cancerous cells.

While it may be possible to administer a compound of the invention alone, in the methods described, the compound administered is generally present as an active ingredient in a desired dosage unit formulation, such as pharmaceutically acceptable composition containing conventional pharmaceutically acceptable carriers. Thus, in another embodiment of the invention, there is provided a pharmaceutical composition comprising a compound of this invention in combination with a pharmaceutically acceptable carrier. Acceptable pharmaceutical carriers generally include diluents, excipients, adjuvants and the like as described herein.

A pharmaceutical composition of the invention may comprise an effective amount of a compound of the invention or an effective dosage amount of a compound of the invention. An effective dosage amount of a compound of the invention includes an amount less than, equal to, or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound may be administered by administering a portion of the composition.

The pharmaceutical compositions may generally be prepared by mixing one or more compounds of Formula I, II or III including stereoisomersor tautomers, solvates, pharmaceutically acceptable salts, derivatives or prodrugs thereof, with pharmaceutically acceptable carriers, excipients, binders, adjuvants, diluents and the like, to form a desired administrable formulation to treat or ameliorate a variety of disorders related to the activity of Lck, particularly inflammation, or related to the activity c-kit, particularly autoimmune disease.

Pharmaceutical compositions can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (2000); and "Pharmaceutics The Science of Dosage Form Design, $2^{nd}$ Ed. (Aulton, ed.) Churchill Livingstone (2002). The following dosage forms are given by way of example and should not be construed as limiting the invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or stereoisomers, solvates, prodrugs, pharmaceutically acceptable salts or tautomers thereof, with at least one additive or excipient such as a starch or other additive and tableted, encapsulated or made into other desirable forms for conventional administration. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration.

For nasal administration, the pharmaceutical formulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms for parenteral administration generally include aqueous suspensions or oil suspensions, which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

The formulations of the invention may be designed to be short-acting, fast-releasing, long-acting, and sustained-releasing as described below. Thus, the pharmaceutical formulations may also be formulated for controlled release or for slow release. The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dosage amount or dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for treating Lck-mediated diseases, C-kit mediated diseases, and other diseases listed above with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Formulations suitable for topical administration include liquid or semi-liquid preparations suitable for penetration through the skin (e.g., liniments, lotions, ointments, creams, or pastes) and drops suitable for administration to the eye, ear, or nose.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

The pharmaceutical compositions may be subjected to conventional pharmaceutical operations such as sterilization and/or may contain conventional adjuvants, such as preservatives, stabilizers, wetting agents, emulsifiers, buffers etc. The pharmaceutically active compounds of this invention can be processed in accordance with conventional methods of pharmacy to produce medicinal agents for administration to patients, including humans and other mammals.

While the compounds of the present invention can be administered as the sole active pharmaceutical agent, they can also be used in combination with one or more compounds of the invention or with one or more other agents. When administered as a combination, the therapeutic agents can be formulated and given to the subject as a single composition or the combination of therapeutic agents can be formulated and given to the subject as separate compositions that are given at the same time or different times.

For example, the compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition modulated by Lck kinase or c-kit kinase. In some embodiments, therapeutic compositions are provided that include a compound of the invention and a second therapeutic agent as a combined preparation for simultaneous, separate or sequential use in the prophylactic treatment of a subject at risk for a disease or condition modulated by Lck kinase or c-kit kinase. In some such embodiments, the components are provided as a single composition. In other embodiments, the compound and the second therapeutic agent are provided separately as parts of a kit.

Treatment may also include administering the pharmaceutical formulations of the present invention in combination with other therapies. For example, the compounds and pharmaceutical formulations of the present invention may be administered before, during, or after surgical procedure and/or radiation therapy. Alternatively, the compounds of the invention can also be administered in conjunction with other anti-proliferative agents including those used in antisense and gene therapy.

One category of suitable antiproliferative agents useful in the present invention is the alkylating agents, a group of highly reactive chemotherapeutics that form covalent linkages with nucleophilic centers (e.g., hydroxyl and carboxyl). Chemically, the alkylating agents can be divided into five groups: nitrogen mustards, ethylenimines, alkylsulfonates, triazenes, and nitrosureas. The nitrogen mustards are frequently useful in, for example, the treatment of chronic lymphocytic leukemia, Hodgkin's disease, malignant lymphoma, small cell lung cancer and breast and testicular cancer. Exemplary nitrogen mustards include chlorambucil, cyclophosphamide, ifosfamide, mechlorethamine, melphalan and uracil mustard. The ethylenimines, the most common of which is thiotepa, may be useful in bladder tumors and in breast and ovarian adenocarcinomas. The alkyl sulfonates are useful in the treatment of chronic myelogenous leukemia and other myeloproliferative disorders. Exemplary alkyl sulfonates include busulfan and piposulfan. The triazines, which include, e.g., dacarbazine, are useful in the treatment of malignant melanomas and sarcomas. Temozolomide, an analog of dacarbazine, may also be used in the methods and compositions of the present invention. Finally, the nitrosureas are especially useful against brain tumors, but also are effective for, e.g., multiple myeloma, malignant melanoma, and lymphoma. Exemplary nitrosureas include carmustine and lomustine.

Another category of antiproliferative agents suitable for use in the present invention is the antimetabolites, structural analogs of normally occurring metabolites that interfere with normal nucleic acid biosynthesis. This category of agents may be subdivided into the folic acid analogs, purine analogs and pyrimidine analogs based on the function of the metabolite with which the agent interferes. The most common folic acid analog is methotrexate, useful in the treatment of choriocarcinoma, leukemias, neoplasms and psoriasis. The purine analogs, such as mercaptopurine, thioguanine and azathioprine, may be useful in leukemias. The pyrimidine analogs are useful in the treatment of, for example, leukemia and carcinomas of the gastrointestinal tract, mammary gland, and bladder. Exemplary pyrimidine analogs include fluorouracil (5-FU), UFT (uracil and ftorafur), capecitabine, gemcitabine and cytarabine.

The vinca alkaloids, natural product-based agents that exert their cytotoxicity by binding to tubulin, represent another category of antiproliferative agents suitable for use in the present invention. The vinca alkaloids are useful in, for example, the treatment of lymphomas, leukemias, and lung, breast, testicular, bladder and head and neck cancers. Exemplary agents include vinblastine, vincristine, vinorelbine and vindesine. The taxanes, agents which promote microtubule assembly, and the podophyllotoxins, agents which inhibit topoisomerases, represent related categories of antiproliferative agents that may be useful in the methods and compositions of the present invention. Exemplary taxanes include paclitaxol and docetaxol, which are useful in breast and lung cancers, among others. Exemplary podophyllotoxins include etoposide (useful in, for example, lymphoma and Hodgkin's disease), teniposide, ironotecan (useful in, for example, colon, rectal and lung cancer) and topotecan, the latter two of which act via inhibition of topoisomerase I.

Antineoplastic antibiotics represent another category of antiproliferative agents useful in the methods and compositions of the present invention. These agents exert their effects by binding to or complexing with DNA. Exemplary agents include daunorubicin, doxorubicin, epirubicin, mitoxantrone, mitomycin, dactinomycin, plicamycin, and bleomycin. The antibiotics are useful in a diverse range of disorders, including Hodgkin's disease, leukemia, lymphoma, and lung cancer.

The methods and compositions of the present invention may comprise other antiproliferative agents, including the platinum complexes (e.g., cisplatin and carboplatin, which are especially useful in the treatment of lung, head and neck, ovarian and breast cancer); enzymes (e.g., L-asparaginase); hormone-related therapy hormone (e.g., tamoxifen, leuprolide, flutamide, megesterol acetate, diethylstilbestrol, prednisone and estradiol cypionate); hydroxyurea; methylhydrazine derivatives such as procarbazine; adrenocortical suppressants, e.g., mitotane, aminoglutethimide; aromatase inhibitors (e.g., anastrozole); and biologic response modifiers (e.g., interferon-A).

Furthermore, the methods and compositions of the present invention may comprise antiproliferative agents that result from the combination of two or more agents including, for example, prednimustine (a conjugate of prednisone and chlorambucil) and estramustine (a conjugate of nornitrogen mustard and estradiol).

The methods and compositions of the present invention may comprise a combination with another kinase inhibitor. Although the present invention is not limited to any particular kinase, kinase inhibitors contemplated for use include, without limitation, tyrphostin AG490 (2-cyano-3-(3,4-dihydroxyphenyl)-N-(benzyl)-2-propenamide), Iressa (ZD1839; Astra Zeneca); Gleevec (STI-571 or imatinib mesylate; Novartis); SU5416 (Pharmacia Corp./Sugen); and Tarceva (OSI-774; Roche/Genentech/OSI Pharmaceuticals).

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

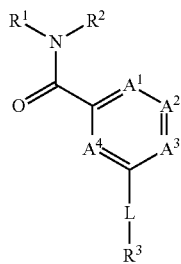

or a stereoisomer, tautomer or pharmaceutically acceptable salt thereof, wherein $A^1$ is $CR^4$;
$A^2$ is $CR^5$;
$A^3$ is $CR^6$;
$A^4$ is $CR^7$; provided that when L is —NHC(O)—, $A^1$ is $CR^4$, $A^2$ is $CR^5$, $A^3$ is $CR^6$ and $A^4$ is $CR^7$, then $R^6$ is H;
L is —C(O)NR$^7$— or —NR$^7$C(O)—;
$R^1$ is quinolinyl or isoquinolinyl, each ring of which is optionally substituted independently with 1-3 substituents of $R^8$, $R^9$, $NR^8R^8$, $NR^8R^9$, $OR^8$, $OR^9$, $SR^8$, $SR^9$, $C(O)R^8$, $C(O)R^9$, $OC(O)R^8$, $C(O)OR^8$, $C(O)NR^8R^8$, $C(O)NR^8R^9$, $NR^8C(O)R^8$, $NR^8C(O)R^9$, $NR^8C(O)NR^8R^8$, $NR^8C(O)NR^8R^9$, $NR^8C(O)OR^8$, $NR^8C(O)OR^9$, $S(O)_2R^8$, $S(O)_2R^9$, $S(O)_2NR^8R^8$, $S(O)_2NR^8R^9$, $NR^8S(O)_2NR^8R^8$, $NR^8S(O)_2NR^8R^9$, $NR^8S(O)_2R^8$ or $NR^8S(O)_2R^9$;
$R^2$ is H, $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 1-3 heteroatoms selected from N, O and S and optionally substituted with 1-3 substituents of $R^9$ or $R^{10}$;
$R^3$ is a ring selected from phenyl and benzo[1.3]dioxolyl wherein said ring is optionally substituted independently with 1-5 substituents of $R^{11}$, $R^{12}$, $R^{13}$, $NR^{11}R^{11}$, $NR^{11}R^{12}$, $OR^{11}$, $SR^{11}$, $OR^{12}$, $SR^{12}$, $C(O)R^{11}$, $C(S)R^{11}$, $CN(CN)R^{11}$, $C(O)R^{12}$, $C(S)R^{12}$, $CN(CN)R^{12}$, $C(O)C(O)R^{11}$, $OC(O)R^{11}$, $COOR^{11}$, $C(O)SR^{11}$, $C(O)C(O)R^{12}$, $OC(O)R^{12}$, $COOR^{12}$, $C(O)SR^{12}$, $C(O)NR^{11}R^{11}$, $C(S)NR^{11}R^{11}$, $C(O)NR^{11}R^{12}$, $C(S)NR^{11}R^{12}$, $OC(O)NR^{11}R^{12}$, $NR^{11}C(O)R^{11}$, $NR^{11}C(O)R^{12}$, $NR^{11}C(S)NR^{11}C(S)R^{12}$, $NR^{11}C(O)NR^{11}R^{11}$, $NR^{11}C(O)NR^{11}R^{12}$, $NR^{11}C(S)NR^{11}R^{11}$, $NR^{11}C(S)NR^{11}R^{12}$, $NR^{11}C(O)OR^{11}$, $NR^{11}C(O)OR^{12}$, $NR^{11}C(O)C(O)R^{11}$, $NR^{11}C(O)C(O)R^{12}$, $NR^{11}C(O)C(O)NR^{11}R^{12}$, $S(O)_2R^{11}$, $S(O)_2R^{12}$, $S(O)_2NR^{11}R^{11}$, $S(O)_2NR^{11}R^{12}$, $NR^{11}S(O)_2NR^{11}R^{12}$, $NR^{11}S(O)_2R^{11}$ or $NR^{11}S(O)_2R^{12}$;
$R^4$ is H or $C_{1-10}$-alkyl;
$R^5$ is H;
$R^6$ is H;
$R^7$ is H;
$R^8$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^9$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{10}$, oxo, $NR^{10}R^{10}$, $OR^{10}$, $SR^{10}$, $C(O)R^{10}$, $COOR^{10}$, $C(O)NR^{10}R^{10}$, $NR^{10}C(O)R^{10}$, $NR^{10}C(O)NR^{10}R^{10}$, $S(O)_2R^{10}$, $S(O)_2NR^{10}R^{10}$ or $NR^{10}S(O)_2R^{10}$;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{11}$ is H, halo, haloalkyl, CN, $NO_2$, acetyl, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^{12}R^{13}$, $NR^{13}R^{13}$, $OR^{12}$, $SR^{12}$, $OR^{13}$, $SR^{13}$, $C(O)R^{12}$, $OC(O)R^{12}$, $COOR^{12}$, $C(O)R^{13}$, $OC(O)R^{13}$, $COOR^{13}$, $C(O)NR^{12}R^{13}$, $C(O)NR^{13}R^{13}$, $NR^{13}C(O)R^{12}$, $NR^{13}C(O)R^{13}$, $NR^{13}C(O)NR^{12}R^{13}$, $NR^{13}C(O)NR^{13}R^{13}$, $NR^{13}C(O)OR^{12}$, $NR^{13}C(O)OR^{13}$, $OC(O)NR^{12}R^{13}$, $OC(O)NR^{13}R^{13}$, $S(O)_2R^{12}$, $S(O)_2NR^{12}R^{13}$, $S(O)_2R^{13}$, $S(O)_2NR^{13}R^{13}$, $NR^{13}S(O)_2NR^{12}R^{13}$, $NR^{13}S(O)_2NR^{13}R^{13}$, $NR^{13}S(O)_2R^{12}$, $NR^{13}S(O)_2R^{13}$ or $R^{13}$;

$R^{12}$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{13}$, oxo, $NR^{13}R^{13}$, $OR^{13}$, $SR^{13}$, $C(O)R^{13}$, $COOR^{13}$, $C(O)NR^{13}R^{13}$, $NR^{13}C(O)R^{13}$, $NR^{13}C$ (O)NR$^{13}$R$^{13}$, OC(O)NR$^{13}$R$^{13}$, S(O)$_2$R$^{13}$, S(O)$_2$NR$^{13}$R$^{13}$ or NR$^{13}$S(O)$_2$R$^{13}$;

alternatively, R$^{11}$ and R$^{12}$ taken together form a partially or fully saturated or unsaturated 5-6 membered ring of carbon atoms optionally including 1-3 heteroatoms selected from O, N, or S, and the ring optionally substituted independently with 1-5 substituents of R$^{13}$; and R$^{13}$ is H, halo, haloalkyl, CN, OH, NO$_2$, NH$_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

2. The compound of claim 1 wherein R$^1$ is

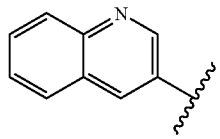 [SMILES: *c1cnc2ccccc2c1]

said ring optionally substituted independently with 1-3 substituents of R$^8$, R$^9$, NR$^8$R$^8$, NR$^8$R$^9$, OR$^8$, OR$^9$, SR$^8$, SR$^9$, C(O)R$^8$, C(O)R$^9$, OC(O)R$^8$, C(O)OR$^8$, C(O)NR$^8$R$^8$, C(O)NR$^8$R$^9$, NR$^8$C(O)R$^8$, NR$^8$C(O)R$^9$, NR$^8$C(O)NR$^8$R$^8$, NR$^8$C(O)NR$^8$R$^9$, NR$^8$C(O)OR$^8$, NR$^8$C(O)OR$^9$, S(O)$_2$R$^8$, S(O)$_2$R$^9$, S(O)$_2$NR$^8$R$^8$, S(O)$_2$NR$^8$R$^9$, NR$^8$S(O)$_2$NR$^8$R$^8$, NR$^8$S(O)$_2$NR$^8$R$^9$, NR$^8$S(O)$_2$R$^8$ or NR$^8$S(O)$_2$R$^9$.

3. The compound of claim 1 wherein
A$^1$ is CR$^4$, wherein R$^4$ is C$_{1-10}$-alkyl;
A$^2$ is CH;
A$^3$ is CH; and
A$^4$ is CH.

4. The compound of claim 1 wherein
R$^1$ is quinolinyl or isoquinolinyl; and
R$^2$ is H or C$_{1-10}$-alkyl.

5. The compound of claim 1 wherein R$^3$ is phenyl optionally substituted as defined in claim 1.

6. The compound of any of claim 1, or a pharmaceutically acceptable salt thereof, selected from:
N3-(6,7-dimethoxyquinolin-3-yl)-4-methyl-N1-(3-((4-methylpiperazin-1-yl)methyl)-5-(trifluoromethyl)phenyl)isophthalamide;
N-(3-((6,7-dimethoxyquinolin-3-yl)carbamoyl)-4-methylphenyl)-2-methyl-3-(trifluoromethyl)benzamide;
N-(3-((6,7-dimethoxyquinolin-3-yl)carbamoyl)-4-methylphenyl)-2,2-difluorobenzo[d][1,3]dioxole-4-carboxamide;
N-(3-((6,7-dimethoxyquinolin-3-yl)carbamoyl)-4-methylphenyl)-2,2-difluorobenzo[d][1,3]dioxole-5-carboxamide;
N3-(6,7-dimethoxyquinolin-3-yl)-N1-(2-fluoro-5-(trifluoromethyl)phenyl)-4-methylisophthalamide;
2-chloro-N-(3-((6,7-dimethoxyquinolin-3-yl)carbamoyl)-4-methylphenyl)-3-(trifluoromethyl)benzamide;
N-(3-((6,7-dimethoxyquinolin-3-yl)carbamoyl)-4-ethylphenyl)-2-methyl-3-(trifluoromethyl)benzamide;
4-methyl-N3-(quinolin-3-yl)-N1-(3-(trifluoromethyl)phenyl)isophthalamide;
4-methyl-N1-(3-((4-methylpiperazin-1-yl)methyl)-5-(trifluoromethyl)phenyl)-N3-(quinolin-3-yl)isophthalamide;
N-(4-methyl-3-((2-(4-(4-methylpiperazin-1-yl)phenylamino)pyrimidin-5-yl)carbamoyl)phenyl)quinoline-4-carboxamide;
N1-(2-fluoro-5-(trifluoromethyl)phenyl)-4-methyl-N3-(quinolin-3-yl)isophthalamide; and
5-(isoquinolin-1-ylamino)-2-methyl-N-(2-(4-(4-methylpiperazin-1-yl)phenylamino)pyrimidin-5-yl)benzamide.

7. A pharmaceutical composition comprising a pharmaceutically acceptable carrier and a compound according to claim 1.

* * * * *